(12) United States Patent
Young et al.

(10) Patent No.: US 10,800,828 B2
(45) Date of Patent: Oct. 13, 2020

(54) SWITCHABLE NON-SCFV CHIMERIC RECEPTORS, SWITCHES, AND METHODS OF USE THEREOF TO TREAT CANCER

(71) Applicant: The Scripps Research Institute, La Jolla, CA (US)

(72) Inventors: Travis Young, La Jolla, CA (US); Chanhyuk Kim, San Diego, CA (US); Peter G. Schultz, La Jolla, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 15/561,274

(22) PCT Filed: Mar. 28, 2016

(86) PCT No.: PCT/US2016/024524
§ 371 (c)(1),
(2) Date: Sep. 25, 2017

(87) PCT Pub. No.: WO2016/154621
PCT Pub. Date: Sep. 29, 2016

(65) Prior Publication Data
US 2018/0118808 A1     May 3, 2018

Related U.S. Application Data

(60) Provisional application No. 62/138,901, filed on Mar. 26, 2015.

(51) Int. Cl.
| | |
|---|---|
| *C07K 14/705* | (2006.01) |
| *C07K 7/08* | (2006.01) |
| *C07K 14/47* | (2006.01) |
| *A61K 38/00* | (2006.01) |
| *C12N 9/12* | (2006.01) |
| *A61K 48/00* | (2006.01) |
| *C07K 14/725* | (2006.01) |
| *A61P 35/00* | (2006.01) |
| *C07K 14/195* | (2006.01) |
| *C07K 14/32* | (2006.01) |
| *C07K 14/78* | (2006.01) |
| *C12N 5/0783* | (2010.01) |
| *C12N 9/22* | (2006.01) |

(52) U.S. Cl.
CPC .............. *C07K 14/705* (2013.01); *C07K 7/08* (2013.01); *C07K 14/47* (2013.01); *C12Y 207/11011* (2013.01); *A61K 38/00* (2013.01); *A61K 48/005* (2013.01); *A61P 35/00* (2018.01); *C07K 14/195* (2013.01); *C07K 14/32* (2013.01); *C07K 14/7051* (2013.01); *C07K 14/70517* (2013.01); *C07K 14/70578* (2013.01); *C07K 14/78* (2013.01); *C07K 2317/522* (2013.01); *C07K 2317/524* (2013.01); *C07K 2317/526* (2013.01); *C07K 2317/53* (2013.01); *C07K 2317/55* (2013.01); *C07K 2317/56* (2013.01); *C07K 2319/00* (2013.01); *C07K 2319/02* (2013.01); *C07K 2319/03* (2013.01); *C07K 2319/20* (2013.01); *C07K 2319/70* (2013.01); *C12N 5/0636* (2013.01); *C12N 9/12* (2013.01); *C12N 9/22* (2013.01); *C12N 2510/00* (2013.01); *C12Y 301/27003* (2013.01)

(58) Field of Classification Search
CPC ...... C07K 14/32; C07K 14/47; C07K 14/195; C07K 14/705; C07K 14/7051; C07K 14/70517; C07K 14/70578; C07K 14/78; C07K 7/08; C07K 2319/00; C07K 2319/02; C07K 2319/03; C07K 2319/20; C07K 2319/70; C07K 2317/522; C07K 2317/524; C07K 2317/526; C07K 2317/53; C07K 2317/55; C07K 2317/56; C12Y 301/27003; C12Y 207/11011; C12N 9/22; C12N 5/0636; C12N 9/12; C12N 2510/00; A61P 35/00; A61K 38/00; A61K 48/005
See application file for complete search history.

(56) References Cited

U.S. PATENT DOCUMENTS

| | | |
|---|---|---|
| 3,773,919 A | 11/1973 | Boswell |
| 3,854,480 A | 12/1974 | Zaffaroni |
| 3,887,699 A | 6/1975 | Yolles |
| 4,452,775 A | 6/1984 | Kent |
| 4,485,045 A | 11/1984 | Regen |

(Continued)

FOREIGN PATENT DOCUMENTS

| | | |
|---|---|---|
| CA | 1176565 | 10/1984 |
| DE | 3218121 | 11/1983 |

(Continued)

OTHER PUBLICATIONS

Rafiq S, et al. (Mar. 2020) Nature Reviews: Clinical Oncology. 17:147-167. (doi.org/10.1038/s41571-019-0297-y).*

(Continued)

*Primary Examiner* — Robert S Landsman
(74) *Attorney, Agent, or Firm* — Cooley LLP

(57) ABSTRACT

Disclosed herein are switchable chimeric receptors, switchable chimeric receptor effector cells and chimeric receptor effector cell switches. The switchable chimeric receptor-ECs are generally T cells. The chimeric receptors have non-antibody extracellular domains that recognize a chimeric receptor binding partner on the chimeric receptor-EC switch or target cell. The chimeric receptor-ECs and switches may be used for the treatment of a disease or condition in a subject in need thereof.

16 Claims, 13 Drawing Sheets

Specification includes a Sequence Listing.

(56) References Cited

U.S. PATENT DOCUMENTS

| | | | |
|---|---|---|---|
| 4,544,545 A | 10/1985 | Ryan et al. | |
| 4,619,794 A | 10/1986 | Hauser | |
| 4,675,189 A | 6/1987 | Kent et al. | |
| 5,133,974 A | 7/1992 | Paradissis et al. | |
| 5,372,930 A | 12/1994 | Colton et al. | |
| 5,407,686 A | 4/1995 | Patel et al. | |
| 5,654,010 A | 8/1997 | Johnson et al. | |
| 5,686,072 A | 11/1997 | Uhr | |
| 5,736,152 A | 4/1998 | Dunn | |
| 5,861,156 A | 1/1999 | George et al. | |
| 5,906,936 A | 5/1999 | Eshhar et al. | |
| 5,912,172 A | 6/1999 | Eshhar et al. | |
| 6,083,751 A | 7/2000 | Feldhaus et al. | |
| 6,372,716 B1 | 4/2002 | Bush et al. | |
| 6,566,329 B1 | 5/2003 | Meyn et al. | |
| 6,686,940 B2 | 2/2004 | Matsuura et al. | |
| 7,258,986 B2 | 8/2007 | Maur et al. | |
| 7,446,190 B2 | 11/2008 | Sadelain et al. | |
| 7,514,537 B2 | 4/2009 | Jensen | |
| 8,802,091 B2 * | 8/2014 | Johnson | C07K 16/2809 424/130.1 |
| 8,802,374 B2 | 8/2014 | Jensen | |
| 8,916,381 B1 | 12/2014 | June et al. | |
| 9,624,276 B2 | 4/2017 | Young et al. | |
| 10,022,427 B2 * | 7/2018 | Chang | C07K 14/555 |
| 2003/0180714 A1 | 9/2003 | Sidhu et al. | |
| 2004/0044177 A1 | 3/2004 | Macke et al. | |
| 2004/0072299 A1 | 4/2004 | Gillies | |
| 2005/0113564 A1 | 5/2005 | Campana et al. | |
| 2005/0129671 A1 | 6/2005 | Cooper et al. | |
| 2006/0083683 A1 | 4/2006 | Hsei | |
| 2007/0172504 A1 | 7/2007 | Shirwan et al. | |
| 2008/0260731 A1 | 10/2008 | Bernett | |
| 2009/0117108 A1 | 5/2009 | Wang et al. | |
| 2010/0178276 A1 | 7/2010 | Sadelain et al. | |
| 2010/0278830 A1 | 11/2010 | Shoemaker et al. | |
| 2010/0297076 A1 | 11/2010 | Morrison | |
| 2010/0324008 A1 | 12/2010 | Low et al. | |
| 2012/0034223 A1 | 2/2012 | Hall et al. | |
| 2012/0213783 A1 | 8/2012 | Rosenberg et al. | |
| 2014/0065171 A1 | 3/2014 | Geierstanger et al. | |
| 2014/0234348 A1 * | 8/2014 | Scholler | C07K 14/465 424/184.1 |
| 2015/0238631 A1 | 8/2015 | Kim et al. | |
| 2017/0246270 A1 | 8/2017 | Young et al. | |

FOREIGN PATENT DOCUMENTS

| | | |
|---|---|---|
| EP | 0036676 | 9/1981 |
| EP | 0058481 | 1/1982 |
| EP | 0052322 | 5/1982 |
| EP | 0088046 | 2/1983 |
| EP | 0102324 | 3/1984 |
| EP | 0133988 | 3/1985 |
| EP | 0142641 | 5/1985 |
| EP | 0143949 | 6/1985 |
| EP | 0158277 | 10/1985 |
| EP | 0517565 | 12/1992 |
| WO | WO-1993/15722 | 8/1993 |
| WO | WO-1994/20069 | 9/1994 |
| WO | WO-96/07399 | 3/1996 |
| WO | WO-96/29998 | 10/1996 |
| WO | WO 96/40072 | 12/1996 |
| WO | WO-97/03692 | 2/1997 |
| WO | WO-1997/015669 A1 | 5/1997 |
| WO | WO-04/009664 | 1/2004 |
| WO | WO-2004/106380 A2 | 12/2004 |
| WO | WO-05/087201 | 9/2005 |
| WO | WO-2007/059312 A2 | 5/2007 |
| WO | WO-2007/070659 A2 | 6/2007 |
| WO | WO-2007/079130 A2 | 7/2007 |
| WO | WO-2007/094916 A2 | 8/2007 |
| WO | WO-2008/025558 A2 | 3/2008 |
| WO | WO 2008//077079 A1 | 6/2008 |
| WO | WO-2008/083346 A1 | 7/2008 |
| WO | WO-2009/026177 A1 | 2/2009 |
| WO | WO-2010/037062 A1 | 4/2010 |
| WO | WO 2010/104749 | 9/2010 |
| WO | WO-2011/028195 A2 | 3/2011 |
| WO | WO-2012/031744 A1 | 3/2012 |
| WO | WO-2012/055961 A1 | 5/2012 |
| WO | WO-2012/079000 A1 | 6/2012 |
| WO | WO 2012//082841 A2 | 6/2012 |
| WO | WO-2012/166559 A1 | 12/2012 |
| WO | WO-2012/166560 A1 | 12/2012 |
| WO | WO-2013/019615 A2 | 2/2013 |
| WO | WO-2013/044225 A1 | 3/2013 |
| WO | WO-2013/093809 A1 | 6/2013 |
| WO | WO-2013/123061 A1 | 8/2013 |
| WO | WO-2014/100615 A1 | 6/2014 |
| WO | WO-2014/153002 A1 | 9/2014 |
| WO | WO-2014/153164 A1 | 9/2014 |

OTHER PUBLICATIONS

Ang et al., "Generating a Chimeric Antigen Receptor to Redirect T-cell Specificity after Infusion," Molecular Therapy 19( Suppl 1): No. 353, p. S137 (2011).

Arcondéguy et al., "Survey and Summary. VEGF-A mRNA processing, stability and translation: a paradigm for intricate regulation of gene expression at the post-transcriptional level," Nucleic Acids Research 41(17): 7997-8010 (2013).

Axup, J. et al., "Synthesis of site-specific antibody-drug conjugates using unnatural amino acids," PNAS 109(40):16101-16106 (2012).

Backer et al., "Self-assembled "dock and lock" system for linking payloads to targeting proteins," Bioconjug Chem. Jul. Aug.;l7(4):912-919 (2006).

Baeuerle et al., "BiTE: Teaching antibodies to engage T-cells for cancer therapy<" Curr Opin Mol Ther 11(1):22-30 (2009).

Beers, S.A., et al., "Antigenic modulation limits the efficacy of anti-CD20 antibodies: implications for antibody selection," Blood 115(25):5191-5201 (2010).

Bibl et al., S"tability of amyloid-beta peptides in plasma and serum," Electrophoresis 33(3):445-450 (2012).

Bluemel et al., "Epitope distance to the target cell membrane and antigen size determine the potency of T cell-mediated lysis by BiTE antibodies specific for a large melanoma surface antigen," Cancer Immunol Immunother 59(8):1197-1209 (2010).

Boder et al., "Directed evolution of antibody fragments with monovalent femtomolar antigen-binding affinity," Proc Natl Acad Sci U S A 97(20):10701-10705 (2000).

Bonini et al., "The suicide gene therapy challenge: how to improve a successful gene therapy approach," Mol Ther 15(7):1248-1252 (2007).

Boulassel and Galal, "Immunotherapy for B-Cell Neoplasms using T Cells expressing Chimeric Antigen Receptors: From antigen choice to clinical implementation," Sultan Qaboos Univ Med J 12(3):273-285 (2012).

Brentjens et al., "Eradication of systemic B-cell tumors by genetically targeted human T lymphocytes co-stimulated by CD80 and interleukin-15," Nature Medicine 9(3): 279-286 (2003).

Brentjens et al., "Genetically Targeted T Cells Eradicate Systemic Acute Lymphoblastic Leukemia Xenografts," Clinical Cancer Research 13(18): 5426-5435, Sep. 15, 2007.

Brentjens et al., "Treatment of chronic lymphocytic leukemia with genetically targeted autologous T cells: case report of an unforeseen adverse event in a phase I clinical trialm" Mol Ther 18(4):666-668 (2010).

Bridgeman et al., "Structural and biophysical determinants of alphabeta T-cell antigen recognition," Immunology 135(1):9-18 (2011).

Cairoet al., "NCI first International Workshop on the biology, prevention, and treatment of relapse after allogeneic hematopoietic stem cell transplantation: report from the committee on the biological considerations of hematological relapse following allogeneic stem cell transplantation unrelated to graft-versus-tumor effects: state of the science," Biol Blood Marrow Transplant 16(6):709-728 (2010).

(56) References Cited

OTHER PUBLICATIONS

Cameron et al., "Identification of a Titin-Derived HLA-A1-Presented Peptide as a Cross-Reactive Target for Engineered MAGE A3-Directed T Cells," Sci Transl Med 197(5):197ra103; 1-11 (2013).
Carpenito et al., "Control of large, established tumor xenografts with genetically retargeted human T cells containing CD28 and CD137 domains," Proc Natl Acad Sci U S A 106(9):3360-3365 (2009).
Carpenter et al., "B-cell maturation antigen is a promising target for adoptive T-cell therapy of multiple myeloma," Clinical Cancer Research 19(8):2048-2060 (2013).
Chatterjee et al., "A Versatile Platform for Single- and Multiple-Unnatural Amino Acid Mutagenesis in *Escherichia coli*.," Biochemistry 52(10):1-23 (2013).
Chiarella et al., "Antigenic features of protein carriers commonly used in immunisation trials," Biotechnol Lett 32(9):1215-1221 (2010).
Chlewicki et al., "High-affinity, peptide-specific T cell receptors can be generated by mutations in CDR1, CDR2 or CDR3," J Mol Biol 346(1):223-239 (2005).
Chung et al., "CD19 is a major B cell receptor-independent activator of MYC-driven B-lymphomagenesis," J Clin Invest 122(6):2257-2266 (2012).
Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462.
Cole et al., "The molecular determinants of CD8 co-receptor function," Immunology 137(2):139-148 (2012).
Connor et al., "Enzymatic N-terminal Addition of Noncanonical Amino Adds to Peptides and Proteins," ChemBioChem 9:366-369 (2008).
Cui et al., "Chemically programmed bispecific antibodies that recruit and activate T cells," Journal of Biological Chemistry 287(34):28206-28214 (2012).
Davila et al., "CD19 CAR-targeted T cells induce long-term remission and B Cell Aplasia in an immunocompetent mouse model of B cell acute lymphoblastic leukemia," PLoS One 8(4) e61338 (2013), 14 pages.
Davis et al., "Therapy of B-Cell Lymphoma with Anti-CD20 Antibodies Can Result in the Loss of CD20 Antigen Expression," Clinical Cancer Research 5: 611-615, (1999).
Dengl et al., "Engineered hapten-binding antibody derivatives for modulation of pharmacokinetic properties of small molecules and targeted payload delivery," Immunological Reviews 270:165-177 (2016).
Dubrovska et al., "A chemically induced vaccine strategy for prostate cancer," ACS Chem Biol 6(11):1223-1231 (2011).
Eppstein et al.,"Biological activity of liposome-encapsulated murine interferon γ is mediated by a cell membrane receptor," Proc. Natl. Acad. Sci. USA, 82: 3688-92 (1985).
Ertl et al., "Considerations for the Clinical Application of Chimeric Antigen Receptor T Cells: Observations from a Recombinant DNA Advisory Committee Symposium Held Jun. 15, 2010," Cancer Research 71(9): 3175-3181 (2011).
Eshhar and Gross, "Chimeric T cell receptor which incorporates the anti-tumour specificity of a monoclonal antibody with the cytolytic activity of T cells: a model system for immunotherapeutical approach," Br. J. Cancer 62: 27-29 (1990).
Eshhar et al., "Specific activation and targeting of cytotoxic lymphocytes through chimeric single chains consisting of antibody-binding domains and the Y or subunits of the immunoglobulin and T-cell receptors," Proc. Natl. Acad. Sci. USA 90:720-724 (1993).
Eshhar, "The T-Body Approach: Redirecting T Cells with Antibody Specificity," Y. Chernajovsky, A. Nissim (eds.), Therapeutic Antibodies. Handbook of Experimental Pharmacology 181. Springer-Verlag Berlin Heidelberg, pp. 329-342 (2008).
Fernando et al., "Targeted Therapy of Colorectal Cancer: Clinical Experience with Bevacizumab," The Oncologist 9(suppl 1):11-18 (2004).

Fitzer-Attas et al., "Harnessing Syk Family Tyrosine Kinases as Signaling Domains for Chimeric Single Chain of the Variable Domain Receptors: Optimal Design for T Cell Activation," The Journal of Immunology 160: 145-154 (1998).
Friedmann-Morvinski et al., "Redirected primary T cells harboring a chimeric receptor require costimulation for their antigen-specific activation," Blood 105: 3087-3093 (2005).
Frost et al., "In Vitro Evaluation of Avidin Antibody Pretargeting Using 211At-Labeled and Biotinylated Poly-L-Lysine as Effector Molecule," Cancer 116(4 suppl): 1101-1110 (2010).
Gamzatova et al., "Human leucocyte antigen (HLA) A2 as a negative clinical prognostic factor in patients with advanced ovarian cancer," Gynecologic Oncology 103: 145-150 (2006).
Gavrilyuk et al., "β-Lactam-based Approach for the Chemical Programming of Aldolase Antibody 38C2," Bioorg Med Chem Lett. 19(5):1421-1424 (2009).
GenBank Accession No. AB064051: *Homo sapiens* IGK mRNA for immunoglobulin kappa light chain VLJ region, partial cds, clone: K10. Jul. 2, 2002, 2 pages.
Gilham et al., CAR-T cells and solid tumors: tuning T cells to challenge an inveterate foe, Trends in Molecular Medicine 18(7):377-384 (2012).
Gillies et al., "Targeting Human Cytotoxic T Lymphocytes to Kill Heterologous Epidermal Growth Factor Receptor-Bearing Tumor Cells. Tumor-Infiltrating Lymphocyte/Hormone Receptor/Recombinant Antibody," J. Immu. 146(3):1067-1071 (1991).
Grada et al., TanCAR: A Novel Bispecific Chimeric Antigen Receptor for Cancer Immunotherapy, Molecular Therapy—Nucleic Acids 2(7):1-11 (2013).
Griffioen, M., et al., Retroviral transfer of human CD20 as a suicide gene for adoptive T-cell therapy. Haematologica 94(9):1316-1320 (2009).
Gross and Eshhar, "Endowing T cells with antibody specificity using chimeric T cell receptors," FASEB J. 6: 3370-3378 (1992).
Gross et al., "Expression of immunoglobulin-T-cell receptor chimeric molecules as functional receptors with antibody-type specificity," Proc Natl Acad Sci U S A 86(24):10024-10028 (1989).
Grupp et al., "Chimeric antigen receptor-modified T cells for acute lymphoid leukemia," N Engl J Med 68(16):1509-1518 (2013).
Guest et al., "The Role of Extracellular Spacer Regions in the Optimal Design of Chimeric Immune Receptors. Evaluation of Four Different scFvs and Antigens," J. Immunother 28(3): 203-211 (2005).
Hanes et al., "Ribosome display efficiently selects and evolves high-affinity antibodies in vitro from immune libraries," Proc Natl Acad Sci U S A 95(24): 14130-1435 (1998).
Herron et al., "High resolution structures of the 4-4-20 Fab-fluorescein complex in two solvent systems: effects of solvent on structure and antigen-binding affinity," Biophys J 67(6):2167-2183 (1994).
Heslop, "Safer CARS," Mol Ther 18(4):661-662 (2010).
Hollatz, G., et al., T cells for suicide gene therapy: activation, functionality and clinical relevance. J Immunol Methods, 2008, pp. 69-81, vol. 331(1-2).
Hombach et al., "T cell activation by recombinant FcεRI γ-chain immune receptors: an extracellular spacer domain impairs antigen-dependent T cell activation but not antigen recognition," Gene Therapy 7: 1067-1075 (2000).
Hotfilder et al., "Leukemic stem cells in childhood high-risk ALL/t(9;22) and t(4;11) are present in primitive lymphoid-restricted CD34+CD19—cells," Cancer Res 65(4):1442-1449 (2005).
Hudecek et al., "Receptor affinity and extracellular domain modifications affect tumor recognition by ROR1-specific chimeric antigen receptor T cells," Clin Cancer Res 19(12):3153-3164 (2013).
Hutchins et al., "Site-Specific Coupling and Sterically Controlled Formation of Multimeric Antibody Fab Fragments with Unnatural Amino Acids. Journal of Molecular Biology," J Mol Biol 406(4):595-603 (2011).
Hutchins et al., Selective formation of covalent protein heterodimers with an unnatural amino acid. Chemistry & Biology 18(3):299-303 (2011).

(56) References Cited

OTHER PUBLICATIONS

Hwang et al., "Hepatic uptake and degradation of unilamellar sphingomyelin/cholesterol liposomes: a kinetic study," Proc. Natl. Acad. Sci. USA, 77: 4030-4034 (1980).
Hwu et al., "Lysis of Ovarian Cancer Cells by Human Lymphocytes Redirected with a Chimeric Gene Composed of an Antibody Variable Region and the Fc Receptor γ Chain," J. Exp. Med. 178: 361-366 (1993).
Johnson et al., "RF1 Knockout Allows Ribosomal Incorporation of Unnatural Amino Acids at Multiple Sites," Nat Chem Biol, 7(11):779-86 (2011).
Johnson et al., "Gene therapy with human and mouse T-cell receptors mediates cancer regression and targets normal tissues expressing cognate antigen," Blood 114: 535-546 (2009).
Jung et al., "Improving in vivo folding and stability of a single-chain Fv antibody fragment by loop grafting," Protein Engineering 10(8):959-966 (1997).
Kalos et al., "T cells with chimeric antigen receptors have potent antitumor effects and can establish memory in patients with advanced leukemia," Science Translational Medicine 3(95):95ra73 (2011), 37 pages.
Kammerer et al., "A conserved trimerization motif controls the topology of short coiled coils," Proc Natl Acad Sci USA 102:13891-13896 (2005).
Kazane et al., "Self-assembled antibody multimers through peptide nucleic acid conjugation," Journal Am Chem Soc 135(1):340-346 (2013).
Kershaw et al., "A Phase I Study on Adoptive Immunotherapy Using Gene-Modified T Cells for Ovarian Cancer," Clinical Cancer Research 12(20 Pt 1):6106-6115 (2006).
Kershaw et al., "Gene-Engineered T Cells as a Superior Adjuvant Therapy for Metastatic Cancer," The Journal of Immunology 173(3): 2143-2150 (2004).
Kim et al., "Protein conjugation with genetically encoded unnatural amin acids," Current Opinion in Chemical Biology 17(3):412-419 (2013).
Kim et al., "Synthesis of Bispecific Antibodies using Genetically Encoded Unnatural Amino Acids," Journal of the American Chemical Society 134(24):9918-9921 (2012).
Kochenderfer et al., Construction and pre-clinical evaluation of an anti-CD19 chimeric antigen receptor, Journal of Immunotherapy 32(7):689-702 (2009).
Kochenderfer et al., "Adoptive transfer of syngeneic T cells transduced with a chimeric antigen receptor that recognizes murine CD19 can eradicate lymphoma and normal B cells," Blood 116(19):3875-3886 (2010).
Kochenderfer et al., "B-cell depletion and remissions of malignancy along with cytokine-associated toxicity in a clinical trial of anti-CD19 chimeric-antigenreceptor-transduced T cells," Blood 119(12):2709-2720 (2012).
Kontermann, "Dual targeting strategies with bispecific antibodies," Mar. 1, 2012 4(2):182-197 (2012).
Kranz et al., "Conjugates of folate and anti-T-cell-receptor antibodies specifically target folate-receptor-positive tumor cells for lysis," Proc. Natl. Acad. Sci. USA 92: 9057-9061 (1995).
Krause et al., "Antigen-dependent CD28 Signaling Selectively Enhances Survival and Proliferation in Genetically Modified Activated Human Primary T Lymphocytes," J. Exp. Med. 188(4):619-626 (1998).
Kudoet al, "T Lymphocytes expressing a CD16 signaling receptor exert antibody-dependent cancer cell killing," Cancer Research 74(1):93-103 (2014), e-pub Nov. 6, 2013.
Kularatne et al., "Prostate-specific membrane antigen targeted imaging and therapy of prostate cancer using a PSMA inhibitor as a homing ligand," Molecular Pharmaceutics 6(3):780-789 (2009).
Kuroki et al., "Strategies to Endow Cytotoxic T Lymphocytes or Natural Killer Cells with Antibody Activity against Carcinoembryonic Antigen," Tumor Biol. 25: 208-216 (2004).
Lamers et al., "Treatment of Metastatic Renal Cell Carcinoma With Autologous T-Lymphocytes Genetically Retargeted Against Carbonic Anhydrase IX: First Clinical Experience," Journal of Clinical Oncology 24(13): e20-e22 (2006).
Lamers et al., "Immune responses to transgene and retroviral vector in patients treated with ex vivo-engineered T cells," Blood 117(1):72-82 (2011), e-pub Oct. 1, 2010.
Lang et al., Genetic encoding of bicyclononynes and trans-cyclooctenes for site-specific protein labeling in vitro and in live mammalian cells via rapid fluorgenic Diels-Alder reactions. Journal of the American Chemical Society, 2012, pp. 10317-10320, vol. 134, No. 25.
le Viseur, C. et al., "In childhood acute lymphoblastic leukemia, blasts at different stages of immunophenotypic maturation have stem cell properties," Cancer Cell, 14(1):47-58 (2008).
Lee and Brentjens, "Retroviral transduction of murine primary T lymphocytes," Methods in Molecular Biology 506:83-96 (2009).
Lin et al., Transglutaminase-Catalyzed Site-Specific Conjugation of Small-Molecules to Proteins in Vitro and on the Surface of Living Cells. J. Am. Chem. Soc. 128:4542-4543 (2006).
Linette et al., "Cardiovascular toxicity and titin cross-reactivity of affinity-enhanced T cells in myeloma and melanoma," Blood 122(6):863-871 (2013).
Litowski et al., "Designing heterodimeric two-stranded alpha-helical coiled-coils. Effects of hydrophobicity and alpha-helical propensity on protein folding, stability, and specificity," J Biol Chem, 277:37272-37279 (2002).
Liu et al., "Adding new chemistries to the genetic code," Annual Review of Biochemistry 79:413-444 (2010).
Lobbestael et al., "Immunohistochemical detection of transgene expression in the brain using small epitope tags," BMC Biotechnology 10, six pages, 2010.
Lu et al., "Site-Specific Antibody-Polymer Conjugates for siRNA Delivery," Journal of American Chemical Society 135(37):13885-13891 (2013).
Lu et al., "Strategy to prevent drug-related hypersensitivity in folate-targeted hapten immunotherapy of cancer," AAPS J 11(3):628-638 (2009).
Ma et al., "Carcinoembryonic antigen-immunoglobulin Fc fusion protein (CEA-Fc) for identification and activation of anti-CEA immunoglobulin-T-cell receptor-modified T cells, representative of a new class of Ig fusion proteins," C. Gene Therapy 11: 297-306 (2004).
Ma et al., Genetically engineered T cells as adoptive immunotherapy of cancer, Cancer Chemother Biol Response Modif 20:315-341 (2002).
Ma et al., "Targeting of antigens to B lymphocytes via CD19 as a means for tumor vaccine development," Journal of Immunology 190(11):5588-5599 (2013).
Maher et al., "Human T-lymphocyte cytotoxicity and proliferation directed by a single chimeric TCRζ/CD28 receptor," Nature Biotechnology 20: 70-75 (2002).
Maher, J., Immunotherapy of malignant disease using chimeric antigen receptor engrafted T cells. International Scholarly Research Notices Oncology, 2012:278093 (2012).
Masir et al., "Loss of CD19 expression in B-cell neoplasms," Histopathology 48(3):239-246 (2006).
Milone et al., "Chimeric receptors containing CD137 signal transduction domains mediate enhanced survival of T cells and increased antileukemic efficacy in vivo," Molecular Therapy 17(8):1453-1464 (2009).
Moore et al., "Application of dual affinity retargeting molecules to achieve optimal redirected T-cell killing of B-cell lymphoma," Blood 117(17):4542-4551 (2011).
Morgan et al., "Case report of a serious adverse event following the administration of T cells transduced with a chimeric antigen receptor recognizing ERBB2," Molecular Therapy 18(4):843-851 (2010).
Mossner et al., "Fast selection of antibodies without antigen purification: adaptation of the protein fragment complementation assay to select antigen-antibody pairs," Journal of Molecular Biology 308(2):115-122 (2001).
Murphy et al., "Elevated expression of il-8 and il-8 receptors in prostate cancer cells correlates with disease progression and resistance to oxaliplatin," Proc. Amer. Assoc. Cancer Res., 2005, 46, abstract No. 1495, 2 pages.

(56) References Cited

OTHER PUBLICATIONS

Nauerth et al., "TCR-ligand koff rate correlates with the protective capacity of antigen-specific CD8+ T cells for adoptive transfer," Science Translational Medicine 5(192):192ra87; pp. 1-10 (2013).
Ogg et al., "Sensitization of tumour cells to lysis by virus-specific CTL using antibody-targeted MHC class I/peptide complexes," British Journal of Cancer 82(5):1058-1062 (2000).
Olejniczak et al., "A quantitative exploration of surface antigen expression in common B-cell malignancies using flow cytometry," Immunol Invest 35(1):93-114 (2006).
Oshimi et al., Increased Lysis of Patient CD10-Positive Leukemic Cells by T Cells Coated With Anti-CD3 Fab' Antibody Cross-Linked to Anti-CD10 Fab' Antibody, Blood 77(5): 1044-1049, (1991).
Park et al., "Adoptive Transfer of Chimeric Antigen Receptor Re-directed Cytolytic T Lymphocyte Clones in Patients with Neuroblastoma," Molecular Therapy 15(4): 825-833 (2007).
Perez et al., "Specific targeting of cytotoxic T cells by anti-T3 linked to anti-target cell antibody," Nature 316: 354-356, Jul. 25, 1985.
Popkov, et al., "Instant immunity through chemically programmable vaccination and covalent self-assembly," Proceedings of the National Academy of Sciences of the United States of America. Early Edition. Jan. 7, 2009, pp. 1-6.
Porter et al., Chimeric antigen receptor-modified T cells in chronic lymphoid leukemia, New England Journal of Medicine 355(8):725-733 (2011).
Pule et al., "Virus-specific T cells engineered to coexpress tumor-specific receptors: persistence and antitumor activity in individuals with neuroblastoma," Nature Medicine 14(11): 1264-1270 (Nov. 2008).
Rabuka et al., "Site-specific chemical protein conjugation using genetically encoded aldehyde tags," Nature Protocols 7(6):1052-1067 (2012).
Rader, et al.,"A Humanized Aldolase Antibody for Selective Chemotherapy and Adaptor Immunotherapy," Journal of Molecular Biology332:889-899 (2003).
Rader, et al., Chemically programmed antibodies, Trends in Biotechnology 32(4)186-197 (2014).
Rader, et al., Chemically programmed monoclonal antibodies for cancer therapy: Adaptor immunotherapy based on a covalent antibody catalyst, PNAS 100(9):5396-5400 (2003).
Reichert, "Biospecific antibodies: A global overview of development as innovative therapeutics," AAPS 2013 National Biotechnology Conference, May 21, 2013, 14 pages.
Reid et al., "Extrinsic Cotton Effects in Hapten-Carrier and Hapten-Antibody Interactions," Proc. Nat. Acad. Sci. USA 68(6): 1184-1187 (1971).
Restifo et al., "Adoptive immunotherapy for cancer: harnessing the T cell response," Nature Reviews Immunology 12(4):269-281 (2012).
Rezvani and Maloneym, Rituximab resistance, Best Pract Res Clin Haematol 24(2):203-216 (2011).
Riddell and Protzer, "Carving the CAR," Gene Therapy 17: 1191-1192 (2010).
Riviere et al., "Effects of retroviral vector design on expression of human adenosine deaminase in murine bone marrow transplant recipients engrafted with genetically modified cells," Proc Natl Acad Sci USA 92(15):6733-6737 (1995).
Roberts et al., "Chemistry for peptide and protein PEGylation," Advanced Drug Delivery Reviews 54:459-476 (2002).
Romer et al., "Preculture of PBMCs at high cell density increases sensitivity of T-cell responses, revealing cytokine release by CD28 superagonist TGN1412," Blood 118(26):6772-6782 (2011).
Rossi et.al., "Stably tethered multifunctional structures of defined composition made by the dock and lock method for use in cancer targeting," Proc Natl Acad Sci US A. May 2;103(18):6841-6846 (2006).
Sadelain et al., "The promise and potential pitfalls of chimeric antigen receptors," Current Opinion in Immunology 21: 215-223 (2009).
Savage et al., "Induction of viral and tumor specific CTL responses using antibody targeted HLA class I peptide complexes," British Journal of Cancer 86: 1336-1342 (2002).
Schmitt-Verhulst et al., "H-2-Restricted Cytotoxic Effectors Generated in Vitro by the Addition of Trinitrophenyl-Conjugated Soluble Proteins," The Journal of Experimental Medicine 147: 352-368 (1978).
Scholler et al., "Decade-long safety and function of retroviral-modified chimeric antigen receptor T cells," Science Translational Medicine 4(132) pp. 132ra53 (2012), 16 pages.
Scott et al., "Immunogenicity of biotinylated hapten-avidin complexes," Mol Immunol 21(11):1055-1060 (1984).
Shirasu et al., "Construction and Molecular Characterization of Human Chimeric T-Cell Antigen Receptors Specific for Carcinoembryonic Antigen," Anticancer Research 30: 2731-2738 (2010).
Sigma-Aldrich Co. LLC, Product Information Monoclanal Anti-CD3, clone UCHT-1 produced in mouse, purified immunoglobulin. Catalog No. C7048, 2012, 2 pages.
Siliciano et al., "The Interaction of Nominal Antigen With T Cell Antigen Receptors. I. Specific Binding of Multivalent Nominal Antigen to Cytolytic T Cell Clone," The Journal of Immunology 135(2):906-914 (1985).
Sinha et al., "Preparation of integrin a(v)β(3)-targeting Ab 38C2 constructs," Nature Protocols 2:449-456 (2007).
Stone et al., "A sensitivity scale for targeting T cells with chimeric antigen receptors (CARs) and bispecific T-cell Engagers (BiTEs)," Oncoimmunology 1(6): 863-873 (2012).
Straathof et al., "An inducible caspase 9 safety switch for T-cell therapy," Blood, 105(11):4247-4254 (2005).
Suhoski et al., "Engineering artificial antigen-presenting cells to express a diverse array of co-stimulatory molecules," Molecular Therapy 15(5):981-988 (2007).
Tai et al., Development of a Peptide-Drug Conjugate for Prostate Cancer Therapy, Molecular Pharmaceutics 8:901-912 (2011).
Tamada et al., "Redirecting Gene-Modified T Cells toward Various Cancer Types Using Tagged Antibodies," Clinical Cancer Research, 18(23):6436-6445 (2012).
Terakuraet al., "Generation of CD19-chimeric antigen receptor modified CD8+ T cells derived from virus-specific central memory T cells," Blood 119(1):72-82 (2012) e-pub Oct. 26, 2011.
Themeli et al., "Generation of tumor-targeted human T lymphocytes from induced pluripotent stem cells for cancer therapy," Nature Biotechnology 31:928-933 (2013).
Thomas et al., "Application of strain-promoted azide-alkyne cycloaddition and tetrazine ligation to targeted Fc-drug conjugates," Bioconjugate Chemistry 23(10): 2007-2013 (2012).
Till et al., "Adoptive immunotherapy for indolent non-Hodgkin lymphoma and mantle cell lymphoma using genetically modified autologous CD20-specific T cells," Blood 112(6): 2261-2271 (2008).
Traversari et al., "The potential immunogenicity of the TK suicide gene does not prevent full clinical benefit associated with the use of TK-transduced donor lymphocytes in HSCT for hematologic malignancies," Blood 109(11):4708-4715 (2007).
Turatti et al., "Redirected activity of human antitumor chimeric immune receptors is governed by antigen and receptor expression levels and affinity of interaction," Journal of Immunotherapy 30(7):684-693 (2007).
Urbanska, et al, "Targeted cancer immunotherapy via combination of designer bispecific antibody and novel gene-engineered T cells," Journal of Translational Medicine 12:347-359 (2014).
Urbanska and Powell, "Development of a novel universal immune receptor for antigen targeting: To Infinity and beyond," Oncoimmunology 1(5):777-779 (2012).
Urbanska, K., et al., "A universal strategy for adoptive immunotherapy of cancer through use of a novel T-cell antigen receptor," Cancer Research 72(7):1844-1852 (2012).
Uttenthal et al., "Challenges in T cell receptor gene therapy," Journal of Gene Med 14(6):386-399 (2012).
Van Dam et al., "Intraoperative tumor-specific fluorescence imaging in ovarian cancer by folate receptor-alpha targeting: first in-human results," Nature Medicine 17(10):1315-1319 (2011).

(56) References Cited

OTHER PUBLICATIONS

Vaughan et al., "Human antibodies with sub-nanomolar affinities isolated from a large non-immunized phage display library," Nat Biotechnol 14(3):309-314 (1996).
Wang et al. "Expanding the genetic code," Angew Chem Int Ed 44:34-66 (2005).
Wang et al., "Reshaping Antibody Diversity," Cell 153: 1379-1393 (Jun. 6, 2013).
Weiden and Breitz, "Pretargeted radioimmunotherapy (PRIT™) for treatment of non-Hodgkin's lymphoma (NHL)," Critical Reviews in Oncology/Hematology 40:37-51 (2001).
Woolfson, "The design of coiled-coil structures and assemblies," Adv Protein Chem, 70: 79-112 (2005).
Xiang et al., "Production of hybrid bispecific antibody recognizing human colorectal carcinoma and CD3 antigen," Mol. Biother. 4: 5-23 (1992).
Xu et al., "Efficacy and safety of adoptive immunotherapy using anti-CD19 chimeric antigen receptor transduced T-cells: a systematic review of phase I clinical trials," Leuk Lymphoma 54(2):255-260 (2013).
Young et al, "Beyond the canonical 20 amino acids: expanding the genetic lexicon," Journal of Biological Chemistry 285(15):11039-11044 (2010).
Young et al., "An enhanced system for unnatural amino acid mutagenesis in *E. coli*.," Journal Molecular Biology 395(2):361-374 (2010), e-pub Oct. 21, 2009.
Yu et al., "A non-transgenic mouse model for B-cell lymphoma: in vivo infection of p53-null bone marrow progenitors by a Myc retrovirus is sufficient for tumorigenesis," Oncogene 21(12):1922-1927 (2002).
Yu et al., "Oscillation between B-lymphoid and myeloid lineages in Myc-induced hematopoietic tumors following spontaneous silencing/reactivation of the EBF/Pax5 pathway," Blood 101(5):1950-1955 (2003), e-pub Oct. 24, 2002.
Zahnd et al., "Directed in vitro evolution and crystallographic analysis of a peptide-binding single chain antibody fragment (scFv) with low picomolar affinity," Journal of Biological Chemistry 279(18):18870-18877 (2004).
Zeidler et al., "Simultaneous Activation of T Cells and Accessory Cells by a New Class of Intact Bispecific Antibody Results in Efficient Tumor Cell Killing," The Journal of Immunology 163: 1246-1252 (1999).
Zhang et al., "Identification and characterization of a new cross-reactive human immunodeficiency virus type 1-neutralizing human monoclonal antibody," Journal of Virology 78(17):9233-9242 (2004).
Zhang et al., "Identification of a novel CD4i human monoclonal antibody Fab that neutralizes HIV-1 primary isolates from different clades," Antiviral Research 61(3):161-164 (2004).
Genbank Accession No. BAF90733.1, two copies of the FLAG epitope and hexahistidine [*Schizosaccharomyces pombe* expression vector pDUAL-FFH1], Genebank database, published on Oct. 1, 2007, 1 page.
Gianpietro Dotti et al., "Design and development of therapies using chimeric antigen receptor-expressing T cells", Immunological Reviews 257(1):107-126 (2013).
Michael C Jensen et al, "Design and implementation of adoptive therapy with chimeric antigen receptor-modified T cells Authors' addresses", Immunological Reviews., 257(1):127-144 (2013).
David T. Rodgers et al: "Switch-medicated activation and retargeting of CAR-T cells for β-cell malignancies," Proceedings National Academy of Sciences PNAS 113(4):E459-E468 (2016).

\* cited by examiner

US 10,800,828 B2

SWITCHABLE NON-SCFV CHIMERIC RECEPTORS, SWITCHES, AND METHODS OF USE THEREOF TO TREAT CANCER

CROSS-REFERENCE

This application is a 371 of international application no. PCT/US2016/024524, filed Mar. 28, 2016, which application claims priority to U.S. Provisional Application No. 62/138,901, filed Mar. 26, 2015, which applications are incorporated by reference herein in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is CIBR_007_01WO_ST25.txt. The text file is 95 KB, was created on Mar. 25, 2016, and is being submitted electronically via EFS-Web.

BACKGROUND OF THE INVENTION

Immunotherapies are becoming attractive alternatives to chemotherapies, including immunotherapies that use adoptive transfer of genetically modified T cells to "reteach" the immune system to recognize and eliminate malignant tumor cells. Genetically modified T cells express chimeric antigen receptors, which generally consist of a signaling endodomain, a CD3-zeta transmembrane domain and an extracellular single-chain variable fragment (scFv) derived from a monoclonal antibody which gives the receptor specificity for a tumor-associated antigen on a target malignant cell. Upon binding the tumor-associated antigen via the chimeric antigen receptor, the chimeric antigen receptor expressing T cell (CAR T-cell) mounts an immune response that is cytotoxic to the malignant cell. Such therapies can circumvent chemotherapy resistance and have been shown to be active against relapsed/refractory disease, resulting in sustained remissions for some chronic lymphocytic leukemia (CLL) and acute lymphoblastic leukemia (ALL) patients. However, these therapies require further investigation and optimization, as they caused undesirable effects such as toxic lymphophenia, chronic hypogammaglobulinemia for hematological targets, fatal off-target cytolysis for solid tumor targets, persistent B cell aplasia with the use of anti-CD19 antibody expressing CAR T-cells, and, in some cases, death.

Introduction of a switch, which controls the activity of the CAR T-cell, would allow CAR T-cell activity and associated immune responses to be turned off after neoplastic cells are eliminated and would allow B cells to reproliferate, or potentially taper cytokine storm. Recent preclinical studies have demonstrated that CAR T-cell systems can be controlled through an antibody-based switch, wherein the antibody binds the target cell (e.g., cancer cell), blocking the CAR T-cell from binding the target cell and "switching off" CAR-T activity. While these systems conceptually allow for switchable targeting of tumors using CAR T-cells, they may suffer from a series of limitations. In the case of hapten-scFv mediated switches, non-specific labeling of antibodies using cysteines or lysines produces heterogeneous products, which include variants that may be non-functional, have unpredictable pharmacokinetics and/or immunogenicity, and that may be difficult to optimize.

SUMMARY OF THE INVENTION

In some embodiments, the present invention provides chimeric receptors comprising: a non-antibody extracellular domain that interacts with a chimeric receptor binding partner, wherein the chimeric receptor binding partner is located on a switch that interacts with a target cell; a transmembrane domain; and an intracellular signaling domain, wherein the intracellular signaling domain signals to an effector cell on which the chimeric receptor is expressed when the non-antibody extracellular domain interacts with the chimeric receptor binding partner. The chimeric receptor binding partner may be present on a switch, wherein the switch comprises the chimeric receptor binding partner and a targeting moiety.

In some embodiments, the present invention provides chimeric receptors comprising: a non-antibody extracellular domain that interacts with a chimeric receptor binding partner, wherein the chimeric receptor binding partner is present on a switch that comprises the chimeric receptor binding partner and a targeting moiety; a transmembrane domain; and an intracellular signaling domain, wherein the intracellular signaling domain signals to an effector cell on which the chimeric receptor is expressed when the non-antibody extracellular domain interacts with the chimeric receptor binding partner.

In some embodiments, the chimeric receptor binding partner comprises a chimeric receptor binding protein. In some embodiments, the chimeric receptor binding protein is selected from an antibody and an antibody fragment. In some embodiments the chimeric receptor binding protein is not selected from an antibody and an antibody fragment. In some embodiments, the chimeric receptor binding partner comprises a chimeric receptor binding peptide. In some embodiments, the chimeric receptor binding partner consists essentially of a chimeric receptor binding peptide. In some embodiments, the chimeric receptor binding peptide comprises a peptide epitope tag. In some embodiments, the targeting moiety is selected from a targeting small molecule, a targeting peptide, a targeting protein, a targeting antibody, and a targeting antibody fragment. In some embodiments, the chimeric receptor binding partner comprises a small molecule. In some embodiments, the targeting moiety is selected from a targeting small molecule, a targeting peptide, and a targeting protein. In some embodiments, the targeting peptide and the targeting protein are not selected from an antibody and an antibody fragment.

In some embodiments, the chimeric receptor binding partner or the non-antibody extracellular domain is selected from a naturally occurring protein, a naturally occurring peptide, portions thereof, homologs thereof, and combinations thereof. In some embodiments, the chimeric receptor binding partner and the non-antibody extracellular domain is selected from a naturally occurring protein, a naturally occurring peptide, portions thereof, homologs thereof, and combinations thereof. In some embodiments, the chimeric receptor binding partner or the non-antibody extracellular domain is selected from a nuclease, a ribonuclease, a transmembrane protein, a cell surface molecule, a cell adhesion molecule, a fibrous protein, an enzyme, and portions thereof. In some embodiments, the chimeric receptor binding partner or the non-antibody extracellular domain is derived from an organism selected form a eukaryote and a prokaryote. In some embodiments, the chimeric receptor binding partner or the non-antibody extracellular domain comprises a non-naturally occurring synthetic peptide. In some embodiments, the chimeric receptor binding partner and the non-antibody extracellular domain form a covalent protein-protein interaction. In some embodiments, the chimeric receptor binding partner and the non-antibody extracellular domain form a non-covalent protein-protein interaction. In some embodiments, the chimeric receptor binding partner comprises barnase and the non-antibody extracellular domain comprises barstar. In some embodiments, the chimeric receptor binding partner comprises barstar and the non-antibody extracellular domain comprises barnase. In some embodiments, the chimeric receptor binding partner and the non-antibody extracellular domain form a covalent protein-peptide interaction. In some embodiments, the chimeric receptor binding partner comprises isopeptag and the non-antibody extracellular domain comprises pilin. In some embodiments, the chimeric receptor binding partner comprises pilin and the non-antibody extracellular domain comprises isopeptag. In some embodiments, the chimeric receptor binding partner comprises spytag and the non-antibody extracellular domain comprises spycatcher. In some embodiments, the chimeric receptor binding partner comprises spycatcher and the non-antibody extracellular domain comprises spytag. In some embodiments, the chimeric receptor binding partner and the non-antibody extracellular domain form a non-covalent protein-peptide interaction. In some embodiments, the chimeric receptor binding partner comprises SNARE and the non-antibody extracellular domain is selected from SNAP25, synaptobrevin, and syntaxin. In some embodiments, the chimeric receptor binding partner comprises SNAP25, synaptobrevin, and syntaxin and the non-antibody extracellular domain comprises SNARE. In some embodiments, the chimeric receptor binding partner comprises Hu-tag and the non-antibody extracellular domain comprises RNAse I. In some embodiments, the chimeric receptor binding partner comprises RNAse I and the non-antibody extracellular domain comprises Hu-tag. In some embodiments, the chimeric receptor binding partner and the non-antibody extracellular domain form a non-covalent peptide-peptide interaction. In some embodiments, the chimeric receptor binding partner comprises a first peptide, which is capable of forming an alpha helix with a second peptide, and the non-antibody extracellular domain comprises the second peptide, which is capable of forming an alpha helix with the first peptide. In some embodiments, the first peptide is selected from any one of the E/K peptides disclosed in Litowski, J. R., and R. S. Hodges. J Biol Chem, 277: 37272-9 (2002), incorporated herein by reference in its entirety (e.g., any one of SEQ ID NOS: 33-34, 61-62, 65-76), and the second peptide is selected from any peptide that is capable of forming an alpha helix with the first peptide. In particular embodiments, the second peptide is an E/K peptide disclosed in Litowski (2002)(e.g., any one of SEQ ID NOS: 33-34, 61-62, 65-76). In some embodiments, the chimeric receptor binding partner comprises the K4 peptide (SEQ ID NO: 33) and the non-antibody extracellular domain comprises the E4 peptide (SEQ ID NO: 34). In some embodiments, the chimeric receptor binding partner comprises the E4 peptide (SEQ ID NO: 34) and the non-antibody extracellular domain comprises a K4 peptide (SEQ ID NO: 33). In some embodiments, the chimeric receptor binding partner comprises a modified K4 peptide and the non-antibody extracellular domain comprises a modified E4 peptide. In some embodiments, the chimeric receptor binding partner comprises a modified E4 peptide and the non-antibody extracellular domain comprises a modified K4 peptide. In some embodiments, the chimeric receptor binding partner comprises a modified K4 peptide and the non-antibody extracellular domain comprises the E4 peptide (SEQ ID NO: 34). In some embodiments, the chimeric receptor binding partner comprises a modified E4 peptide and the non-antibody extracellular domain comprises the K4 peptide (SEQ ID NO: 33). In some embodiments, the chimeric receptor binding partner comprises the K4 peptide (SEQ ID NO: 33) and the non-antibody extracellular domain comprises a modified E4 peptide. In some embodiments, the chimeric receptor binding partner comprises the E4 peptide (SEQ ID NO: 34) and the non-antibody extracellular domain comprises a modified K4 peptide. In some embodiments, the chimeric receptor binding partner consists of or consists essentially of a sequence of SEQ ID NO: 33 and the non-antibody extracellular domain consists of or consists essentially of a sequence of SEQ ID NO: 34. In some embodiments, the chimeric receptor binding partner consists of or consists essentially of a sequence of SEQ ID NO: 34 and the non-antibody extracellular domain consists of or consists essentially of a sequence of SEQ ID NO: 33. In some embodiments, the chimeric receptor binding partner comprises a sequence that has at least 85%, at least 90%, at least 95% or greater identity to SEQ ID NO: 33 and the non-antibody extracellular domain comprises a sequence that has at least 85%, at least 90%, at least 95% or greater identity to SEQ ID NO: 34. In some embodiments, the chimeric receptor binding partner comprises a sequence that has at least 85%, at least 90%, at least 95% or greater identity to SEQ ID NO: 34 and the non-antibody extracellular domain comprises a sequence that has at least 85%, at least 90%, at least 95% or greater identity to SEQ ID NO: 33. In some embodiments, the chimeric receptor binding partner comprises a sequence that has at least 85%, at least 90%, at least 95% or greater identity to any one of SEQ ID NOS: 61-62, 65-76. In some embodiments, the non-antibody extracellular domain comprises a sequence that has at least 85%, at least 90%, at least 95% or greater identity to any one of SEQ ID NOS: 61-62, 65-76. In some embodiments, the chimeric receptor binding partner comprises first mouse coronin 1A alpha helix and the non-antibody extracellular domain comprises a second mouse coronin 1A alpha helix. In some embodiments, the chimeric receptor binding partner is selected from an anchor domain of an A-kinase anchor protein and a regulatory subunit of cAMP-dependent protein kinase A, and the non-antibody extracellular domain comprises a dimerization and docking domain of cAMP-dependent protein kinase. In some embodiments, the chimeric receptor binding partner comprises a dimerization and docking domain of cAMP-dependent protein kinase and the non-antibody extracellular domain is selected from an anchor domain of an A-kinase anchor protein and a regulatory subunit of cAMP-dependent protein kinase A. In some embodiments, the chimeric receptor binding partner and the non-antibody extracellular domain form a covalent peptide-peptide interaction. In some embodiments, the chimeric receptor binding partner is selected from an anchor domain of an A-kinase anchor protein and a regulatory subunit of cAMP-dependent protein kinase A, and the non-antibody extracellular domain comprises a dimerization and docking domain of cAMP-dependent protein kinase, wherein the dimerization and docking domain comprises a cysteine and the anchor domain comprises a cysteine. In some embodiments, the chimeric receptor binding partner comprises a dimerization and docking domain of cAMP-dependent protein kinase and the non-antibody extracellular domain is selected from an anchor domain of an A-kinase anchor protein and a regulatory subunit of cAMP-dependent protein kinase A, wherein the dimerization and docking domain comprises a cysteine and the anchor domain comprises a cysteine. The anchor domain may have a sequence selected from SEQ ID NO: 8 and SEQ ID NO: 10. In some embodiments, the dimerization and docking domain has a sequence selected from SEQ ID NO: 9 and SEQ ID NO: 11. In some embodiments, the the non-antibody extracellular domain consists essentially of a non-antibody peptide. In some embodiments, the non-antibody peptide is selected from isopeptag, spytag, SNARE, Hu-tag, a coronin alpha helix, an anchor domain of an A-kinase anchor protein, and a dimerization and docking domain of a cAMP dependent protein kinase A. In some embodiments, the non-antibody extracellular domain consists essentially of a non-antibody peptide. In some embodiments, the non-antibody peptide is selected from isopeptag, spytag, SNARE, Hu-tag, a coronin alpha helix, the K4 alpha helix peptide (SEQ ID NO: 33), the E4 alpha helix peptide (SEQ ID NO: 34), any one E/K alpha helix peptide having a sequence selected from SEQ ID NOS: 33-34 and 61-62, 65-76), an anchor domain of an A-kinase anchor protein, and a dimerization and docking domain of a cAMP dependent protein kinase A. In some embodiments, the non-antibody extracellular domain interacts tightly with the target. In some embodiments, the non-antibody extracellular domain is capable of forming a covalent interaction with the target. In some embodiments, the covalent interaction comprises a disulfide bond. In some embodiments, the non-antibody extracellular domain forms a non-covalent interaction with the target. In some embodiments, the chimeric receptor is encoded by a polynucleotide having a sequence selected from SEQ ID NOS: 1-2. In some embodiments, the chimeric receptor is encoded by a polynucleotide having a sequence selected from SEQ ID NOS: 35-36. In some embodiments, the chimeric receptor is encoded by an amino acid having a sequence selected from SEQ ID NOS: 41-42. In some embodiments, the chimeric receptor is encoded by an amino acid having a sequence selected from SEQ ID NOS: 47-48.

Further disclosed herein are effector cells comprising a chimeric receptor, wherein the chimeric receptor comprises: a non-antibody extracellular domain that interacts with a chimeric receptor binding partner, wherein the chimeric receptor binding partner is located on a switch that interacts with the target cell; a transmembrane domain; and an intracellular signaling domain, wherein the intracellular signaling domain signals to an effector cell on which the chimeric receptor is expressed when the non-antibody extracellular domain interacts with the chimeric receptor binding partner. In some embodiments, the chimeric receptor binding partner is present on a switch. In some embodiments, the chimeric receptor binding partner is present on a switch, wherein the switch comprises the chimeric receptor binding partner and a targeting moiety. In some embodiments, the chimeric receptor binding partner comprises a chimeric receptor binding protein. In some embodiments, the chimeric receptor binding protein is selected from an antibody and an antibody fragment. In some embodiments, the chimeric receptor binding protein is not selected from an antibody and an antibody fragment. In some embodiments, the chimeric receptor binding partner comprises a chimeric receptor binding peptide. In some embodiments, the chimeric receptor binding partner consist essentially of a chimeric receptor binding peptide. In some embodiments, the chimeric receptor binding peptide comprises a peptide epitope tag. In some embodiments, the targeting moiety is selected from a targeting small molecule, a targeting peptide, a targeting protein, a targeting antibody, and a targeting antibody fragment. In some embodiments, the chimeric receptor binding partner comprises a small molecule. In some embodiments, the targeting moiety may be selected from a targeting small molecule, a targeting peptide, and a targeting protein. In some embodiments, the targeting peptide and the targeting protein may not be selected from an antibody and an antibody fragment. In some embodiments, the chimeric receptor binding partner or the non-antibody extracellular domain is selected from a naturally occurring protein, a naturally occurring peptide, portions thereof, homologs thereof, and combinations thereof. In some embodiments, the chimeric receptor binding partner or the non-antibody extracellular domain is selected from a nuclease, a ribonuclease, a transmembrane protein, a cell surface molecule, a cell adhesion molecule, a fibrous protein, an enzyme, and portions thereof. In some embodiments, the chimeric receptor binding partner or the non-antibody extracellular domain is derived from an organism selected form a eukaryote and a prokaryote. In some embodiments, the chimeric receptor binding partner or the non-antibody extracellular domain comprises a non-naturally occurring synthetic peptide. In some embodiments, the chimeric receptor binding partner and the non-antibody extracellular domain form a covalent protein-protein interaction. In some embodiments, the chimeric receptor binding partner and the non-antibody extracellular domain form a non-covalent protein-protein interaction. In some embodiments, the chimeric receptor binding partner comprises barnase and the non-antibody extracellular domain comprises barstar. In some embodiments, the chimeric receptor binding partner comprises barstar and the non-antibody extracellular domain comprises barnase. In some embodiments, the chimeric receptor binding partner and the non-antibody extracellular domain form a covalent protein-peptide interaction. In some embodiments, the chimeric receptor binding partner comprises isopeptag and the non-antibody extracellular domain comprises pilin. In some embodiments, the chimeric receptor binding partner comprises pilin and the non-antibody extracellular domain comprises isopeptag. In some embodiments, the chimeric receptor binding partner comprises spytag and the non-antibody extracellular domain comprises spycatcher. In some embodiments, the chimeric receptor binding partner comprises spycatcher and the non-antibody extracellular domain comprises spytag. In some embodiments, the chimeric receptor binding partner and the non-antibody extracellular domain form a non-covalent protein-peptide interaction. In some embodiments, the chimeric receptor binding partner comprises SNARE and the non-antibody extracellular domain is selected from SNAP25, synaptobrevin, and syntaxin. In some embodiments, the chimeric receptor binding partner comprises SNAP25, synaptobrevin, and syntaxin and the non-antibody extracellular domain comprises SNARE. In some embodiments, the chimeric receptor binding partner comprises Hu-tag and the non-antibody extracellular domain comprises RNAse I. In some embodiments, the chimeric receptor binding partner comprises RNAse I and the non-antibody extracellular domain comprises Hu-tag. In some embodiments, the chimeric receptor binding partner and the non-antibody extracellular domain form a non-covalent peptide-peptide interaction. In some embodiments, the chimeric receptor binding partner comprises first mouse coronin 1A alpha helix and the non-antibody extracellular domain comprises a second mouse coronin 1A alpha helix. In some embodiments, the chimeric receptor binding partner is selected from an anchor domain of an A-kinase anchor protein and a regulatory subunit of cAMP-dependent protein kinase A, and the non-antibody extracellular domain comprises a dimerization and docking domain of cAMP-dependent protein kinase. In some embodiments, the chimeric receptor binding partner comprises a dimerization and docking domain of cAMP-dependent protein kinase and the non-antibody extracellular domain is selected from an anchor domain of an A-kinase anchor protein and a regulatory subunit of cAMP-dependent protein kinase A. In some embodiments, the chimeric receptor binding partner and the non-antibody extracellular domain may form a covalent peptide-peptide interaction. In some embodiments, the chimeric receptor binding partner is selected from an anchor domain of an A-kinase anchor protein and a regulatory subunit of cAMP-dependent protein kinase A, and the non-antibody extracellular domain comprises a dimerization and docking domain of cAMP-dependent protein kinase, wherein the dimerization and docking domain comprises a cysteine and the anchor domain comprises a cysteine. In some embodiments, the chimeric receptor binding partner comprises a dimerization and docking domain of cAMP-dependent protein kinase and the non-antibody extracellular domain is selected from an anchor domain of an A-kinase anchor protein and a regulatory subunit of cAMP-dependent protein kinase A, wherein the dimerization and docking domain comprises a cysteine and the anchor domain comprises a cysteine. In some embodiments, the anchor domain has a sequence selected from SEQ ID NO: 8 and SEQ ID NO: 10. In some embodiments, the dimerization and docking domain has a sequence selected from SEQ ID NO: 9 and SEQ ID NO: 11. In some embodiments, the non-antibody extracellular domain consists essentially of a non-antibody peptide. In some embodiments, the non-antibody peptide is selected from isopeptag, spytag, SNARE, Hu-tag, a coronin alpha helix, an anchor domain of an A-kinase anchor protein, and a dimerization and docking domain of a cAMP dependent protein kinase A. In some embodiments, the non-antibody extracellular domain interacts tightly with the target. In some embodiments, the non-antibody extracellular domain is capable of forming a covalent interaction with the target. In some embodiments, the covalent interaction comprises a disulfide bond. In some embodiments, the non-antibody extracellular domain forms a non-covalent interaction with the target. In some embodiments, the chimeric receptor is encoded by a polynucleotide having a sequence selected from SEQ ID NOS: 1-2. In some embodiments, the chimeric receptor is encoded by a polynucleotide having a sequence selected from SEQ ID NOS: 35-36. In some embodiments, the chimeric receptor is encoded by an amino acid having a sequence selected from SEQ ID NOS: 41-42. In some embodiments, the chimeric receptor is encoded by an amino acid having a sequence selected from SEQ ID NOS: 47-48.

In some embodiments, the effector cell is a T cell.

Disclosed herein are chimeric receptor-effector cell switches comprising: a chimeric receptor binding partner that interacts with a non-antibody extracellular domain of a chimeric receptor on an effector cell; and a targeting moiety that interacts with a cell surface molecule on a target cell. In some embodiments, the chimeric receptor binding partner comprises a chimeric receptor binding protein. In some embodiments, the chimeric receptor binding protein is selected from an antibody and an antibody fragment. In some embodiments, the chimeric receptor binding protein is not be an antibody or antibody fragment. In some embodiments, the binding partner comprises a chimeric receptor binding peptide. In some embodiments, the chimeric receptor binding partner may consist essentially of a chimeric receptor binding peptide. In some embodiments, the chimeric receptor binding peptide comprises a peptide epitope tag. In some embodiments, the targeting moiety is selected from a targeting small molecule, a targeting peptide, a targeting protein, a targeting antibody, and a targeting antibody fragment. In some embodiments, the chimeric receptor binding partner comprises a small molecule. In some embodiments, the targeting moiety is selected from a targeting small molecule, a targeting peptide, and a targeting protein. In some embodiments, the targeting peptide and the targeting protein are not selected from an antibody and an antibody fragment. In some embodiments, the chimeric binding partner comprises barnase and the non-antibody extracellular domain comprises barstar. In some embodiments, the chimeric receptor binding partner comprises barstar and the non-antibody extracellular domain comprises barnase. In some embodiments, the chimeric receptor binding partner comprises isopeptag and the non-antibody extracellular domain comprises pilin. In some embodiments, the chimeric receptor binding partner comprises pilin and the non-antibody extracellular domain comprises isopeptag. In some embodiments, the chimeric receptor binding partner comprises spytag and the non-antibody extracellular domain comprises spycatcher. In some embodiments, the chimeric receptor binding partner comprises spycatcher and the non-antibody extracellular domain comprises spytag. In some embodiments, the chimeric receptor binding partner comprises SNARE and the non-antibody extracellular domain may be selected from SNAP25, synaptobrevin, and syntaxin. In some embodiments, the chimeric receptor binding partner is selected from SNAP25, synaptobrevin, and syntaxin and the non-antibody extracellular domain comprises SNARE. In some embodiments, the chimeric receptor binding partner comprises Hu-tag and the non-antibody extracellular domain comprises RNAse I. In some embodiments, the chimeric receptor binding partner comprises RNAse I and the non-antibody extracellular domain comprises Hu-tag. In some embodiments, the chimeric receptor binding partner comprises coronin and the non-antibody extracellular domain comprises a ccCorl peptide. In some embodiments, the chimeric receptor binding partner comprises a ccCorl peptide and the non-antibody extracellular domain comprises coronin. In some embodiments, the chimeric receptor binding partner is selected from an anchor domain of an A-kinase anchor protein and a regulatory subunit of cAMP-dependent protein kinase A, and the non-antibody extracellular domain comprises a dimerization and docking domain of cAMP-dependent protein kinase. In some embodiments, the chimeric receptor binding partner comprises a dimerization and docking domain of cAMP-dependent protein kinase and the non-antibody extracellular domain is selected from an anchor domain of an A-kinase anchor protein and a regulatory subunit of cAMP-dependent protein kinase A. In some embodiments, the anchor domain has a sequence selected from SEQ ID NO: 8 and SEQ ID NO: 10. In some embodiments, the dimerization and docking domain has a sequence selected from SEQ ID NO: 9 and SEQ ID NO: 11. In some embodiments, the chimeric receptor binding partner is at least partially encoded by a sequence selected from SEQ ID NOS: 6-11. In some embodiments, the targeting moiety comprises a targeting peptide. In some embodiments, the targeting moiety is selected from a targeting antibody and a targeting antibody fragment. In some embodiments, the targeting antibody or antibody fragment is selected from the group consisting of: an immunoglobulin, an Fc null immunoglobulin, and a Fab, and fragments thereof. In some embodiments, the targeting moiety is selected from the group consisting of: an anti-EGFR antibody, an anti-Her2 antibody, anti-EGFRvIII antibody, an anti-CD33 antibody, an anti-CLL-1 antibody, an anti-CEA antibody, an anti-CD19 antibody, an anti-CD22 antibody, an anti-BCMA antibody, and an anti-CS1 antibody, and fragments thereof. In some embodiments, the targeting moiety comprises a small molecule. In some embodiments, the small molecule does not contain a peptide. In some embodiments, the small molecule does not contain two or more amino acids connected by an amide bond. In some embodiments, the small molecule is selected from a small molecule that binds a folate receptor and a small molecule that binds a prostate specific membrane antigen. In some embodiments, the small molecule that binds a folate receptor is folate and the small molecule that binds a prostate specific membrane antigen may be 2-[3-(1,3-dicarboxypropy)ureidol] pentanedioic acid. In some embodiments, the chimeric receptor binding partner is selected from a chimeric receptor binding protein and a chimeric receptor binding peptide, and the targeting moiety is selected from a targeting antibody and a targeting antibody fragment. In some embodiments, the chimeric receptor binding partner is fused to a terminus of the targeting antibody or the targeting antibody fragment. In some embodiments, the chimeric receptor binding partner is fused to a region of the targeting antibody or the targeting antibody fragment selected from the group consisting of: an N terminus of a light chain, a C terminus of a light chain, an N terminus of a heavy chain, a C terminus of a Fab heavy chain, and a C terminus of a constant region heavy chain. In some embodiments, the chimeric receptor binding partner is grafted into the targeting antibody or the targeting antibody fragment. In some embodiments, the chimeric receptor binding partner is grafted into a region of the targeting antibody or the targeting antibody fragment selected from a CH1 domain, a CH2 domain, a CH3 domain, a CL domain, a VH domain, a VL domain, and a hinge region. In some embodiments, the chimeric receptor binding partner is grafted between two regions of the targeting antibody or the targeting antibody fragment selected from a CH1 domain, a CH2 domain, a CH3 domain, a CL domain, a VH domain, a VL domain, a heavy chain, a light chain, and a hinge region, wherein the two regions are adjacent. In some embodiments, the chimeric receptor binding partner is grafted into a loop of the targeting antibody or targeting antibody fragment. In some embodiments, the loop is in a constant domain of the targeting antibody or antibody fragment. In some embodiments, the target cell is a cancer cell. In some embodiments, the cell surface molecule is a tumor associated antigen. In some embodiments, the cell surface molecule is selected from the group consisting of: a cluster of differentiation protein, a receptor, an integral membrane protein and a glycoprotein. In some embodiments, the chimeric receptor-effector cell switch is at least partially encoded by a sequence selected from SEQ ID NOS: 3-5.

Further disclosed herein are pharmaceutical compositions comprising: a chimeric receptor-effector cell switch comprising: a chimeric receptor binding partner that interacts with a non-antibody extracellular domain of a chimeric receptor on an effector cell; and a targeting moiety that interacts with a cell surface molecule on a target cell; and a pharmaceutically acceptable salt, carrier, excipient and/or vehicle.

Disclosed herein are kits comprising: a chimeric receptor-effector cell switch comprising: a chimeric receptor binding partner that interacts with a non-antibody extracellular domain of a chimeric receptor on an effector cell; and a targeting moiety that interacts with a cell surface molecule on a target cell; and a chimeric receptor-effector cell comprising a chimeric receptor that binds to the chimeric receptor binding partner of the chimeric receptor-effector cell switch. In some embodiments, the kits comprise a first chimeric receptor-effector cell switch and a second chimeric receptor-effector cell switch, wherein the first chimeric receptor-effector cell switch comprises a first chimeric receptor binding partner and a first targeting moiety and the second chimeric receptor-effector cell switch comprises a second chimeric receptor binding partner and a second targeting moiety. In some embodiments, the first chimeric receptor binding partner and the second chimeric receptor binding partner are the same. In some embodiments, the first targeting moiety binds a first cell surface molecule on a first target cell and the second targeting moiety binds a second cell surface molecule on a second target cell, wherein the first cell surface molecule and the second cell surface molecule are different. In some embodiments, the effector cell is selected from a T cell, an effector B cell, a natural killer cell, a macrophage, and a progenitor thereof. The effector cell may be selected from a naive T cell, a memory stem cell T cell, a central memory T cell, an effector memory T cell, a helper T cell, a CD4+ T cell, a CD8+ T cell, a CD8/CD4+ T cell, an $\alpha\beta$ T cell, a $\gamma\delta$ T cell, a cytotoxic T cell, a natural killer T cell, a natural killer cell, and a macrophage.

Further disclosed herein are vectors comprising a polynucleotide having a sequence that encodes a chimeric receptor, wherein the chimeric receptor comprises a non-antibody extracellular domain. In some embodiments, the extracellular domain binds a chimeric receptor binding partner on a switch.

Disclosed herein are methods of treating a disease or condition in a subject in need thereof, comprising administering to the subject a chimeric receptor-effector cell switch comprising: a chimeric receptor binding partner that interacts with a non-antibody extracellular domain of a chimeric receptor on an effector cell; and a targeting moiety that interacts with a cell surface molecule on a target cell. In some embodiments, the subject hosts a chimeric receptor-effector cell comprising a chimeric receptor that binds to the chimeric receptor binding partner of the chimeric receptor-effector cell switch. In some embodiments, the method further comprises administering a chimeric receptor-effector cell comprising a chimeric receptor that binds to the chimeric receptor binding partner of the chimeric receptor-effector cell switch. In some embodiments, the method comprises administering a first chimeric receptor-effector cell switch and a second chimeric receptor-effector cell switch, wherein the first chimeric receptor-effector cell switch comprises a first chimeric receptor binding partner and a first targeting moiety and the second chimeric receptor-effector cell switch comprises a second chimeric receptor binding partner and a second targeting moiety. In some embodiments, the first chimeric receptor binding partner and the second chimeric receptor binding partner are the same. In some embodiments, the first targeting moiety binds a first cell surface molecule on a first target cell and the second targeting moiety binds a second cell surface molecule on a second target cell, wherein the first cell surface molecule and the second cell surface molecule are different. In some embodiments, the method further comprises dose-titrating the chimeric receptor-effector cell switch.

Further disclosed herein are methods of killing a target cell expressing a target antigen, comprising contacting a chimeric receptor-effector cell disclosed herein with a chimeric receptor-effector cell switch disclosed herein, wherein the chimeric receptor-effector cell expresses a chimeric receptor with a non-antibody extracellular domain that binds to a chimeric receptor binding partner on the chimeric receptor effector cell switch, and wherein the chimeric receptor effector cell switch comprises the binding domain that binds the non-antibody extracellular domain of the chimeric receptor and the switch comprises a targeting moiety that binds an antigen on the target cell. In some embodiments, the method results in the target cell being lysed by the effector cell. In some embodiments, the EC50 for killing the target cell ranges from about 0.1 pM to about 500 pM of the switch. In some embodiments, the methods result in the target cell being lysed. In some embodiments, the EC50 for killing the target cell ranges from about 1 pM to about 100 pM of the switch. In some embodiments, the target antigen is expressed on the surface of a target cell. In some embodiments, the target cell has a disease or condition. In some embodiments, the disease or condition is selected from a cancer, an inflammatory disease or condition, a metabolic disease and a genetic disorder. In some embodiments, the disease is cancer. In some embodiments, the contacting occurs in vivo in a subject (e.g., a human).

Further disclosed herein are methods of activating a target cell, comprising contacting a chimeric receptor-effector cell disclosed herein with a chimeric receptor-effector cell switch disclosed herein, wherein the chimeric receptor-effector cell is only activated if the contacting includes both (i) binding of the chimeric receptor binding partner on the chimeric receptor effector cell switch to the non-antibody extracellular domain of the chimeric receptor expressed on the chimeric receptor-effector cell and (ii) concurrent binding of the targeting moiety on the chimeric receptor effector cell switch to its target antigen. In some embodiments, the target antigen is expressed on the surface of a target cell. In some embodiments, the target cell has a disease or condition. In some embodiments, the disease or condition is selected from a cancer, an inflammatory disease or condition, a metabolic disease and a genetic disorder. In some embodiments, the disease is cancer. In some embodiments, activating the effector cell induces effector cell-mediated killing of the target cell. In some embodiments, the contacting occurs in vivo in a subject (e.g., a human). Further disclosed herein are methods of treating a disease or condition in a subject in need thereof, comprising (A) administering to the subject a chimeric receptor-effector cell comprising a chimeric receptor, wherein the chimeric receptor comprises (i) a non-antibody extracellular domain that interacts with a chimeric receptor binding partner, wherein the chimeric receptor binding partner is present on a switch that comprises the chimeric receptor binding partner and a targeting moiety; (ii) a transmembrane domain; and (iii) an intracellular signaling domain, wherein the intracellular signaling domain signals to an effector cell on which the chimeric receptor is expressed when the non-antibody extracellular domain interacts with the chimeric receptor binding partner; and (B) administering to the subject a chimeric receptor-effector cell switch comprising (i) a chimeric receptor binding partner that interacts with a non-antibody extracellular domain of a chimeric receptor on an effector cell and (ii) a targeting moiety that interacts with a cell surface molecule on a target cell. In some embodiments, the chimeric receptor-effector cell is administered to the subject prior to the administering of the chimeric receptor-effector cell switch. In some embodiments, the disease or condition is selected from a cancer, an inflammatory disease or condition, a metabolic disease and a genetic disorder.

DETAILED DESCRIPTION OF THE INVENTION

Figure 1:
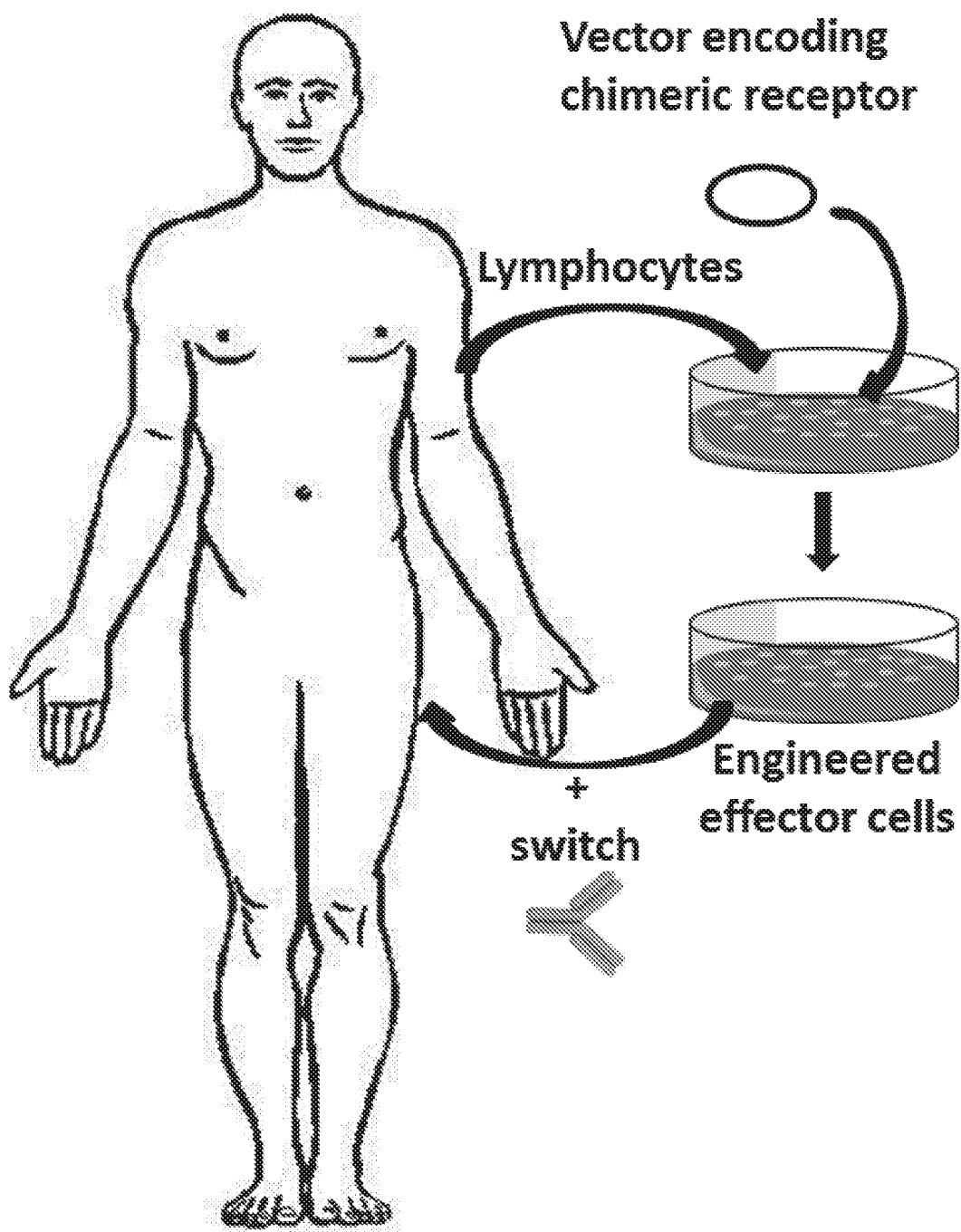
FIG. 1 illustrates a general overview of switchable chimeric receptor-T cell therapy disclosed herein. Lymphocytes are isolated from a subject and an expression vector encoding a chimeric receptor is subsequently introduced to the lymphocytes to produce chimeric receptor effector cells. Chimeric receptor effector cells are administered to the subject, along with a switch.
Figure 2:
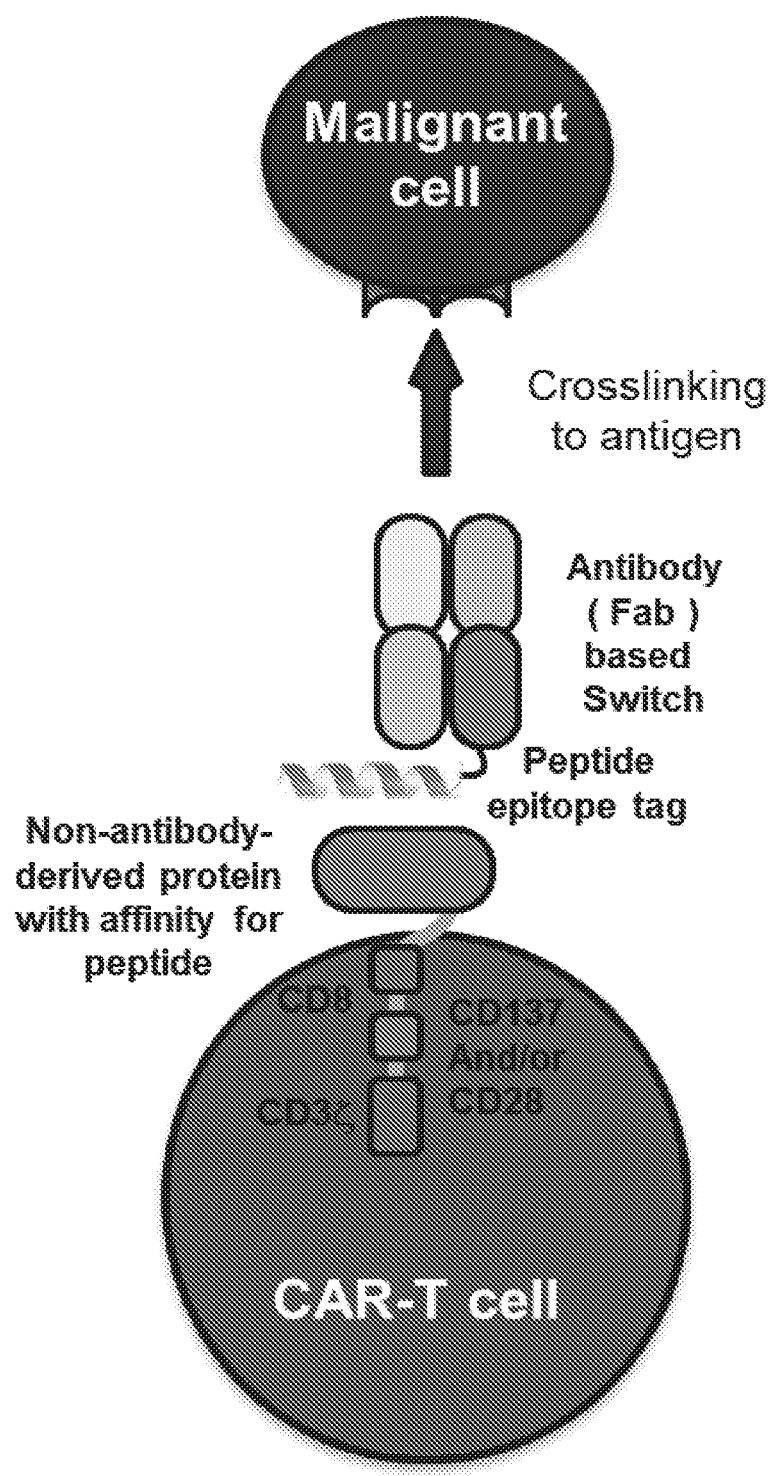
FIG. 2 illustrates a protein-peptide switchable chimeric receptor-T cell platform, the switch comprising a peptide that binds to an extracellular protein of a chimeric receptor and a targeting antibody that binds to a cell surface molecule on a target cell, functioning to bring the target cell in proximity of the effector cell. Binding of the switch to both the chimeric receptor and target cell induces an immune response that would be cytotoxic the proximal target cell.
Figure 3:
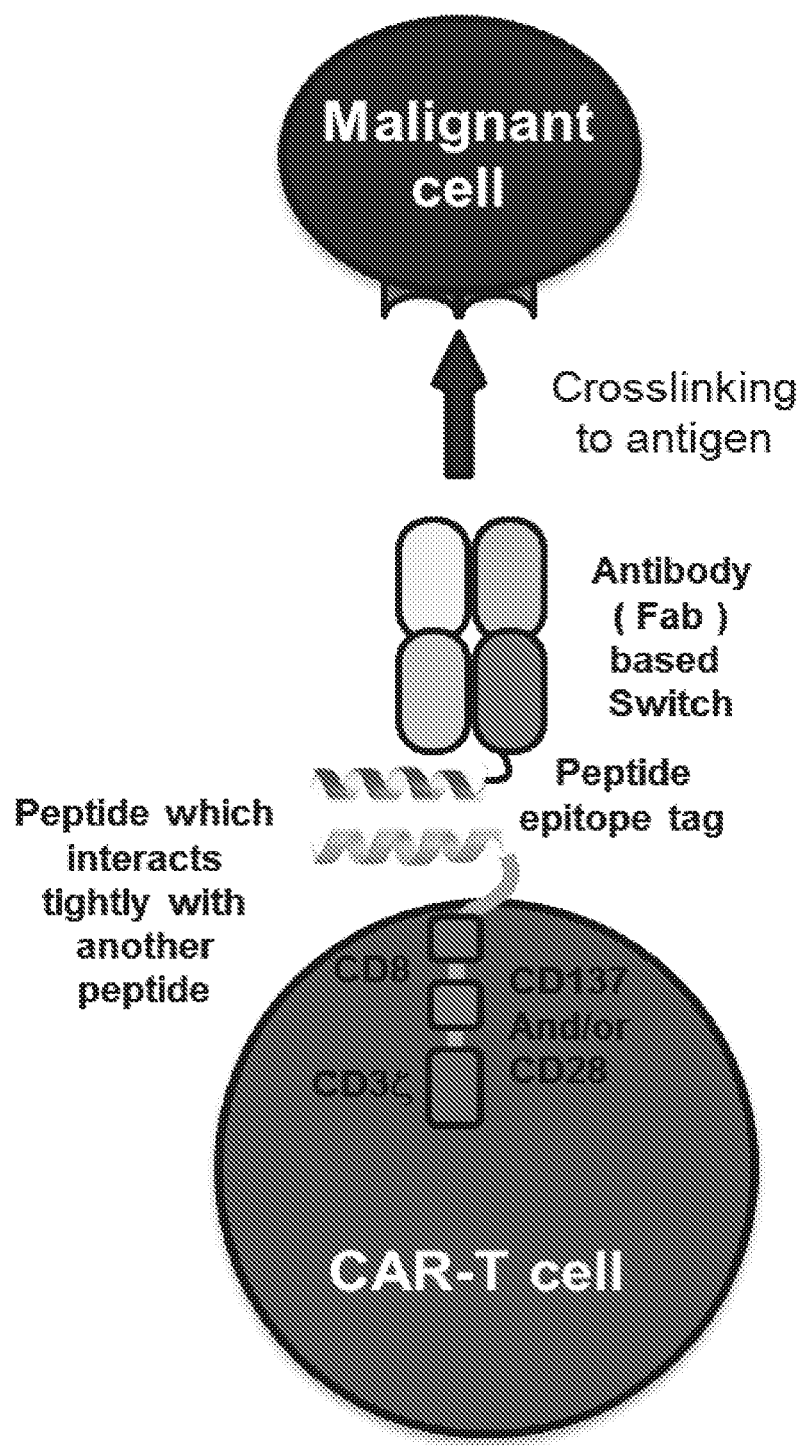
FIG. 3 illustrates a peptide-peptide switchable chimeric receptor-T cell platform, the switch comprising a peptide that binds to an extracellular peptide of a chimeric receptor and a targeting antibody that binds to a cell surface protein on a target cell, functioning to bring the target cell in proximity of the effector cell. Binding of the switch to both the chimeric receptor at the target cell induces an immune response that would be cytotoxic the proximal target cell.

Disclosed herein are compositions and methods for selectively activating and deactivating chimeric receptor T cells (CAR T cell), which may provide for a safer and more versatile immunotherapy than conventional CAR-T cell designs currently being tested in clinical trials by providing control over the therapy. Disclosed herein are switchable chimeric receptor effector cells and chimeric receptor effector cell switches, referred to as "switches," herein, wherein the switches have a first region that is bound by an effector cell chimeric receptor and a second region that binds a cell surface molecule on target cell. The second region of the switch that binds the cell surface molecule on a target cell may be selected from a non-antibody protein, a peptide, an antibody, an antibody fragment or a non-peptide small molecule (e.g., vitamin, metabolite). Chimeric receptor binding of the switch may stimulate an immune response from the effector cell that is cytotoxic to the bound target cell. In general, the effector cell is a T cell. The switch may act as an "on-switch" or an "off switch" for effector cell activity. Activity may be "turned off" by reducing or ceasing administration of the switch. These switches may be used with the effector cells disclosed herein, as well as existing CAR T-cells, for the treatment of a disease or condition, such as cancer, wherein the target cell is a malignant cell. Such treatment may be referred to herein as switchable immunotherapy, for which an exemplary schematic overview is depicted in FIG. 1.

The chimeric receptors disclosed herein generally comprise a non-antibody extracellular domain that interacts with a chimeric receptor binding partner; a transmembrane domain; and an intracellular signaling domain, wherein the intracellular signaling domain signals to an effector cell on which the chimeric receptor is expressed when the non-antibody extracellular domain interacts with the chimeric receptor binding partner. In various embodiments, the term "CAR," which is known is the art to refer to a "chimeric antigen receptor," is used to describe the chimeric receptors disclosed herein, despite the fact that the receptors disclosed herein do not comprise antibodies or antibody domains that recognize antigens and are not, technically, antigen receptors. The extracellular domain may be a non-antibody protein or a non-antibody peptide. Unlike canonical CARs, the extracellular domain does not comprise an antibody or antibody fragment. The chimeric receptor binding partner is located on the switch. The chimeric receptor binding partner may be non-antibody protein or peptide. Thus, the chimeric receptor and the switch may have a protein-protein interaction, a peptide-peptide interaction or a protein-peptide/peptide-protein interaction.

One advantage of using protein-peptide or peptide-peptide interactions is reduced immunogenicity. Peptides and proteins derived entirely from human proteins may be less immunogenic than scFvs, which are commonly derived from humanization of murine antibodies. For example, peptides derived from human RNA polymerase are human-derived and therefore not expected to have immunogenicity.

Another advantage of peptide-peptide interactions is size. A scFv is typically on the order of 750 nucleotides (250 amino acids). In contrast, a peptide encoding the AD1 module of the dock and lock platform, for example, is as small as 17 amino acids. Similarly, a peptide encoding a K4 or E4 alpha helix-forming peptide (e.g., SEQ ID NO: 33 or 34, respectively), for example, is as small as 28 amino acids. As used herein, reference to "K4" or a "K4 peptide" refers to a peptide having the sequence of SEQ ID NO: 33: As used herein, reference to "E4" or an "E4 peptide" refers to a peptide having the sequence of SEQ ID NO: 34. In some embodiments, unless otherwise indicated, reference to the "K4/E4" peptides means SEQ ID NOS: 33 and 34, respectively, and reference to a "K4/E4" switch means a switch comprising either one of SEQ ID NOS: 33 and 34. The terms "K4/E4" and "E4/K4" are used interchangeably. Reference to the term "E/K", e.g., an E/K peptide or an "E/K analog" means a peptide that forms an E/K coil when it is bound to another complementary E/K peptide. E/K coils and peptides that form E/K coils are known in the art (see, e.g., Litowski, (2002), e.g., SEQ ID NOS: 61-62, 65-76). The reduced size has two advantages. First, the small gene results in less genetic content which needs to be transferred into the cell. In the case of lenti and retro viruses, smaller genes are more efficient to incorporate. Therefore, peptide-peptide based chimeric receptors have higher transduction efficiencies. Second, the size of the peptide vs the size of the scFv is important in formation of the immunological synapse between the target cell, T cell, and switch. Because the peptide is relatively small, it enables the T cell and target cell to be closer together than the scFv-based chimeric receptor. In general a shorter distance from T cell-to-target cell results in more efficient target cell lysis and T cell activation. This is a major advantage of peptide-peptide chimeric receptors (see, e.g., Ma, J. S., et. al., Proc Natl Acad Sci USA, 113: E450-8 (2016); Rodgers, D. T., et. al., Proc Natl Acad Sci USA, 113: E459-68 (2016)).

Further disclosed herein are pharmaceutical compositions comprising a chimeric receptor-effector cell switch, wherein the chimeric receptor-effector cell switch comprises a chimeric receptor binding partner that interacts with a non-antibody extracellular domain of a chimeric receptor on an effector cell; and a targeting moiety that interacts with a cell surface molecule on a target cell; and a pharmaceutically acceptable salt, carrier, excipient and/or vehicle.

Disclosed herein are kits comprising a chimeric receptor-effector cell switch, wherein the chimeric receptor-effector cell switch comprises: a chimeric receptor binding partner that interacts with a non-antibody extracellular domain of a chimeric receptor on an effector cell; and a targeting moiety that interacts with a cell surface molecule on a target cell; and a chimeric receptor-effector cell comprising a chimeric receptor that binds to the chimeric receptor binding partner of the chimeric receptor-effector cell switch.

Further disclosed herein are vectors comprising a polynucleotide having a sequence that encodes a chimeric receptor, wherein the chimeric receptor comprises a non-antibody extracellular domain.

Disclosed herein are methods of treating a disease or condition in a subject in need thereof, comprising administering to the subject a chimeric receptor-effector cell switch comprising: a chimeric receptor binding partner that interacts with a non-antibody extracellular domain of a chimeric receptor on an effector cell; and a targeting moiety that interacts with a cell surface molecule on a target cell.

Unless otherwise specified, the terms "switch" and "chimeric receptor-effector cell switch", as used herein, are used interchangeably and may refer to a peptide switch. The antibody portion of the peptide antibody switch may comprise at least a portion of an antibody or an entire antibody. For example, the antibody portion of the peptide antibody switch may comprise at least a portion of a heavy chain, a portion of a light chain, a portion of a variable region, a portion of a constant region, a portion of a complementarity determining region (CDR), or a combination thereof. The antibody portion of the peptide antibody switch and/or small molecule antibody switch may comprise at least a portion of the Fc (fragment, crystallizable) region. The antibody portion of the peptide antibody switch may comprise at least a portion of the complementarity determining region (e.g., CDR1, CDR2, CDR3). The antibody portion of the peptide antibody switch may comprise at least a portion of the Fab (fragment, antigen-binding) region. The peptide switch may be a peptide-Fab switch. The peptide switch may be a peptide-IgG switch. The peptide switch may be a peptide-scFv switch.

Before the present methods, kits and compositions are described in greater detail, it is to be understood that this invention is not limited to particular method, kit or composition described, as such may, of course, vary. It is also to be understood that the terminology used herein is for the purpose of describing particular embodiments only, and is not intended to be limiting, since the scope of the present invention will be limited only by the appended claims. Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be chimeric receptor carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods, kits and compositions are provided for producing chimeric receptor-EC platforms and switches used to bring an effector cell together with a target in a subject. These methods, kits and compositions find therapeutic use in a number of diseases and conditions. For example, heterogeneous tumors and blood cell malignancies (e.g., acute lymphoblastic leukemia and chronic lymphocytic leukemia) may be more effectively treated with a chimeric receptor-EC platform when the length, valency and orientation of the chimeric receptor-EC switch linkage as well as the chimeric receptor-EC switch cell targeting moiety is optimized. Heterogeneous tumors may be more effectively treated with multiple Switches that target more than one tumor antigens. Advantages and features of the invention will become apparent to those persons skilled in the art upon reading the details of the compositions and methods as more fully described below.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

I. Chimeric Receptor

Disclosed herein are chimeric receptors comprising: a non-antibody extracellular domain that interacts with a chimeric receptor binding partner; a transmembrane domain; and an intracellular signaling domain, wherein the intracellular signaling domain signals to an effector cell on which the chimeric receptor is expressed when the non-antibody extracellular domain interacts with the chimeric receptor binding partner, wherein the chimeric receptor binding partner is located on a switch that interacts with the target cell.

The chimeric receptor may be an activating chimeric receptor. The activating chimeric receptor may comprise a chimeric receptor which provides an activating signal to the effector cell. The activating signal may trigger an immune response in the effector cell. The immune response may comprise a cytotoxic effect on nearby cells (e.g., target cells). The transmembrane domain and/or the intracellular domain of the chimeric receptor may comprise at least a portion of a cytoplasmic signaling domain. The intracellular domain may comprise at least a portion of a signaling molecule selected from the group comprising CD3zeta, CD28, and 4-1BB. The intracellular domain may comprise an Fc receptor or a portion thereof. The Fc receptor or portion thereof may be CD16 or a portion thereof. The signaling molecule may comprise CD3zeta. The signaling molecule may comprise CD28. The signaling molecule may comprise 4-1BB. The intracellular domain may comprise at least a portion of CD3zeta. The intracellular domain may comprise at least a portion of CD28, The intracellular domain may comprise at least a portion of 4-1BB, The intracellular domain may comprise at least a portion of OX-40, The intracellular domain may comprise at least a portion of CD30, The intracellular domain may comprise at least a portion of CD40, The intracellular domain may comprise at least a portion of CD2. The intracellular domain may comprise at least a portion of CD27. The intracellular domain may comprise at least a portion of ICOS. The intracellular domain may comprise at least a portion of lymphocyte function-associated antigen-1 (LFA-1). The intracellular domain may comprise at least a portion of CD7. The intracellular domain may comprise at least a portion of LIGHT. The intracellular domain may comprise at least a portion of NKG2C. The intracellular domain may comprise at least a portion of B7-H3. The intracellular domain may comprise at least a portion of a cytoplasmic signaling domain from one or more signaling molecules. The intracellular domain may comprise at least a portion of two or more cytoplasmic signaling domains. The two or more cytoplasmic signaling domains may be from two or more different signaling molecules. The intracellular domain may comprise at least a portion of three or more cytoplasmic signaling domains. The intracellular domain may comprise at least a portion of four or more cytoplasmic signaling domains. The intracellular domain may comprise at least a portion of a ligand that binds to one or more signaling molecules. The intracellular domain may comprise at least a portion of a ligand that binds to CD83.

Protein-Protein Interactions

The CAR may comprise a non-antibody extracellular domain, wherein the extracellular domain comprises a non-antibody protein. The non-antibody protein may interact with the chimeric receptor binding partner, wherein the chimeric receptor binding partner comprises a chimeric receptor binding protein, constituting a protein-protein interaction. The protein-protein interaction may be loose. A loose interaction may be an interaction wherein the chimeric receptor binding partner and the non-antibody peptide bind with a $K_D$ of about $10^{-4}$ M, about $10^{-3}$M, about $10^{-2}$M, about $10^{-1}$ M, or with a $K_D$ that is larger than about $10^{-1}$ M. The protein-protein interaction may be a tight interaction. A tight interaction may be an interaction wherein the chimeric receptor binding partner and the non-antibody peptide bind with a $K_D$ of about $10^{-5}$M, about $10^{-6}$M, about $10^{-7}$ M, about $10^{-8}$M, about $10^{-9}$M, about $10^{-10}$ M, about $10^{-11}$ M or about $10^{-12}$M. The protein-protein interaction may comprise a covalent protein-protein interaction. The protein-protein interaction may comprise a non-covalent protein-protein interaction. The non-antibody protein and/or chimeric receptor binding protein may comprise an enzyme. The enzyme may be a nuclease. The nuclease may be a ribonuclease. The ribonuclease may be prokaryotic. The non-antibody protein and/or chimeric receptor binding protein may comprise a substrate. The non-antibody protein may comprise barnase and the chimeric receptor binding protein may comprise barstar. The non-antibody protein may comprise barstar and the chimeric receptor binding protein may comprise barnase. Barnase is an amino acid ribonuclease from *Bacillus amyloliquefaciens*. Barstar is a natural intracellular inhibitor of barnase. Barnase interacts with barstar with high affinity, having a protein-protein binding on-rate of 10^8/s/M (Buckle A M, Schreiber G, Fersht A R; Biochemistry 33 (30): 8878-8 (August 1994), incorporated herein by reference in its entirety). Barnase, barstar, and their interactions are described in Mossakowska D E, Nyberg K, Fersht A R; Biochemistry 28 (9): 3843-50 (May 1989), which is incorporated herein by reference in its entirety.

Protein-Peptide Interactions

The non-antibody protein may interact with the chimeric receptor binding partner, wherein the chimeric receptor binding partner comprises a chimeric receptor binding peptide, constituting a protein-peptide interaction. Alternatively, the non-antibody extracellular domain may comprise a non-antibody peptide that interacts with the chimeric receptor binding partner, wherein the chimeric receptor binding partner comprises a chimeric receptor binding protein, constituting the protein-peptide interaction. The protein-peptide interaction may be a loose interaction. A loose interaction may be an interaction wherein the chimeric receptor binding partner and the non-antibody peptide bind with a $K_D$ of about $10^{-4}$ M, about $10^{-3}$M, about $10^{-2}$M, about $10^{-1}$M, or with a $K_D$ that is larger than about $10^{-1}$ M. The protein-peptide interaction may be a tight interaction. A tight interaction may be an interaction wherein the chimeric receptor binding protein and the non-antibody peptide (or the chimeric receptor binding peptide and the non-antibody protein) bind with $K_D$ of about $10^{-5}$M, about $10^{-6}$M, about $10^{-7}$ M, about $10^{-8}$M, about $10^{-9}$M, about $10^{-10}$ M, about $10^{-11}$M or about $10^{12}$M. The non-antibody protein and/or chimeric receptor binding protein may be selected from a fibrous protein, an adhesion molecule protein and a membrane protein.

The protein-peptide interaction may comprise a covalent protein-peptide interaction. For example, the non-antibody protein may comprise a *Streptococcus pyogenes* pilin protein and the chimeric receptor binding peptide may comprise an isopeptag. Alternatively, the non-antibody peptide may comprise an isopeptag and the chimeric receptor binding protein may comprise a *Streptococcus pyogenes* pilin protein. The interactions between isopeptag and *Streptococcus pyogenes* pilin protein are described in Kang, H. J., Coulibaly, F., Clow, F., Proft, T., and Baker, E. N. Science 318, 1625-1628 (2007) and Zakeri, B. and Howarth, M.; J. Am. Chem. Soc. 132, 4526-4527 (2010), each of which is incorporated herein by reference in its entirety. The isopeptag sequence is shown in Table 3. Also, by way of non-limiting example, the non-antibody protein may comprise a *Streptococcus pyogenes* fibronectin binding protein (SpyCatcher), and the chimeric receptor binding peptide may comprise a SpyTag. Alternatively, the non-antibody peptide may comprise a SpyTag and the chimeric receptor binding protein may comprise a *Streptococcus pyogenes* fibronectin binding protein (SpyCatcher). The covalent interaction between SpyCatcher and SpyTag are described in Zakeri B, Howarth M, JACS, vol. 109 no. 12, (2012), which is incorporated herein by reference in its entirety.

The protein-peptide interaction may comprise a non-covalent protein-peptide interaction. For example, non-antibody protein may be selected from a synaptobrevin, a SNAP25 and a syntaxin, and portions thereof (e.g., alpha helix), and the chimeric receptor binding peptide may comprise a SNARE. Alternatively, the non-antibody peptide may comprise a SNARE and the chimeric receptor binding protein may be selected from a synaptobrevin, a SNAP25 and a syntaxin, and portions thereof (e.g., alpha helix). The interactions between SNARE and synaptobrevin, SNAP25 and a syntaxin are described in Söllner T, et al., Nature 362:318-324 (1993); Sutton R B, Fasshauer D, Jahn R, Brunger A T, Nature 395:347-353 (1998); and Darios, F, Proc. Natl. Acad. Sci. U. S. A 107, 18197-18201 (2010), each of which is incorporated herein by reference in its entirety. Also, by way of non-limiting example, the non-antibody protein may comprise an RNAseI and the chimeric receptor binding peptide may comprise a Hu-tag. Alternatively, the non-antibody peptide may comprise a Hu-tag and the chimeric receptor binding protein may comprise an RNAseI. Also, by way of non-limiting example, the non-antibody protein may comprise a HuS adapter protein and the chimeric receptor binding peptide may comprise a Hu-tag. Alternatively, the non-antibody peptide may comprise a Hu-tag and the chimeric receptor binding protein may comprise a HuS adapter protein. Interactions between Hu-tag and RNase I and Hu-tag and HuS adapter protein are described in Backer, M. V., et. al., Adapter protein for site-specific conjugation of payloads for targeted drug delivery. Bioconjugate Chem. 15, 1021-1029 (2004), which is incorporated herein by reference in its entirety.

Peptide-Peptide Interactions

The CAR may comprise a non-antibody extracellular domain, wherein the extracellular domain comprises a non-antibody peptide. The non-antibody peptide may interact with the chimeric receptor binding partner, wherein the chimeric receptor binding partner comprises a chimeric receptor binding peptide, constituting a peptide-peptide interaction. The peptide-peptide interaction may be a loose interaction. A loose interaction may be an interaction wherein the chimeric receptor binding partner and the non-antibody peptide bind with a $K_D$ of about $10^{-4}$ M, about $10^{-3}$ M, about $10^{-2}$ M, about $10^{-1}$ M, or with a $K_D$ that is larger than about $10^{-1}$ M. The peptide-peptide interaction may be a tight interaction. A tight interaction may be an interaction wherein the chimeric receptor binding peptide and the non-antibody peptide (or the chimeric receptor binding peptide and the non-antibody peptide) bind with a $K_D$ of about $10^{-5}$ M, about $10^{-6}$ M, about $10^{-7}$ M, about $10^{-8}$ M, about $10^{-9}$ M, about $10^{10}$ M, about $10^{-11}$ M or about $10^{-12}$ M. The non-antibody peptide and/or chimeric receptor binding peptide may comprise be selected from a secondary structure of a protein (e.g., alpha helix, beta sheet), a protein domain, an enzyme domain, a dimerization domain, and a multimerization domain.

The peptide-peptide interaction may comprise a non-covalent peptide—peptide interaction. The non-antibody peptide may comprise a first alpha helix of a protein, and the chimeric receptor binding peptide may comprise a second alpha helix of a protein. The first alpha helix and the second alpha helix may form a coiled coil structure. For example, but not to be limited in any way, the first peptide may be selected from any one of the E/K peptides disclosed in Litowski, J. R. (2002)(e.g., any one of SEQ ID NOS: 33-34, and 61-62, 65-76), and the second peptide may be selected from any peptide that is capable of forming an alpha helix with the first peptide. The second peptide may be an E/K peptide disclosed in Litowski (2002)(e.g., any one of SEQ ID NOS: 33-34, 61-62, 65-76) The non-antibody protein may comprise the K4 peptide (SEQ ID NO: 33) and the chimeric receptor binding protein may comprise the E4 peptide (SEQ ID NO: 34). The non-antibody protein may comprise the E4 peptide (SEQ ID NO: 34) and the chimeric receptor binding protein may comprise the K4 peptide (SEQ ID NO: 33). The interactions between the K4 and E4 peptides are described in Litowski, J. R., and R. S. Hodges. J Biol Chem, 277: 37272-9 (2002) and Woolfson, D. N., Adv Protein Chem, 70: 79-112 (2005), each of which is incorporated herein by reference in its entirety. The non-antibody protein may comprise a modified K4 peptide and the chimeric receptor binding protein may comprise a modified E4 peptide. The non-antibody protein may comprise a modified E4 peptide and the chimeric receptor binding protein may comprise a modified K4 peptide. The non-antibody protein may comprise a modified K4 peptide and the chimeric receptor binding protein may comprise the E4 peptide (SEQ ID NO: 34). The non-antibody protein may comprise a modified E4 peptide and the chimeric receptor binding protein may comprise a K4 peptide (SEQ ID NO: 33). The non-antibody protein may comprise the K4 peptide (SEQ ID NO: 33) and the chimeric receptor binding protein may comprise a modified E4 peptide. The non-antibody protein may comprise the E4 peptide (SEQ ID NO: 34) and the chimeric receptor binding protein may comprise a modified K4 peptide. The non-antibody protein may consist or consist essentially of a peptide having the sequence of SEQ ID NO: 33 and the chimeric receptor binding protein may consist or consist essentially of a peptide having the sequence of SEQ ID NO: 34. The non-antibody protein may consist or consist essentially of a peptide having the sequence of SEQ ID NO: 34 and the chimeric receptor binding protein may consist or consist essentially of a peptide having the sequence of SEQ ID NO: 33. The non-antibody protein may comprise a peptide having a sequence that has at least 85%, at least 90%, at least 95% or greater identity to SEQ ID NO: 33 and the chimeric receptor binding protein may comprise a peptide having a sequence that has at least 85%, at least 90%, at least 95% or greater identity to SEQ ID NO: 34. The non-antibody protein may comprise a peptide having a sequence that has at least 85%, at least 90%, at least 95% or greater identity to SEQ ID NO: 34 and the chimeric receptor binding protein may comprise a peptide having a sequence that has at least 85%, at least 90%, at least 95% or greater identity to SEQ ID NO: 33.

Also, by way of non-limiting example, the non-antibody peptide may comprise a first alpha helix of a mouse coronin 1A protein, and the chimeric receptor binding peptide may comprise a second alpha helix of a mouse coronin 1A protein. The coiled-coil interactions of mouse coronin 1A proteins are described in Kammerer R A, et al., Proc Natl Acad Sci USA 102:13891-13896 (2005), which is incorporated herein by reference in its entirety.

Also, by way of non-limiting example, the non-antibody peptide may comprise an anchoring domain (AD) of an A-kinase anchoring protein (AKAP) and the chimeric receptor binding peptide may comprise a dimerization and docking domain (DDD) of cAMP-dependent protein kinase A. The interaction of ADs with DDDs, known as the Dock and Lock system, have been describe in Rossi E A, Goldenberg D M, Chang C H, Bioconjug Chem. March 21; 23(3):309-23 (2012); Rossi E A, et. al., Proc Natl Acad Sci USA. May 2; 103(18):6841-6 (2006); and Backer M V, Patel V, Jehning B T, Backer J M., Bioconjug Chem. July-August; 17(4):912-9 (2006), each of which is incorporated herein by reference in its entirety.

Thus, by way of non-limiting example, the non-antibody peptide may comprise an anchoring domain (AD1) of an A-kinase anchoring protein and the chimeric receptor binding peptide may comprise a dimerization and docking domain (DDD1) of cAMP-dependent protein kinase A. Alternatively, the non-antibody peptide may comprise the DDD1 and the chimeric receptor binding peptide may comprise the anchoring domain (AD1).

The peptide-peptide interaction may comprise a covalent peptide—peptide interaction. By way of non-limiting example, the non-antibody peptide may comprise an anchoring domain (AD2) of an A-kinase anchoring protein and the chimeric receptor binding peptide may comprise a dimerization and docking domain (DDD2) of cAMP-dependent protein kinase A, wherein the AD2 and DDD2 have been modified with cysteines that form disulfide bonds between the AD and the DDD. Alternatively, the non-antibody peptide may comprise the DDD2 and the chimeric receptor binding peptide may comprise the AD2, wherein the AD2 and DDD2 have been modified with cysteines that form disulfide bonds between the AD2 and the DDD2. These disulfide bonds may form a covalent interaction between AD2 and the DDD2. This may be advantageous to increase affinity of the non-antibody peptide for the chimeric receptor binding peptide, or vice versa.

The effector cell may comprise a plurality of chimeric receptors. Two or more of the plurality of chimeric receptors may be the same. Two or more of the plurality of chimeric receptors may be different. Two or more of the plurality of chimeric receptors may each comprise an extracellular domain that comprises a DDD (e.g., DDD1 or DDD2). The DDDs of the two or more of the plurality of chimeric receptors may self-homo-multimerize, to produce multimerized DDDs. The DDDs may self-homo-dimerize, to produce dimerized DDDs. The multimerized or dimerized DDDs may bind to one or more ADs. The multimerized or dimerized DDDs bound to one or more ADs may increase signal transduction and/or activation of the effector cell, relative to a chimeric receptor that comprises one or no DDDs.

The chimeric receptor may comprise an extracellular domain, wherein the extracellular domain comprises the AD. The switch may comprise the DDD. The switch may be bivalent for the AD because the DDD self-homo-dimerizes upon binding the AD (e.g., see FIG. 4). The DDD self-homo-dimerizing upon binding the AD may increase the avidity of the switch for the target cell and may improve the sensitivity of the switch for the target. This may be relevant for target cells with low surface density (or expression) of the cell surface molecule.

Figure 4:
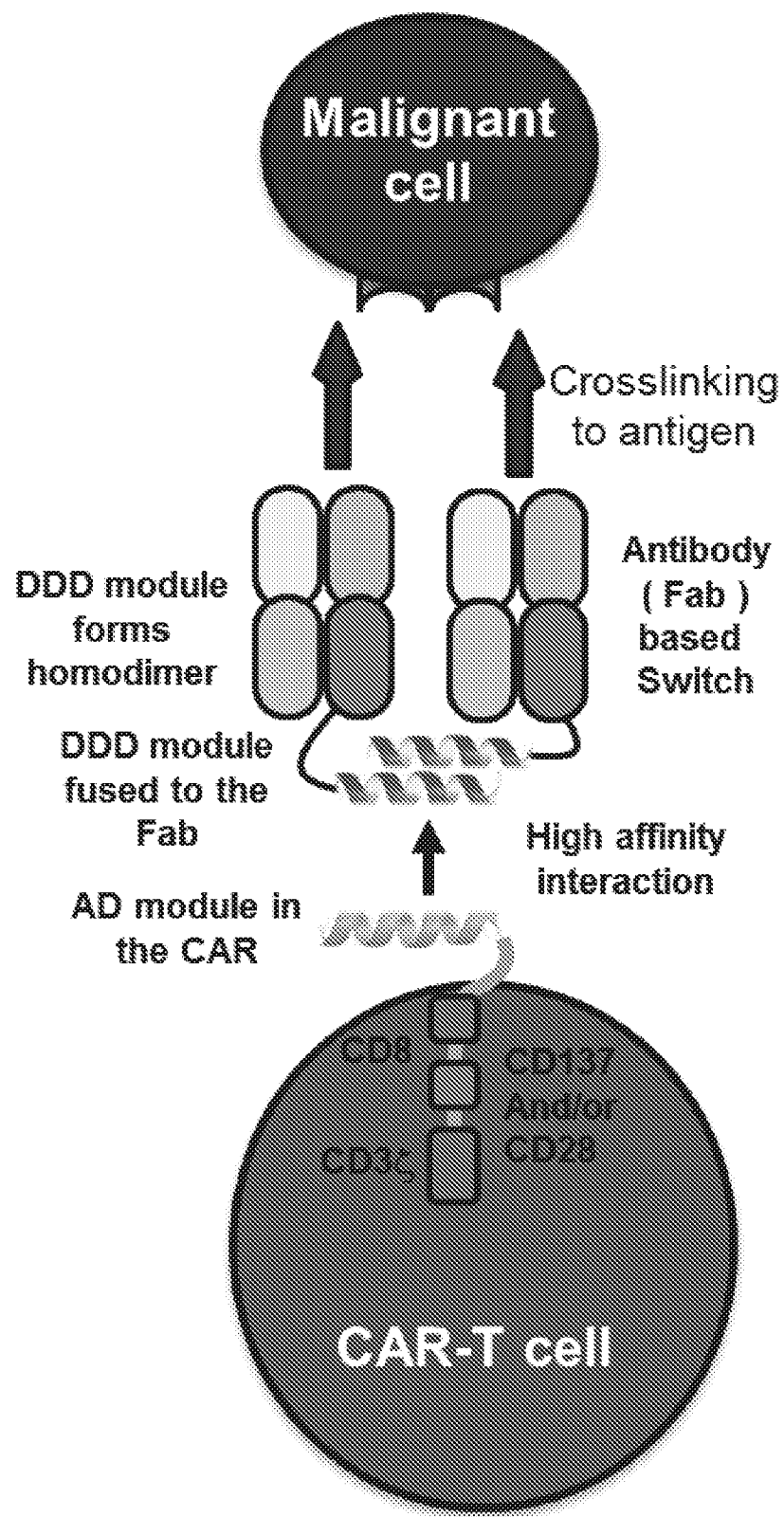
FIG. 4 illustrates an example of a dock and lock switchable chimeric receptor-T cell platform in which the DDD-module is on the switch and the AD-module is on the chimeric receptor extracellular domain.

The switch may comprise the AD and the chimeric receptor may comprise the DDD (e.g., see FIG. 5) or the switch may comprise the DDD and the chimeric receptor may comprise the AD, resulting in a DDD/AD pair (e.g., see FIG. 4). The DDD/AD pair may be smaller than an scFcv/peptide pair resulting from a chimeric antigen receptor comprising an scFv and a switch comprising a peptide, providing a size and geometry to the pair that is optimal for chimeric receptor binding to the chimeric receptor binding partner and subsequent chimeric receptor activation/signaling.

The chimeric effector receptor cell may be activated by multimerization of crosslinking multiple switches to multiple antigens on the target cell. The minimum number of switches to cause activation may be greater than two. The multimerized or dimerized DDDs may have generally potentiated signaling because it requires fewer crosslinks with switches than a canonical chimeric antigen receptor (e.g., without a dimerized/multimerized extracellular domain or portion thereof) to achieve activation.

The non-antibody extracellular domain may have a binding affinity for the chimeric receptor binding partner of less than about 0.01 pM, about 0.02 pM, about 0.03 pM, about 0.04 pM, 0.05 pM, about 0.06 pM, about 0.07 pM, about 0.08 pM, about 0.09 pM, about 0.1 pM, about 0.2 pM, 0.3 pM, about 0.4 pM, about 0.5 pM, about 0.6 pM, about 0.7 pM, about 0.8 pM, about 0.9 pM or about 1 pM, about 2 pM, about 3 pM, about 4 pM, about 5 pM, about 6 pM, about 7 pM, about 8 pM, about 9 pM, about 10 pM, about 0.01 nM, about 0.02 nM, about 0.03 nM, about 0.04 nM, about 0.05 nM, about 0.06 nM, about 0.07 nM, about 0.08 nM, about 0.09 nM, about 0.1 nM, about 0.2 nM, about 0.3 nM, about 0.4 nM, about 0.5 nM, about 0.6 nM, about 0.7 nM, about 0.8 nM, about 0.9 nM, about 1 nM, about 2 nM, about 2.5 nM, about 3 nM, about 4 nM, about 5 nM, about 6 nM, about 7 nM, about 8 nM, about 9 nM, about 10 nM, about 12 nM, about 14 nM, about 16 nM, about 18 nM, about 20 nM, about 22 nM, about 24 nM, about 26 nM, about 28 nM or about 30 nM.

II. Chimeric Receptor Effector Cells

The methods, platforms and kits disclosed herein may comprise one or more chimeric receptor effector cells (chimeric receptor-EC) or uses thereof. The chimeric receptor effector cells disclosed herein express a chimeric receptor. The chimeric receptor may be any chimeric receptor disclosed herein. Wherein the methods, platforms, or kits comprise two or more effector cells, the two or more effector cells may be of the same cell type. The two or more effector cells may be of a different cell type. The two or more effector cells may be of the same cell lineage. The two or more effector cells may be of different cell lineages. The two or more effector cells may comprise two or more identical chimeric receptors. The two or more effector cells may comprise two or more different chimeric receptors. The two or more effector cells may comprise two or more similar chimeric receptors.

The effector cell may be a T cell. The effector cell may be a cell of a T cell lineage. The effector cell may be a mature T cell. The effector cell may be a precursor T cell. The effector cell may be a cytotoxic T cell. The effector cell may be a naive T cell. The effector cell may be a memory stem cell T cell ($T_{MSC}$). The effector cell may be a central memory T cell ($T_{CM}$). The effector cell may be an effector T cell (TE). The effector cell may be a CD4+ T cell. The T cell may be a CD8+ T cell. The effector cell may be a CD4+ and CD8+ cell. The effector cell may be an alpha-beta T cell. The effector cell may be a gamma-delta T cell. The effector cell may be a natural killer T cell. The effector cell may be a helper T cell.

While preferred embodiments of the present disclosure describe methods, kits and platforms comprising T cells, one skilled in the art may also understand that other cell types may be used in place of a T cell. The effector cell may be an effector cell that has an effect on a target or target cell when brought into proximity of the target or target cell. The effector cell may be a cell that has a cytotoxic effect on a target or target cell when brought into proximity of the target or target cell. The effector cell may be an immune cell. The effector cell may be selected from a B cell, a monocyte, a thrombocyte, a leukocyte, a neutrophil, an eosinophil, a basophil, or a lymphocyte. The effector cell may be a lymphocyte. The effector cell may be a macrophage. The effector cell may be a phagocytic cell. The effector cell may be an effector B cell. The effector cell may be a natural killer cell. The effector cell may isolated or derived from a subject suffering from a disease or condition. The effector cell may be a cell derived from a subject to be treated with a chimeric receptor-EC switch or chimeric receptor-EC platform disclosed herein.

The T cell may express a chimeric receptor disclosed herein.

The T cell may express a chimeric receptor encoded by a polynucleotide having the sequence of SEQ ID NO: 1. The T cell may express a chimeric receptor encoded by one or more polynucleotides based on or derived from SEQ ID NO: 1. The polynucleotide may be at least about 5%, 10%, 15%, 20%, 25%, 30%, 35%, 40%, 45%, 50%, 55%, 60%, 65%, 70%, 75%, 80%, 85%, 90% or 95% identical to one or more polynucleotides based on or derived from SEQ ID NO: 1. The polynucleotide may be at least about 70% identical to one or more polynucleotides based on or derived from SEQ ID NO: 1. The polypeptide encoded by one or more polynucleotides may be based on or derived from SEQ ID NO: 1. The polypeptide may be encoded by a polynucleotide that is at least about 5%, 10%, 15%, 20%, 25%, 30%, 35%, 40%, 45%, 50%, 55%, 60%, 65%, 70%, 75%, 80%, 85%, 90% or 95% identical to one or more polynucleotides based on or derived from SEQ ID NO: 1. The polynucleotide may be constitutively expressed. The polynucleotide may be conditionally expressed.

The T cell may express a chimeric receptor encoded by a polynucleotide having the sequence of SEQ ID NO: 2. The T cell may express a chimeric receptor encoded by one or more polynucleotides based on or derived from SEQ ID NO: 2. The polynucleotide may be at least about 5%, 10%, 15%, 20%, 25%, 30%, 35%, 40%, 45%, 50%, 55%, 60%, 65%, 70%, 75%, 80%, 85%, 90% or 95% identical to one or more polynucleotides based on or derived from SEQ ID NO: 1. The polynucleotide may be at least about 70% identical to one or more polynucleotides based on or derived from SEQ ID NO: 1. The polypeptide encoded by one or more polynucleotides may be based on or derived from SEQ ID NO: 1. The polypeptide may be encoded by a polynucleotide that is at least about 5%, 10%, 15%, 20%, 25%, 30%, 35%, 40%, 45%, 50%, 55%, 60%, 65%, 70%, 75%, 80%, 85%, 90% or 95% identical to one or more polynucleotides based on or derived from SEQ ID NO: 2. The polynucleotide may be constitutively expressed. The polynucleotide may be conditionally expressed.

The T cell may express a chimeric receptor encoded by a polynucleotide having the sequence of SEQ ID NO: 35. The T cell may express a chimeric receptor encoded by one or more polynucleotides based on or derived from SEQ ID NO: 35. The polynucleotide may be at least about 5%, 10%, 15%, 20%, 25%, 30%, 35%, 40%, 45%, 50%, 55%, 60%, 65%, 70%, 75%, 80%, 85%, 90% or 95% identical to one or more polynucleotides based on or derived from SEQ ID NO: 35. The polynucleotide may be at least about 70% identical to one or more polynucleotides based on or derived from SEQ ID NO: 35. The polypeptide encoded by one or more polynucleotides may be based on or derived from SEQ ID NO: 35. The polypeptide may be encoded by a polynucleotide that is at least about 5%, 10%, 15%, 20%, 25%, 30%, 35%, 40%, 45%, 50%, 55%, 60%, 65%, 70%, 75%, 80%, 85%, 90% or 95% identical to one or more polynucleotides based on or derived from SEQ ID NO: 35. The polynucleotide may be constitutively expressed. The polynucleotide may be conditionally expressed.

The T cell may express a chimeric receptor encoded by a polynucleotide having the sequence of SEQ ID NO: 36. The T cell may express a chimeric receptor encoded by one or more polynucleotides based on or derived from SEQ ID NO: 36. The polynucleotide may be at least about 5%, 10%, 15%, 20%, 25%, 30%, 35%, 40%, 45%, 50%, 55%, 60%, 65%, 70%, 75%, 80%, 85%, 90% or 95% identical to one or more polynucleotides based on or derived from SEQ ID NO: 36. The polynucleotide may be at least about 70% identical to one or more polynucleotides based on or derived from SEQ ID NO: 36. The polypeptide encoded by one or more polynucleotides may be based on or derived from SEQ ID NO: 36. The polypeptide may be encoded by a polynucleotide that is at least about 5%, 10%, 15%, 20%, 25%, 30%, 35%, 40%, 45%, 50%, 55%, 60%, 65%, 70%, 75%, 80%, 85%, 90% or 95% identical to one or more polynucleotides based on or derived from SEQ ID NO: 36. The polynucleotide may be constitutively expressed. The polynucleotide may be conditionally expressed.

The T cell may express a chimeric receptor encoded by a polypeptide having the sequence of SEQ ID NO: 41. The T cell may express a chimeric receptor encoded by one or more polypeptides based on or derived from SEQ ID NO: 41. The polypeptide may be at least about 5%, 10%, 15%, 20%, 25%, 30%, 41%, 40%, 45%, 50%, 55%, 60%, 65%, 70%, 75%, 80%, 85%, 90% or 95% identical to one or more polypeptides based on or derived from SEQ ID NO: 41. The polypeptide may be at least about 70% identical to one or more polypeptides based on or derived from SEQ ID NO: 41. The polypeptide encoded by one or more polypeptides may be based on or derived from SEQ ID NO: 41. The polypeptide may be encoded by a polypeptide that is at least about 5%, 10%, 15%, 20%, 25%, 30%, 41%, 40%, 45%, 50%, 55%, 60%, 65%, 70%, 75%, 80%, 85%, 90% or 95% identical to one or more polypeptides based on or derived from SEQ ID NO: 41. The polypeptide may be constitutively expressed. The polypeptide may be conditionally expressed.

The T cell may express a chimeric receptor encoded by a polypeptide having the sequence of SEQ ID NO: 42. The T cell may express a chimeric receptor encoded by one or more polypeptides based on or derived from SEQ ID NO: 42. The polypeptide may be at least about 5%, 10%, 15%, 20%, 25%, 30%, 35%, 40%, 45%, 50%, 55%, 60%, 65%, 70%, 75%, 80%, 85%, 90% or 95% identical to one or more polypeptides based on or derived from SEQ ID NO: 42. The polypeptide may be at least about 70% identical to one or more polypeptides based on or derived from SEQ ID NO: 42. The polypeptide encoded by one or more polypeptides may be based on or derived from SEQ ID NO: 42. The polypeptide may be encoded by a polypeptide that is at least about 5%, 10%, 15%, 20%, 25%, 30%, 35%, 40%, 45%, 50%, 55%, 60%, 65%, 70%, 75%, 80%, 85%, 90% or 95% identical to one or more polypeptides based on or derived from SEQ ID NO: 42. The polypeptide may be constitutively expressed. The polypeptide may be conditionally expressed.

The T cell may express a chimeric receptor encoded by a polypeptide having the sequence of SEQ ID NO: 47. The T cell may express a chimeric receptor encoded by one or more polypeptides based on or derived from SEQ ID NO: 47. The polypeptide may be at least about 5%, 10%, 15%, 20%, 25%, 30%, 35%, 40%, 45%, 50%, 55%, 60%, 65%, 70%, 75%, 80%, 85%, 90% or 95% identical to one or more polypeptides based on or derived from SEQ ID NO: 47. The polypeptide may be at least about 70% identical to one or more polypeptides based on or derived from SEQ ID NO: 47. The polypeptide encoded by one or more polypeptides may be based on or derived from SEQ ID NO: 47. The polypeptide may be encoded by a polypeptide that is at least about 5%, 10%, 15%, 20%, 25%, 30%, 35%, 40%, 45%, 50%, 55%, 60%, 65%, 70%, 75%, 80%, 85%, 90% or 95% identical to one or more polypeptides based on or derived from SEQ ID NO: 47. The polypeptide may be constitutively expressed. The polypeptide may be conditionally expressed.

The T cell may express a chimeric receptor encoded by a polypeptide having the sequence of SEQ ID NO: 48. The T cell may express a chimeric receptor encoded by one or more polypeptides based on or derived from SEQ ID NO: 48. The polypeptide may be at least about 5%, 10%, 15%, 20%, 25%, 30%, 35%, 40%, 45%, 50%, 55%, 60%, 65%, 70%, 75%, 80%, 85%, 90% or 95% identical to one or more polypeptides based on or derived from SEQ ID NO: 48. The polypeptide may be at least about 70% identical to one or more polypeptides based on or derived from SEQ ID NO: 48. The polypeptide encoded by one or more polypeptides may be based on or derived from SEQ ID NO: 48. The polypeptide may be encoded by a polypeptide that is at least about 5%, 10%, 15%, 20%, 25%, 30%, 35%, 40%, 45%, 50%, 55%, 60%, 65%, 70%, 75%, 80%, 85%, 90% or 95% identical to one or more polypeptides based on or derived from SEQ ID NO: 48. The polypeptide may be constitutively expressed. The polypeptide may be conditionally expressed.

Disclosed herein are methods of producing a chimeric receptor effector cell (chimeric receptor-EC), the methods comprising introducing one or more polynucleotides encoding a chimeric receptor or a chimeric receptor complex into an effector cell. The effector cell may be a T cell. Introducing one or more polynucleotides encoding a chimeric receptor or a chimeric receptor complex into an effector cell may comprise transfecting the effector cell with the one or more polynucleotides. Introducing one or more polynucleotides encoding a chimeric receptor or a chimeric receptor complex into an effector cell may comprise virally infecting the effector cell with one or more viruses comprising the one or more polynucleotides encoding a chimeric receptor disclosed herein. Introducing one or more polynucleotides encoding a chimeric receptor or a chimeric receptor complex into an effector cell may comprise transducing the effector cell with one or more viruses comprising the one or more polynucleotides encoding a chimeric receptor disclosed herein. The virus may be a lentivirus. The virus may be an adenovirus. The virus may be a retrovirus. The virus may be an adeno-associated virus. The virus may be a self-complementary adeno-associated virus (scAAV). The virus may be a modified human immunodeficiency (HIV) virus. The virus may be a modified herpes simplex virus (HSV) virus. Other methods of producing the -EC may comprise a method of transferring one or more polynucleotides encoding a chimeric receptor into a cell, wherein the methods comprise adding a transposon, a zinc finger nuclease, a TALEN or a CRISPR to the cell. The transposon may be a sleeping beauty transposon. The one or more polynucleotides may have the sequence of SEQ ID NO: 1. The one or more polynucleotides may be based on or derived from SEQ ID NO: 1. The one or more polynucleotides may have the sequence of SEQ ID NO: 2. The one or more polynucleotides may be based on or derived from SEQ ID NO: 2. The one or more polynucleotides may have the sequence of SEQ ID NO: 35. The one or more polynucleotides may be based on or derived from SEQ ID NO: 35. The one or more polynucleotides may have the sequence of SEQ ID NO: 36. The one or more polynucleotides may be based on or derived from SEQ ID NO: 36.

III. Switch

Disclosed herein are chimeric receptor-effector cell switches comprising: a chimeric receptor binding partner that interacts with a chimeric receptor on an effector cell; and a targeting moiety that binds a cell surface molecule on a target.

Chimeric Receptor Binding Partner

The chimeric receptor binding partner may be anything suitable for being bound by a non-antibody extracellular domain of a chimeric receptor disclosed herein. For example, the chimeric receptor biding partner may be a naturally occurring protein, a naturally occurring peptide, portions thereof, homologs thereof, and combinations thereof. The chimeric receptor binding partner may be derived from a naturally occurring protein, derived from a naturally occurring peptide, portions thereof, homologs thereof, and combinations thereof. The chimeric receptor binding partner may be derived from an organism selected form a eukaryote and a prokaryote. The chimeric receptor binding partner may be non-naturally occurring. For example, the chimeric receptor biding partner may be a non-naturally occurring protein, a non-naturally occurring peptide, portions thereof, homologs thereof, and combinations thereof. The chimeric receptor binding partner may be a non-naturally occurring synthetic peptide.

The chimeric receptor binding partner may be a small molecule.

The chimeric receptor binding partner may bind to a non-antibody extracellular domain of a chimeric receptor disclosed herein via a covalent protein-protein interaction. The chimeric receptor binding partner may bind to a non-antibody extracellular domain of a chimeric receptor disclosed herein via a non-covalent protein-protein interaction.

The chimeric receptor binding partner may bind to a non-antibody extracellular domain of a chimeric receptor disclosed herein via a covalent protein-peptide interaction. The chimeric receptor binding partner may bind to a non-antibody extracellular domain of a chimeric receptor disclosed herein via a non-covalent protein-peptide interaction.

The chimeric receptor binding partner may bind to a non-antibody extracellular domain of a chimeric receptor disclosed herein via a covalent peptide-peptide interaction. The chimeric receptor binding partner may bind to a non-antibody extracellular domain of a chimeric receptor disclosed herein via a non-covalent peptide-peptide interaction.

The chimeric receptor binding partner may be a chimeric receptor binding protein. The chimeric receptor binding protein may comprise an antibody or antibody fragment. The chimeric receptor binding protein may not comprise an antibody or antibody fragment. The chimeric receptor binding partner may be a chimeric receptor binding peptide. The chimeric receptor binding peptide may comprise an antibody fragment. The chimeric receptor binding peptide may not comprise an antibody fragment. The chimeric receptor binding partner may comprise a chimeric receptor binding small molecule.

In some embodiments, the chimeric receptor binding partner is selected from (i) a chimeric receptor binding protein, (ii) a chimeric receptor binding peptide, and (iii) a chimeric receptor binding small molecule.

Chimeric Receptor Binding Protein

The chimeric receptor binding partner may be a chimeric receptor binding protein that is bound by a chimeric receptor. The chimeric receptor binding protein may have high proteolytic stability and low immunogenicity in humans relative to a protein in general. The chimeric receptor binding protein may comprise a foreign protein or portion thereof. The chimeric receptor binding protein may not comprise a foreign protein or portion thereof. The chimeric receptor binding protein may be selected from a hormone, a cytokine, a chemokine, a growth factor, a cell adhesion molecule, a signaling peptide, a receptor, a cell surface peptide and fragments thereof. The chimeric receptor binding protein may be a ligand or a fragment thereof. The ligand may be a hormonal ligand. The chimeric receptor binding protein may have a length of more than about 100 amino acids, more than about 200 amino acids, more than about 300 amino acids, more than about 400 amino acids, more than about 500 amino acids, more than about 600 amino acids, more than about 700 amino acids, more than about 800 amino acids, more than about 900 amino acids, or more than about 1000 amino acids. The chimeric receptor binding protein may have a length of about 100 amino acids, about 200 amino acids, about 300 amino acids, about 400 amino acids, about 500 amino acids, about 600 amino acids, about 700 amino acids, about 800 amino acids, about 900 amino acids, or about 1000 amino acids. The chimeric receptor binding protein may be an antigen.

The chimeric receptor binding protein may comprise an antibody or antibody fragment. The chimeric receptor binding protein may not comprise an antibody or antibody fragment. The chimeric receptor binding protein may comprise at least about 100, at least about 200, at least about 300, at least about 400, or at least about 500 amino acids of an antibody or antibody fragment. The antibody or antibody fragment may comprise a variable domain or portion thereof. The antibody or antibody fragment may comprise a constant domain or portion thereof.

The chimeric receptor binding protein may comprise a non-naturally occurring protein. The chimeric receptor binding protein may comprise a synthetic protein. The chimeric receptor binding protein may comprise a non-animal protein (e.g., a protein not expressed in an animal). The chimeric receptor binding protein may comprise a non-mammalian protein. The chimeric receptor binding protein may comprise a non-human protein. The chimeric receptor binding protein may comprise a protein derived from a plant, a yeast, a bacteria, a reptile, a bird or an insect.

The chimeric receptor binding protein may comprise a protease cleavage site. The protease cleavage site may be recognized by thrombin, factor Xa, TEV protease, a matrix metalloprotease (MMP) or enterokinase. The MMP may be MMP8. The MMP may be MMP9.

The chimeric receptor binding protein may be based on or derived from a naturally occurring protein. The peptide may be based on or derived from a human protein. The chimeric receptor binding protein may be based on or derived from an protein expressed in animal selected from a chimpanzee, a monkey, a rat, a mouse, a bird, a fish, a pig, a horse, a cow, a goat, a chicken, a rabbit and a guinea pig. The chimeric receptor binding protein may be based on or derived from a mammalian protein. The chimeric receptor binding peptide may be based on or derived from a non-mammalian protein. The chimeric receptor binding protein may be based on or derived from a protein expressed in a plant. The chimeric receptor binding protein may be based on or derived from a protein expressed in a bacterium. The chimeric receptor binding protein may be based on or derived from a prokaryotic protein. The chimeric receptor binding protein may be based on or derived from a eukaryotic protein. The chimeric receptor binding pep protein tide may be based on or derived from a protein expressed by a yeast.

Thus, in various non-limiting embodiments, the chimeric receptor binding protein may comprise an enzyme. The enzyme may be a nuclease. The nuclease may be a ribonuclease. The ribonuclease may be prokaryotic. The chimeric receptor binding protein may comprise a substrate. The chimeric receptor binding protein may comprise barstar. The chimeric receptor binding protein may comprise barnase. In some embodiments, the chimeric receptor binding protein may be a protein selected from a fibrous protein, an adhesion molecule protein and a membrane protein. The chimeric receptor binding protein may comprise a *Streptococcus pyogenes* pilin protein. The chimeric receptor binding protein may comprise a *Streptococcus pyogenes* fibronectin binding protein (SpyCatcher). The chimeric receptor binding protein may comprise a protein or a portion of a protein selected from a synaptobrevin, a SNAP25 and a syntaxin, and portions thereof (e.g., alpha helix). The chimeric receptor binding protein may comprise an RNAseI. The chimeric receptor binding protein may comprise a HuS adapter protein.

Chimeric Receptor Binding Peptide

The chimeric receptor binding partner may be a chimeric receptor binding peptide that is bound by a chimeric receptor. The chimeric receptor binding peptide may have high proteolytic stability and low immunogenicity in humans relative to peptides in general. The chimeric receptor binding peptide may be selected from a hormone, a cytokine, a chemokine, a growth factor, a cell adhesion molecule, a signaling peptide, a receptor, a cell surface peptide and fragments thereof. The chimeric receptor binding peptide may be a ligand or a fragment thereof. The chimeric receptor binding small peptide may be a ligand or a fragment thereof. The ligand may be a hormonal ligand. The ligand may be a peptide ligand. The chimeric receptor binding peptide may be a cyclic peptide. The chimeric receptor binding peptide may be a linear peptide. The chimeric receptor binding peptide may have a length of between about 2 and about 10, about 10 and about 20, about 20 and about 30, about 30 and about 40, about 40 and about 50, about 50 and about 60, about 60 and about 70, about 70 and about 80, and about 80 and about 90 amino acids. The chimeric receptor binding peptide may be an antigen. The chimeric receptor binding peptide may be an epitope. The chimeric receptor binding peptide may be a nonlinear epitope. The chimeric receptor binding peptide may further comprise a second peptide.

The chimeric receptor binding peptide may not comprise an antibody or antibody fragment. The chimeric receptor binding peptide may comprise less than 10 amino acids of an antibody or antibody fragment. The chimeric receptor binding peptide may comprise less than 12 amino acids of an antibody or antibody fragment. The chimeric receptor binding peptide may comprise less than 15 amino acids of an antibody or antibody fragment. The chimeric receptor binding peptide may comprise less than 20 amino acids of an antibody or antibody fragment. The chimeric receptor binding peptide may comprise less than 22 amino acids of an antibody or antibody fragment. The chimeric receptor binding peptide may comprise less than 30 amino acids of an antibody or antibody fragment. The chimeric receptor binding peptide may comprise a paratope of an antibody or antibody fragment.

In some embodiments, the present invention provides chimeric receptor effector cell switches comprising a targeting moiety and a chimeric receptor binding peptide, wherein the targeting moiety is a targeting polypeptide. The targeting polypeptide may comprise a targeting antibody or antibody fragment. The targeting antibody or antibody fragment may comprise a variable domain. The variable domain may be selected from a VH domain and a VL domain. The chimeric receptor binding peptide may be located at or near the N terminus of the VH domain. The chimeric receptor binding peptide may be located at or near the N terminus of the VL domain.

The chimeric receptor binding peptide may comprise a non-naturally occurring peptide. The chimeric receptor binding peptide may comprise a synthetic peptide. The chimeric receptor binding peptide may comprise a non-animal peptide (e.g., a peptide not expressed in an animal). The chimeric receptor binding peptide may comprise a non-mammalian peptide. The chimeric receptor binding peptide may comprise a non-human peptide. The chimeric receptor binding peptide may comprise a peptide derived from a plant, a yeast, a bacteria, a reptile, a bird or an insect.

The chimeric receptor binding peptide may comprise a myc-tag. The chimeric receptor binding peptide may comprise His-tag. The chimeric receptor binding peptide may comprise an HA-tag. The chimeric receptor binding peptide may comprise peridinin chlorophyll protein complex. The chimeric receptor binding peptide may comprise green fluorescent protein (GFP). The chimeric receptor binding peptide may comprise red fluorescent protein (RFP). The chimeric receptor binding peptide may comprise phycoerythrin (PE). The chimeric receptor binding peptide may comprise streptavidin. The chimeric receptor binding peptide may comprise avidin. The chimeric receptor binding peptide may comprise horse radish peroxidase (HRP). The chimeric receptor binding peptide may comprise alkaline phosphatase. The chimeric receptor binding peptide may comprise glucose oxidase. The chimeric receptor binding peptide may comprise glutathione-S-transferase (GST). The chimeric receptor binding peptide may comprise maltose binding protein. The chimeric receptor binding peptide, by non-limiting example, may be a c-myc tag, polyhistidine tag, V5, VSVG, softag 1, softag 3, express tag, S tag, palmitoylation, nitrosylation, SUMO tag, thioredoxin, poly (NANP), poly-Arg, calmodulin binding protein, PurF fragment, ketosteroid isomerase, PaP3.30, TAF12 histone fold domain, FKBP-tag, SNAP tag, Halo-tag, peptides from RNAse I. The chimeric receptor binding peptide may comprise a protease cleavage site. The protease cleavage site may be recognized by thrombin, factor Xa, TEV protease or enterokinase.

The chimeric receptor binding peptide may be based on or derived from a naturally occurring peptide. The peptide may be based on or derived from a human peptide. The chimeric receptor binding peptide may be based on or derived from an peptide expressed in animal selected from a chimpanzee, a monkey, a rat, a mouse, a bird, a fish, a pig, a horse, a cow, a goat, a chicken, a rabbit and a guinea pig. The chimeric receptor binding peptide may be based on or derived from a mammalian peptide. The chimeric receptor binding peptide may be based on or derived from a non-mammalian peptide. The chimeric receptor binding peptide may be based on or derived from a peptide expressed in a plant. The chimeric receptor binding peptide may be based on or derived from a peptide expressed in a bacterium. The chimeric receptor binding peptide may be based on or derived from a prokaryotic peptide. The chimeric receptor binding peptide may be based on or derived from a eukaryotic peptide. The chimeric receptor binding peptide may be based on or derived from a peptide expressed by a yeast.

Thus, in some embodiments, by way of non-limiting example, the chimeric receptor binding peptide may comprise an isopeptag. The chimeric receptor binding peptide may comprise a SpyTag. The chimeric receptor binding peptide may comprise a SNARE. The chimeric receptor binding peptide may comprise a Hu-tag. The chimeric receptor binding partner may comprise a first alpha helix peptide that binds to a second alpha helix peptide such that the first alpha helix and the second alpha helix may form a coiled coil structure when bound. The chimeric receptor binding peptide may comprise the E4 peptide (SEQ ID NO: 34). The chimeric receptor binding peptide may comprise the K4 peptide (SEQ ID NO: 33). The chimeric receptor binding peptide may comprise a modified E4 peptide. The chimeric receptor binding peptide may comprise a modified K4 peptide. The chimeric receptor binding peptide may consist of or consist essentially of a peptide having the sequence of SEQ ID NO: 34. The chimeric receptor binding peptide may consist of or consist essentially of a peptide having the sequence of SEQ ID NO: 33. The chimeric receptor binding peptide may comprise a peptide having a sequence that has at least 85%, at least 90%, at least 95% or greater identity to SEQ ID NO: 33. The chimeric receptor binding peptide may comprise a peptide having a sequence that has at least 85%, at least 90%, at least 95% or greater identity to SEQ ID NO: 34. The chimeric receptor binding peptide may comprise a peptide having a sequence that has at least 85%, at least 90%, at least 95% or greater identity to any one of SEQ ID NOS: 61-62, 65-76. The chimeric receptor binding peptide may comprise a peptide having the sequence of any one of SEQ ID NOS: 61-62, 65-76.

Also, by way of non-limiting example, the chimeric receptor binding peptide may comprise an alpha helix of a mouse coronin 1A protein. Also, by way of non-limiting example, the chimeric receptor binding peptide may comprise a dimerization and docking domain (DDD) of cAMP-dependent protein kinase A. The chimeric receptor binding peptide may comprise an anchoring domain (AD) of an A-kinase anchoring protein (AKAP). The chimeric receptor binding peptide may comprise DDD1. The chimeric receptor binding peptide may comprise AD1. The chimeric receptor binding peptide may comprise DDD2. The chimeric receptor binding peptide may comprise AD2.

Also, by way of non-limiting example, the chimeric receptor binding peptide may comprise a dimerization and docking domain of cAMP-dependent protein kinase A (e.g., DDD1 or DDD2), wherein the DDD has been modified with cysteines that form disulfide bonds between the DDD and an AD partner on a chimeric receptor (e.g., on the non-antibody extracellular domain). The chimeric receptor binding peptide may comprise a AD (e.g., AD1 or AD2), wherein the AD has been modified with cysteines that form disulfide bonds between the AD and a DDD partner on a chimeric receptor (e.g., on the non-antibody extracellular domain). These disulfide bonds may form a covalent interaction between AD1 and the DDD1 or between the AD2 and the DDD2. This may be advantageous to increase affinity of the non-antibody peptide for the chimeric receptor binding peptide, or vice versa.

Chimeric Receptor Binding Small Molecule.

The chimeric receptor binding partner may comprise a small molecule. The small molecule may not comprise a peptide. The small molecule may not comprise two or more amino acids linked by an amide bond. The small molecule may be a small molecule that is bound by a protein or peptide. The small molecule may be a small molecule that is bound by a protein or peptide, wherein the protein or peptide is present in the non-antibody extracellular domain of the chimeric receptor. The small molecule may be a small molecule that is bound by a protein or peptide with a high affinity. The small molecule may be a drug. The small molecule may be an inorganic compound. The small molecule may be an organic compound. The small molecule may be naturally occurring. The small molecule may not be naturally occurring. The small molecule may be synthetic. The small molecule may be selected from a steroid, a vitamin, a vitamer, a ligand, a receptor agonist, a receptor antagonist, an enzyme inhibitor, a DNA aptamer, a peptide nucleic acid (PNA), a PNA aptamer, a petoid, a substrate, a substrate analog, a metabolite, an antibiotic, a monosaccharide, a disaccharide, a lipid, a fatty acid, a nucleic acid, an alkaloid, a glycoside, a phenzine, a polyketide, a terpene and a tetrapyrrole, and portions thereof. By way of non-limiting example, the small molecule may be selected from the group consisting of DOTA, dinitrophenol, quinone, biotin, aniline, atrazine, an aniline-derivative, o-aminobenzoic acid, p-aminobenzoic acid, m-aminobenzoic acid, hydralazine, halothane, digoxigenin, benzene arsonate, lactose, trinitrophenol, biotin or a derivative thereof.

The small molecule may comprise a vitamin or a derivative thereof. The vitamin, by non-limiting example may be selected from Vitamin A, Vitamin B, Vitamin C, Vitamin D, Vitamin E and Vitamin K. The vitamin may be Vitamin C. The vitamin may be Vitamin D. The vitamin may comprise folate or a derivative thereof. The small molecule may comprise a vitamer. The small molecule may comprise a vitamin metabolite or vitamin precursor. The vitamer, by non-limiting example, may be selected from retinol, retinal, beta carotene, a carotenoid, thiamine, riboflavin, niacin, niacinamide, pantothenic acid, pyridoxine, pyridoxamine, pyridozl, biotin, folic acid, folinic acid, cyanocobalamin, hydroxycobalamin, methylcobalamin, ascorbic acid, cholecalciferol, ergocalciferol, a tocopherol, a tocotrienol, a phylloquinone, and a menaquinone or a derivative thereof. The small molecule may comprise an antioxidant or a derivative thereof.

The small molecule may be an enzyme inhibitor. The small molecule may be selected, by non-limiting example, from a tyrosine kinase inhibitor, a protease inhibitor, a growth factor receptor inhibitor, a hormone receptor inhibitor, a janus kinase inhibitor, an anaplastic lymphoma kinase (ALK) inhibitor, a Bcl-2 inhibitor, a poly ADP ribose polymerase (PARP) inhibitor, a PI3K inhibitor, a Braf inhibitor, a MAP kinase inhibitor, a cyclin dependent kinase inhibitor and a heat shock protein inhibitor. The enzyme inhibitor may be selected from apatinib, bortezomib, imatinib, ibrutinib, seliciclib, bosutinib, cabozantinib, crizotinib, dabrafenib, dasatinib, doxorubicin, erlotinib, everolimus, gefitinib, imatinib, iniparib, lapatinib, LEE011, LGX818, milotinib, obatoclax, olaparib, pazopanib, PD-0332991, perifosine, ponatinib, regorafenib, ruxolitinib, salinomycin, sorafebnib, sunitinib, tamoxifen, temsirolimus, tofacitinib, trametinib, vandetanib and vemurafenib or a derivative thereof.

The small molecule may be less than about 1000 Da, 1100 Da, 1200 Da, 1300 Da, 1400 Da, 1500 Da, 1600 Da, 1700 Da, 1800 Da, 1900 Da, 2000 Da, 2100 Da, 2200 Da, 2300 Da, 2400 Da, 2500 Da, 2600 Da, 2700 Da, 2800 Da, 2900, Da or less than about 3000 Da. The switch may be less than about 1200 Da. The switch may be less than about 1500 Da. The CAR-EC switch may be less than about 2000 Da.

The small molecule may have a size on the order of about $10^{-8}$ m, about $10^{-9}$ m, about $10^{-10}$ m. The small molecule may have a size of less than about $10^{-7}$ m. The small molecule may have a size of less than about $10^{-8}$ m. The small molecule may have a size of less than about $10^{-9}$ m. The small molecule may have a size of less than about $10^{-10}$ m. The small molecule may have a size of less than about $10^{-11}$ m. The small molecule may be less than about 10 nm, less than about 20 nm, less than about 30 nm, less than about 40 nm, less than about 50 nm, less than about 60 nm, less than about 70 nm, less than about 80 nm, less than about 90 nm, less than about 100 nm, less than about 110 nm, less than about 120 nm, less than about 130 nm, less than about 140 nm, less than about 150 nm, less than about 160 nm, less than about 170 nm, less than about 180 nm, less than about 190 nm, or less than about 200 nm wide at its widest dimension. The small molecule may be less than about 100 nm, less than about 200 nm wide, less than about 300 nm, less than about 400 nm, less than about 500 nm, less than about 600 nm, less than about 700 nm, less than about 800 nm, less than about 900 nm, or less than about 1000 nm wide, at its widest dimension.

Targeting Moiety

Disclosed herein are switches comprising a targeting moiety that binds a cell surface molecule on a target. The targeting moiety may be selected from a protein, a peptide, an antibody, an antibody fragment, a nucleic acid, and a sugar. The nucleic acid may be selected from a ribonucleic acid (RNA), a deoxyribonucleic acid, and combinations thereof. The nucleic acid may comprise an RNA aptamer. The nucleic acid may comprise a peptide nucleic acid (PNA). The sugar may comprise a glycan.

The targeting moiety may be a targeting protein. The targeting protein may comprise a targeting peptide that binds the cell surface molecule. The targeting protein may comprise a non-antibody protein or a non-antibody fragment protein. The targeting protein may comprise a soluble monoclonal TCR. The targeting protein may comprise a knottin (e.g., a protein with a knot or knot fold, a protein with a trefoil knot fold). The targeting protein may comprise a domain. The targeting protein may comprise a designed ankyrin repeat protein (DARPin) or portion thereof. The targeting protein may comprise a beta sandwich protein. The beta sandwich protein may comprise an adnectin. The targeting protein may comprise an anticalin or portion thereof.

The targeting protein may comprise a targeting antibody or antibody fragment. The targeting antibody or antibody fragment may be an immunoglobulin (Ig). The immunoglobulin may selected from an IgG, an IgA, an IgD, an IgE, an IgM, a fragment thereof, a portion thereof, and a modification thereof. The immunoglobulin may be IgG. The IgG may be IgG1. The IgG may be IgG2. The IgG may have one or more Fc mutations for modulating endogenous T cell FcR binding to the switch. The IgG may have one or more Fc mutations for removing the Fc binding capacity to the FcR of FcR-positive cells. Removal of the Fc binding capacity may reduce the opportunity for crosslinking of the chimeric receptor-EC to FcR positive cells, wherein crosslinking of the chimeric receptor-EC to FcR positive cells would activate the chimeric receptor-EC in the absence of the target cell. As such, modulating the endogenous T cell FcR binding to the chimeric receptor-EC switch may reduce an ineffective or undesirable immune response. The one or more Fc mutations may remove a glycosylation site. The one or more Fc mutations may be selected from E233P, L234V, L235A, delG236, A327G, A330S, P331S, N297Q and any combination thereof. The one or more Fc mutations may be in IgG1. The one or more Fc mutations in the IgG1 may be L234A, L235A, or both. Alternatively, or additionally, the one or more Fc mutations in the IgG1 may be L234A, L235E, or both. Alternatively, or additionally, the one or more Fc mutations in the IgG1 may be N297A. Alternatively, or additionally, the one or more mutations may be in IgG2. The one or more Fc mutations in the IgG2 may be V234A, V237A, or both.

The targeting antibody or antibody fragment may be an Fc null immunoglobulin or a fragment thereof.

As used herein, the term "antibody fragment" refers to any form of an antibody other than the full-length form. Antibody fragments herein include antibodies that are smaller components that exist within full-length antibodies, and antibodies that have been engineered. Antibody fragments include, but are not limited to, Fv, Fc, Fab, and (Fab')2, single chain Fv (scFv), diabodies, triabodies, tetrabodies, bifunctional hybrid antibodies, CDR1, CDR2, CDR3, combinations of CDRs, variable regions, framework regions, constant regions, heavy chains, light chains, alternative scaffold non-antibody molecules, and bispecific antibodies. Unless specifically noted otherwise, statements and claims that use the term "antibody" or "antibodies" may specifically include "antibody fragment" and "antibody fragments."

The targeting antibody fragment may be human, fully human, humanized, human engineered, non-human, and/or chimeric antibody. The non-human antibody may be humanized to reduce immunogenicity to humans, while retaining the specificity and affinity of the parental non-human antibody. Chimeric antibodies may refer to antibodies created through the joining of two or more antibody genes which originally encoded for separate antibodies. A chimeric antibody may comprise at least one amino acid from a first antibody and at least one amino acid from a second antibody, wherein the first and second antibodies are different. At least a portion of the targeting antibody or antibody fragment may be from a bovine species, a human species, or a murine species. At least a portion of the targeting antibody or antibody fragment may be from a rat, a goat, a guinea pig or a rabbit. At least a portion of the targeting antibody or antibody fragment may be from a human. At least a portion of the targeting antibody or antibody fragment antibody may be from cynomolgus monkey. The targeting antibody fragment may be a single domain antibody. The single domain antibody may be a camelid.

The targeting antibody or antibody fragment may be based on or derived from an antibody or antibody fragment from a mammal, bird, fish, amphibian, reptile. Mammals include, but are not limited to, carnivores, rodents, elephants, marsupials, rabbits, bats, primates, seals, anteaters, cetaceans, odd-toed ungulates and even-toed ungulates. The mammal may be a human, non-human primate, mouse, sheep, cat, dog, cow, horse, goat, or pig.

The targeting antibody or an antibody fragment may target an antigen selected from, by non-limiting example, CD19, Her2, CLL-1, CD33, EGFRvIII, CD20, CD22, BCMA or a fragment thereof. The antigen may comprise a wildtype antigen. The antigen may comprise one or more mutations.

The targeting antibody or antibody fragment may be an anti-CD19 antibody or a fragment thereof. The targeting antibody or antibody may be an anti-CD22 antibody. The targeting antibody or antibody may be an anti-BCMA antibody or a fragment thereof. The targeting antibody or antibody may be an anti-CS1 antibody or a fragment thereof. The targeting antibody or antibody may be an anti-EGFRvIII antibody or a fragment thereof. The targeting antibody or antibody may be an anti-Her2 antibody or a fragment thereof. The targeting antibody or antibody may comprise an anti-CD20 antibody or antibody fragment. The targeting antibody or antibody may comprise rituximab. The targeting antibody or antibody may comprise an anti-EGFR antibody or antibody fragment. The targeting antibody or antibody may comprise an anti-CEA antibody or antibody fragment. The targeting antibody or antibody may comprise an anti-CLL-1 antibody or antibody fragment. The targeting antibody or antibody may comprise an anti-CD33 antibody or antibody fragment. The targeting antibody or antibody may not comprise an anti-EpCAM antibody or fragment thereof.

The targeting antibody or antibody fragment may be selected from any commercially available antibody. The targeting antibody or antibody fragment may be selected from ado-trastuzumab emtansine, alemtuzumab, bevacizumab, brentuximab, vedotin, gemtuzumab, ozogamicin, ipilimumab, ibritumomab, tiuxetan, panitumumab, cetuximab, erbitux, rituximab, trastuzumab and fragments thereof.

The targeting antibody or antibody fragment may comprise an anti-CD19 antibody or fragment thereof. The targeting antibody or fragment thereof may comprise a light chain of the anti-CD19 antibody or fragment thereof. The light chain of the anti-CD19 antibody or fragment may comprise an amino acid sequence based on or derived from SEQ ID NO: 30. The amino acid sequence may be about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO: 30. The targeting antibody or fragment thereof may comprise a heavy chain of the anti-CD19 or fragment thereof. The targeting antibody or fragment thereof may comprise a heavy chain of an anti-CD19 IgG. The heavy chain of the anti-CD19 IgG may comprise a sequence based on or derived from SEQ ID NO: 31. The amino acid sequence may be about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO: 31. The targeting antibody or fragment thereof may comprise a heavy chain of an anti-CD19 Fab. The heavy chain of the anti-CD19 Fab may comprise a sequence based on or derived from SEQ ID NO: 32. The amino acid sequence may be about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous to SEQ ID NO: 32.

The targeting antibody or antibody fragment may comprise an amino acid sequence selected from SEQ ID NOs: 24-32. The targeting polypeptide may be based on or derived from an amino acid sequence selected from SEQ ID NOs: 24-32.

The targeting moiety may comprise a targeting peptide. The targeting peptide may have a length of between about 2 and about 10, about 10 and about 20, about 20 and about 30, about 30 and about 40, about 40 and about 50, about 50 and about 60, about 60 and about 70, about 70 and about 80, and about 80 and about 90 amino acids. The targeting peptide may have a length of less than about 100 amino acids. The targeting moiety may consist essentially of a targeting peptide. The targeting peptide may not comprise an antibody or antibody fragment or portion thereof. The targeting peptide may comprise an antigen binding site of the targeting antibody or antibody fragment. The targeting peptide may be at least a portion of an antibody fragment and the cell surface molecule may be an antigen. The targeting moiety may comprise one or more peptides that recognize and/or bind one or more antigens. The targeting moiety may comprise one or more peptides that recognize and/or bind only one antigen. The targeting peptide may be selected from a kunitz domain, an adnectin, an affibody, and portions thereof.

The targeting moiety may comprise a targeting small molecule. The targeting moiety may comprise a non-peptidic small molecule. The non-peptidic small molecule may not comprise two amino acids, wherein the two amino acids are connected by an amide bond. The targeting small molecule may be a cell-targeting molecule, an inorganic chemical ligand, a nucleic acid, a ligand, a receptor agonist, a receptor antagonist, an enzyme inhibitor, a DNA aptamer, a peptide nucleic acid (PNA), a PNA aptamer, a vitamin, a substrate or a substrate analog. The chimeric receptor binding partner and the targeting small molecule may be site-specifically linked. The chimeric receptor binding partner may comprise an unnatural amino acid. The chimeric receptor binding partner and the targeting small molecule may be site-specifically linked by the unnatural amino acid. The targeting small molecule may bind a cell surface molecule on a target cell. The cell surface molecule may be selected from an antigen, a protein, a peptide, a lipid, a sterol, a glycolipid and a cell surface marker. The targeting small molecule may be 2-[3-(1,3-dichimeric receptorboxypropyl) ureido]pentanedioic acid.

The targeting small molecule may comprise a vitamin or a derivative thereof. The vitamin, by non-limiting example may be selected from Vitamin A, Vitamin B, Vitamin C, Vitamin D, Vitamin E and Vitamin K. The vitamin may be Vitamin C. The vitamin may be Vitamin D. The vitamin may comprise folate or a derivative thereof. The vitamin may be folate or a derivative thereof. The targeting may be folate. The TID may comprise a vitamer. The TID may comprise a vitamin metabolite or vitamin precursor. The vitamer, by non-limiting example, may be selected from retinol, retinal, beta carotene, a carotenoid, thiamine, riboflavin, niacin, niacinamide, pantothenic acid, pyridoxine, pyridoxamine, pyridozl, biotin, folic acid, folinic acid, cyanocobalamin, hydroxycobalamin, methylcobalamin, ascorbic acid, cholecalciferol, ergocalciferol, a tocopherol, a tocotrienol, a phylloquinone, and a menaquinone or a derivative thereof. The targeting may comprise an antioxidant or a derivative thereof.

The targeting small molecule may be an enzyme inhibitor. The targeting may be selected, by non-limiting example, from a tyrosine kinase inhibitor, a protease inhibitor, a growth factor receptor inhibitor, a hormone receptor inhibitor, a janus kinase inhibitor, an anaplastic lymphoma kinase (ALK) inhibitor, a Bcl-2 inhibitor, a poly ADP ribose polymerase (PARP) inhibitor, a PI3K inhibitor, a Braf inhibitor, a MAP kinase inhibitor, a cyclin dependent kinase inhibitor and a heat shock protein inhibitor. The enzyme inhibitor may be selected from apatinib, bortezomib, imatinib, ibrutinib, seliciclib, bosutinib, cabozantinib, crizotinib, dabrafenib, dasatinib, doxorubicin, erlotinib, everolimus, gefitinib, imatinib, iniparib, lapatinib, LEE011, LGX818, milotinib, obatoclax, olaparib, pazopanib, PD-0332991, perifosine, ponatinib, regorafenib, ruxolitinib, salinomycin, sorafebnib, sunitinib, tamoxifen, temsirolimus, tofacitinib, trametinib, vandetanib and vemurafenib or a derivative thereof.

The targeting small molecule may be sufficiently small to penetrate a tumor. The targeting small molecule may be sufficiently small to penetrate a tumor when it is conjugated to the chimeric receptor binding partner.

The targeting moiety may bind to a cell surface molecule on a target. The cell surface molecule may comprise an antigen. The cell surface molecule may be selected from a protein, a lipid moiety, a glycoprotein, a glycolipid, a carbohydrate, a polysaccharide, a nucleic acid, an MHC-bound peptide, or a combination thereof. The cell surface molecule may comprise parts (e.g., coats, capsules, cell walls, flagella, fimbrae, and toxins) of bacteria, viruses, and other microorganisms. The cell surface molecule may be expressed by the target cell. The cell surface molecule may not be expressed by the target cell. By way of non-limiting example, the cell surface molecule may be a ligand expressed by a cell that is not the target cell and that is bound to the target cell or a cell surface molecule of the target cell. Also, by non-limiting example, the cell surface molecule may be a toxin, exogenous molecule or viral protein that is bound to a cell surface or cell surface receptor of the target cell.

Linkers

The switch may further comprise a linker. The linker may provide the switch a flexibility, length or geometry optimal for facilitating an interaction or effect of the effector cell on the target cell. The switch may further comprise one or more linkers. The switch may comprise two linkers. The linker may comprise a peptide. The linker may comprise a rigid peptide. The linker may be at least about 1, at least about 2, at least about 3, at least about 4, at least about 5, at least about 6, at least about 7, at least about 8, at least about 9 or at least about 10 amino acids in length. The one or more linkers may comprise about 5, about 10, about 15, about 20, about 25, about 30, about 35, about 40, about 45, about 50, about 55, about 60, about 70, about 80, about 90 or about 100 amino acids. The linker may be located at the N terminus or the C terminus of the chimeric receptor binding partner to graft the chimeric receptor binding partner to the targeting moiety. A first linker may be fused to the N terminus of the chimeric receptor binding partner and a second linker may be fused to the C terminus of the chimeric receptor binding partner. The chimeric receptor binding partner may be grafted into an internal site of the targeting polypeptide with a linker on either end of the chimeric receptor binding partner. The linker may be located at the N terminus or the C terminus of the targeting moiety to graft the targeting moiety into the chimeric receptor binding partner. A first linker may be fused to the N terminus of the targeting moiety and a second linker may be fused to the C terminus of the targeting moiety. The targeting moiety may be grafted into an internal site of the chimeric receptor binding partner with a linker on either end of the targeting moiety. The linker may be comprised of the sequence $(GGGGS)_n$, (SEQ ID NO:12), wherein n may be 1, 2, 3, 4, 5 or more. The linker may be comprised of the sequence $(GGS)_n$, (SEQ ID NO:14), wherein n may be 1, 2, 3, 4, 5 or more. The linker may comprise a sequence selected from SEQ ID NOS: 12-23. The linker may comprise the sequence GGGGS (SEQ ID NO: 67).

Conjugated Switches

Disclosed herein are switches, wherein the chimeric receptor binding partner is conjugated to the targeting moiety, wherein the targeting moiety is a small molecule. The switch may be made by a method wherein the small molecule is conjugated to a linker to create a small molecule-linker intermediate. The small molecule or the small molecule-linker intermediate may comprise one or more reactive functional groups that may react with a complementary reactive functional group on the chimeric receptor binding partner, previous to incorporation into the switch. The linker or the small molecule-linker intermediate may be bifunctional. The linker or the small molecule-linker intermediate may be heterobifunctional.

The small molecule-linker intermediate or the switch may be the product of a bioorthogonal reaction, non-limiting examples of which are reviewed in Kim et al., Curr Opin Chem Bio 17:412-419 (2013). The small molecule-linker intermediate, linker or the switch may comprise an oxime, a tetrazole, a Diels Alder adduct, a hetero Diels Alder adduct, an aromatic substitution reaction product, a nucleophilic substitution reaction product, an ester, an amide, a chimeric receptorbamate, an ether, a thioether, or a Michael reaction product. The small molecule-linker intermediate, linker or the switch be a cycloaddition product, a metathesis reaction product, a metal-mediated cross-coupling reaction product, a radical polymerization product, an oxidative coupling product, an acyl-transfer reaction product, or a photo click reaction product. The cycloaddition may be a Huisgen-cycloaddition. The cycloaddition may be a copper-free [3+2] Huisgen-cycloaddition. The cycloaddition may be a Diels-Alder reaction. The cycloaddition may be a hetero Diels-Alder reaction. The small molecule-linker intermediate may be the product of an enzyme-mediated reaction. The small molecule-linker intermediate may be a product of a transglutaminase-mediated reaction, non-limiting examples of which are described in Lin et al., J. Am. Chem. Soc. 128:4542-4543 (2006) and WO 2013/093809. The small molecule-linker intermediate, linker or the switch may comprise a disulfide bridge that connects two cysteine residues, such as ThioBridge™ technology by PolyTherics. The small molecule-linker intermediate, linker or the switch may comprise a maleimide bridge that connects two amino acid residues. The small molecule-linker intermediate, linker or the switch may comprise a maleimide bridge that connects two cysteine residues.

The small molecule-linker intermediate or linker may comprise an alkoxy-amine (or aminooxy) group, azide group and/or cyclooctyne group at one or more termini. The small molecule-linker intermediate or linker may comprise an alkoxy-amine at one terminus and an azide group at the other terminus. The small molecule-linker intermediate or linker may comprise an alkoxy-amine at one terminus and a cyclooctyne group at the other terminus. The alkoxy-amine may form a stable oxime with a ketone group on an amino acid. The alkoxy-amine may form a stable oxime with a ketone group on an unnatural amino acid. The ketone group may be on ap-acetyl phenylalanine (pAcF).

Grafted/Fused Switches

Disclosed herein are switches, wherein the chimeric receptor binding partner is grafted or fused to the targeting moiety. The chimeric receptor binding partner may comprise a non-antibody protein or a non-antibody peptide and the targeting moiety may comprise a targeting polypeptide, protein or peptide. The chimeric receptor binding partner may comprise a non-antibody protein or a non-antibody peptide and the targeting moiety may comprise a targeting antibody or antibody fragment. The targeting antibody or antibody fragment may be selected from an immunoglobulin, a Fab, a Fab', a F(ab')$_2$ and an scFv. The targeting antibody or antibody fragment may comprise a light chain. The targeting antibody or antibody fragment may comprise a heavy chain.

The chimeric receptor binding partner may be grafted into the targeting moiety (e.g., between chosen amino acids of the targeting antibody or antibody fragment). The chimeric receptor binding partner may be fused to a terminus of the targeting antibody or antibody fragment. Alternatively, the targeting antibody or antibody fragment may be grafted into or fused to the chimeric receptor binding partner.

The chimeric receptor binding partner may be fused to an N terminus of the light chain of the targeting antibody or antibody fragment. The chimeric receptor binding partner may be fused to a C terminus of the light chain of the targeting antibody or antibody fragment. The chimeric receptor binding partner may be fused to an N terminus of the heavy chain of the targeting antibody or antibody fragment. The chimeric receptor binding partner may be fused to a C terminus of the heavy chain of the targeting antibody or antibody fragment. The chimeric receptor binding partner may be fused to an N terminus of a VL domain of the targeting antibody or antibody fragment. The chimeric receptor binding partner may be fused to an N terminus of a VH domain of the targeting antibody or antibody fragment. The chimeric receptor binding partner may be fused to a C terminus of a CL domain of the targeting antibody or antibody fragment. The chimeric receptor binding partner may be fused to a C terminus of an Fc domain of the targeting antibody or antibody fragment. The chimeric receptor binding partner may be fused to an N terminus of a VL domain of an IgG. The chimeric receptor binding partner may be fused to an N terminus of a VH domain of an IgG. The chimeric receptor binding partner may be fused to a C terminus of a CL domain of an IgG. The chimeric receptor binding partner may be fused to a C terminus of an Fc domain of an IgG. The chimeric receptor binding partner may be fused to an N terminus of a VL domain of a Fab. The chimeric receptor binding partner may be fused to an N terminus of a VH domain of a Fab. The chimeric receptor binding partner may be fused to a C terminus of a CL domain of a Fab. The chimeric receptor binding partner may be fused to a C terminus of a $CH_1$ domain of the Fab.

The chimeric receptor binding partner may be grafted into an internal site of a targeting antibody or antibody fragment (e.g., between chosen amino acids of the targeting antibody or antibody fragment). The chimeric receptor binding partner may be grafted into a heavy chain of a targeting antibody or antibody fragment. The chimeric receptor binding partner may be grafted into a light chain of a targeting antibody or antibody fragment. The chimeric receptor binding partner may be grafted into a constant domain/region of a targeting antibody or antibody fragment. The chimeric receptor binding partner may be grafted into a variable domain/region of a targeting antibody or antibody fragment. The chimeric receptor binding partner may be grafted into an internal site of a Fab. The chimeric receptor binding partner may be grafted into an internal site of an immunoglobulin (e.g., IgG). The chimeric receptor binding partner may be grafted into a domain of the targeting antibody or fragment thereof selected from a CL domain, a $CH_1$ domain, a $CH_2$ domain, a $CH_3$ domain, a VL domain, a VH domain and a hinge domain. The chimeric receptor binding partner may be grafted between two domains of the antibody or fragment thereof selected from a CL domain, a $CH_1$ domain, a $CH_2$ domain, a $CH_3$ domain, a VL domain, a VH domain and a hinge domain, wherein the two domains are adjacent. The chimeric receptor binding partner may be grafted into a CL domain of the antibody or fragment thereof. The chimeric receptor binding partner may be grafted into a $CH_1$ domain of the antibody or fragment thereof. The chimeric receptor binding partner may be grafted into a hinge domain of the antibody or fragment thereof. The chimeric receptor binding partner may be grafted into a loop of the antibody or fragment thereof. The chimeric receptor binding partner may be grafted into a CL domain loop of the antibody or fragment thereof.

The chimeric receptor binding partner may be grafted into the C terminus of the targeting antibody or antibody fragment and therefore the distance between the chimeric receptor and the target may differ substantially depending on the size of chimeric receptor-EC switch (approximately 40 Å for scFv, 70 Å for Fab, and 120 Å for IgG). While a larger distance may negatively impact efficacy in vitro, the increased residence time of the full length antibody may be superior in vivo.

Multivalent Switches

Exemplified herein are switches comprising a chimeric receptor binding partner and a targeting moiety. However, one skilled in the art would understand that these switches could further comprise additional targeting moieties and/or additional chimeric receptor binding partners. One or more chimeric receptor binding partners may be grafted into one or more grafting sites of the targeting moiety, and vice versa. One or more chimeric receptor binding partners may be fused to one or more termini of the targeting moiety, and vice versa. One or more chimeric receptor binding partners may be conjugated to one or more termini of the targeting moiety, and vice versa. This may be advantageous, as several grafting/fusing sites may be predicted to provide optimal binding of the chimeric receptor binding partner to the chimeric receptor. For example, a first chimeric receptor binding partner may be grafted into a first domain of the targeting moiety and a second chimeric receptor binding partner may be grafted into a second domain of the targeting moiety. The first domain and the second domain may be the same. The first domain and the second domain may be different. By way of non-limiting example, the first chimeric receptor binding partner may be grafted into a light chain of a targeting antibody or antibody fragment and a second chimeric receptor binding partner may be grafted into heavy chain of the targeting antibody or antibody fragment. The first chimeric receptor binding partner may be fused to a first terminus of the targeting polypeptide and a second chimeric receptor binding partner may be fused to a second terminus of the targeting polypeptide. By way of non-limiting example, the first chimeric receptor binding partner may be fused to a C terminus of a light chain of a targeting antibody or antibody fragment and a second chimeric receptor binding partner may be fused to an N terminus of a heavy chain of the targeting antibody or antibody fragment. The first chimeric receptor binding partner may be fused to a terminus of the targeting polypeptide and a second chimeric receptor binding partner may be grafted within a domain of the targeting polypeptide. The first chimeric receptor binding partner and the second chimeric receptor binding partner may be the same or similar, such that the switch may be used with an effector cell that expresses one chimeric receptor. The first chimeric receptor binding partner and the second chimeric receptor binding partner may be different, such that the switch may be used with an effector cell that expresses one or more chimeric receptors or multiple effector cells that express different chimeric receptors.

The switches disclosed herein may comprise one or more chimeric receptor binding partners. The switches disclosed herein may comprise two or more chimeric receptor binding partners. The switches disclosed herein may comprise three or more chimeric receptor binding partners. The switches disclosed herein may comprise 1, 2, 3, 4, 5, 6, 7 or more chimeric receptor binding partners. The one or more chimeric receptor binding partners may be fused or grafted to the targeting moiety via one or more linkers. Thus, the switches disclosed herein may comprise one or more linkers. The switches disclosed herein may comprise two or more linkers. The switches disclosed herein may comprise three or more linkers. The switches disclosed herein may comprise 1, 2, 3, 4, 5, 6, 7 or more linkers.

IV. Chimeric Receptor-Effector Cell Platform

Disclosed herein are chimeric receptor effector cell platforms comprising a chimeric receptor-effector cell switch, wherein the switch comprises a chimeric receptor binding partner that interacts with a non-antibody extracellular domain of a chimeric receptor on an effector cell and a targeting moiety that interacts with a cell surface molecule on a target cell; and a chimeric receptor-effector cell comprising a chimeric receptor that binds to the chimeric receptor binding partner of the chimeric receptor-effector cell switch. The chimeric receptor effector cell platforms are referred to as "platforms," herein.

The platforms may comprise two or more switches. The platforms may comprise 3, 4, 5, 6, 7, 8, 9, 10, 11, 12, 13, 14, 15, 16, 17, 18, 19, 20 or more Switches. The platforms may comprise may comprise more than 20, more than 25, more than 30, more than 35, more than 40, more than 45 or more than 50 Switches. The two or more switches may be selected from one or more switches disclosed herein or a combination thereof.

The platforms disclosed herein may further comprise a first switch and a second switch, wherein the first switch comprises a first chimeric receptor binding partner and a first targeting moiety and the second switch comprises a second chimeric receptor binding partner and a second targeting moiety. The first chimeric receptor binding partner and the second chimeric receptor binding partner may be the same. The first chimeric receptor binding partner and the second chimeric receptor binding partner may be different. The first chimeric receptor binding partner and the second chimeric receptor binding partner may be about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous. The first targeting moiety and the second targeting polypeptide may be the same. The first targeting moiety and the second targeting moiety may be different. The first targeting moiety and the second targeting moiety may be about 99%, about 98%, about 97%, about 96%, about 95%, about 92%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or about 2% homologous.

V. Targets

Disclosed herein are chimeric receptors and chimeric receptor switches that interact with a cell surface molecule on a target cell. Generally, binding of the effector cell and the target cell to the switch brings the target cell into proximity with the effector cell sufficiently close for an activity of the effector cell to have an effect on the target cell. For example, when the effector cell (e.g., T cell) and the target cell are bound to the switch, the T cell may produce an immune response that has a cytotoxic effect on the target cell.

The switches may interact with a plurality of target cells. The target cell may be an infected cell. The target cell may be a pathogenically infected cell. The target cell may be a diseased cell. The target cell may be a genetically-modified cell. The target cell may not be a host cell. The target cell may come from an invading organism (e.g., yeast, worm, bacteria, fungus). Further disclosed herein are Switches that interact with a molecule on a non-cell target. The non-cell target may be a virus or a portion thereof. The non-cell target may be a fragment of a cell. The non-cell target may be an extracellular matrix component or protein.

The target cell may be derived from a tissue. The tissue may be selected from brain, esophagus, breast, colon, lung, glia, ovary, uterus, testes, prostate, gastrointestinal tract, bladder, liver, thymus, bone and skin. The target cell may be derived from one or more endocrine glands. Alternatively, or additionally, the target cell may be derived from one or more endocrine glands. The endocrine gland may be a lymph gland, pituitary gland, thyroid gland, parathyroid gland, pancreas, gonad or pineal gland.

The target cell may be selected from a stem cell, a pluripotent cell, a hematopoietic stem cell or a progenitor cell. The target cell may a circulating cell. The target cell may be an immune cell.

The target cell may be a cancer stem cell. The target cell may be a cancer cell. The cancer cell may be derived from a tissue. The tissue may be selected from, by way of non-limiting example, a brain, an esophagus, a breast, a colon, a lung, a glia, an ovary, a uterus, a testicle, a prostate, a gastrointestinal tract, a bladder, a liver, a thyroid and skin. The cancer cell may be derived from bone. The cancer cell may be derived from blood. The cancer cell may be derived from a B cell, a T cell, a monocyte, a thrombocyte, a leukocyte, a neutrophil, an eosinophil, a basophil, a lymphocyte, a hematopoietic stem cell or an endothelial cell progenitor. The cancer cell be derived from a CD19-positive B lymphocyte. The cancer cell may be derived from a stem cell. The cancer cell may be derived from a pluripotent cell. The cancer cell may be derived from one or more endocrine glands. The endocrine gland may be a lymph gland, pituitary gland, thyroid gland, parathyroid gland, pancreas, gonad or pineal gland.

The cancer cell may be a CD19-positive cell. The cancer cell may be a CD19-positive B lymphocyte. The cancer cell may be a Her2-positive cell. The Her2-positive cell may be a Her2-positive breast cancer cell. The target cell may be a BCMA-positive cell. The cancer cell may be a BCMA-positive multiple myeloma cell. The cancer cell may be a CS1-positive cell. The CS1-positive cell may be a multiple myeloma cell. The cancer cell may be an EGFRvIII-positive cell. The cancer cell may be an EGFRvIII-positive glioblastoma cell. The cancer cell may be a CD20-positive cell. The cancer cell may be a CD22-positive cell.

Cell Surface Molecule

The cell surface molecule may be an antigen. The antigen may be at least a portion of a surface antigen or a cell surface marker on a cell. The antigen may be a receptor or a co-receptor on a cell. The antigen may refer to a molecule or molecular fragment that may be bound by a major histocompatibility complex (MHC) and presented to a T-cell receptor. The term "antigen" may also refer to an immunogen. The immunogen may provoke an adaptive immune response if injected on its own into a subject. The immunogen may induce an immune response by itself. The antigen may be a superantigen, T-dependent antigen or a T-independent antigen. The antigen may be an exogenous antigen. Exogenous antigens are typically antigens that have entered the body from the outside, for example by inhalation, ingestion, or injection. Some antigens may start out as exogenous antigens, and later become endogenous (for example, intracellular viruses). The antigen may be an endogenous antigen. The endogenous antigen may be an antigen that has been generated within cells as a result of normal cell metabolism, or because of pathogenic infections (e.g., viral, bacterial, fungal, parasitic). The antigen may be an autoantigen. The autoantigen may be a normal protein or complex of proteins (and sometimes DNA or RNA) that is recognized by the immune system of patients suffering from a specific autoimmune disease. These antigens should, under normal conditions, not be the target of the immune system, but, due to genetic and/or environmental factors, the normal immunological tolerance for such an antigen is not present in these patients. The antigen may be present or overexpressed due to a disease or condition. The disease or condition may be a cancer or leukemia. The disease or condition may be an inflammatory disease or condition. The disease or condition may be a metabolic disease. The disease or condition may be a genetic disorder.

The cell surface molecule may be an antigen that has been designated as a tumor antigen. Tumor antigens or neoantigens may be antigens that are presented by MHC I or MHC II molecules on the surface of tumor cells. These antigens may sometimes be presented by tumor cells and never by the normal ones. In this case, they are called tumor-specific antigens (TSAs) and, in general, result from a tumor-specific mutation. More common are antigens that are presented by tumor cells and normal cells, and they are called tumor-associated antigens (TAAs). Cytotoxic T lymphocytes that recognize these antigens may be able to destroy the tumor cells before they proliferate or metastasize. Tumor antigens may also be on the surface of the tumor in the form of, for example, a mutated receptor, in which case they may be recognized by B cells. Unless otherwise specified, the terms "tumor antigen," "tumor specific antigen" and "tumor associated antigen," are used interchangeably herein.

The cell surface molecule may be a receptor. The receptor may be an extracellular receptor. The receptor may be a cell surface receptor. By way of non-limiting example, the receptor may bind a hormone, a neurotransmitter, a cytokine, a growth factor or a cell recognition molecule. The receptor may be a transmembrane receptor. The receptor may be an enzyme-linked receptor. The receptor may be a G-protein couple receptor (GPCR). The receptor may be a growth factor receptor. By way of non-limiting example, the growth factor receptor may be selected from an epidermal growth factor receptor, a fibroblast growth factor receptor, a platelet derived growth factor receptor, a nerve growth factor receptor, a transforming growth factor receptor, a bone morphogenic protein growth factor receptor, a hepatocyte growth factor receptor, a vascular endothelial growth factor receptor, a stem cell factor receptor, an insulin growth factor receptor, a somatomedin receptor, an erythropoietin receptor and homologs and fragments thereof. The receptor may be a hormone receptor. The receptor may be an insulin receptor. By way of non-limiting example, the receptor may selected from an eicosanoid receptor, a prostaglandin receptor, an estrogen receptor, a follicle stimulating hormone receptor, a progesterone receptor, a growth hormone receptor, a gonadotropin-releasing hormone receptor, homologs thereof and fragments thereof. The receptor may be an adrenergic receptor. The receptor may be an integrin. The receptor may be an Eph receptor. The receptor may be a luteinizing hormone receptor. The cell surface molecule may be at least about 50% homologous to a luteinizing hormone receptor. The receptor may be an immune receptor. By way of non-limiting example, the immune receptor may be selected from a pattern recognition receptor, a toll-like receptor, a NOD like receptor, a killer activated receptor, a killer inhibitor receptor, an Fc receptor, a B cell receptor, a complement receptor, a chemokines receptor and a cytokine receptor. By way of non-limiting example, the cytokine receptor may be selected from an interleukin receptor, an interferon receptor, a transforming growth factor receptor, a tumor necrosis factor receptor, a colony stimulating factor receptor, homologs thereof and fragments thereof. The receptor may be a receptor kinase. The receptor kinase may be a tyrosine kinase receptor. The receptor kinase may be a serine kinase receptor. The receptor kinase may be a threonine kinase receptor. By way of non-limiting example, the receptor kinase may activate a signaling protein selected from a Ras, a Raf, a PI3K, a protein kinase A, a protein kinase B, a protein kinase C, an AKT, an AMPK, a phospholipase, homologs thereof and fragments thereof. The receptor kinase may activate a MAPK/ERK signaling pathway. The receptor kinase may activate Jak, Stat or Smad.

The cell surface molecule may be a non-receptor cell surface protein. The cell surface molecule may be a cluster of differentiation proteins. By way of non-limiting example, the cell surface molecule may be selected from CD34, CD31, CD117, CD45, CD11b, CD15, CD24, CD114, CD182, CD14, CD11a, CD91, CD16, CD3, CD4, CD25, CD8, CD38, CD22, CD61, CD56, CD30, CD13, CD33, fragments thereof, and homologs thereof.

The cell surface molecule may be a molecule that does not comprise a peptide. The cell surface molecule may comprise a lipid. The cell surface molecule may comprise a lipid moiety or a lipid group. The lipid moiety may comprise a sterol. The lipid moiety may comprise a fatty acid. The antigen may comprise a glycolipid. The cell surface molecule may comprise a carbohydrate.

VI. Kits, Vectors and Polynucleotides

Disclosed herein are kits comprising one or more switches disclosed herein. The kit may further comprise two or more switches. The kit may comprise three switches. The kit may comprise about 3, 4, 5, 6, 7, 8, 9, 10, 12, 15, 20, 24, 30, 35, 48, 50, 55, 60, 65, 70, 75, 80, 85, 90, 96, 100, 120, 150, 200, 300, 384, 400, 500, 600, 700, 800, 900 or 1000 switches. The kit may be employed for biological research. The kit may be used for diagnosing a disease or a condition. The kit may be used for treating a disease or condition. The switches of the kit may be used with effector cells disclosed herein or existing CAR T-cells clinically used or tested. The kit may further comprise one or more effector cells. The effector cell may be a T cell. The T cell may express one or more chimeric receptors. The kit may further comprise a polynucleotide encoding one or more chimeric receptors. The kit may further comprise a vector comprising a polynucleotide encoding one or more chimeric receptors. The chimeric receptor may be selected from any of the chimeric receptors disclosed herein. The kit may comprise one or more polynucleotides encoding a chimeric receptor-EC switch disclosed herein or a portion thereof (e.g., antibody, antibody fragment, peptide).

Further disclosed herein are and vectors and polynucleotides encoding switches and portions thereof, wherein the switch comprises a chimeric receptor binding partner and a targeting protein/peptide, wherein the targeting protein/peptide binds a cell surface molecule on a target cell. The polynucleotides may be DNA. The polynucleotides may be RNA. Unless otherwise specified, the terms "polynucleotide" and "vector," as used herein, are used interchangeably. The targeting polypeptide may be an antibody or antibody fragment. The vector may comprise a sequence encoding a heavy chain of the antibody or antibody fragment. The vectors may comprise a sequence encoding a light chain of the antibody or antibody fragment. The vectors may comprise the sequence encoding the light chain of the antibody or antibody fragment and the sequence encoding the heavy chain of the antibody or antibody fragment. The light chain and the heavy chain may be expressed from the same vector. The light chain and the heavy chain may be expressed from two separate vectors.

Disclosed herein are vectors and polynucleotides encoding chimeric receptors, wherein the chimeric receptors comprise a non-antibody extracellular domain. The non-antibody extracellular domain may not comprise an antibody or antibody fragment. The non-antibody extracellular domain may comprise a non-antibody protein. The non-antibody extracellular domain may comprise a non-antibody peptide. The polynucleotide may have a sequence selected from SEQ ID NO: 1 or SEQ ID NO: 2.

Vectors comprising sequences encoding chimeric receptors and/or chimeric receptor effector cell switches and portions thereof, disclosed herein, may be selected from any commercially available expression vector. The expression vector may be a prokaryotic expression vector. The expression vector may be a eukaryotic expression vector. The expression vector may be a mammalian expression vector. The expression vector may be a viral expression vector. The expression vector may have a constitutive promoter for constitutive expression of the chimeric receptor and/or switch encoding sequences. The expression vector may have an inducible promoter for conditional expression of the chimeric receptor and/or switch encoding sequences.

VII. Therapeutic Use

Disclosed herein are methods, platforms and kits for treating a disease or condition in a subject in need thereof, the method comprising administering a chimeric receptor effector cell switch to the subject, wherein the switch comprises: a chimeric receptor-binding partner; and a targeting moiety. Disclosed herein are methods of treating a disease or condition in a subject in need thereof, the method comprising administering any one of the switches disclosed herein.

The methods may comprise administering an effector cell expressing a chimeric receptor and one or more switches. The methods may comprise administering about 1, 2, 3, 4, 5, 6, 7, 8, 9, 10, 12, 15, 20, 24, 30, 35, 48, 50, 55, 60, 65, 70, 75, 80, 85, 90, 96, 100, 120, 150, 200, 300, 384, 400, 500, 600, 700, 800, 900, 1000 or more switches. The methods may comprise administering two or more switches. The two or more switches may comprise the same chimeric receptor-binding partner. The two more switches may comprise the same cell targeting polypeptide. The two or more switches may comprise one or more different chimeric receptor-binding partner. The two more switches may comprise one or more different targeting moieties. The methods may comprise administering a plurality of chimeric receptor-EC cells and one or more switches.

Disclosed herein are methods of treating a disease or condition in a subject in need thereof, the method comprising administering a chimeric receptor effector cell (chimeric receptor-EC) switch to the subject, wherein the chimeric receptor-EC switch comprises: a chimeric receptor binding partner; and a targeting moiety that binds a cell surface molecule on a target.

The methods may comprise administering one or more chimeric receptor effector cells. The methods may comprise administering one or more T cells. The one or more effector cells may be selected from T cell is selected from a naive T cell, a memory stem cell T cell, a central memory T cell, an effector memory T cell, a helper T cell, a CD4+ T cell, a CD8+ T cell, a CD8/CD4+ T cell, an αβ T cell, a γδ T cell, a cytotoxic T cell, a natural killer T cell, a natural killer cell, a macrophage.

The switch may have a therapeutic effect that is at least partially dependent on bringing an effector cell in proximity of a target cell. The therapeutic effect on the intended indication of the switch may be at least partially due to the switch recruiting an effector cell to the target cell. The therapeutic effect on the intended indication of the switch may be predominantly due to the recruiting an effector cell to the target cell. The therapeutic effect of the switch may be at least partially dependent on stimulating an immune response in the chimeric receptor-EC cell.

Administering the switch may not have any therapeutic effect without further administering an effector cell. The switch may not have a significant, desirable and/or intended therapeutic effect without further administering an effector cell. The switch may not have any therapeutic effect towards an intended indication of the chimeric receptor-EC platform without further administering an effector cell. A portion or component of the switch may not have a therapeutic effect towards the intended indication of the switch without being conjugated to a second portion or component of the switch (e.g., chimeric receptor binding partner or targeting moiety). The dose of a portion or component of the switch (e.g., chimeric receptor binding partner or targeting moiety) when administered as part of the chimeric receptor-EC platform to provide a therapeutic effect may not have a therapeutic effect when the portion or component of the switch is administered alone at that dose. The portion or component of the switch may not be intended to have any therapeutic effect besides recruiting the T cell to the target cell. Administering the portion or component of the switch alone may have a therapeutic effect on the target cell, wherein the therapeutic effect is negligible relative to the therapeutic effect of administering the switch and the chimeric receptor-EC cell. Administering the portion or component of the switch may have a therapeutic effect on the target cell, wherein the therapeutic effect is less than the therapeutic effect of administering the switch and the chimeric receptor-EC cell.

Disclosed herein are uses of switches disclosed herein to treat a disease or condition in a subject in need thereof. Further disclosed herein are uses of switches disclosed herein in the manufacture of a medicament for the treatment of a disease or condition.

The disease or condition may be a cell proliferative disorder. The cell proliferative disorder may be selected from a solid tumor, a lymphoma, a leukemia and a liposarcoma. The cell proliferative disorder may be acute, chronic, recurrent, refractory, accelerated, in remission, stage I, stage II, stage III, stage IV, juvenile or adult. The cell proliferative disorder may be selected from myelogenous leukemia, lymphoblastic leukemia, myeloid leukemia, an acute myeloid leukemia, myelomonocytic leukemia, neutrophilic leukemia, myelodysplastic syndrome, B-cell lymphoma, burkitt lymphoma, large cell lymphoma, mixed cell lymphoma, follicular lymphoma, mantle cell lymphoma, hodgkin lymphoma, recurrent small lymphocytic lymphoma, hairy cell leukemia, multiple myeloma, basophilic leukemia, eosinophilic leukemia, megakaryoblastic leukemia, monoblastic leukemia, monocytic leukemia, erythroleukemia, erythroid leukemia and hepatocellular carcinoma. The cell proliferative disorder may comprise a hematological malignancy. The hematological malignancy may comprise a B cell malignancy. The cell proliferative disorder may comprise a chronic lymphocytic leukemia. The cell proliferative disorder may comprise an acute lymphoblastic leukemia. The cell proliferative disorder may comprise a CD19-positive Burkitt's lymphoma.

The disease or condition may be a cancer, a pathogenic infection, autoimmune disease, inflammatory disease, or genetic disorder.

In some instances, the disease or condition (e.g., one or more diseases or conditions) comprises a cancer. The cancer may comprise a recurrent and/or refractory cancer. Examples of cancers include, but are not limited to, sarcomas, carcinomas, lymphomas or leukemias.

The cancer may comprise a neuroendocrine cancer. The cancer may comprise a pancreatic cancer. The cancer may comprise an exocrine pancreatic cancer. The cancer may comprise a thyroid cancer. The thyroid cancer may comprise a medullary thyroid cancer. The cancer may comprise a prostate cancer.

The cancer may comprise an epithelial cancer. The cancer may comprise a breast cancer. The cancer may comprise an endometrial cancer. The cancer may comprise an ovarian cancer. The ovarian cancer may comprise a stromal ovarian cancer. The cancer may comprise a cervical cancer.

The cancer may comprise a skin cancer. The skin cancer may comprise a neo-angiogenic skin cancer. The skin cancer may comprise a melanoma.

The cancer may comprise a kidney cancer.

The cancer may comprise a lung cancer. The lung cancer may comprise a small cell lung cancer. The lung cancer may comprise a non-small cell lung cancer.

The cancer may comprise a colorectal cancer. The cancer may comprise a gastric cancer. The cancer may comprise a colon cancer.

The cancer may comprise a brain cancer. The brain cancer may comprise a brain tumor. The cancer may comprise a glioblastoma. The cancer may comprise an astrocytoma.

The cancer may comprise a blood cancer. The blood cancer may comprise a leukemia. The leukemia may comprise a myeloid leukemia. The cancer may comprise a lymphoma. The lymphoma may comprise a non-Hodgkin's lymphoma.

The cancer may comprise a sarcoma. The sarcoma may comprise an Ewing's sarcoma.

Sarcomas are cancers of the bone, cartilage, fat, muscle, blood vessels, or other connective or supportive tissue. Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g., alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous, melanoma, nonmelanoma, or actinic (solar) keratosis.

In some instances, the cancer is a lung cancer. Lung cancer may start in the airways that branch off the trachea to supply the lungs (bronchi) or the small air sacs of the lung (the alveoli). Lung cancers include non-small cell lung carcinoma (NSCLC), small cell lung carcinoma, and mesotheliomia. Examples of NSCLC include squamous cell carcinoma, carcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

Alternatively, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. In some instances, the cancer is a meningioma.

The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic leukemia.

Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenström macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

The cancer may comprise a solid tumor. The cancer may comprise a sarcoma. The cancer may be selected from a group consisting of a bladder cancer, a breast cancer, a colon cancer, a rectal cancer, an endometrial cancer, a kidney cancer, a lung cancer, melanoma, a myeloma, a thyroid cancer, a pancreatic cancer, a glioma, a malignant glioma of the brain, a glioblastoma, an ovarian cancer, and a prostate cancer. The cancer may have non-uniform antigen expression. The cancer may have modulated antigen expression. The antigen may be a surface antigen. The cancer may not comprise a myeloma. The cancer may not comprise a melanoma. The cancer may not comprise a colon cancer. The cancer may be acute lymphoblastic leukemia (ALL). The cancer may be relapsed ALL. The cancer may be refractory ALL. The cancer may be relapsed, refractory ALL. The cancer may be chronic lymphocytic leukemia (CLL). The cancer may be relapsed CLL. The cancer may be refractory CLL. The cancer may be relapsed, refractory CLL.

The cancer may comprise a breast cancer. The breast cancer may be triple positive breast cancer (estrogen receptor, progesterone receptor and Her2 positive). The breast cancer may be triple negative breast cancer (estrogen receptor, progesterone receptor and Her2 negative). The breast cancer may be estrogen receptor positive. The breast cancer may be estrogen receptor negative. The breast cancer may be progesterone receptor positive. The breast cancer may be progesterone receptor negative. The breast cancer may comprise a Her2 negative breast cancer. The breast cancer may comprise a low-expressing Her2 breast cancer. The breast cancer may comprise a Her2 positive breast cancer. Cell lines expressing Her2 have been well-characterized for antigen density, reflecting clinical immunohistochemistry characterization which classifies malignancies as 0 (<20,000 Her2 antigens per cell), 1+(100,000 Her2 antigens per cell), 2+(500,000 Her2 antigens per cell), and 3+(>2,000,000 Her2 antigens per cell). The present invention provides for methods of treating breast cancers of these classifications. The breast cancer may comprise a breast cancer classified as Her2 0. The breast cancer may comprise a breast cancer classified as Her2 1+. The breast cancer may comprise a breast cancer classified as Her2 2+. The breast cancer may comprise a breast cancer classified as a Her2 3+.

The disease or condition may be a pathogenic infection. Pathogenic infections may be caused by one or more pathogens. In some instances, the pathogen is a bacterium, fungi, virus, or protozoan.

Exemplary pathogens include but are not limited to: *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio*, or *Yersinia*. In some cases, the disease or condition caused by the pathogen is tuberculosis and the heterogeneous sample comprises foreign molecules derived from the bacterium *Mycobacterium tuberculosis* and molecules derived from the subject. In some instances, the disease or condition is caused by a bacterium is tuberculosis, pneumonia, which may be caused by bacteria such as *Streptococcus* and *Pseudomonas*, a foodborne illness, which may be caused by bacteria such as *Shigella, Campylobacter* and *Salmonella*, and an infection such as tetanus, typhoid fever, diphtheria, syphilis and leprosy. The disease or condition may be bacterial vaginosis, a disease of the vagina caused by an imbalance of naturally occurring bacterial flora. Alternatively, the disease or condition is a bacterial meningitis, a bacterial inflammation of the meninges (e.g., the protective membranes covering the brain and spinal cord). Other diseases or conditions caused by bacteria include, but are not limited to, bacterial pneumonia, a urinary tract infection, bacterial gastroenteritis, and bacterial skin infection. Examples of bacterial skin infections include, but are not limited to, impetigo which may be caused by *Staphylococcus aureus* or *Streptococcus pyogenes*; erysipelas which may be caused by a *streptococcus* bacterial infection of the deep epidermis with lymphatic spread; and cellulitis which may be caused by normal skin flora or by exogenous bacteria.

The pathogen may be a fungus, such as, *Candida, Aspergillus, Cryptococcus, Histoplasma, Pneumocystis,* and *Stachybotrys*. Examples of diseases or conditions caused by a fungus include, but are not limited to, jock itch, yeast infection, ringworm, and athlete's foot.

The pathogen may be a virus. Examples of viruses include, but are not limited to, adenovirus, coxsackievirus, Epstein-Barr virus, Hepatitis virus (e.g., Hepatitis A, B, and C), herpes simplex virus (type 1 and 2), cytomegalovirus, herpes virus, HIV, influenza virus, measles virus, mumps virus, papillomavirus, parainfluenza virus, poliovirus, respiratory syncytial virus, rubella virus, and varicella-zoster virus. Examples of diseases or conditions caused by viruses include, but are not limited to, cold, flu, hepatitis, AIDS, chicken pox, rubella, mumps, measles, warts, and poliomyelitis.

The pathogen may be a protozoan, such as *Acanthamoeba* (e.g., *A. astronyxis, A. castellanii, A. culbertsoni, A. hatchetti, A. polyphaga, A. rhysodes, A. healyi, A. divionensis*), *Brachiola* (e.g., *B. connori, B. vesicularum*), *Cryptosporidium* (e.g., *C. parvum*), *Cyclospora* (e.g., *C. cayetanensis*), *Encephalitozoon* (e.g., *E. cuniculi, E. hellem, E. intestinalis*), *Entamoeba* (e.g., *E. histolytica*), *Enterocytozoon* (e.g., *E. bieneusi*), *Giardia* (e.g., *G. lamblia*), *Isospora* (e.g, *I. belli*), Microsporidium (e.g., *M. africanum, M. ceylonensis*), *Naegleria* (e.g., *N. fowleri*), *Nosema* (e.g., *N. algerae, N. ocularum*), *Pleistophora, Trachipleistophora* (e.g., *T. anthropophthera, T. hominis*), and *Vittaforma* (e.g., *V. corneae*).

The disease or condition may be an autoimmune disease or autoimmune related disease. An autoimmune disorder may be a malfunction of the body's immune system that causes the body to attack its own tissues. Examples of autoimmune diseases and autoimmune related diseases include, but are not limited to, Addison's disease, alopecia areata, ankylosing spondylitis, antiphospholipid syndrome (APS), autoimmune aplastic anemia, autoimmune hemolytic anemia, autoimmune hepatitis, autoimmune myocarditis, Behcet's disease, celiac sprue, Crohn's disease, dermatomyositis, eosinophilic fasciitis, erythema nodosum, giant cell arteritis (temporal arteritis), Goodpasture's syndrome, Graves' disease, Hashimoto's disease, idiopathic thrombocytopenic purpura (ITP), IgA nephropathy, juvenile arthritis, diabetes, juvenile diabetes, Kawasaki syndrome, Lambert-Eaton syndrome, lupus (SLE), mixed connective tissue disease (MCTD), multiple sclerosis, myasthenia gravis, pemphigus, polyarteritis nodosa, type I, II, & III autoimmune polyglandular syndromes, polymyalgia rheumatica, polymyositis, psoriasis, psoriatic arthritis, Reiter's syndrome, relapsing polychondritis, rheumatoid arthritis, sarcoidosis, scleroderma, Sjogren's syndrome, sperm & testicular autoimmunity, stiff person syndrome, Takayasu's arteritis, temporal arteritis/giant cell arteritis, ulcerative colitis, uveitis, vasculitis, vitiligo, and Wegener's granulomatosis.

The disease or condition may be an inflammatory disease. Examples of inflammatory diseases include, but are not limited to, alveolitis, amyloidosis, angiitis, ankylosing spondylitis, avascular necrosis, Basedow's disease, Bell's palsy, bursitis, carpal tunnel syndrome, celiac disease, cholangitis, chondromalacia patella, chronic active hepatitis, chronic fatigue syndrome, Cogan's syndrome, congenital hip dysplasia, costochondritis, Crohn's Disease, cystic fibrosis, De Quervain's tendinitis, diabetes associated arthritis, diffuse idiopathic skeletal hyperostosis, discoid lupus, Ehlers-Danlos syndrome, familial mediterranean fever, fasciitis, fibrositis/fibromyalgia, frozen shoulder, ganglion cysts, giant cell arteritis, gout, Graves' Disease, HIV-associated rheumatic disease syndromes, hyperparathyroid associated arthritis, infectious arthritis, inflammatory bowel syndrome/irritable bowel syndrome, juvenile rheumatoid arthritis, lyme disease, Marfan's Syndrome, Mikulicz's Disease, mixed connective tissue disease, multiple sclerosis, myofascial pain syndrome, osteoarthritis, osteomalacia, osteoporosis and corticosteroid-induced osteoporosis, Paget's Disease, palindromic rheumatism, Parkinson's Disease, Plummer's Disease, polymyalgia rheumatica, polymyositis, pseudogout, psoriatic arthritis, Raynaud's Phenomenon/Syndrome, Reiter's Syndrome, rheumatic fever, rheumatoid arthritis, sarcoidosis, sciatica (lumbar radiculopathy), scleroderma, scurvy, sickle cell arthritis, Sjogren's Syndrome, spinal stenosis, spondyloisthesis, Still's Disease, systemic lupus erythematous, Takayasu's (Pulseless) Disease, Tendinitis, tennis elbow/golf elbow, thyroid associated arthritis, trigger finger, ulcerative colitis, Wegener's Granulomatosis, and Whipple's Disease.

Methods of treatment disclosed herein may comprise off-target activity as measured by cytokine levels. The method may reduce the off-target activity, as measured by cytokine levels, when compared to other CHIMERIC RECEPTOR-EC therapies. The method may reduce the off-target activity as measured by interferon gamma levels. Other off-target activities that may be reduced include toxic lymphophenia, fatal cytolysis of solid tumor targets and chronic hypogammaglobulinemia for hematological targets. Methods of treatment and compositions disclosed herein may be used to treat a cancer comprising CD19-mediated B cell aplasia. The methods and compositions may minimize the CD19-mediated B cell aplasia. The method may avoid long-term B-cell aplasia.

The chimeric receptor-EC platforms, methods and compositions disclosed herein may be used to treat a heterogeneous tumor or a heterogeneous blood cell malignancy in a subject in need thereof. The "pan-B cell" marker CD20 is the most prevalently targeted antigen for B cell neoplasms and the FDA-approved antibody rituximab is a vital component in the treatment of many leukemias and lymphomas. However, resistance mechanisms related to modulation of CD20 antigen expression occurs in a significant number of patients. It is clear that targeting with either CD19 or CD20 antigen alone is insufficient for a curative therapy. The methods disclosed herein provide for construction and administration of two or more switches with different specificities (e.g., an anti-CD19 antibody chimeric receptor-EC switch and an anti-CD20 antibody chimeric receptor-EC switch). The methods disclosed herein provide for construction and administration of two or more switches with different specificities (e.g., an anti-CD19 antibody chimeric receptor-EC switch and an anti-CD22 antibody chimeric receptor-EC switch). This methodology may offer a significant advantage against the propensity for relapse in the clinic while avoiding persistent loss of B cells. A heterogeneous tumor or heterogeneous blood cell malignancy may also be treated with an anti-CD19 antibody chimeric receptor-EC switch and an anti-CD22 antibody chimeric receptor- EC switch. One or more Switches may be administered sequentially or simultaneously.

The chimeric receptor-EC switch may be administered with one or more additional therapeutic agents. The one or more additional therapeutic agents may be selected from a group consisting of an immunotherapy, a chemotherapy and a steroid. The one or more additional therapeutic agents may be a chemotherapy drug. The chemotherapy drug may be an alkylating agent, an antimetabolite, an anthracycline, a topoisomerase inhibitor, a mitotic inhibitor, a corticosteroid or a differentiating agent. The chemotherapy drug may be selected from actinomycin-D, bleomycin, altretamine, bortezomib, busulfan, carboplatin, capecitabine, carmustine, chlorambucil, cisplatin, cladribine, clofarabine, cyclophosphamide, cytarabine, dachimeric receptorbazine, daunorubicin, docetaxel, doxorubicin, epirubicin, etoposide, estramustine, floxuridine, fludarabine, fluorouracil, gemcitbine (Gemzar), hydroxyurea, idarubicin, ifosfamide, irinotecan (Camptosar), ixabepilone, L-asparaginase, lomustine, mechlorethamine, melphalan, 6-mercaptopurine, methotrexate, mitomycin-C, paclitaxel (Taxol), pemetrexed, pentostatin, streptozocin, temozolomide, teniposide, thioguanine, thiotepa, topotecan (Hycamtin), vincristine, vinblastine, vinorelbine, retinoids, tretinoin (ATRA or Atralin), bexarotene (Targretin) and arsenic trioxide (Arsenox). The chemotherapy may be administered as a pill to swallow, as an injection into the muscle or fat tissue, intravenously, topically or directly into a body cavity.

The one or more additional therapeutic agents may comprise an angiogenesis inhibitor. The angiogenesis inhibitor may be selected from bevacizumab, itraconazole, carboxyamidotriazole, TNP-470, CM101, IFN alpha, IL-12, platelet factor 4, suramin, SU5416, thrombospondin, a VEGFR antagonist, an angiostatic steroid with heparin, CHIMERIC RECEPTOR-ECilage-derived angiogenesis inhibitory factor, matrix metalloprotease inhibitors, angiostatin, endostatin, sorafenib, sunitinib, pazopanib, everolimus, 2-methoxyestradiol, tecogalan, tetrathiomolybdate, thalidomide, prolactin, $\alpha v \beta_3$ inhibitor, linomide, tasquinimod, soluble VEGFR-1, soluble NRP-1, angiopoietin 2, vasostatin, calreticulin, TIMP, CDAI, Meth-1, Meth-2, interferon-alpha, interferon-beta, interferon-gamma, CXCL10, IL-4, IL-12, IL-18, prothrombin, antithrombin III fragment, prolactin, VEGI, SPARC, osteopontin, maspin, canstatin, proliferin-related protein and restin.

The one or more additional therapeutic agents may comprise a hormone therapy. The hormone therapy may be selected from an anti-estrogen (e.g., fulvestrant (Faslodex®), tamoxifen, toremifene (Fareston®)); an aromatase inhibitor (e.g., anastrozole (Arimidex®) exemestane (Aromasin®), letrozole (Ferrara®) ); a progestin (e.g., megestrol acetate (Megace®) ); an estrogen; an anti-androgen (e.g., bicalutamide (Casodex®) flutamide (Eulexin®) nilutamide (Nilandron®) ); a gonadotropin-releasing hormone (GnRH) or luteinizing hormone-releasing hormone (LHRH) agonist or analog (e.g., leuprolide (Lupron®), goserelin (Zoladex®) ).

The one or more additional therapeutic agents may comprise a steroid. The steroid may be a corticosteroid. The steroid may be cortisol or a derivative thereof. The steroid may be selected from prednisone, methylprednisolone (Solumedrol®) or dexamethasone.

The switch may be administered with one or more additional therapies. The one or more additional therapies may comprise laser therapy. The one or more additional therapies may comprise radiation therapy. The one or more additional therapies may comprise surgery.

Disclosed herein are platforms, kits and methods for treating a disease or condition in a subject. The subject may be a healthy subject. The subject may be suffering from a disease or condition. The subject may be suffering from more than one disease or condition. The subject may be suffering from chronic lymphocytic leukemia. The subject may be suffering from acute lymphoblastic leukemia. The subject may be an animal. The subject may be a mammal. The mammal may be a human, a chimpanzee, a gorilla, a monkey, a bovine, a horse, a donkey, a mule, a dog, a cat, a pig, a rabbit, a goat, a sheep, a rat, a hamster, a guinea pig or a mouse. The subject may be a bird or a chicken. The subject may be a human. The subject may be a child. The child may be suffering from acute lymphoblastic leukemia. The subject may be less than 6 months old. The subject may be about 1 year old, about 2 years old, about 3 years old, about 4 years old, about 5 years old, about 6 years old, about 7 years old, about 8 years old, about 9 years old, about 10 years old, about 11 years old, about 12 years old, about 13 years old, about 14 years old, about 15 years old, about 18 years old, about 20 years old, about 25 years old, about 30 years old, about 35 years old, about 40 years old, about 45 years old, about 50 years old, about 55 years old, about 60 years old, about 65 years old, about 70 years old, about 75 years old, about 80 years old, about 85 years old, about 90 years old, about 95 years old, about 100 years old or about 105 years old.

VIII. Methods of Killing or Activating Target Cells

Further disclosed herein are methods of killing a target cell, comprising contacting a chimeric receptor-effector cell disclosed herein with a chimeric receptor-effector cell switch disclosed herein, wherein the chimeric receptor-effector cell expresses a chimeric receptor with a non-antibody extracellular domain that binds to a chimeric receptor binding partner on the chimeric receptor effector cell switch, and wherein the chimeric receptor effector cell switch comprises the binding domain that binds the non-antibody extracellular domain of the chimeric receptor and the switch comprises a targeting moiety that binds an antigen on the target cell.

The contacting may occur in vitro. The contacting may occur in vivo in a subject. The subject may be any of the subjects disclosed herein. The subject may have a disease. The disease may be any one or more of the diseases disclosed herein. The disease may be cancer. The contacting may be via administration, via the methods described herein. The administering may comprise administering the chimeric receptor-effector cell switch to a subject that has already been administered chimeric receptor-effector cells expressing a chimeric receptor that binds the switch. The administering may comprise administering to a subject the chimeric receptor-effector cell switch and further administering to the subject a chimeric receptor-effector cell expressing a chimeric receptor that binds the chimeric receptor-effector cell switch.

The contacting may induce lysis of the targeted cell. The contacting may kill the target cell. The contacting may kill target cells with an EC50 for killing that ranges from about 1 pM to about 100 pM. The contacting may kill target cells with an eC50 for killing that is lower than 1 pM. The contacting may kill a cell that has a disease. The cell may have any disease disclosed herein. The disease may be cancer.

The switch may be any switch disclosed herein. The switch may be a K4/E4 switch. The targeting moiety may bind any antigen disclosed herein. The targeting moiety may bind CD19.

Further disclosed herein are methods of activating a target cell, comprising contacting a chimeric receptor-effector cell disclosed herein with a chimeric receptor-effector cell switch disclosed herein, wherein the chimeric receptor-effector cell is only activated if the contacting includes both (i) binding of the chimeric receptor binding partner on the chimeric receptor effector cell switch to the non-antibody extracellular domain of the chimeric receptor expressed on the chimeric receptor-effector cell and (ii) concurrent binding of the targeting moiety on the chimeric receptor effector cell switch to its target antigen.

The contacting may occur in vitro. The contacting may occur in vivo in a subject. The subject may be any of the subjects disclosed herein. The subject may have a disease. The disease may be any one or more of the diseases disclosed herein. The disease may be cancer. The contacting may be via administration, via the methods described herein. The administering may comprise administering the chimeric receptor-effector cell switch to a subject that has already been administered chimeric receptor-effector cells expressing a chimeric receptor that binds the switch. The administering may comprise administering to a subject the chimeric receptor-effector cell switch and further administering to the subject a chimeric receptor-effector cell expressing a chimeric receptor that binds the chimeric receptor-effector cell switch.

The contacting may induce lysis of the targeted cell. The contacting may kill the target cell. The contacting may kill target cells with an EC50 for killing that ranges from about 1 pM to about 100 pM. The contacting may kill target cells with an eC50 for killing that is lower than 1 pM. The contacting may kill a cell that has a disease. The cell may have any disease disclosed herein. The disease may be cancer.

The switch may be any switch disclosed herein. The switch may be a K4/E4 switch. The targeting moiety may bind any antigen disclosed herein. The targeting moiety may bind CD19.

IX. Method of Clearing Effector Cells

Further disclosed herein are methods of clearing chimeric receptor-EC cells in a subject, comprising administering a chimeric receptor-EC off switch. The chimeric receptor-EC off switch may comprise an antibody or antibody fragment that targets a cell surface marker on the effector cell. The chimeric receptor-EC off switch may comprise a peptide that is bound by the chimeric receptor of the chimeric receptor-EC. The chimeric receptor-EC off switch may comprise a chimeric receptor binding partner that is bound by the chimeric receptor of the chimeric receptor effector cell. The chimeric receptor-EC off switch may comprise a chimeric receptor binding partner that is bound by the chimeric receptor of the chimeric receptor effector cell and a targeting moiety that does not bind the cell surface molecule on the target cell.

The chimeric receptor-EC off switch may comprise the targeting moiety that is bound by the cell surface molecule of the target cell. The chimeric receptor-EC off switch may comprise the targeting moiety that is bound by the cell surface molecule of the target cell and not comprise the chimeric receptor binding partner.

The chimeric receptor-EC off switch may consist essentially of the chimeric receptor binding partner that is bound by the chimeric receptor of the chimeric receptor effector cell. The chimeric receptor-EC off switch may comprise excess and/or soluble chimeric receptor binding partner.

The chimeric receptor-EC off switch may consist essentially of the targeting moiety that is bound by the cell surface molecule of the target cell. The chimeric receptor-EC off switch may comprise excess and/or soluble targeting moiety.

The chimeric receptor binding partner may comprise DDD and the off-switch may consist essentially of AD. The chimeric receptor binding partner may comprise AD and the off-switch may consist essentially of DDD.

The antibody, antibody fragment or peptide of the chimeric receptor-EC off switch may be conjugated to a drug or a toxin. The drug or toxin may be selected from maytasine (e.g., DM1, DM4), monomethylauristatin E, monomethylauristatin F, Ki-4.dgA, dolastatin 10, calicheamicin, SN-38, duocarmycin, irinotecan, ricin, saporin, gelonin, poke weed antiviral protein, *Pseudomonas aeruginosa* exotoxin A or diphtheria toxin. The toxin may comprise a poison, a bacterial toxin (e.g., bacterial toxins causing tetanus, diphtheria), a plant toxin or animal toxin. The toxin may be a snake venom. The toxin may comprise vinblastine. The toxin may comprise auristatin. The toxin may be contained in a liposome membrane-coated vesicle. Wherein the toxin is contained in a liposome membrane-coated vesicle, the antibody is attached to the vesicle.

The cell surface marker may be a viral protein or fragment thereof. Alternatively or additionally, the effector cell expresses a viral protein or fragment thereof that is not a cell surface marker. The effector cell expressing a viral protein or fragment thereof may be targeted with a drug. Wherein the effector cell comprises a viral protein or fragment thereof, the drug may be selected from a group comprising abacavir, acyclovir, acyclovir, adefovir, amantadine, amprenavir, ampligen, arbidol, atazanavir, atripla, balavir, boceprevirertet, cidofovir, combivir, darunavir, delavirdine, didanosine, docosanol, edoxudine, efavirenz, emtricitabine, enfuvirtide, entecavir, an entry inhibitor, famciclovir, a fixed dose combination antiretroviral drug, fomivirsen, fosamprenavir, foscarnet, fosfonet, a fusion inhibitor, ganciclovir, ibacitabine, imunovir, idoxuridine, imiquimod, indinavir, inosine, integrase inhibitor, interferon type III, interferon type II, interferon type I, interferon, lamivudine, lopinavir, loviride, maraviroc, moroxydine, methisazone, nelfinavir, nevirapine, nexavir, nucleoside analogue, oseltamivir, peginterferon alfa-2a, penciclovir, peramivir, pleconaril, podophyllotoxin, protease inhibiro, raltegravir, a reverse transcriptase inhibitor, ribavirin, rimantadine, ritonavir, pyramidine, saquinavir, sofosbuvir, stavudine, a synergistic enhancer retroviral durg, tea tree oil, telaprevir, tenofovir, tenofovir disoproxil, tipranavir, trifluridine, trizivir, tromantadine, truvada, valaciclovir, vicriviroc, vidarabine, viramidine, zacitabine, zanamivir or zidovudine. The drug may be ganciclovir. The drug may be acyclovir.

The chimeric receptor-EC off switch may be expressed by the effector cell. The chimeric receptor-EC off switch may be located within the cytoplasm of the effector cell. The chimeric receptor-EC off switch may comprise a caspase signaling domain or portion thereof. The chimeric receptor-EC off switch may comprise a caspase activity. The caspase activity may be inducible. The caspase activity may be induced by a small molecule, a protein or a peptide. The caspase activity may be inducible by rimiducid.

X. Pharmaceutical Compositions

Disclosed herein is a pharmaceutical composition comprising one or more of the Switches disclosed herein. The compositions may further comprise one or more pharmaceutically acceptable salts, excipients or vehicles. Pharmaceutically acceptable salts, excipients, or vehicles for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with serum albumin are exemplary appropriate carriers. The pharmaceutical compositions may include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also may be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers may be conventional buffers such as acetate, borate, citrate, phosphate, bicarbonate, or Tris-HCl. Acetate buffer may be about pH 4-5.5, and Tris buffer may be about pH 7-8.5. Additional pharmaceutical agents are set forth in Remington's Pharmaceutical Sciences, 18th Edition, A. R. Gennaro, ed., Mack Publishing Company, 1990.

The composition may be in liquid form or in a lyophilized or freeze-dried form and may include one or more lyoprotectants, excipients, surfactants, high molecular weight structural additives and/or bulking agents (see, for example, U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g., polysorbate 20, polysorbate 80); poloxamers (e.g., poloxamer 188); poly(ethylene glycol) phenyl ethers (e.g., Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; and the MONAQUAT™ series (Mona Industries, Inc., Paterson, N.J.), polyethyl glycol, polypropyl glycol, and copolymers of ethylene and propylene glycol (e.g., Pluronics, PF68 etc). Exemplary amounts of surfactant that may be present in the pre-lyophilized formulation are from about 0.001-0.5%. High molecular weight structural additives (e.g., fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions may be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980.

Pharmaceutical compositions described herein may be formulated for controlled or sustained delivery in a manner that provides local concentration of the product (e.g., bolus, depot effect) and/or increased stability or half-life in a particular local environment. The compositions may comprise the formulation of Switches, polypeptides, nucleic acids, or vectors disclosed herein with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then may be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., antibodies comprising an ultralong CDR3). See, for example, the description of controlled release porous polymeric microparticles for the delivery of pharmaceutical compositions in WO 93/15722. Suitable materials for this purpose include polylactides (see, e.g., U.S. Pat. No. 3,773,919), polymers of poly-(a-hydroxycarboxylic acids), such as poly-D-(−)-3-hydroxybutyric acid (EP 133,988A), copolymers of L-glutamic acid and gamma ethyl-L-glutamate (Sidman et al., Biopolymers, 22: 547-556 (1983)), poly(2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(−)-3-hydroxybutyric acid. Other biodegradable polymers include poly(lactones), poly(acetals), poly(orthoesters), and poly(orthocarbonates). Sustained-release compositions also may include liposomes, which may be prepared by any of several methods known in the art (see, e.g., Eppstein et al., Proc. Natl. Acad. Sci. USA, 82: 3688-92 (1985)). The carrier itself, or its degradation products, should be nontoxic in the target tissue and should not further aggravate the condition. This may be determined by routine screening in animal models of the target disorder or, if such models are unavailable, in normal animals. Microencapsulation of recombinant proteins for sustained release has been performed successfully with human growth hormone (rhGH), interferon-(rhIFN-), interleukin-2, and MN rgp120. Johnson et al., Nat. Med., 2:795-799 (1996); Yasuda, Biomed. Ther., 27:1221-1223 (1993); Hora et al., Bio/Technology. 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010. The sustained-release formulations of these proteins were developed using poly-lactic-coglycolic acid (PLGA) polymer due to its biocompatibility and wide range of biodegradable properties. The degradation products of PLGA, lactic and glycolic acids may be cleared quickly within the human body. Moreover, the degradability of this polymer may be depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41. Additional examples of sustained release compositions include, for example, EP 58,481A, U.S. Pat. No. 3,887,699, EP 158,277A, Canadian Patent No. 1176565, U. Sidman et al., Biopolymers 22, 547 [1983], R. Langer et al., Chem. Tech. 12, 98 [1982], Sinha et al., J. Control. Release 90, 261 [2003], Zhu et al., Nat. Biotechnol. 18, 24 [2000], and Dai et al., Colloids Surf B Biointerfaces 41, 117 [2005].

Bioadhesive polymers are also contemplated for use in or with compositions of the present disclosure. Bioadhesives are synthetic and naturally occurring materials able to adhere to biological substrates for extended time periods. For example, carbopol and polycarbophil are both synthetic cross-linked derivatives of poly(acrylic acid). Bioadhesive delivery systems based on naturally occurring substances include for example hyaluronic acid, also known as hyaluronan. Hyaluronic acid is a naturally occurring mucopolysaccharide consisting of residues of D-glucuronic and N-acetyl-D-glucosamine. Hyaluronic acid is found in the extracellular tissue matrix of vertebrates, including in connective tissues, as well as in synovial fluid and in the vitreous and aqueous humor of the eye. Esterified derivatives of hyaluronic acid have been used to produce microspheres for use in delivery that are biocompatible and biodegradable (see, for example, Cortivo et al., Biomaterials (1991) 12:727-730; EP 517,565; WO 96/29998; Illum et al., J. Controlled Rel. (1994) 29:133-141).

Both biodegradable and non-biodegradable polymeric matrices may be used to deliver compositions of the present disclosure, and such polymeric matrices may comprise natural or synthetic polymers. Biodegradable matrices are preferred. The period of time over which release occurs is based on selection of the polymer. Typically, release over a period ranging from between a few hours and three to twelve months is most desirable. Exemplary synthetic polymers which may be used to form the biodegradable delivery system include: polymers of lactic acid and glycolic acid, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyanhydrides, polyurethanes and co-polymers thereof, poly(butic acid), poly(valeric acid), alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), polyvinyl acetate, poly vinyl chloride, polystyrene and polyvinylpyrrolidone. Exemplary natural polymers include alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The polymer optionally is in the form of a hydrogel (see, for example, WO 04/009664, WO 05/087201, Sawhney, et al., Macromolecules, 1993, 26, 581-587) that can absorb up to about 90% of its weight in water and further, optionally is cross-linked with multi-valent ions or other polymers.

Delivery systems also include non-polymer systems that are lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the product is contained in a form within a matrix such as those described in U.S. Pat. Nos. 4,452,775, 4,675,189 and 5,736,152 and (b) diffusional systems in which a product permeates at a controlled rate from a polymer such as described in U.S. Pat. Nos. 3,854,480, 5,133,974 and 5,407,686. Liposomes containing the product may be prepared by methods known methods, such as for example (DE 3,218,121; Epstein et al., Proc. Natl. Acad. Sci. USA, 82: 3688-3692 (1985); Hwang et al., Proc. Natl. Acad. Sci. USA, 77: 4030-4034 (1980); EP 52,322; EP 36,676; EP 88,046; EP 143,949; EP 142,641; JP 83-118008; U.S. Pat. Nos. 4,485,045 and 4,544,545; and EP 102,324).

Alternatively or additionally, the compositions may be administered locally via implantation into the affected area of a membrane, sponge, or other appropriate material on to which a switch disclosed herein has been absorbed or encapsulated. Where an implantation device is used, the device may be implanted into any suitable tissue or organ, and delivery of a switch, nucleic acid, or vector disclosed herein may be directly through the device via bolus, or via continuous administration, or via catheter using continuous infusion.

A pharmaceutical composition comprising a switch disclosed herein may be formulated for inhalation, such as for example, as a dry powder. Inhalation solutions also may be formulated in a liquefied propellant for aerosol delivery. In yet another formulation, solutions may be nebulized. Additional pharmaceutical composition for pulmonary administration include, those described, for example, in WO 94/20069, which discloses pulmonary delivery of chemically modified proteins. For pulmonary delivery, the particle size should be suitable for delivery to the distal lung. For example, the particle size may be from 1 µm to 5 µm; however, larger particles may be used, for example, if each particle is fairly porous.

Certain formulations containing Switches disclosed herein may be administered orally. Formulations administered in this fashion may be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents may be included to facilitate absorption of a selective binding agent. Diluents, flavorings, low melting point waxes, vegetable oils, lubricants, suspending agents, tablet disintegrating agents, and binders also may be employed.

Another preparation may involve an effective quantity of a CHIMERIC RECEPTOR-EC switch disclosed herein in a mixture with non-toxic excipients which are suitable for the manufacture of tablets. By dissolving the tablets in sterile water, or another appropriate vehicle, solutions may be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Suitable and/or preferred pharmaceutical formulations may be determined in view of the present disclosure and general knowledge of formulation technology, depending upon the intended route of administration, delivery format, and desired dosage. Regardless of the manner of administration, an effective dose may be calculated according to patient body weight, body surface area, or organ size. Further refinement of the calculations for determining the appropriate dosage for treatment involving each of the formulations described herein are routinely made in the art and is within the ambit of tasks routinely performed in the art. Appropriate dosages may be ascertained through use of appropriate dose-response data.

XI. Chimeric Receptor—EC Switch Production Methods

Disclosed herein are methods of producing Switches comprising expressing one or more polypeptides from one or more vectors comprising one or more polynucleotide having one or more sequences that encode a chimeric receptor-effector cell switch or a portion thereof, wherein the chimeric receptor-effector cell switch comprises a chimeric receptor binding partner and a targeting moiety. The targeting moiety may comprise a targeting polypeptide. In general, the methods comprise fusing or grafting the chimeric receptor binding partner to a polynucleotide encoding the targeting polypeptide. Fusing or grafting may be carried out by any standard cloning method known to one skilled in the art. Fusing or grafting the polynucleotides encoding the chimeric receptor binding partner and targeting polypeptide may comprise enzymatic digestion of the polynucleotides, ligation of the polynucleotides and/or amplification of the polynucleotides.

The chimeric receptor binding partner may be fused to an N terminus of the targeting polypeptide. The chimeric receptor binding partner may be fused to a C terminus of the targeting polypeptide. The chimeric receptor binding partner may be grafted within the targeting polypeptide. The targeting polypeptide may comprise a targeting antibody or antibody fragment. The chimeric receptor binding partner may be fused to an N terminus of the targeting antibody or antibody fragment. The chimeric receptor binding partner may be fused to a C terminus of the targeting antibody or antibody fragment.

As will be clear to one skilled in the art, many of the sequences disclosed herein include leader peptides, which will be cleaved during polypeptide expression if expression is in a cell comprising a secretory pathway. The location of the leader peptide is at the N-terminus of the protein, and the leader sequences are readily apparent to one skilled in the art and can be easily identified using, e.g., the SignalP server (available at the world wide web address: cbs.dtu.dk/services/SignalP/).

As used herein, the term "fused" may refer to adjoining a terminus of the chimeric receptor binding partner with a terminus of the targeting polypeptide. The chimeric receptor binding partner may be fused to the terminus of the targeting polypeptide without replacing or removing any amino acids of the targeting polypeptide. Fusing the chimeric receptor binding partner to the terminus of the targeting polypeptide may comprise removing or replacing amino acids at the terminus of the targeting polypeptide. Removing or replacing amino acids at the terminus of the targeting polypeptide may comprise removing or replacing about 1 to about 20 amino acids at the terminus of the targeting polypeptide. The chimeric receptor binding partner may be fused to the terminus of the targeting polypeptide via a linker. The linker may be fused to the chimeric receptor binding partner to produce a chimeric receptor binding partner-linker intermediate. The linker may be fused to a chimeric receptor binding partner N terminus to produce the chimeric receptor binding partner-linker intermediate. The linker may be fused to a chimeric receptor binding partner C terminus to produce the chimeric receptor binding partner-linker intermediate. The chimeric receptor binding partner-linker intermediate may be fused to the targeting polypeptide. The chimeric receptor binding partner linker intermediate may be fused to the N terminus of the targeting polypeptide. The chimeric receptor binding partner-linker intermediate may be fused to the C terminus of the targeting polypeptide. A first chimeric receptor binding partner linker intermediate may be fused to the N terminus of the targeting polypeptide and a second chimeric receptor binding partner linker intermediate may be fused to the C terminus of the targeting polypeptide. The chimeric receptor binding partner of the first chimeric receptor binding partner linker intermediate may be the same or similar to the chimeric receptor binding partner of the second chimeric receptor binding partner linker intermediate. The chimeric receptor binding partner of the first chimeric receptor binding partner linker intermediate may be different from the chimeric receptor binding partner of the second chimeric receptor binding partner linker intermediate.

As used herein, the term "grafted" may refer to inserting a chimeric receptor binding partner within a targeting polypeptide (e.g., between two amino acids of the targeting polypeptide). The chimeric receptor binding partner may be grafted within the targeting polypeptide without replacing or removing any amino acids of the targeting polypeptide. Grafting the chimeric receptor binding partner within the targeting polypeptide may comprise removing or replacing amino acids within the targeting polypeptide. Removing or replacing amino acids within the targeting polypeptide may comprise removing or replacing about 1 to about 20 amino acids within the targeting polypeptide. The chimeric receptor binding partner may be grafted within the targeting polypeptide via one linker. The chimeric receptor binding partner may be grafted within the targeting polypeptide via two linkers. The linker may be fused to the chimeric receptor binding partner N terminus to produce a chimeric receptor binding partner-linker intermediate. The linker may be fused to the chimeric receptor binding partner C terminus to produce a chimeric receptor binding partner-linker intermediate. A first linker may be fused to the chimeric receptor binding partner N terminus and a second linker may be fused to the chimeric receptor binding partner C terminus to produce a chimeric receptor binding partner-linker intermediate. The chimeric receptor binding partner linker intermediate may be grafted with in the targeting polypeptide. A first chimeric receptor binding partner linker intermediate may be grafted within the targeting polypeptide and a second chimeric receptor binding partner linker intermediate may be grafted within the targeting polypeptide. The first chimeric receptor binding partner linker intermediate may be grafted within a first domain of the targeting polypeptide and a second chimeric receptor binding partner linker intermediate may be grafted within a second domain of the targeting polypeptide. The first domain of the targeting polypeptide may be the same as the second domain of the targeting polypeptide. The first domain of the targeting polypeptide may be different from the second domain of the targeting polypeptide. The chimeric receptor binding partner of the first chimeric receptor binding partner linker intermediate may be the same or similar to the chimeric receptor binding partner of the second chimeric receptor binding partner linker intermediate. The chimeric receptor binding partner of the first chimeric receptor binding partner linker intermediate may be different from the chimeric receptor binding partner of the second chimeric receptor binding partner linker intermediate. Unless otherwise specified, the terms "graft" and "insert", as used herein, are used interchangeably.

The targeting moiety may comprise an antibody or antibody fragment. The antibody or antibody fragment may comprise a heavy chain and a light chain or fragments thereof. The methods may comprise expressing a heavy chain wherein the chimeric receptor binding partner is fused to a terminus of the heavy chain. The methods may comprise expressing a heavy chain wherein the chimeric receptor binding partner is grafted within the heavy chain. The methods may comprise expressing a light chain wherein the chimeric receptor binding partner is fused to a terminus of the light chain. The methods may comprise expressing a light chain wherein the chimeric receptor binding partner is grafted within the light chain.

The methods may further comprise cloning one or more polynucleotides encoding the targeting polypeptide and/or the chimeric receptor binding partner into an expression vector. The methods may further comprise ligation of the one or more polynucleotides encoding the targeting polypeptide and/or chimeric receptor binding partner into an expression vector. The expression vector may be a prokaryotic expression vector. The expression vector may be a eukaryotic expression vector. The expression vector may be a mammalian expression vector. The expression vector may be a viral expression vector. The methods may further comprise validating the cloning of the one or more polynucleotides encoding the targeting polypeptide and/or chimeric receptor binding partner into the expression vector comprising sequencing the expression vector, running gel electrophoresis of the vector and/or viewing the targeting polypeptide and/or chimeric receptor binding partner on an SDS page gel.

The methods may further comprise amplifying a polynucleotide encoding the targeting polypeptide and/or chimeric receptor binding partner and cloning the targeting polypeptide and/or chimeric receptor binding partner into the expression vector. Amplifying the polynucleotide encoding the targeting polypeptide and/or the chimeric receptor binding partner may comprise synthesizing oligonucleotides at least partially complementary to the gene. The oligonucleotides may be sufficiently complementary to the gene to anneal to the polynucleotide. The oligonucleotides may comprise linker sequences. The linker sequences may be selected from SEQ ID NOs: 12-23.

The methods may further comprise transfecting or infecting a cell with the expression vector. The methods may further comprise expressing the targeting polypeptide and/or chimeric receptor binding partner in the cell. The methods may further comprise expressing the targeting polypeptide and/or chimeric receptor binding partner in a cell free system. The methods may further comprise producing a virus comprising the expression vector. The methods may further comprise propagating the virus. The methods may further comprise infecting a cell with the virus comprising the expression vector. The methods may further comprise propagating the cell.

Disclosed herein are methods of grafting the antibody or antibody fragment, the chimeric receptor binding partner or the targeting peptide to produce a switch. The method may comprise grafting the chimeric receptor binding partner to the antibody or antibody fragment. The method may comprise grafting the chimeric receptor binding partner to an n terminus, c terminus or internal site of the antibody or antibody fragment. The chimeric receptor binding partner may be grafted to a CL domain of the antibody or antibody fragment. The chimeric receptor binding partner may be grafted to a loop of the CL domain of the antibody or antibody fragment. The method may comprise grafting the antibody or antibody fragment to the chimeric receptor binding partner. The method may comprise grafting the antibody or antibody fragment to an N terminus, C terminus or internal site of the chimeric receptor binding partner. the method may comprise grafting the chimeric receptor binding partner to the targeting peptide. The method may comprise grafting the chimeric receptor binding partner to an N terminus, C terminus or internal site of the targeting peptide. The method may comprise grafting the targeting peptide to the chimeric receptor binding partner. The method may comprise grafting the targeting peptide to an N terminus, C terminus or internal site of the chimeric receptor binding partner.

The chimeric receptor binding partner, targeting peptide, antibody or antibody fragment may comprise one or more linkers, wherein the linker is located at the N terminus and/or C terminus of the chimeric receptor binding partner, targeting peptide, antibody or antibody fragment. The method may comprise grafting the antibody or antibody fragment, the chimeric receptor binding partner or the targeting peptide through the linker. The linker may comprise (GGGGS)$_n$ (SEQ ID 12).

Grafting may comprise producing a switch encoding nucleic acid. Producing the switch encoding nucleic acid may comprise one or more polymerase chain reactions. Producing the switch encoding nucleic acid may comprise one or more nucleic acid enzymatic digestions. The enzymatic digestion may be site specific. Producing the switch encoding nucleic acid may comprise one or more ligations. The methods of producing the switch may comprise incorporating the switch encoding nucleic acid into a switch vector. The vector may be an expression vector. The expression vector may comprise a constitutive promoter, an inducible promoter and/or a conditional promoter. The switch encoding nucleic acid or vector may be expressed in a cell and the resulting switch isolated and purified. The cell may be a prokaryotic cell. The cell may be an *E. coli*. The cell may be a eukaryotic cell. The cell may be a mammalian cell. The switch encoding nucleic acid or switch vector may be expressed in a cell-free system. Alternatively or additionally the switch may be synthesized from free amino acids.

Purification of Switches and Portions Thereof

Disclosed herein are methods of purifying switches disclosed herein, comprising separating the Switches disclosed herein from components of a switch production system (e.g., cellular debris, free amino acids). Purifying the switch may comprise use of one or more concentrator columns, electrophoresis, filtration, centrifugation, chromatography or a combination thereof. Chromatography may comprise size-exclusion chromatography. Additional chromatography methods include, but are not limited to, hydrophobic interaction chromatography, ion exchange chromatography, affinity chromatography, metal binding, immunoaffinity chromatography, and high performance liquid chromatography or high pressure liquid chromatography. Electrophoresis may comprise denaturing electrophoresis or non-denaturing electrophoresis.

The switches may comprise one or more peptide tags. The methods of purifying switches may comprise binding one or more peptide tags of the Switches to a capturing agent. The capturing agent may be selected from an antibody, a column, a bead and a combination thereof. The one or more tags may be cleaved by one or more proteases. Examples of tags include, but are not limited to, polyhistidine, FLAG® tag, HA, c-myc, V5, chitin binding protein (CBP), maltose binding protein (MBP), and glutathione-S-transferase (GST). The peptide tag may be HTP. The peptide tag may be yeast transcription factor GCN4.

The methods may further comprise lyophilization or ultracentrifugation of the chimeric receptor binding partners, targeting polypeptides and/or the switches.

The purity of the chimeric receptor binding partners, targeting polypeptides and/or the Switches may be equal to or greater than 50%, 55%, 60%, 65%, 70%, 75%, 80%, 85%, 90%, 91%, 92%, 93%, 94%, 95%, 96%, 97%, 98%, 99% or more. The purity of the chimeric receptor binding partners, targeting polypeptides and/or the switches may be equal to or greater than 85%. The purity of the chimeric receptor binding partners, targeting polypeptides and/or the switches may be equal to or greater than 90%. The purity of the chimeric receptor binding partners, targeting polypeptides and/or the Switches may be equal to or greater than 95%. The purity of the chimeric receptor binding partners, targeting polypeptides and/or the switches may be equal to or greater than 97%.

The methods of producing switches disclosed herein may comprise producing switches that are structurally homogeneous. The method of producing the switch from a polynucleotide may result in one or more switches that have the same or similar form, features, binding affinities (e.g., for the chimeric receptor or the target), geometry and/or size. The homogeneity of the Switches may be equal to or greater than 50%, 55%, 60%, 65%, 70%, 75%, 80%, 85%, 90%, 91%, 92%, 93%, 94%, 95%, 96%, 97%, 98%, 99% or more. The homogeneity of the switches may be equal to or greater than 85%. The homogeneity switches may be equal to or greater than 90%. The homogeneity of the switches may be equal to or greater than 95%. The homogeneity of the Switches may be equal to or greater than 97%. The homogeneity may be a structural homogeneity. The homogeneity may be a structural homogeneity prior to administering the cell to a subject. The homogeneity may be a structural homogeneity prior to modifications to the switch by cellular activities (methylation, acetylation, glycosylation, etc.). These high percentages of homogeneity may provide a more predictable effect of the switch. These high percentages of homogeneity may provide for less off-target effects of the switch, when combined with a chimeric receptor-EC to treat a condition in a subject.

TABLE 1

Chimeric Receptor-Nucleotide Sequence

| NAME | SEQ ID NO | SEQUENCE |
|---|---|---|
| CHIMERIC RECEPTOR with DDD1 module | 1 | atggccttaccagtgaccgccttgctcctgccgctggccttgctgctccacgccgccaggccgTCA CATATCCAGATCCCCCCCGGACTGACTGAACTGCTGCAGGGCT ATACCGTGGAAGTGCTGAGACAGCAGCCTCCCGACCTGGTGG AGTTCGCCGTGGAATACTTTACCCGGCTGAGGGAGGCACGGG CTGGAGGCGGAGGTTCAGGAGGAGGAGGGAGTGGCGGAGGC GGTAGCaccacgacgccagcgccgcgaccaccaacaccggcgccaccatcgcgtcgcagc ccctgtccctgcgcccagaggcgtgccggccagcggcgggggggcgcagtgcacacgaggggggct ggacttcgcctgtgatatctacatctgggcgcccttggccgggacttgtggggtccttctcctgtcactgg ttatcaccattactgcaaacggggcagaaagaaactctgtatatattcaaacaaccatttatgagacca gtacaaactactcaagaggaagatggctgtagctgccgatttccagaagaagaagaaggaggatgtga actgagagtgaagttcagcaggagcgcagacgccccgcgtacaagcagggccagaaccagctcta taacgagctcaatctaggacgaagagaggagtacgatgttttggacaagagacgtggccgggaccct |

TABLE 1-continued

Chimeric Receptor-Nucleotide Sequence

| NAME | SEQ ID NO | SEQUENCE |
|---|---|---|
| | | gagatggggggaaagccgagaaggaagaaccctcaggaaggcctgtacaatgaactgcagaaaga<br>taagatggcggaggcctacagtgagattgggatgaaaggcgagcgccggaggggcaaggggcacg<br>atggcctttaccagggtctcagtacagccaccaaggacacctacgacgcccttcacatgcaggccctg<br>ccccctcgctaa |
| CHIMERIC RECEPTOR with AD1 module | 2 | atggccttaccagtgaccgccttgctcctgccgctggccttgctgctccacgccgccaggccgCAG<br>ATTGAGTACCTGGCTAAACAGATTGTGGATAACGCTATTCAGC<br>AGGCAGGCGGAGGTGGATCTGGAGGCGGTGGGTCAGGTGGA<br>GGCGGAAGTaccacgacgccagccgccgcgaccaccaacaccggcgcccaccatcgcgtcg<br>cagcccctgtccctgcgcccagaggcgtgccggccagcggcgggggggcgcagtgcacacgaggg<br>ggctggacttcgcctgtgatatctacatctgggcgcccttggccgggacttgtggggtccttctcctgtca<br>ctggttatccccttttactgcaaacggggcagaaagaaactcctgtatatattcaaacaaccatttatgag<br>accagtacaaactactcaagaggaagatggctgtagctgccgatttccagaagaagaagaaggagga<br>tgtgaactgagagtgaagttcagcaggagcgcagacgcccccgcgtacaagcagggccagaaccag<br>ctctataacgagctcaatctaggacgaagagaagtacgatgtttttggacaagagacgtggccggga<br>ccctgagatggggggaaagccgagaaggaagaaccctcaggaaggcctgtacaatgaactgcagaa<br>agataagatggcggaggcctacagtgagattgggatgaaaggcgagcgccggaggggcaaggggc<br>acgatggcctttaccagggtctcagtacagccaccaaggacacctacgacgcccttcacatgcaggcc<br>ctgccccctcgctaa |

TABLE 2

Switch-Nucleotide Sequence

| NAME | SEQ ID NO | SEQUENCE |
|---|---|---|
| Switch with DDD1 module and anti-CD19 huB4 heavy chain | 3 | atgtacaggatgcaactcctgtcttgcattgcactaagtcttgcacttgtcacgaattcgCAGGTGC<br>AGCTGGTCCAGCCAGGGGCAGAGGTCGTCAAGCCAGGAGCAT<br>CCGTCAAACTGTCATGTAAAACAAGCGGGTATACTTTCACCAG<br>CAATTGGATGCACTGGGTGAAGCAGGCCCCCGGACAGGGCCT<br>GGAGTGGATCGGGGAAATTGACCCTAGTGATTCATACACTAA<br>CTACAACCAGAACTTCCAGGGAAAGGCCAAACTGACCGTGGA<br>CAAAAGCACCTCCACAGCTTATATGGAGGTGAGCAGCCTGCG<br>GTCCGACGATACTGCAGTCTACTATTGCGCCAGAGGCTCTAAC<br>CCTTACTATTACGCTATGGATTACTGGGGGCAGGGAACAAGC<br>GTGACTGTCTCTAGTGCATCAACAAAGGGACCAAGCGTGTTTC<br>CACTGGCCCCCTCAAGCAAGAGCACCTCCGGAGGGACAGCCG<br>CTCTGGGATGTCTGGTGAAAGACTACTTCCCCGAGCCTGTGAC<br>TGTCTCTTGGAATAGTGGCGCTCTGACCTCCGGGGTGCACACA<br>TTTCCAGCAGTCCTGCAGTCCTCTGGACTGTATTCTCTGAGTTC<br>AGTGGTCACCGTGCCCAGCTCCTCTCTGGGCACTCAGACCTAC<br>ATCTGCAATGTCAACCATAAGCCTAGTAACACAAAAGTGGAT<br>AAGAAAGTCGAACCAAAGAGCTGTGGCGGAGGGAGCGGAGG<br>AGGCGGTAGCGGCGGGGAGGCTCACATATCCAGATTCCACC<br>AGGGCTGACAGAACTGCTGCAGGGCTACACCGTGGAGGTCCT<br>GCGGCAGCAGCCCCCTGACCTGGTGGAGTTCGCTGTGGAATA<br>CTTTACAAGGCTGCGGGAGGCTCGGGCTtaa |
| Switch with AD1 module and anti-CD19 huB4 heavy chain | 4 | atgtacaggatgcaactectgtatgcattgcactaagtcttgcacttgtcacgaattcgCAGGTGC<br>AGCTGGTCCAGCCAGGGGCAGAGGTCGTCAAGCCAGGAGCAT<br>CCGTCAAACTGTCATGTAAAACAAGCGGGTATACTTTCACCAG<br>CAATTGGATGCACTGGGTGAAGCAGGCCCCCGGACAGGGCCT<br>GGAGTGGATCGGGGAAATTGACCCTAGTGATTCATACACTAA<br>CTACAACCAGAACTTCCAGGGAAAGGCCAAACTGACCGTGGA<br>CAAAAGCACCTCCACAGCTTATATGGAGGTGAGCAGCCTGCG<br>GTCCGACGATACTGCAGTCTACTATTGCGCCAGAGGCTCTAAC<br>CCTTACTATTACGCTATGGATTACTGGGGGCAGGGAACAAGC<br>GTGACTGTCTCTAGTGCATCAACAAAGGGACCAAGCGTGTTTC<br>CACTGGCCCCCTCAAGCAAGAGCACCTCCGGAGGGACAGCCG<br>CTCTGGGATGTCTGGTGAAAGACTACTTCCCCGAGCCTGTGAC<br>TGTCTCTTGGAATAGTGGCGCTCTGACCTCCGGGGTGCACACA<br>TTTCCAGCAGTCCTGCAGTCCTCTGGACTGTATTCTCTGAGTTC<br>AGTGGTCACCGTGCCCAGCTCCTCTCTGGGCACTCAGACCTAC<br>ATCTGCAATGTCAACCATAAGCCTAGTAACACAAAAGTGGAT<br>AAGAAAGTCGAACCAAAGAGCTGTGGCGGAGGGAGCGGAGG<br>AGGCGGTAGCGGCGGGGAGGCTCACATATCCAGATTCCACC<br>AGGGCTGACAGAACTGCTGCAGGGCTACACCGTGGAGGTCCT<br>GCGGCAGCAGCCCCCTGACCTGGTGGAGTTCGCTGTGGAATA<br>CTTTACAAGGCTGCGGGAGGCTCGGGCTtaa |

TABLE 2-continued

Switch-Nucleotide Sequence

| NAME | SEQ ID NO | SEQUENCE |
|---|---|---|
| Anti-CD19 huB4 light chain | 5 | atgtacaggatgcaactcctgtatgcattgcactaagtcttgcacttgtcacgaattcgGACATCC<br>AGATGACACAGACTACATCCTCCCTGTCTGCCTCTCTGGGAGA<br>CAGAGTCACCATCAGTTGCAGGGCAAGTCAGGACATTAGTAA<br>ATATTTAAATTGGTATCAGCAGAAACCAGATGGAACTGTTAA<br>ACTCCTGATCTACCATACATCAAGATTACACTCAGGAGTCCCA<br>TCAAGGTTCAGTGGCAGTGGGTCTGGAACAGATTATTCTCTCA<br>CCATTAGCAACCTGGAGCAAGAAGATATTGCCACTTACTTTTG<br>CCAACAGGGTAATACGCTTCCGTACACGTTCGGAGGGGGGAC<br>CAAGCTTGAGATCaaacgaactgtggctgcaccatctgtatcatcttcccgccatctgatga<br>gcagttgaaatctggaactgcctctgtcgtgtgcctgctgaataacttctatcccagagaggccaaagta<br>cagtggaaggtggataacgcctccaatcgggtaactcccaggagagtgtcacagagcaggacagc<br>AAGgacagcacctacagcctcagcagcaccctgacgctgagcaaagcagactacgagaaacaca<br>aagtctacgcctgcgaagtcacccatcagggcctgtcctcgcccgtcacaaagagatcaacagggga<br>gagtgttaa |

TABLE 3

Chimeric Receptor and Switch non-antibody peptides-Amino Acid Sequence

| NAME | SEQ ID NO | SEQUENCE |
|---|---|---|
| Isopeptag | 6 | TDKDMTITFTNKKDAE |
| Spytag | 7 | AHIVMVDAYKPTK |
| AD1 w/out cysteines | 8 | QIEYLAKQIVDNAIQQA |
| DDD1 without cysteines | 9 | (S)HIQIPPGLTELLQGYTVEVLRQQPPDLVEFAVEYFTRLREARA |
| AD1 with cysteines | 10 | CGQIEYLAKQIVDNAIQQAGC |
| DDD1 with cysteines | 11 | CGHIQIPPGLTELLQGYTVEVLRQQPPDLVEFAVEYFTRLREARA |
| K4 | 33 | KVAALKEKVAALKEKVAALKEKVAALKE |
| E4 | 34 | EVAALEKEVAALEKEVAALEKEVAALEK |

TABLE 4

| NAME | SEQ ID NO | SEQUENCE |
|---|---|---|
| Linker 1 | 12 | (GGGGS)$_n$, n is at least 1 |
| Linker 2 | 13 | (GGGS)$_n$, n is at least 1 |
| Linker 3 | 14 | (GGS)$_n$, n is at least 1 |
| Linker 4 | 15 | (G$_m$S)$_n$, n is at least 1, m is at least 1 |
| Linker 5 | 16 | (X$_m$S)$_n$, n is at least 1, m is at least 1 and X is an amino acid |
| Linker 6 | 17 | LVGEAAAKEAAAKA |
| Linker 7 | 18 | AEAAAKEAAAKA |
| Linker 8 | 19 | EAAAKEAAAKEAAAKA |
| Linker 9 | 20 | KESGSVSSEQLAQFRSLD |

TABLE 4-continued

| NAME | SEQ ID NO | SEQUENCE |
|---|---|---|
| Linker 10 | 21 | EGKSSGSGSESKST |
| Linker 11 | 22 | GSAGSAAGSGEF |
| Linker 12 | 23 | APAPAPAPAPAPAP |

Bold indicates grafted region (peptide and/orlinker(s)). Underline indicates peptide.

TABLE 5

Switch targeting polypeptides-Amino Acid Sequence

| NAME | SEQ ID NO | SEQUENCE |
|---|---|---|
| Light chain of wildtype anti-CS1 antibody | 12 | DIQMTQSPSSLSASVGDRVTITCKASQDVGIAVAWYQQKPG KVPKLLIYWASTRHTGVPDRFSGSGSGTDFTLTISSLQPEDV ATYYCQQYSSYPYTFGQGTKLEIKRTVAAPSVFIFPPSDEQL KSGTASVVCLLNNFYPREAKVQWKVDNALQSGNSQESVTE QDSKDSTYSLSSTLTLSKADYEKHKVYACEVTHQGLSSPVT KSFNRGEC |
| Heavy chain of wildtype anti-CS1 antibody Fab | 13 | EVQLVESGGGLVQPGGSLRLSCAASGFDFSRYWMSWVRQ APGKGLEWIGEINPDSSTINYAPSLKDKFIISRDNAKNSLYLQ MNSLRAEDTAVYYCARPDGNYWYFDVWGQGTLVTVSSAS TKGPSVFPLAPSSKSTSGGTAALGCLVKDYFPEPVTVSWNS GALTSGVHTFPAVLQSSGLYSLSSVVTVPSSSLGTQTYICNV NHKPSNTKVDKKVEPKSC |
| Light chain of anti-EGFRvIII antibody (Hu806) Fab | 14 | DIQMTQSPSSMSVSVGDRVTITCHSSQDINSNIGWLQQKPGK SFKGLIYHGTNLDDGVPSRFSGSGSGTDYTLTISSLQPEDFAT YYCVQYAQFPWTFGGGTKLEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKS FNRGEC |
| Heavy chain of anti-EGFRvIII antibody (Hu806) Fab | 15 | QLQESGPGLVKPSQTLSLTCTVSGYSISSDFAWNWIRQPPGK GLEWMGYISYSGNTRYQPSLKSRITISRDTSKNQFFLKLNSV TAADTATYYCVTAGRGFPYWGQGTLVTVSSASTKGPSVFPP LAPSSKSTSGGTAALGCLVKDYFPEPVTVSWNSGALTSGVH TFPAVLQSSGLYSLSSVVTVPSSSLGTQTYICNVNHKPSNTK VDKKVEPKSC |
| Light chain of anti-BCMA antibody (BCMA98) Fab | 16 | DIQMTQSPSSLSASVGDRVTITCRANQGISNNLNWYQQKPG KAPKPLIYYTSNLQSGVPSRFSGSGSGTDYTLTISSLQPEDFA TYYCQQFTSLPYTFGQGTKLEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKS FNRGEC |
| Heavy chain of anti-BCMA antibody (BCMA98) Fab | 17 | EVQLVESGGGLVQPGGSLRLSCAASGFTFSNFDMAWVRQA PGKGLVWVSSITTGGGDTYYADSVKGRFTISRDNAKSTLYL QMDSLRSEDTAVYYCVRHGYYDGYHLFDYWGQGTLVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSC |
| Light Chain of anti-CD19 antibody | 18 | DIQMTQTTSSLSASLGDRVTISCRASQDISKYLNWYQQKPD GTVKLLIYHTSRLHSGVPSRFSGSGSGTDYSLTISNLEQEDIA TYFCQQGNTLPYTFGGGTKLEIKRTVAAPSVFIFPPSDEQLK SGTASVVCLLNNFYPREAKVQWKVDNALQSGNSQESVTEQ DSKDSTYSLSSTLTLSKADYEKHKVYACEVTHQGLSSPVTK SFNRGEC |
| Heavy Chain of anti-CD19 antibody IgG | 19 | EVKLQESGPGLVAPSQSLSVTCTVSGVSLPDYGVSWIRQPPR KGLEWLGVIWGSETTYYNSALKSRLTIIKDNSKSQVFLKMN SLQTDDTAIYYCAKHYYYGGSYAMDYWGQGTSVTVSSAS TKGPSVFPLAPSSKSTSGGTAALGCLVKDYFPEPVTVSWNS GALTSGVHTFPAVLQSSGLYSLSSVVTVPSSSLGTQTYICNV NHKPSNTKVDKKVEPKSCDKTHTCPPCPAPPVAGPSVFLFPP KPKDTLMISRTPEVTCVVVDVSHEDPEVKFNWYVDGVEVH NAKTKPREEQYNSTYRVVSVLTVLHQDWLNGKEYKCKVS NKGLPSSIEKTISKAKGQPREPQVYTLPPSRDELTKNQVSLT CLVKGFYPSDIAVEWESNGQPENNYKTTPPVLDSDGSFFLY SKLTVDKSRWQQGNVFSCSVMHEALHNHYTQKSLSLSPGK |

TABLE 5-continued

Switch targeting polypeptides-Amino Acid Sequence

| NAME | SEQ ID NO | SEQUENCE |
| --- | --- | --- |
| Heavy Chain of anti-CD19 antibody Fab | 20 | EVKLQESGPGLVAPSQSLSVTCTVSGVSLPDYGVSWIRQPPR KGLEWLGVIWGSETTYYNSALKSRLTIIKDNSKSQVFLKMN SLQTDDTAIYYCAKHYYYGGSYAMDYWGQGTSVTVSSAS TKGPSVFPLAPSSKSTSGGTAALGCLVKDYFPEPVTVSWNS GALTSGVHTFPAVLQSSGLYSLSSVVTVPSSSLGTQTYICNV NHKPSNTKVDKKVEPKSC |

TABLE 6

E4/K4 Lentivirus Chimeric Receptor-Nucleotide Sequence

| NAME | SEQ ID NO | SEQUENCE |
| --- | --- | --- |
| E4 Chimeric Receptor | 35 | ATGGCCTTACCAGTGACCGCCTTGCTCCTGCCGCTGGCCT TGCTGCTCCACGCCGCCAGGCCGGAGGTTGCTGCCCTGG AGAAGGAGGTGGCTGCACTGGAGAAAGAGGTGGCCGCC CTGGAAAAAGAAGTGGCAGCCTTGGAGAAGGAAAGCAA GTATGGCCCACCTTGTCCACCTTGTCCCGATATCTACATC TGGGCGCCCTTGGCCGGGACTTGTGGGGTCCTTCTCCTGT CACTGGTTATCACCCTTTACTGCAAACGGGGCAGAAAGA AACTCCTGTATATATTCAAACAACCATTTATGAGACCAGT ACAAACTACTCAAGAGGAAGATGGCTGTAGCTGCCGATT TCCAGAAGAAGAAGAAGGAGGATGTGAACTGAGAGTGA AGTTCAGCAGGAGCGCAGACGCCCCCGCGTACAAGCAGG GCCAGAACCAGCTCTATAACGAGCTCAATCTAGGACGAA GAGAGGAGTACGATGTTTTGGACAAGAGACGTGGCCGGG ACCCTGAGATGGGGGGAAAGCCGAGAAGGAAGAACCCT CAGGAAGGCCTGTACAATGAACTGCAGAAAGATAAGAT GGCGGAGGCCTACAGTGAGATTGGGATGAAAGGCGAGC GCCGGAGGGGCAAGGGGCACGATGGCCTTTACCAGGGTC TCAGTACAGCCACCAAGGACACCTACGACGCCCTTCACA TGCAGGCCCTGCCCCCTCGCTAA |
| K4 Chimeric Receptor | 36 | ATGGCCTTACCAGTGACCGCCTTGCTCCTGCCGCTGGCCT TGCTGCTCCACGCCGCCAGGCCGAAAGTGGCAGCCCTGA AGGAGAAAGTTGCGGCTCTCAAAGAGAAAGTGGCTGCAC TGAAAGAAAAGGTTGCCGCCCTCAAGGAGGAAAGCAAG TATGGCCCACCTTGTCCACCTTGTCCCGATATCTACATCT GGGCGCCCTTGGCCGGGACTTGTGGGGTCCTTCTCCTGTC ACTGGTTATCACCCTTTACTGCAAACGGGGCAGAAAGAA ACTCCTGTATATATTCAAACAACCATTTATGAGACCAGTA CAAACTACTCAAGAGGAAGATGGCTGTAGCTGCCGATTT CCAGAAGAAGAAGAAGGAGGATGTGAACTGAGAGTGAA GTTCAGCAGGAGCGCAGACGCCCCCGCGTACAAGCAGGG CCAGAACCAGCTCTATAACGAGCTCAATCTAGGACGAAG AGAGGAGTACGATGTTTTGGACAAGAGACGTGGCCGGGA CCCTGAGATGGGGGGAAAGCCGAGAAGGAAGAACCCTC AGGAAGGCCTGTACAATGAACTGCAGAAAGATAAGATG GCGGAGGCCTACAGTGAGATTGGGATGAAAGGCGAGCG CCGGAGGGGCAAGGGGCACGATGGCCTTTACCAGGGTCT CAGTACAGCCACCAAGGACACCTACGACGCCCTTCACAT GCAGGCCCTGCCCCCTCGCTAA |
| Fmc63 HCCT E4 switch Heavy Chain | 37 | ATGTACAGGATGCAACTCCTGTCTTGCATTGCACTAAGTC TTGCACTTGTCACGAATTCGGAGGTGAAACTGCAGGAGT CAGGACCTGGCCTGGTGGCGCCCTCACAGAGCCTGTCCG TCACATGCACTGTCTCAGGGGTCTCATTACCCGACTATGG TGTAAGCTGGATTCGCCAGCCTCCACGAAAGGGTCTGGA GTGGCTGGGAGTAATATGGGGTAGTGAAACCACATACTA TAATTCAGCTCTCAAATCCAGACTGACCATCATCAAGGA CAACTCCAAGAGCCAAGTTTTCTTAAAAATGAACAGTCT GCAAACTGATGACACAGCCATTTACTACTGTGCCAAACA TTATTACTACGGTGGTAGCTATGCTATGGACTACTGGGGC CAAGGAACCTCAGTCACCGTCTCCTCAGCCTCCACCAAG GGCCCATCGGTCTTCCCCCTGGCACCCTCCTCCAAGAGCA CCTCTGGGGGCACAGCGGCCCTGGGCTGCCTGGTCAAGG ACTACTTCCCCGAACCGGTGACGGTGTCGTGGAACTCAG GCGCCCTGACCAGCGGCGTGCACACCTTCCCGGCTGTCCT ACAGTCCTCAGGACTCTACTCCCTCAGCAGCGTGGTGACT GTGCCCTCTAGCAGCTTGGGCACCCAGACCTACATCTGC AACGTGAATCACAAGCCCAGCAACACCAAGGTGGACAA GAAAGTTGAGCCCAAATCTTGTGGCGGAGGCGGGAGCGA |

TABLE 6-continued

| E4/K4 Lentivirus Chimeric Receptor-Nucleotide Sequence | | |
|---|---|---|
| NAME | SEQ ID NO | SEQUENCE |
| | | GGTTGCTGCCCTGGAGAAGGAGGTGGCTGCACTGGAGAA<br>AGAGGTGGCCGCCCTGGAAAAAGAAGTGGCAGCCTTGG<br>AGAAGTGA |
| Fmc63 HCCT<br>K4 switch<br>Heavy Chain | 38 | ATGTACAGGATGCAACTCCTGTCTTGCATTGCACTAAGTC<br>TTGCACTTGTCACGAATTCGGAGGTGAAACTGCAGGAGT<br>CAGGACCTGGCCTGGTGGCGCCCTCACAGAGCCTGTCCG<br>TCACATGCACTGTCTCAGGGGTCTCATTACCCGACTATGG<br>TGTAAGCTGGATTCGCCAGCCTCCACGAAAGGGTCTGGA<br>GTGGCTGGGAGTAATATGGGGTAGTGAAACCACATACTA<br>TAATTCAGCTCTCAAATCCAGACTGACCATCATCAAGGA<br>CAACTCCAAGAGCCAAGTTTTCTTAAAAATGAACAGTCT<br>GCAAACTGATGACACAGCCATTTACTACTGTGCCAAACA<br>TTATTACTACGGTGGTAGCTATGCTATGGACTACTGGGGC<br>CAAGGAACCTCAGTCACCGTCTCCTCAGCCTCCACCAAG<br>GGCCCATCGGTCTTCCCCCTGGCACCCTCCTCCAAGAGCA<br>CCTCTGGGGGCACAGCGGCCCTGGGCTGCCTGGTCAAGG<br>ACTACTTCCCCGAACCGGTGACGGTGTCGTGGAACTCAG<br>GCGCCCTGACCAGCGGCGTGCACACCTTCCCGGCTGTCCT<br>ACAGTCCTCAGGACTCTACTCCCTCAGCAGCGTGGTGACT<br>GTGCCCTCTAGCAGCTTGGGCACCCAGACCTACATCTGC<br>AACGTGAATCACAAGCCCAGCAACACCAAGGTGGACAA<br>GAAAGTTGAGCCCAAATCTTGTGGCGGAGGCGGGAGCAA<br>AGTGGCAGCCCTGAAGGAGAAAGTTGCGGCTCTCAAAGA<br>GAAAGTGGCTGCACTGAAAGAAAAGGTTGCCGCCCTCAA<br>GGAGTGAT |
| Fmc63 HC WT<br>switch Heavy<br>Chain | 39 | ATGTACAGGATGCAACTCCTGTCTTGCATTGCACTAAGTC<br>TTGCACTTGTCACGAATTCGGAGGTGAAACTGCAGGAGT<br>CAGGACCTGGCCTGGTGGCGCCCTCACAGAGCCTGTCCG<br>TCACATGCACTGTCTCAGGGGTCTCATTACCCGACTATGG<br>TGTAAGCTGGATTCGCCAGCCTCCACGAAAGGGTCTGGA<br>GTGGCTGGGAGTAATATGGGGTAGTGAAACCACATACTA<br>TAATTCAGCTCTCAAATCCAGACTGACCATCATCAAGGA<br>CAACTCCAAGAGCCAAGTTTTCTTAAAAATGAACAGTCT<br>GCAAACTGATGACACAGCCATTTACTACTGTGCCAAACA<br>TTATTACTACGGTGGTAGCTATGCTATGGACTACTGGGGC<br>CAAGGAACCTCAGTCACCGTCTCCTCAGCCTCCACCAAG<br>GGCCCATCGGTCTTCCCCCTGGCACCCTCCTCCAAGAGCA<br>CCTCTGGGGGCACAGCGGCCCTGGGCTGCCTGGTCAAGG<br>ACTACTTCCCCGAACCGGTGACGGTGTCGTGGAACTCAG<br>GCGCCCTGACCAGCGGCGTGCACACCTTCCCGGCTGTCCT<br>ACAGTCCTCAGGACTCTACTCCCTCAGCAGCGTGGTGACT<br>GTGCCCTCTAGCAGCTTGGGCACCCAGACCTACATCTGC<br>AACGTGAATCACAAGCCCAGCAACACCAAGGTGGACAA<br>GAAAGTTGAGCCCAAATCTTGTTGAT |
| Fmc63 LC WT<br>switch Light<br>Chain | 40 | ATGTACAGGATGCAACTCCTGTCTTGCATTGCACTAAGTC<br>TTGCACTTGTCACGAATTCGGACATCCAGATGACACAGA<br>CTACATCCTCCCTGTCTGCCTCTCTGGGAGACAGAGTCAC<br>CATCAGTTGCAGGGCAAGTCAGGACATTAGTAAATATTT<br>AAATTGGTATCAGCAGAAACCAGATGGAACTGTTAAACT<br>CCTGATCTACCATACATCAAGATTACACTCAGGAGTCCC<br>ATCAAGGTTCAGTGGCAGTGGGTCTGGAACAGATTATTC<br>TCTCACCATTAGCAACCTGGAGCAAGAAGATATTGCCAC<br>TTACTTTTGCCAACAGGGTAATACGCTTCCGTACACGTTC<br>GGAGGGGGGACCAAGCTTGAGATCAAACGAACTGTGGCT<br>GCACCATCTGTCTTCATCTTCCCGCCATCTGATGAGCAGT<br>TGAAATCTGGAACTGCCTCTGTCGTGTGCCTGCTGAATAA<br>CTTCTATCCCAGAGAGGCCAAAGTACAGTGGAAGGTGGA<br>TAACGCCCTCCAATCGGGTAACTCCCAGGAGAGTGTCAC<br>AGAGCAGGACAGCAAGGACAGCACCTACAGCCTCAGCA<br>GCACCCTGACGCTGAGCAAAGCAGACTACGAGAAACAC<br>AAAGTCTACGCCTGCGAAGTCACCCATCAGGGCCTGTCC<br>TCGCCCGTCACAAAGAGCTTCAACAGGGGAGAGTGTTGA |

TABLE 7

Lentivirus Chimeric Receptor-Protein Sequence

| NAME | SEQ ID NO | SEQUENCE |
|---|---|---|
| E4 Chimeric Receptor | 41 | MALPVTALLLPLALLLHAARPEVAALEKEVAALEKEVAAL EKEVAALEKESKYGPPCPPCPDIYIWAPLAGTCGVLLLSLVI TLYCKRGRKKLLYIFKQPFMRPVQTTQEEDGCSCRFPEEEE GGCELRVKFSRSADAPAYKQGQNQLYNELNLGRREEYDVL DKRRGRDPEMGGKPRRKNPQEGLYNELQKDKMAEAYSEIG MKGERRRGKGHDGLYQGLSTATKDTYDALHMQALPPR. |
| K4 Chimeric Receptor | 42 | MALPVTALLLPLALLLHAARPKVAALKEKVAALKEKVAAL KEKVAALKEESKYGPPCPPCPDIYIWAPLAGTCGVLLLSLVI TLYCKRGRKKLLYIFKQPFMRPVQTTQEEDGCSCRFPEEEE GGCELRVKFSRSADAPAYKQGQNQLYNELNLGRREEYDVL DKRRGRDPEMGGKPRRKNPQEGLYNELQKDKMAEAYSEIG MKGERRRGKGHDGLYQGLSTATKDTYDALHMQALPPR. |
| Fmc63 HCCT E4 switch Heavy Chain | 43 | MYRMQLLSCIALSLALVTNSEVKLQESGPGLVAPSQSLSVT CTVSGVSLPDYGVSWIRQPPRKGLEWLGVIWGSETTYYNSA LKSRLTIIKDNSKSQVFLKMNSLQTDDTAIYYCAKHYYYGG SYAMDYWGQGTSVTVSSASTKGPSVFPLAPSSKSTSGGTAA LGCLVKDYFPEPVTVSWNSGALTSGVHTFPAVLQSSGLYSL SSVVTVPSSSLGTQTYICNVNHKPSNTKVDKKVEPKSCGGG GSEVAALEKEVAALEKEVAALEKEVAALEK. |
| Fmc63 HCCT K4 switch Heavy Chain | 44 | MYRMQLLSCIALSLALVTNSEVKLQESGPGLVAPSQSLSVT CTVSGVSLPDYGVSWIRQPPRKGLEWLGVIWGSETTYYNSA LKSRLTIIKDNSKSQVFLKMNSLQTDDTAIYYCAKHYYYGG SYAMDYWGQGTSVTVSSASTKGPSVFPLAPSSKSTSGGTAA LGCLVKDYFPEPVTVSWNSGALTSGVHTFPAVLQSSGLYSL SSVVTVPSSSLGTQTYICNVNHKPSNTKVDKKVEPKSCGGG GSKVAALKEKVAALKEKVAALKEKVAALKE. |
| Fmc63 HC WT Heavy Chain | 45 | MYRMQLLSCIALSLALVTNSEVKLQESGPGLVAPSQSLSVT CTVSGVSLPDYGVSWIRQPPRKGLEWLGVIWGSETTYYNSA LKSRLTIIKDNSKSQVFLKMNSLQTDDTAIYYCAKHYYYGG SYAMDYWGQGTSVTVSSASTKGPSVFPLAPSSKSTSGGTAA LGCLVKDYFPEPVTVSWNSGALTSGVHTFPAVLQSSGLYSL SSVVTVPSSSLGTQTYICNVNHKPSNTKVDKKVEPKSC. |
| Fmc63 LC WT Light Chain | 46 | MYRMQLLSCIALSLALVTNSDIQMTQTTSSLSASLGDRVTIS CRASQDISKYLNWYQQKPDGTVKLLIYHTSRLHSGVPSRFS GSGSGTDYSLTISNLEQEDIATYFCQQGNTLPYTFGGGTKLE IKRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGEC. |

TABLE 8

Lentivirus Chimeric Receptor-Protein Sequence

| NAME | SEQ ID NO | SEQUENCE |
|---|---|---|
| 2X-E4 Chimeric Receptor | 47 | MALPVTALLLPLALLLHAARPEVAALEKEVAALEKEVAAL EKEVAALEKGGGGSEVAALEKEVAALEKEVAALEKEVAAL EKESKYGPPCPPCPDIYIWAPLAGTCGVLLLSLVITLYCKRG RKKLLYIFKQPFMRPVQTTQEEDGCSCRFPEEEEGGCELRV KFSRSADAPAYKQGQNQLYNELNLGRREEYDVLDKRRGRD PEMGGKPRRKNPQEGLYNELQKDKMAEAYSEIGMKGERR RGKGHDGLYQGLSTATKDTYDALHMQALPPR. |
| 2X-K4 Chimeric Receptor | 48 | MALPVTALLLPLALLLHAARPKVAALKEKVAALKEKVAAL KEKVAALKEGGGGSKVAALKEKVAALKEKVAALKEKVAA LKEESKYGPPCPPCPDIYIWAPLAGTCGVLLLSLVITLYCKR GRKKLLYIFKQPFMRPVQTTQEEDGCSCRFPEEEEGGCELR VKFSRSADAPAYKQGQNQLYNELNLGRREEYDVLDKRRGR DPEMGGKPRRKNPQEGLYNELQKDKMAEAYSEIGMKGER RRGKGHDGLYQGLSTATKDTYDALHMQALPPR. |
| Fmc63 HCCT 2X-E4 switch Heavy Chain | 49 | MYRMQLLSCIALSLALVTNSEVKLQESGPGLVAPSQSLSVT CTVSGVSLPDYGVSWIRQPPRKGLEWLGVIWGSETTYYNSA LKSRLTIIKDNSKSQVFLKMNSLQTDDTAIYYCAKHYYYGG SYAMDYWGQGTSVTVSSASTKGPSVFPLAPSSKSTSGGTAA LGCLVKDYFPEPVTVSWNSGALTSGVHTFPAVLQSSGLYSL SSVVTVPSSSLGTQTYICNVNHKPSNTKVDKKVEPKSCGGG |

TABLE 8-continued

Lentivirus Chimeric Receptor-Protein Sequence

| NAME | SEQ ID NO | SEQUENCE |
| --- | --- | --- |
|  |  | GSEVAALEKEVAALEKEVAALEKEVAALEKGGGGSEVAAL<br>EKEVAALEKEVAALEKEVAALEK. |
| Fmc63 HCCT<br>2X-K4 switch<br>Heavy Chain | 50 | MYRMQLLSCIALSLALVTNSEVKLQESGPGLVAPSQSLSVT<br>CTVSGVSLPDYGVSWIRQPPRKGLEWLGVIWGSETTYYNSA<br>LKSRLTIIKDNSKSQVFLKMNSLQTDDTAIYYCAKHYYYGG<br>SYAMDYWGQGTSVTVSSASTKGPSVFPLAPSSKSTSGGTAA<br>LGCLVKDYFPEPVTVSWNSGALTSGVHTFPAVLQSSGLYSL<br>SSVVTVPSSSLGTQTYICNVNHKPSNTKVDKKVEPKSCGGG<br>GSKVAALKEKVAALKEKVAALKEKVAALKEGGGGSKVAA<br>LKEKVAALKEKVAALKEKVAALKE. |

TABLE 9

Switch Sequences For Additional Grafting Positions.-Protein Sequence

| NAME | SEQ ID NO | SEQUENCE |
| --- | --- | --- |
| Fmc63 LCCT<br>E4 switch<br>Light Chain | 51 | MYRMQLLSCIALSLALVTNSDIQMTQTTSSLSASLGDRVTIS<br>CRASQDISKYL,NWYQQKPDGTVKLLIYHTSRLHSGVPSRFS<br>GSGSGTDYSLTISNLEQEDIATYFCQQGNTLPYTFGGGTKLE<br>IKRTVAAPSVFIFPPSDEQLKSGTASVVCLLNNFYPREAKVQ<br>WKVDNALQSGNSQESVTEQDSKDSTYSLSSTLTLSKADYEK<br>HKVYACEVTHQGLSSPVTKSFNRGECGGGGSEVAALEKEV<br>AALEKEVAALEKEVAALEK. |
| Fmc63 LCCT<br>K4 switch<br>Light Chain | 52 | MYRMQLLSCIALSLALVTNSDIQMTQTTSSLSASLGDRVTIS<br>CRASQDISKYLNWYQQKPDGTVKLLIYHTSRLHSGVPSRFS<br>GSGSGTDYSLTISNLEQEDIATYFCQQGNTLPYTFGGGTKLE<br>IKRTVAAPSVFIFPPSDEQLKSGTASVVCLLNNFYPREAKVQ<br>WKVDNALQSGNSQESVTEQDSKDSTYSLSSTLTLSKADYEK<br>HKVYACEVTHQGLSSPVTKSFNRGECGGGGSKVAALKEKV<br>AALKEKVAALKEKVAALKE. |
| Fmc63 HCNT<br>E4 switch<br>Heavy Chain | 53 | MEVAALEKEVAALEKEVAALEKEVAALEKGGGSYRMQLL<br>SCIALSLALVTNSEVKLQESGPGLVAPSQSLSVTCTVSGVSL<br>PDYGVSWIRQPPRKGLEWLGVIWGSETTYYNSALKSRLTIIK<br>DNSKSQVFLKMNSLQTDDTAIYYCAKHYYYGGSYAMDYW<br>GQGTSVTVSSASTKGPSVFPLAPSSKSTSGGTAALGCLVKD<br>YFPEPVTVSWNSGALTSGVHTFPAVLQSSGLYSLSSVVTVPS<br>SSLGTQTYICNVNHKPSNTKVDKKVEPKSC. |
| Fmc63 HCNT<br>K4 switch<br>Heavy Chain | 54 | MKVAALKEKVAALKEKVAALKEKVAALKEGGGSYRMQL<br>LSCIALSLALVTNSEVKLQESGPGLVAPSQSLSVTCTVSGVS<br>LPDYGVSWIRQPPRKGLEWLGVIWGSETTYYNSALKSRLTII<br>KDNSKSQVFLKMNSLQTDDTAIYYCAKHYYYGGSYAMDY<br>WGQGTSVTVSSASTKGPSVFPLAPSSKSTSGGTAALGCLVK<br>DYFPEPVTVSWNSGALTSGVHTFPAVLQSSGLYSLSSVVTV<br>PSSSLGTQTYICNVNHKPSNTKVDKKVEPKSC. |
| Fmc63 LCNT<br>E4 switch<br>Light Chain | 55 | MEVAALEKEVAALEKEVAALEKEVAALEKGGGSYRMQLL<br>SCIALSLALVTNSDIQMTQTTSSLSASLGDRVTISCRASQDIS<br>KYLNWYQQKPDGTVKLLIYHTSRLHSGVPSRFSGSGSGTDY<br>SLTISNLEQEDIATYFCQQGNTLPYTFGGGTKLEIKRTVAAP<br>SVFIFPPSDEQLKSGTASVVCLLNNFYPREAKVQWKVDNAL<br>QSGNSQESVTEQDSKDSTYSLSSTLTLSKADYEKHKVYACE<br>VTHQGLSSPVTKSFNRGEC. |
| Fmc63 LCNT<br>K4 switch<br>Light Chain | 56 | MKVAALKEKVAALKEKVAALKEKVAALKEGGGSYRMQL<br>LSCIALSLALVTNSDIQMTQTTSSLSASLGDRVTISCRASQDI<br>SKYLNWYQQKPDGTVKLLIYHTSRLHSGVPSRFSGSGSGTD<br>YSLTISNLEQEDIATYFCQQGNTLPYTFGGGTKLEIKRTVAA<br>PSVFIFPPSDEQLKSGTASVVCLLNNFYPREAKVQWKVDNA<br>LQSGNSQESVTEQDSKDSTYSLSSTLTLSKADYEKHKVYAC<br>EVTHQGLSSPVTKSFNRGEC. |
| Fmc63 HCC1<br>E4 switch<br>Heavy Chain | 57 | MYRMQLLSCIALSLALVTNSEVKLQESGPGLVAPSQSLSVT<br>CTVSGVSLPDYGVSWIRQPPRKGLEWLGVIWGSETTYYNSA<br>LKSRLTIIKDNSKSQVFLKMNSLQTDDTAIYYCAKHYYYGG<br>SYAMDYWGQGTSVTVSSASTKGPSVFPLAPSSGGGGSEVA<br>ALEKEVAALEKEVAALEKEVAALEKGGSGTAALGCLVKD<br>YFPEPVTVSWNSGALTSGVHTFPAVLQSSGLYSLSSVVTVPS<br>SSLGTQTYICNVNHKPSNTKVDKKVEPKSC. |

TABLE 9-continued

Switch Sequences For Additional Grafting Positions.-Protein Sequence

| NAME | SEQ ID NO | SEQUENCE |
|---|---|---|
| Fmc63 HCC1 K4 switch Heavy Chain | 58 | MYRMQLLSCIALSLALVTNSEVKLQESGPGLVAPSQSLSVT CTVSGVSLPDYGVSWIRQPPRKGLEWLGVIWGSETTYYNSA LKSRLTIIKDNSKSQVFLKMNSLQTDDTAIYYCAKHYYYGG SYAMDYWGQGTSVTVSSASTKGPSVFPLAPSSGGGGSKVA ALKEKVAALKEKVAALKEKVAALKEGGSGGTAALGCLVK DYFPEPVTVSWNSGALTSGVHTFPAVLQSSGLYSLSSVVTV PSSSLGTQTYICNVNHKPSNTKVDKKVEPKSC. |
| Fmc63 LCC1A E4 switch Light Chain | 59 | MYRMQLLSCIALSLALVTNSDIQMTQTTSSLSASLGDRVTIS CRASQDISKYLNWYQQKPDGTVKLLIYHTSRLHSGVPSRFS GSGSGTDYSLTISNLEQEDIATYFCQQGNTLPYTFGGGTKLE IKRTVAAPSVFIFPPSDEQLKSGTASVVCLLNNFYPREAKVQ WKVDNALQSGNSQESVTEQDSGGGGSEVAALEKEVAALE KEVAALEKEVAALEKGGGGSDSTYSLSSTLTLSKADYEKH KVYACEVTHQGLSSPVTKSFNRGEC. |
| Fmc63 LCC1A K4 switch Light Chain | 60 | MYRMQLLSCIALSLALVTNSDIQMTQTTSSLSASLGDRVTIS CRASQDISKYLNWYQQKPDGTVKLLIYHTSRLHSGVPSRFS GSGSGTDYSLTISNLEQEDIATYFCQQGNTLPYTFGGGTKLE IKRTVAAPSVFIFPPSDEQLKSGTASVVCLLNNFYPREAKVQ WKVDNALQSGNSQESVTEQDSGGGGSKVAALKEKVAALK EKVAALKEKVAALKEGGGGSDSTYSLSSTLTLSKADYEKH KVYACEVTHQGLSSPVTKSFNRGEC. |
| Fmc63 LC BV E4 switch light chain | 63 | MEVAALEKEVAALEKEVAALEKEVAALEKGGGSYRMQLL SCIALSLALVTNSDIQMTQTTSSLSASLGDRVTISCRASQDIS KYLNWYQQKPDGTVKLLIYHTSRLHSGVPSRFSGSGSGTDY SLTISNLEQEDIATYFCQQGNTLPYTFGGGTKLEIKRTVAAP SVFIFPPSDEQLKSGTASVVCLLNNFYPREAKVQWKVDNAL QSGNSQESVTEQDSKDSTYSLSSTLTLSKADYEKHKVYACE VTHQGLSSPVTKSFNRGECGGGGSEVAALEKEVAALEKEV AALEKEVAALEK |
| Fmc63 HC BV E4 switch light chain | 64 | MEVAALEKEVAALEKEVAALEKEVAALEKGGGSYRMQLL SCIALSLALVTNSEVKLQESGPGLVAPSQSLSVTCTVSGVSL PDYGVSWIRQPPRKGLEWLGVIWGSETTYYNSALKSRLTIIK DNSKSQVFLKMNSLQTDDTAIYYCAKHYYYGGSYAMDYW GQGTSVTVSSASTKGPSVFPLAPSSKSTSGGTAALGCLVKD YFPEPVTVSWNSGALTSGVHTFPAVLQSSGLYSLSSVVTVPS SSLGTQTYICNVNHKPSNTKVDKKVEPKSCGGGGSEVAALE KEVAALEKEVAALEKEVAALEK. |

EXAMPLES

The following illustrative examples are representative of embodiments of the software applications, systems, and methods described herein and are not meant to be limiting in any way.

Example 1—Production and Evaluation of a Dock and Lock Switchable Chimeric Receptor Platform To create a switchable chimeric receptor cell based on a peptide-peptide interaction, the dock and lock system is used. The DDD1 module is genetically fused in the chimeric receptor in place of the canonical scFv. The DDD1 module self-assembles into homodimers which form a trimeric complex with the AD1 domain. The chimeric receptor gene from N terminus to C terminus is: CD8 leader peptide, DDD1 module, CD8 hinge, CD8 transmembrane domain, 4-1BB costimulatory domain, CD3 zeta activation domain (SEQ ID NO:1). The mature chimeric receptor protein from N terminus to C terminus is: DDD1 module, CD8 hinge, CD8 transmembrane domain, 4-1BB costimulatory domain, CD3 zeta activation domain Note that alternative hinges, transmembrane domains, and costimulatory domains are feasible. The genes are fused to create a single open reading frame which encodes the DDD1 chimeric receptor. This chimeric receptor is placed in a lentiviral vector which is transferred into T cells using lentivirus. The cells are expanded over 2 weeks using CD3/CD28 beads.

To create a switch for the DDD1 chimeric receptor, the AD1 module is fused to the C-terminus of the heavy chain of anti-CD19 antibody huB4 Fab (SEQ ID NO: 4). Note the fusion could be made to the C-terminus of the light chain as well.

The huB4 AD1 Fab switch is expressed from a pFUSE vector in HEK (mammalian cells) at 37 degrees over 7 days by combining the huB4 AD1 heavy chain Fab (SEQ ID NO: 4) with the pFUSE vector harboring the huB4 light chain (SEQ ID NO: 5). After expression the switch is purified using standard techniques on protein G resin. The purified switch is then used in cytotoxicity assays.

The activity of the dock and lock chimeric receptor-T cells is tested in cytotoxicity assays. DDD1 chimeric receptor is co-cultured with CD19-positive RS4; 11 cells at an effector to target ratio of 10:1. The huB4 AD1 switch is added at various concentrations to form a cytotoxicity curve from which an EC50 concentration for the switch can be determined. Cytotoxicity is assessed by LDH release in the culture supernatant after 24 hrs. More LDH release indicates higher cytotoxicity. Alternatively, cytotoxicity is assessed by flow cytometry by staining the target cells with 7-AAD and annexin V. Optimally there is high cytotoxicity of the RS4; 11 cells at low concentrations of the AD1 switch.

T cell activation is measured by assessing cytokine release in the culture supernatant from the cytotoxicity assay by flow cytometry or ELISA. Cytokines analyzed are IL-2, TNFa, and INF-g. Increased cytokines indicates increased T cell activation. T cell activation is also measured by staining T cells for CD25 and CD69 expression after 24 hour cytotoxicity coculture.

Off-target activity and specificity of the DDD1 chimeric receptor-T cells with the AD1 switch is assessed by measuring cytotoxicity and T cell activation in the presence of CD19-negative cell K562. Optimally there is no cytotoxicity of K562 and no T fell activation even at high concentrations of the AD1 switch.

Figure 5:
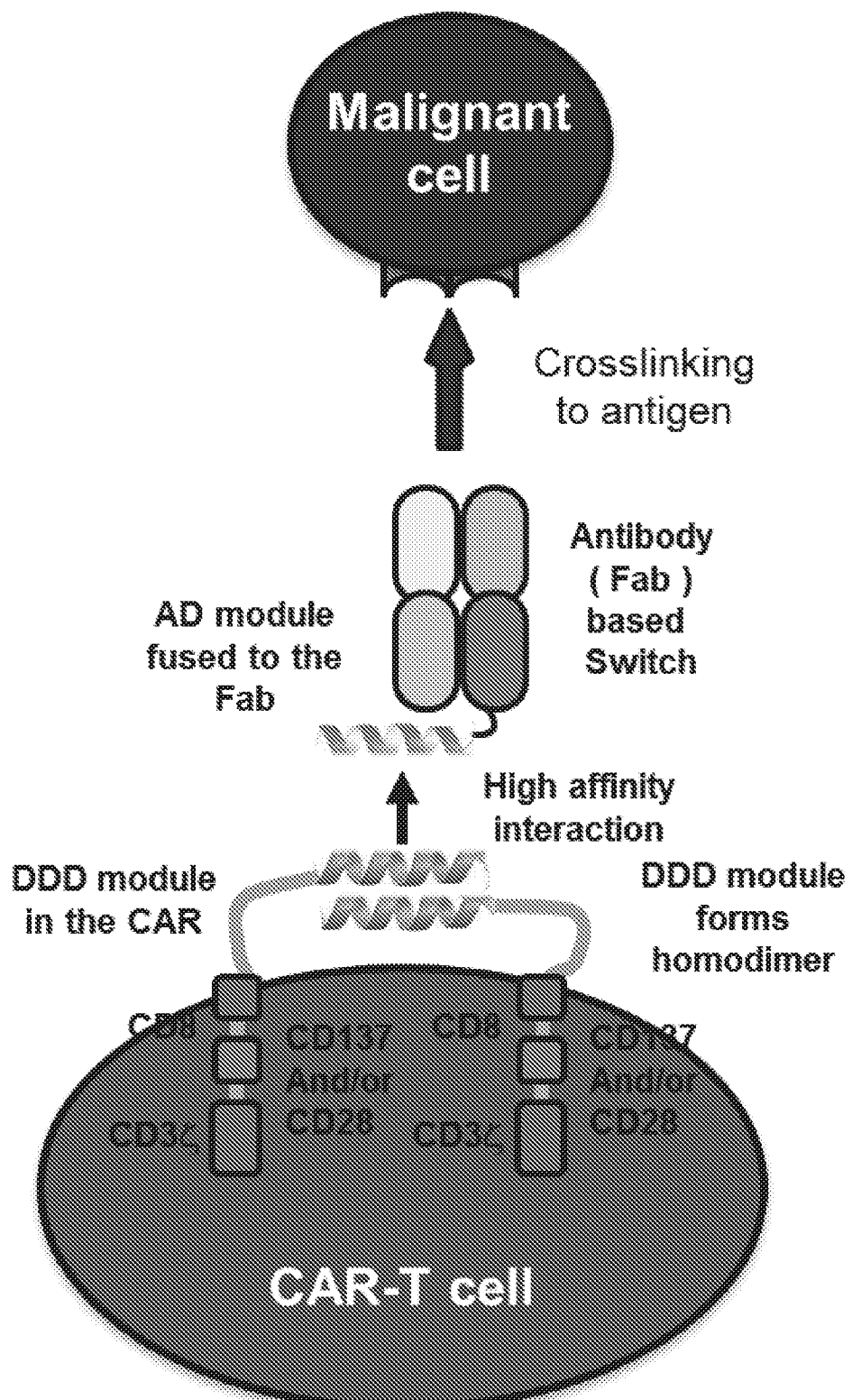
FIG. 5 illustrates an example of a dock and lock switchable chimeric receptor-T cell platform in which the DDD-module is on chimeric receptor extracellular domain the and the AD-module is on the switch.
Figure 6:
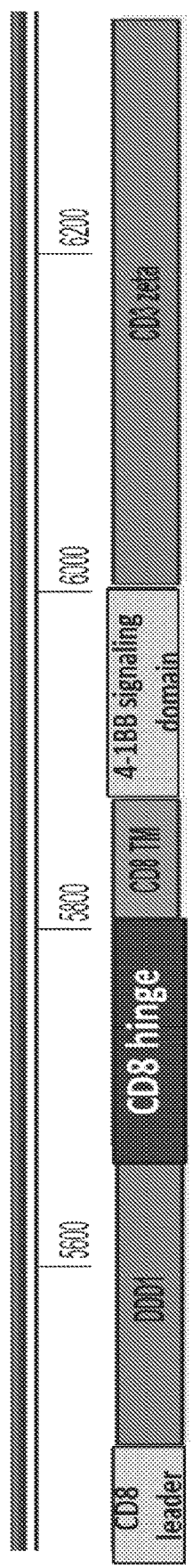
FIG. 6 illustrates an exemplary chimeric receptor, from N terminus to C terminus: CD8 leader peptide, DDD1 module, CD8 hinge, CD8 transmembrane domain, 4-1BB costimulatory domain, CD3 zeta activation domain.
Figure 7:
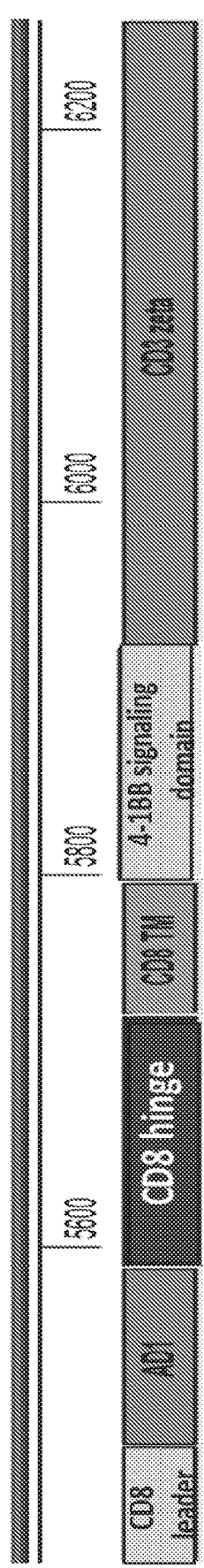
FIG. 7 illustrates an exemplary chimeric receptor with an AD1 module
Figure 8:
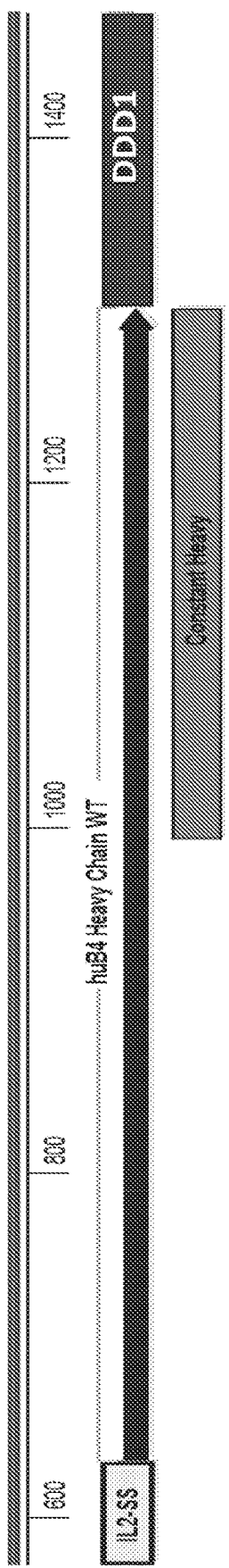
FIG. 8 illustrates an exemplary switch with a DDD1 module fused to the C-terminus of the heavy chain of anti-CD19 antibody huB4.
Figure 9:
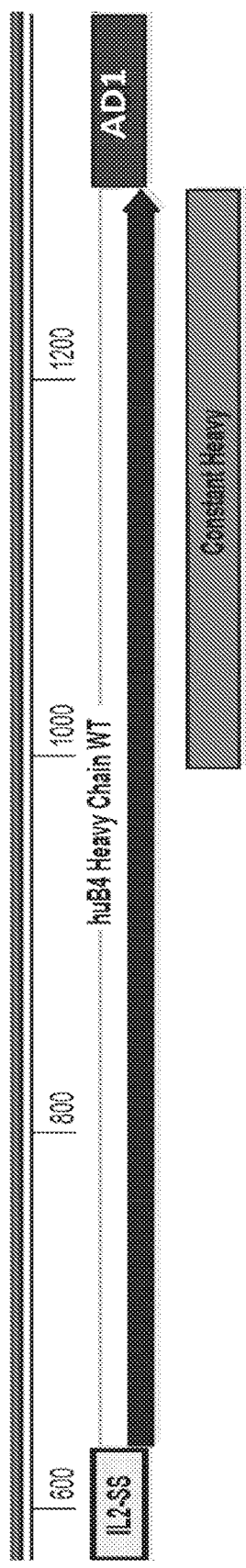
FIG. 9 illustrates an exemplary switch with an AD1 module fused to the C-terminus of the heavy chain of anti-CD19 antibody huB4.
Figure 10:
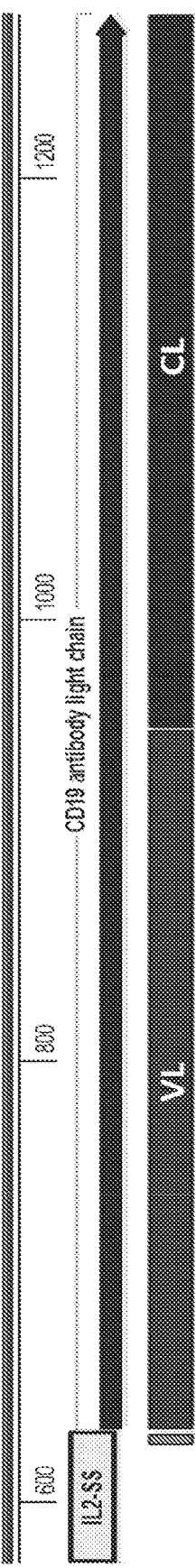
FIG. 10 illustrates a wild type anti-CD19 antibody huB4 light chain which is paired with the anti-CD19 antibody huB4 heavy chain from FIG. 8 or FIG. 9 during protein expression.

Development of the DDD1 chimeric receptor and AD1 switch enables a dimeric chimeric receptor to be activated by a monomeric switch (FIG. 5). This is because the DDD1 module self-assembles into homodimers. This results in a single AD1 switch that signals through two DDD1 chimeric receptors. This may be advantageous in chimeric receptor activation as dimeric chimeric receptors have been shown to increase T cell response and persistence. This may also increase sensitivity to the switch.

Alternatively the dock and lock platform is accomplished by incorporation of the AD1 module (SEQ ID NO: 2) in the chimeric receptor and the DDD1 module in the switch (SEQ ID NO: 3) (FIG. 4). In this case the chimeric receptor is monomeric and the switch is dimeric (bivalent) because the DDD1 domain self-assembles into a homodimer. This increases sensitivity to the antigen.

Example 2—Production of a Protein Coil Switchable Chimeric Receptor Platform

We created switchable chimeric receptor cells based on the coil-coil interactions of two peptides: K4, (KVAALKEKVAALKEKVAALKEKVAALKE (SEQ ID NO: 33)) and E4 (EVAALEKEVAALEKEVAALEKEVAALEK (SEQ ID NO: 34)) These peptides interact with one another to form an alpha helical coiled coil ("coil") when lysine residues on K4 form electrostatic interactions with glutamic acid residues on E4. The K4/E4 peptides and their interactions have been described by Litowski, J R, (2002), incorporated by reference herein in its entirety and generally reviewed (Woolfson 2005), incorporated by reference herein in its entirety. The affinity of this interaction is reported to be with an apparent $K_D$ of $4 \times 10^{-9}$M (Litowski and Hodges 2002).

To exploit this coil interaction in a switch/sCAR system, one peptide of a K4/E4 pair was expressed as part of the CAR on the surface of a transduced effector cell, e.g., a T cell, and the other peptide was fused genetically with the Fab switch which recognizes the cancer antigen. This system shows dose titratable anti-tumor activity as has been observed for other switches in vitro which results in target cell killing and cytokine release, indicative of T cell activation. This interaction is dependent on the specificity of the switch molecule to bind to the target cell. No killing or T cell activation is observed when target cells lack the antigen (CD19) recognized by the Fab switch.

Switch Cloning and Expression

The switch constructs utilized in this example are shown in Tables 6 and 7 (DNA and protein sequences, respectively). Gene fragments encoding the switches, which included FMC63 (anti-CD19) heavy chains fused to either one of the E4 or K4 peptides, were synthesized (Integrated DNA Technologies, Coralville, Iowa, USA) and cloned into appropriate expression vectors. In general to produce a switch requires two chains, one selected from the heavy chain sequences and one selected from the light chain sequences. In general these sequences must be derived from the same antibody clone (ie Fmc63 light chains are paired with Fmc63 heavy chains). To create the wild type Fab protein (lacking a peptide that could bind to the chimeric receptor), wild type light chain is paired with wild type heavy chain. To create a monovalent switch, one wild type (WT) chain is replaced with a chain containing a peptide that will bind to the chimeric receptor. For example to create the Fmc63 HCCT E4 switch, the Fmc63 HCCT E4 switch heavy chain SEQ ID NO: 43 is paired with the Fmc63 LC WT light chain SEQ ID NO: 46. Thus the expressed antibody will contain a single E4 peptide. To express a bivalent switch, two peptide chains may be used that each contain the peptide sequence. For example to create a Fmc63 bivalent CT switch, the Fmc63 HCCT E4 switch heavy chain SEQ ID NO: 43 is paired with the Fmc63 LCCT E4 switch light chain SEQ ID NO: 51. Still another way to produce a bivalent switch would be to place two peptides that are the target of the chimeric receptor in the same chain. For example Fmc63 LC BV SEQ ID NO: 63 is paired with Fmc63 HC WT heavy chain SEQ ID NO: 45. For another example Fmc63 HC BV SEQ ID NO: 64 is paired with Fmc63 LC WT heavy chain SEQ ID NO: 46. In this way two peptides are expressed on the light chain or heavy chain, respectively. Expression was carried out as follows: Briefly, HEK293F cells were transfected at a density of $1 \times 10$ 6 cells/ml with a 1:2 ratio of plasmid DNA to 293fectin (Thermo). Small scale expressions (30-50 ml) used a 1:1 ratio of heavy chain to light chain, whereas larger scale expressions ($\geq 100$ ml) required a 3:2 ratio of heavy chain to light chain. Expression medium containing the secreted proteins was harvested 72 hours post-transfection by centrifugation at 400×g. Fab switches were purified by Protein G or Protein A respectively (GE Healthcare Life Sciences, CA). Switches were eluted with 0.1 M glycine pH 2.8 and neutralized by the addition of 10% v/v 1M Tris-HCl pH 8. Switches were then buffer exchanged into phosphate buffered saline with PD10 desalting columns (GE Healthcare Life Sciences, CA) and filter sterilized for subsequent use. Switch integrity was confirmed by SDS page and QTOF analysis (data not shown).

CAR Cloning and Expression

For this experiment, two CAR constructs were created, one construct having the K4 peptide at the N-terminus, in place of the canonical CAR scFv, and the other construct instead utilizing the E4 peptide at the N-terminus. The CAR construct designs were as follows:
  (i) E4 CAR-T chimeric receptor: from N terminus to C terminus: [CD8 leader peptide, E4 peptide (protein sequence: SEQ ID NO: 34), IgG4m hinge, CD8 transmembrane domain, 4-1BB costimulatory domain, CD3 zeta activation domain] (chimeric receptor DNA sequence: SEQ ID NO: 35).
  (ii) K4 CAR-T chimeric receptor: from N terminus to C terminus: [CD8 leader peptide, K4 peptide (protein sequence: SEQ ID NO: 33), IgG4m hinge, CD8 transmembrane domain, 4-1BB costimulatory domain, CD3 zeta activation domain] (chimeric receptor DNA sequence: SEQ ID NO: 36).

Note that alternative hinges, transmembrane domains, and costimulatory domains are feasible. The domain components are fused to create a single open reading frame which encodes the E4 or K4 chimeric receptor. Gene fragments encoding the CAR constructs were synthesized (Integrated DNA Technologies, Coralville, Iowa, USA), sub-cloned into the lentiviral vector, and virus were produced as described below.

Viral Production

Lentivirus encoding the E4 or K4 chimeric receptor sequence (SEQ ID NOS: 35 and 36, respectively, as shown in Table 6) were produced in HEK293FT cells. HEK293FT cells were maintained in D10 (DMEM supplemented with 10% v/v heat-inactivated fetal bovine serum, 1% v/v L-glutamine, sodium pyruvate, and minimal non-essential amino acids, and penicillin-streptomycin). HEK293FT cells were plated in 10 cm tissue-cultured treated plates at a density of $5 \times 10^6$ cells. The next day, cells were transfected with 7.5 µg K4 or E4 lentiviral plasmid, 2.5 µg pMDG, 6 µg pMDL, 6 µg pREV using the Fugene HD reagent (Promega) at a 3:1 ratio per the manufacturer's recommendation. 24 hours after transfection, the media was removed and replaced with a fresh 10 ml of D10. The cell culture supernatant was centrifuged at 3000 rpm for 15 minutes at 4° C. and the clarified supernatant was poured into a clean, sterile tube and stored at 4° C. This procedure was repeated at 48 and 72 hours post-transfection. All supernatants were pooled and centrifuged at 25,000 rpm for 1.5 hours at 4° C. The supernatant was poured off and the viral pellet was incubated in 500 ul Aim-V overnight at 4° C.

T Cell Transduction

PBMC were isolated from healthy donors by Ficoll-Pacque density gradient and allowed to rest for 1 hour in Aim-V medium supplemented with 1% pen-strep and 5% human serum, to remove adherent cells. The non-adherent cell fraction was washed twice with complete Aim-V medium and resuspended at a concentration of $1 \times 10^6$ cells/ml with rIL-2 (300 IU/ml R&D systems) and Dynabeads® Human T-Activator CD3/CD28 (at a 3:1 bead to cell ratio, prepared as per manufactures instructions). For lentivirus transduction, a 24-well non-tissue culture treated plates were coated with retronectin (Clontech; 10 µg/cm$^2$ in PBS) overnight at 4° C. The wells were then blocked with 1% BSA PBS for 30 minutes at room temperature before being washed twice with PBS, at which point $1 \times 10^6$ activated T cells were added to each well in complete Aim-V media containing rIL-2, 5 µg/ml polybrene (Santa Cruz Biotech) and 100 µl of concentrated lentivirus. The 24-well plate was centrifuged at 1000×g for 1 hour 30 minutes at 33° C. with no brake. The cells were placed in a 37° C., 5% CO$_2$ incubator overnight. Following a 24-hour incubation, cells were collected and the virus was removed by centrifugation at 500×g for 5 minutes. The cells were resuspended in fresh media containing rIL-2, polybrene and 100 µl of concentrated lentivirus as before, and added to a fresh retronectin-coated plate. The 24-well plate was then centrifuged at 1000×g for 1 hour 30 minutes at 33° C. with no brake, and the cells were placed in a 37° C., 5% CO$_2$ incubator overnight. Following a 24-hour incubation the cells were collected and resuspended in complete Aim-V and cultured at a concentration of $0.5-2 \times 10^6$ cells/ml.

Example 3—Evaluation of Cytotoxicity Induced by E4 and K4 CAR-T Cell/Switches

Cytotoxicity Assay

Cytotoxicity assays were performed in media R5 (RPMI supplemented with 5% v/v heat-inactivated fetal bovine serum, 1% v/v L-glutamine, sodium pyruvate, minimal non-essential amino acids, and penicillin-streptomycin). Fmc63 HCCT E4 and Fmc63 HCCT K4 switches (see Table 6) were prepared in a standard 96-well plate R10 (RPMI supplemented with 10% v/v heat-inactivated fetal bovine serum, 1% v/v L-glutamine, sodium pyruvate, minimal non-essential amino acids, and penicillin-streptomycin). Switches were diluted to 500 nM in 200 ul R5 then filter sterilized. Serial 10-fold dilutions were made transferring 10 ul of switch into 90 ul R10. Target cells (Raji luc cells transduced to express firefly luciferase, or K562) were collected and resuspended in R5 media at a density of $2 \times 10^5$ cells/ml. Raji luc cells are CD19 positive, whereas K562 cells are CD19 negative. 50 ul of cells were then added to all wells except media-only control. CAR-T cells were collected and resuspended in R5 at a density of $2 \times 10^6$ cells/ml. 50 ul of E4 or K4 CAR-T cells were added to all wells except media-only control, maximum kill, and spontaneous kill wells. 2 ul of switch dilutions were added to cytotoxicity wells. Plates were incubated overnight at 37° C., 5% CO$_2$ for 16-20 hours.

LDH Release Assay

LDH release assays were performed using the Promega CytoTox 96® Non-Radioactive Cytotoxicity Assay (cat. number G1780). After the 16-20 hour overnight incubation (discussed in the cytotoxicity assay above), 10× lysis solution was added to maximum kill wells containing only target cells. Wells were mixed well to lyse cells and plates were returned to the incubator for 45 minutes. After 45 minute incubation, plates were centrifuged at 500×g for 5 minutes to pellet cells. 30 ul of supernatants were transferred to a regular 96-well plate. 30 ul of CytoTox 96® Reagent was added and plate was incubated in the dark at room temperature for 30 minutes. 30 ul of Stop Solution was added and plate was immediately measured for absorbance at 495 nm on a plate reader. Cytotoxicity was calculated using the following formula: 100×((Sample OD495−No switch OD495)/(maximum kill OD495−spontaneous kill OD495)).

Figure 11:
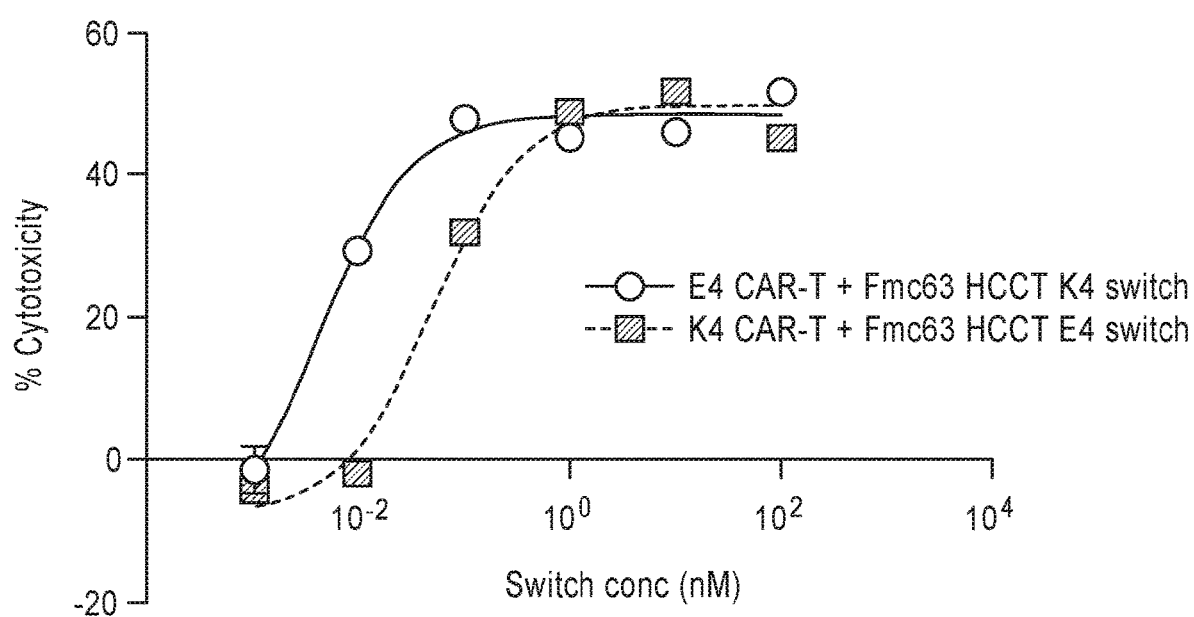
FIG. 11 shows results of a cytotoxicity assay measuring CAR-T cell-induced killing of CD19 positive Raji luc cells with increasing concentrations of a complementary anti-CD19 (Fmc63) switch peptide. The switch/CAR-T interaction is mediated by the E4/K4 alpha helical coiled coil peptides. Increased target cell killing is observed by E4 CAR-T cells and K4 CAR-T cells, respectively, as the concentration of their corresponding K4-Fmc63 and E4-Fmc63 switches are increased.
Figure 12:
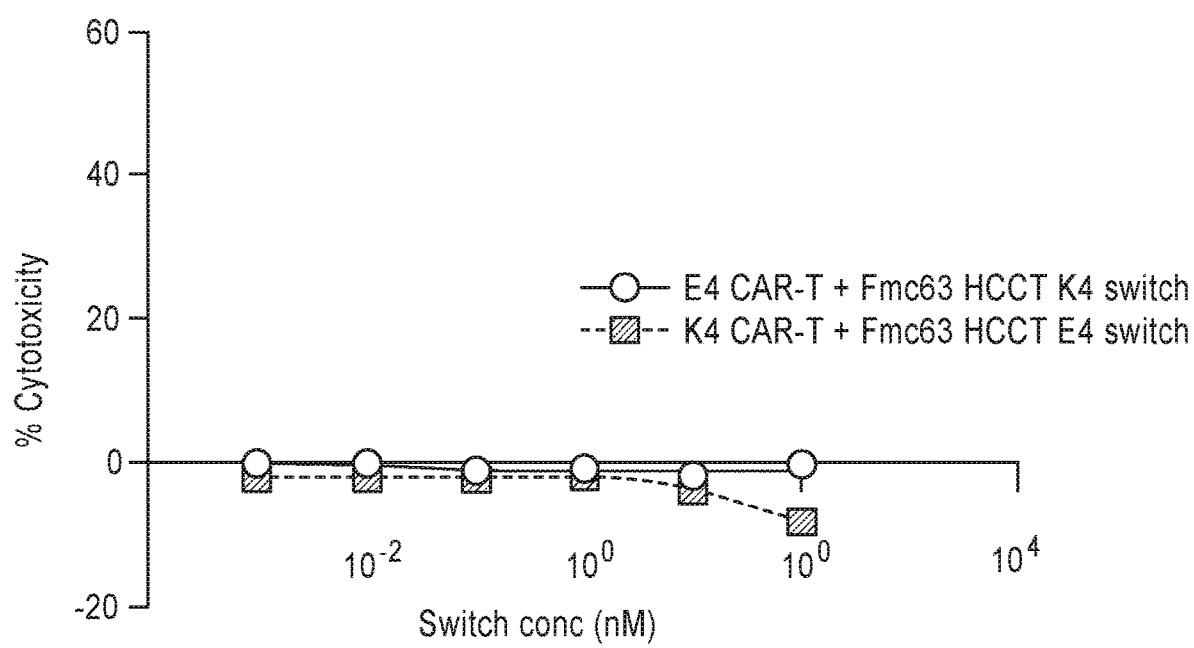
FIG. 12 shows results of a cytotoxicity assay measuring CAR-T cell-induced killing of CD19 negative K562 cells with increasing concentrations of a complementary anti-CD19 (Fmc63) switch peptide. The E4/K4 switches and E4/K4 CAR-T cells shown are the same as in FIG. 11. No target cell killing is observed due to the lack of switch binding in the absence of CD19 on the target cell surface.

Results of this experiment are shown in FIGS. 11 and 12. We find that in the presence of increasing concentration of switch, CAR-T cells are able to induce killing of target Raji luc cells, which express CD19 (FIG. 11), but not K562 cells, which lack the CD19 target for switch binding (FIG. 12). This shows both that the switch with the E4 or K4 coil attached to the C-terminus of the heavy chain is able to recognize its CD19 antigen on the target cell, and also that the CAR-T cell expressing the K4 or E4 coil is able to bind to the switch and become activated to cause target cell death only on cells that are positive for the target antigen.

Table 10 shows calculated EC50s for the K4 and E4 switch cytotoxicity assays in Raji luc cells. Table 11 shows average percent cytotoxicity in Raji luc cells of three replicates (see also the graphical representation of this data, which is shown in FIG. 11).

TABLE 10

Calculated EC50s for K4 and E4 switches from cytotoxicity assay.

|  | E4 CAR-T + Fmc63 HCCT K4 switch | K4 CAR-T + Fmc63 HCCT E4 switch |
|---|---|---|
| EC50 (nM) | 0.004315 | 0.05068 |

TABLE 11

Average cytotoxicity of three replicates as shown in FIG. 11

| Switch concentration (nM) | E4 CAR-T + Fmc63 HCCT K4 switch percent cytotoxicity | K4 CAR-T + Fmc63 HCCT E4 switch percent cytotoxicity |
|---|---|---|
| 100 | 51.72885 | 45.20702 |
| 10 | 46.19895 | 51.85736 |
| 1 | 45.34356 | 48.80928 |
| 0.1 | 47.87358 | 32.15935 |
| 0.01 | 29.50082 | −1.92362 |
| 0.001 | −1.55817 | −4.04401 |

The percentage of cell killing and EC50 for these switches are on par with results we have obtained previously using an antigen/scFv switch/CAR-T cells system (see, e.g., Rodgers, D. T., Proc Natl Acad Sci USA, 113: E459-68 (2016)).

Table 12 shows average percent cytotoxicity of three replicates in K562 cells, which are CD19 negative (see also the graphical representation of this data, which is shown in FIG. 12). The lack of any cell death induced by the E4 and K4 CAR-Ts in K562 confirms the specificity of the CAR-Ts for CD19 positive cells.

TABLE 12

Average cytotoxicity of three replicates as shown in FIG. 12

| Switch concentration (nM) | E4 CAR-T + Fmc63 HCCT K4 switch percent cytotoxicity | K4 CAR-T + Fmc63 HCCT E4 switch percent cytotoxicity |
|---|---|---|
| 100 | −0.18785 | −8.14425 |
| 10 | −1.72277 | −3.82866 |
| 1 | −0.75881 | −1.81917 |
| 0.1 | −1.04059 | −2.11577 |
| 0.01 | −0.03213 | −2.30857 |
| 0.001 | 0.10134 | −2.05645 |

Example 4—Evaluation of Cytokine Release Induced by E4 and K4 CAR-T Cell/Switches CBA Cytokine Array The cytotoxicity assay described in Example 3 was performed again using only 1 nM E4 or K4 switch concentration in triplicate. The WT Fmc63 switch (aka WT Fab) was also used at 1 nM as a negative control to compare responses for the same anti-CD19 switch with and without peptide recognized by the CAR-T cell. Assays were performed using both CD19+ Raji luc cells and CD19-K562 cells.

CBA assay was performed using BD™ Cytometric Bead Array (CBA) Human Th1/Th2 Cytokine kit (cat. no. 550749). 30 ul of cytotoxicity assay supernatant was transferred to a U-bottom 96-well plate. Assay beads were prepared by mixing 5 ul of each Capture bead per well and 30 ul per well Human Th1/Th2 PE Detection Reagent. 30 ul of the Capture bead/PE Detection Reagent mix was then added to the 30 ul of supernatant and the plate was incubated for 3 hours at room temperature in the dark. After incubation, the plate was centrifuged at 500×g for 5 minutes to pellet the Capture beads and supernatant was flicked off. Beads were then washed with 200 ul Wash Buffer and finally resuspended in 100 ul Wash Buffer for analysis on the BD Accuri.

Figure 13A:
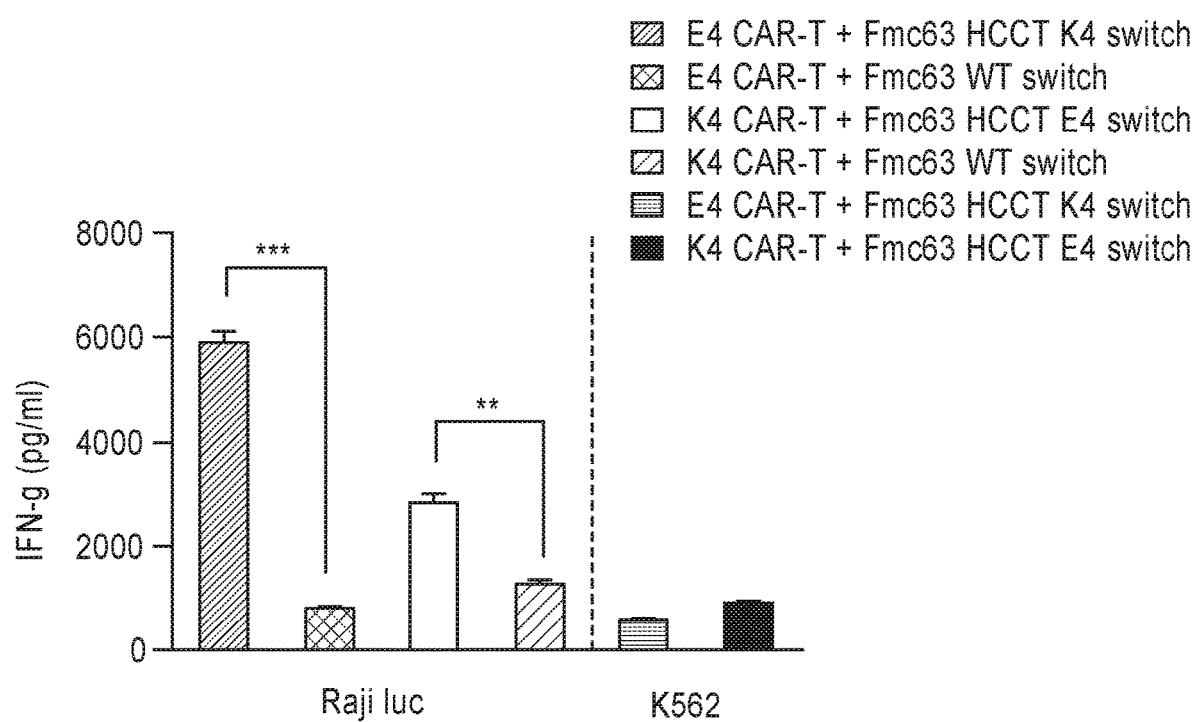
FIG. 13A shows IFN-g production induced by the E4 and K4 CAR-T cells in the presence or absence of complementary switch peptides in CD19-positive Raji luc cells and CD19-negative K562 cells.
Figure 13B:
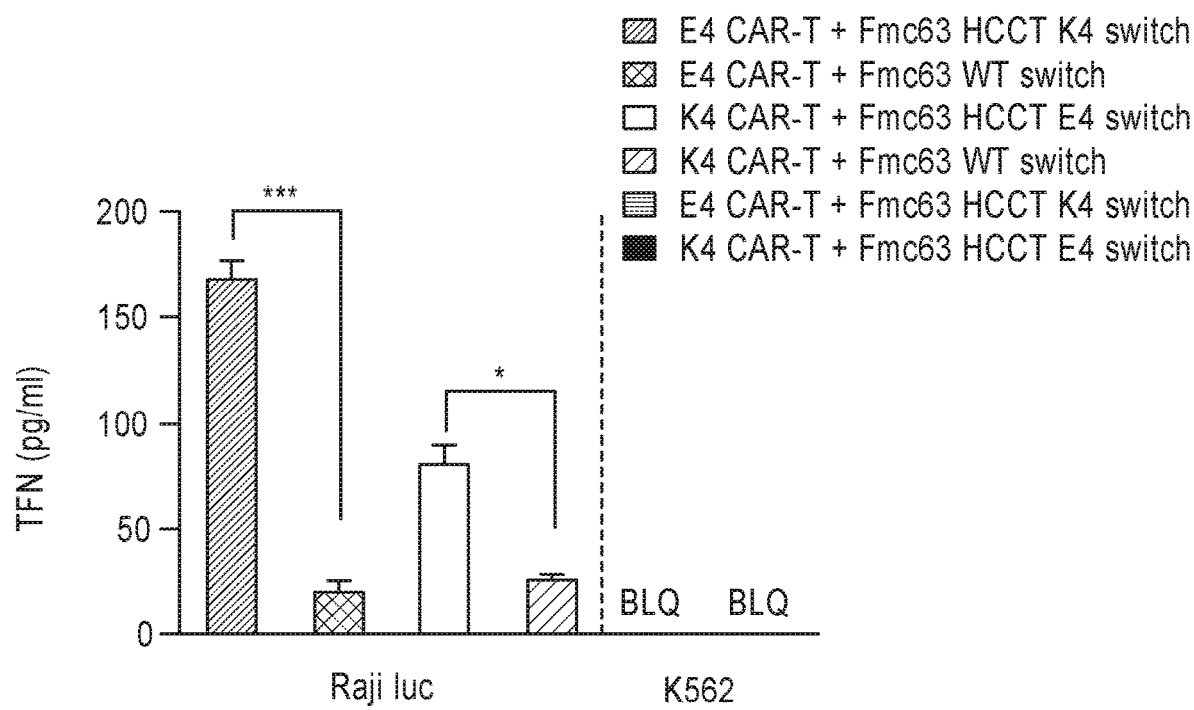
FIG. 13B shows TNF production induced by the E4 and K4 CAR-T cells in the presence or absence of complementary switch peptides in CD19-positive Raji luc cells and CD19-negative K562 cells. BLQ indicates below limit of quantification for the assay.
Figure 13C:
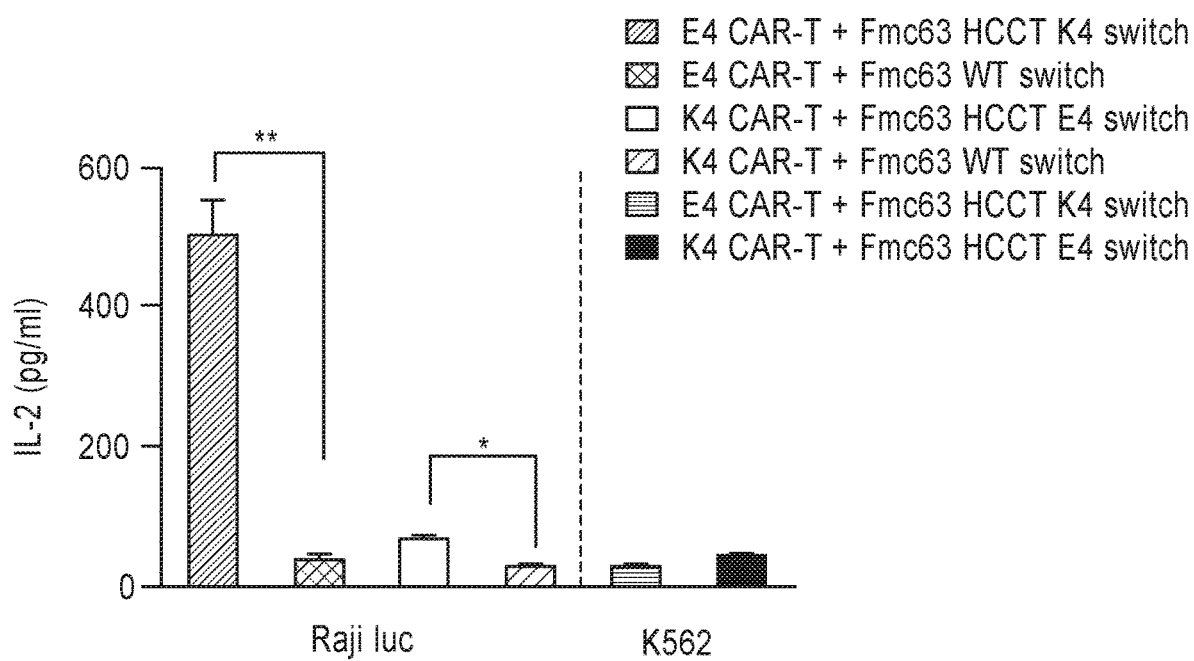
FIG. 13C shows IL-2 production induced by the E4 and K4 CAR-T cells in the presence or absence of complementary switch peptides in CD19-positive Raji luc cells and CD19-negative K562 cells.

Results of the cytokine array are shown in FIG. 13a through FIG. 13c. For Raji luc target cells (CD19+), significantly greater amounts of cytokine were induced by switches containing the E4 or K4 peptide compared with the wild type Fmc63 Fab which did not contain the E4 or K4 peptide (WT Fmc63 switch). This indicated that the K4 or E4 chimeric receptor needed to bind to the E4 or K4 peptide, respectively, in ordered to induce cytokine release. Furthermore, switches containing the E4 or K4 peptide with the K4 or E4 chimeric receptor transduced T cells (respectively) were unable to induce significant cytokine release against K562 (CD19−) cells. This indicated that switches require crosslinking of the chimeric receptor transduced T cells to an antigen positive cell in order to induce cytokine release. Soluble switch that is not cross linked to a target cell is unable to activate the cells in the absence of the antigen positive target cells. This is important because it indicates in translation to a therapeutic strategy that the switch will not activate the chimeric receptor transduced T cells prior to engaging the appropriate antigen positive target cell.

Example 5—Optimization of E4 and K4-Based Chimeric Receptors and Switches

The simple system tested in Examples 3 and 4, in which one coil is expressed by the CAR and one coil is expressed on the Fab switch, can be elaborated in many ways to provide altered, and perhaps more robust, anti-tumor activity. Such modifications include the use of coil peptides with modified affinities, construction of switch peptides and corresponding CARs that each express a plurality of coil peptides, and modification of the position of the peptide on the switch to optimize interaction with the corresponding anti-switch CAR. Certain examples of these modifications are discussed below.

CARs/Switches with Modified E4/K4 Peptide Sequences

In Examples 3 and 4, we tested a coiled-coil pair that interacts with an apparent $K_D$ of $4\times10^{-9}$ M. However, by altering the properties of the coils, the affinity of this interaction can be altered, as described by Litowski, (2002). For example, by altering the alanine residues within the core of the helix to serines (protein sequence: EVSALEKEVSALEKEVSALEKEVSALEK (SEQ ID NO: 61) for the E4 switch and protein sequence: KVSALKEKVSALKEKVSALKEKVSALKE (SEQ ID NO: 62) for the K4 switch), the affinity of the interaction is reduced by almost two-orders of magnitude to $9\times10^{-7}$ M. This may be advantageous in certain aspects such as the ability for the engineered cells and switches to engage in serial killing (or killing of multiple target cells by each effector cell). Additional E/K coil peptides suitable for use in the CARs/switches disclosed herein include those disclosed in Litowski, (2002), (e.g., any one of SEQ ID NOS: 65-76).

CARs/Switches with Two or More E4/K4 Peptide Sequences

Table 8 shows K4 and E4 switches, and corresponding CAR constructs with complementary coil peptides, which were designed such that each switch and CAR has two tandem coils joined by a G45 linker. In this way, the number of peptide-peptide interactions between the switch and the CAR is doubled. The number of coils expressed by both the CAR-T cell and the switch could be increased until maximum T cell activity is observed. The rationale for increasing the number of coils is to increase the avidity of the CAR switch interaction which may be advantageous in certain aspects such as the ability for the engineered cells and switches to target cells with low antigen density.

Modified E4/K4 Graft Position on Fab Switches

The position of the peptide on the switch can also be altered in order to find optimal positions that allows for the most productive interaction between the switch and the target cell. In Examples 3 and 4, the peptide was grafted onto the C-terminus of the heavy chain of the Fab (HCCT); however, numerous other potential grafting positions exist (see, e.g., FIG. 14 and Table 9, discussed below).

Figure 14:
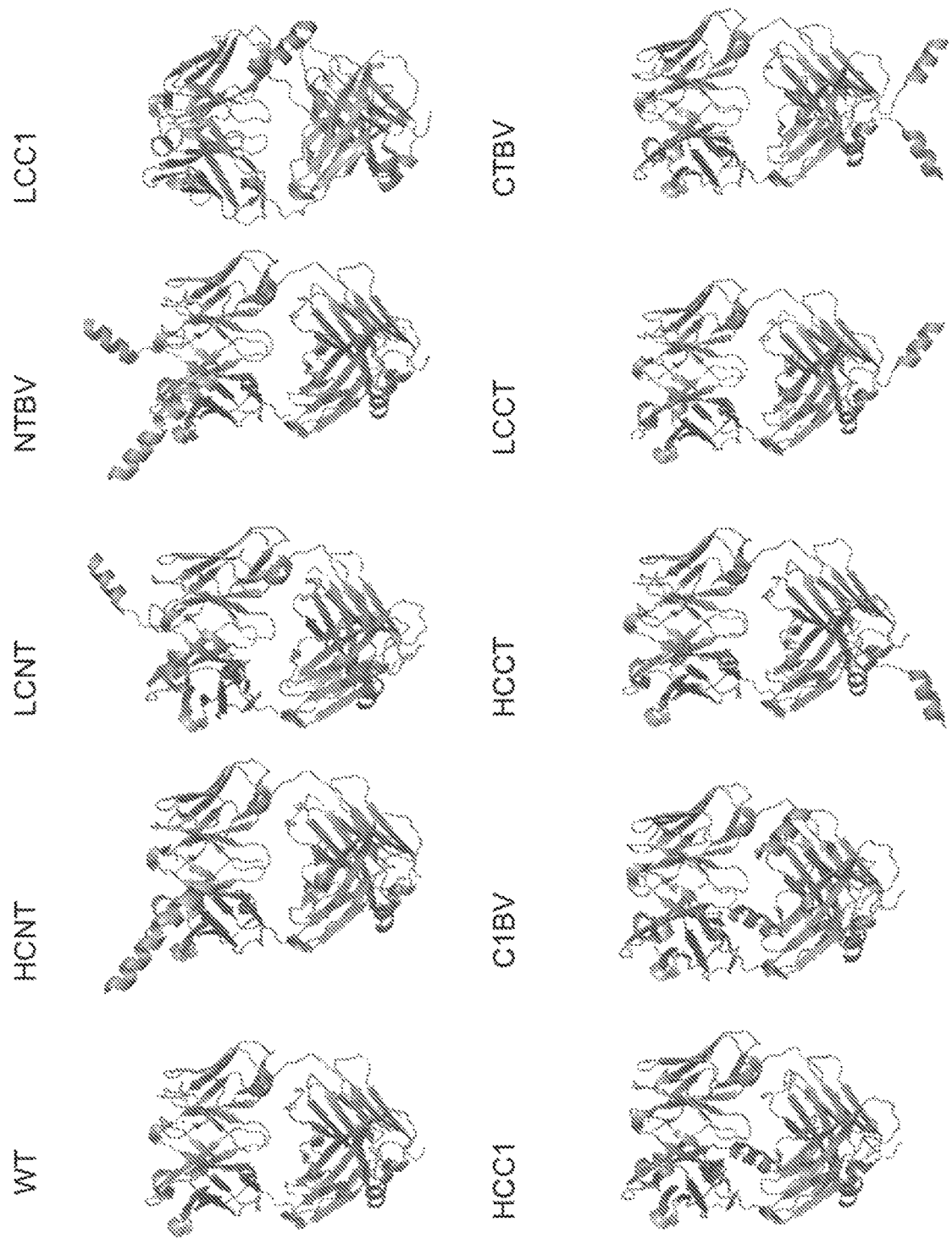
FIG. 14 shows alternative positions for grafting E4 or K4 coils peptides to Fabs to generate Fab-based coiled-coil switches.

Table 9 shows K4 and E4 switches in which the peptide is grafted to various different locations: (i) the C-terminus of the light chain (LCCT); (ii) the C-terminus of both the heavy and light chain (CTBV); (iii) the N-terminus of the light chain (LCNT); (iv) the N-terminus of the heavy chain (HCNT); or both the N-terminus and the C-terminus of the light chain to give a bivalent construct (NTBV). Additionally, the peptide could be grafted into the middle of the Fab protein at loops in the constant region of either the light chain (LCC1A), heavy chain (HCC1), or both (C1ABV). All of these constructs are depicted in FIG. 14. Alternatively two peptides could be grafted in the same chain LC BV or HC BC (not shown).

By altering the sequence, number, and/or graft location of coil peptides on the switch peptides and the CARs described herein, the affinity of the switch/CAR interaction and/or the efficiency with which the switch/CAR-T cell is able to induce targeted cytokine release and cytotoxicity may be modulated. This system allows for optimization of the immunological synapse formed by the target antigen/switch/CAR-T complex.

This technology is not limited to CD19. It can similarly be applied to target other antigens. For example, we have previously shown that the scFv/epitope switchable CAR-T system can also be used to direct T cell activity against target cells expressing CD20 by grafting the epitope onto an anti-CD20 Fab. Similarly, we could graft the E4 or K4 coil(s) onto an anti-CD20 antibody. Again, the coils could be grafted to either the N- or C-termini, or in loops in the constant region for the heavy chain, light chain, or both of the anti-CD20 Fab. We could also increase the number of coils on the switch and/or CAR-T cell to provide the maximum benefit. A similar strategy is expected to work for any Fab targeting an antigen of interest.

What is claimed is:

1. A chimeric receptor comprising:
   a. a non-antibody extracellular domain comprising a first peptide capable of forming an alpha helix that binds to a chimeric receptor binding peptide;
   b. transmembrane domain; and c. intracellular signaling domain, wherein the intracellular signaling domain signals to the chimeric receptor effector cell on which the chimeric receptor is expressed when the non-antibody extracellular domain binds to the chimeric receptor binding peptide; and wherein the chimeric receptor binding peptide comprises a second peptide capable of forming an alpha helix and binding to the first peptide.

2. The chimeric receptor of claim 1, wherein the chimeric receptor binding peptide is present on a switch, wherein the switch comprises the chimeric receptor binding peptide and a targeting moiety.

3. The chimeric receptor of claim 2, wherein the chimeric receptor binding peptide comprises a peptide epitope tag.

4. The chimeric receptor of claim 2, wherein the targeting moiety is selected from (i) a targeting small molecule, (ii) a targeting peptide, (iii) a targeting protein, and (iv) a targeting antibody, or an antibody fragment thereof.

5. The chimeric receptor of claim 2, wherein the chimeric receptor binding peptide and/or the non-antibody extracellular domain comprises a non-naturally occurring synthetic peptide.

6. The chimeric receptor of claim 2, wherein a. the chimeric receptor binding peptide and the non-antibody extracellular domain form a non-covalent protein-peptide interaction;

b. the chimeric receptor binding peptide comprises soluble NSF attachment protein Receptor (SNARE) and the non-antibody extracellular domain is selected from synaptosome Associated Protein 25 (SNAP25), synaptobrevin, and syntaxin;

c. the chimeric receptor binding partner and the non-antibody extracellular domain form a non-covalent peptide-peptide interaction.

7. The chimeric receptor of claim 2, wherein the and the second peptide bind together by forming a coiled-coil.

8. The chimeric receptor of claim 2, wherein a. the first peptide is the K4 peptide and the second peptide is the E4 peptide or b. the first peptide is the E4 peptide and the second peptide is the K4.

9. The chimeric receptor of claim 7, wherein a. the first peptide comprises the sequence SEQ ID NO: 33 and the second peptide comprises the sequence SEQ ID NO: 34 or b. the first peptide comprises the sequence SEQ ID NO: 34 and the second peptide comprises the sequence SEQ ID NO: 33.

10. The chimeric receptor of claim 7, wherein a. the first peptide comprises a sequence that has at least 95% or greater identity to SEQ ID NO: 33 and the second peptide comprises a sequence that has at least 95% or greater identity to SEQ ID NO: 34 or b. the first peptide comprises a sequence that has at least 95% or greater identity to SEQ ID NO: 34 and the second peptide comprises a sequence that has at least 95% or greater identity to SEQ ID NO: 33.

11. The chimeric receptor of claim 2, wherein a. the chimeric receptor binding peptide comprises a first mouse coronin 1A alpha helix and the non-antibody extracellular domain comprises a second mouse coronin 1A alpha helix;

b. the chimeric receptor binding peptide is selected from an anchor domain of an A-kinase anchor protein and a regulatory subunit of cAMP-dependent protein kinase A, and the non-antibody extracellular domain comprises a dimerization and docking domain of cAMP-dependent protein kinase;

c. the chimeric receptor binding peptide comprises a dimerization and docking domain of cAMP-dependent protein kinase and the non-antibody extracellular domain is selected from an anchor domain of an A-kinase anchor protein and a regulatory subunit of cAMP-dependent protein kinase A;

d. the chimeric receptor binding peptide is selected from an anchor domain of an A-kinase anchor protein and a regulatory subunit of cAMP-dependent protein kinase A, and the non-antibody extracellular domain comprises a dimerization and docking domain of cAMP-dependent protein kinase, wherein the dimerization and docking domain comprises a cysteine and the anchor domain comprises a cysteine; or e. the chimeric receptor binding peptide comprises a dimerization and docking domain of cAMP-dependent protein kinase and the non-antibody extracellular domain is selected from an anchor domain of an A-kinase anchor protein and a regulatory subunit of cAMP-dependent protein kinase A, wherein the dimerization and docking domain comprises a cysteine and the anchor domain comprises a cysteine.

12. The chimeric receptor of claim 11(d) or 11 (e), wherein the anchor domain has a sequence selected from SEQ ID NO: 8 and SEQ ID NO: 10 and the dimerization and docking domain has a sequence selected from SEQ ID NO: 9 and SEQ ID NO: 11.

13. The chimeric receptor of claim 1, wherein the non-antibody extracellular domain consists essentially of a non-antibody peptide selected from SNARE, a coronin alpha helix, the K4 alpha helix peptide, the E4 alpha helix peptide, an anchor domain of an A-kinase anchor protein, and a dimerization and docking domain of a cAMP dependent protein kinase A.

14. The chimeric receptor of claim 1, wherein the chimeric receptor is encoded by a polynucleotide having a sequence selected from SEQ ID NOS: 1-2 and SEQ ID NOS: 35-36.

15. A kit comprising:

a. a chimeric receptor-effector cell switch comprising:

1) a chimeric receptor binding peptide comprising a first peptide capable of forming an alpha helix and binding to a non-antibody extracellular domain of a chimeric receptor on an effector cell; and 2) a targeting moiety that interacts with a cell surface molecule on a target cell; and b. a chimeric receptor-effector cell comprising a chimeric receptor that comprises:

1) a non-antibody extracellular domain comprising a second peptide capable of forming an alpha helix that binds to the alpha helix of the first peptide;

2) a transmembrane domain; and 3) an intracellular signaling domain, wherein the intracellular signaling domain signals to the chimeric receptor effector cell when the first peptide binds to the second peptide.

16. A method of treating cancer in a subject in need thereof, comprising:
  A. administering to the subject a chimeric receptor-effector cell comprising:
    i. a chimeric receptor comprising:
      a. a non-antibody extracellular domain comprising a first peptide capable of forming an alpha helix that binds to a second peptide capable of forming an alpha helix, wherein the second peptide present on a chimeric receptor-effector cell switch;
      b. a transmembrane domain; and
      c. an intracellular signaling domain, wherein the intracellular signaling domain signals to the chimeric receptor effector cell on which the chimeric receptor is expressed when the non-antibody extracellular domain binds to the chimeric receptor binding peptide; and
  B. administering to the subject the chimeric receptor-effector cell switch; said switch comprising:
    i. the chimeric receptor binding peptide comprising the second peptide; and
    ii. a targeting moiety that interacts with a cell surface molecule on a target cell.

* * * * *

SEQUENCE LISTING

```
<160> NUMBER OF SEQ ID NOS: 76

<210> SEQ ID NO 1
<211> LENGTH: 912
<212> TYPE: DNA
<213> ORGANISM: Artificial Sequence
<220> FEATURE:
<223> OTHER INFORMATION: Chimeric receptor with DDD1 module

<400> SEQUENCE: 1
atggccttac cagtgaccgc cttgctcctg ccgctggcct tgctgctcca cgccgccagg      60
ccgtcacata tccagatccc ccccggactg actgaactgc tgcagggcta taccgtggaa     120
gtgctgagac agcagcctcc cgacctggtg gagttcgccg tggaatactt tacccggctg     180
agggaggcac gggctggagg cggaggttca ggaggaggag ggagtggcgg aggcggtagc     240
accacgacgc cagcgccgcg accaccaaca ccggcgccca ccatcgcgtc gcagcccctg     300
tccctgcgcc cagaggcgtg ccggccagcg gcggggggcg cagtgcacac gaggggggctg     360 gacttcgcct gtgatatcta catctgggcg cccttggccg ggacttgtgg ggtccttctc     420
ctgtcactgg ttatcaccct ttactgcaaa cggggcagaa agaaactcct gtatatattc     480
aaacaaccat ttatgagacc agtacaaact actcaagagg aagatggctg tagctgccga     540
tttccagaag aagaagaagg aggatgtgaa ctgagagtga agttcagcag gagcgcagac     600 gccccccgcgt acaagcaggg ccagaaccag ctctataacg agctcaatct aggacgaaga     660
gaggagtacg atgttttgga caagagacgt ggccgggacc ctgagatggg gggaaagccg     720
agaaggaaga accctcagga aggcctgtac aatgaactgc agaaagataa gatggcggag     780
gcctacagtg agattgggat gaaaggcgag cgccggaggg gcaaggggca cgatggcctt     840
taccagggtc tcagtacagc caccaaggac acctacgacg cccttcacat gcaggccctg     900 cccctcgct aa                                                         912
```

<210> SEQ ID NO 2
<211> LENGTH: 831
<212> TYPE: DNA
<213> ORGANISM: Artificial Sequence
<220> FEATURE:
<223> OTHER INFORMATION: Chimeric receptor with AD1 module

<400> SEQUENCE: 2

```
atggccttac cagtgaccgc cttgctcctg ccgctggcct tgctgctcca cgccgccagg      60
ccgcagattg agtacctggc taaacagatt gtggataacg ctattcagca ggcaggcgga     120
ggtggatctg gaggcggtgg gtcaggtgga ggcggaagta ccacgacgcc agcgccgcga     180
ccaccaacac cggcgcccac catcgcgtcg cagcccctgt ccctgcgccc agaggcgtgc     240
cggccagcgg cggggggcgc agtgcacacg aggggctgg  acttcgcctg tgatatctac     300
atctgggcgc ccttggccgg gacttgtggg gtccttctcc tgtcactggt tatcacccct     360
tactgcaaac ggggcagaaa gaaactcctg tatatattca acaaccatt  tatgagacca     420 gtacaaacta ctcaagagga agatggctgt agctgccgat tccagaaga  agaagaagga     480 ggatgtgaac tgagagtgaa gttcagcagg agcgcagacg cccccgcgta caagcagggc     540
cagaaccagc tctataacga gctcaatcta ggacgaagag aggagtacga tgttttggac     600
aagagacgtg gccgggaccc tgagatgggg ggaaagccga aggaagaa   ccctcaggaa     660 ggcctgtaca tgaactgca  gaaagataag atggcggagg cctacagtga gattgggatg     720
aaaggcgagc gccggagggg caaggggcac gatggccttt accagggtct cagtacagcc     780
accaaggaca cctacgacgc ccttcacatg caggccctgc cccctcgcta a              831
```

<210> SEQ ID NO 3
<211> LENGTH: 903
<212> TYPE: DNA
<213> ORGANISM: Artificial Sequence
<220> FEATURE:
<223> OTHER INFORMATION: Switch with DDD1 module and anti-CD19 huB4
heavy chain

<400> SEQUENCE: 3

```
atgtacagga tgcaactcct gtcttgcatt gcactaagtc ttgcacttgt cacgaattcg      60
caggtgcagc tggtccagcc aggggcagag gtcgtcaagc caggagcatc cgtcaaactg     120
tcatgtaaaa caagcgggta tactttcacc agcaattgga tgcactgggt gaagcaggcc     180 ccggacagg  gcctggagtg gatcgggaa  attgaccta  gtgattcata cactaactac     240
aaccagaact tccagggaaa ggccaaactg accgtggaca aaagcacctc cacagcttat     300
atggaggtga gcagcctgcg gtccgacgat actgcagtct actattgcgc cagaggctct     360
aacccttact attacgctat ggattactgg ggcagggaa  caagcgtgac tgtctctagt     420
gcatcaacaa agggaccaag cgtgtttcca ctggcccct  caagcaagag cacctccgga     480
gggacagccg ctctgggatg tctggtgaaa gactacttcc ccgagcctgt gactgtctct     540
tggaatagtg gcgctctgac ctccggggtg cacacatttc cagcagtcct gcagtcctct     600
ggactgtatt ctctgagttc agtggtcacc gtgcccagct cctctctggg cactcagacc     660
tacatctgca atgtcaacca taagcctagt aacacaaaag tggataagaa agtcgaacca     720
aagagctgtg gcggaggag  cggaggaggc ggtagcggcg gggaggctc  acatatccag     780 attccaccag gctgacaga  actgctgcag ggctacaccg tggaggtcct gcggcagcag     840 cccccctgacc tggtggagtt cgctgtggaa tactttacaa ggctgcggga ggctcgggct     900
```

| taa | 903 |

<210> SEQ ID NO 4
<211> LENGTH: 903
<212> TYPE: DNA
<213> ORGANISM: Artificial Sequence
<220> FEATURE:
<223> OTHER INFORMATION: Switch with AD1 module and anti-CD19 huB4 heavy
      chain

<400> SEQUENCE: 4

| atgtacagga tgcaactcct gtcttgcatt gcactaagtc ttgcacttgt cacgaattcg | 60 |
| caggtgcagc tggtccagcc aggggcagag gtcgtcaagc caggagcatc cgtcaaactg | 120 |
| tcatgtaaaa caagcgggta ctttcacc agcaattgga tgcactgggt gaagcaggcc | 180 |
| cccggacagg gcctggagtg gatcggggaa attgacccta gtgattcata cactaactac | 240 |
| aaccagaact tccagggaaa ggccaaactg accgtggaca aaagcacctc cacagcttat | 300 |
| atggaggtga gcagcctgcg gtccgacgat actgcagtct actattgcgc cagaggctct | 360 |
| aacccttact attacgctat ggattactgg gggcagggaa caagcgtgac tgtctctagt | 420 |
| gcatcaacaa agggaccaag cgtgtttcca ctggccccct caagcaagag caccctccgga | 480 |
| gggacagccg ctctgggatg tctggtgaaa gactacttcc ccgagcctgt gactgtctct | 540 |
| tggaatagtg gcgctctgac ctccggggtg cacacatttc cagcagtcct gcagtcctct | 600 |
| ggactgtatt ctctgagttc agtggtcacc gtgcccagct cctctctggg cactcagacc | 660 |
| tacatctgca atgtcaacca taagcctagt aacacaaaag tggataagaa agtcgaacca | 720 |
| aagagctgtg gcggagggag cggaggaggc ggtagcggcg ggggaggctc acatatccag | 780 |
| attccaccag gcctgacaga actgctgcag ggctacaccg tggaggtcct gcggcagcag | 840 |
| cccccctgacc tggtggagtt cgctgtgaa tactttacaa ggctgcggga ggctcgggct | 900 |
| taa | 903 |

<210> SEQ ID NO 5
<211> LENGTH: 705
<212> TYPE: DNA
<213> ORGANISM: Artificial Sequence
<220> FEATURE:
<223> OTHER INFORMATION: Anti-CD19 huB4 light chain

<400> SEQUENCE: 5

| atgtacagga tgcaactcct gtcttgcatt gcactaagtc ttgcacttgt cacgaattcg | 60 |
| gacatccaga tgacacagac tacatcctcc ctgtctgcct ctctgggaga cagagtcacc | 120 |
| atcagttgca gggcaagtca ggacattagt aaatatttaa attggtatca gcagaaacca | 180 |
| gatggaactg ttaaactcct gatctaccat acatcaagat acactcagg agtcccatca | 240 |
| aggttcagtg gcagtgggtc tggaacagat tattctctca ccattagcaa cctggagcaa | 300 |
| gaagatattg ccacttactt ttgccaacag ggtaatacgc ttccgtacac gttcggaggg | 360 |
| gggaccaagc ttgagatcaa acgaactgtg gctgcaccat ctgtcttcat cttcccgcca | 420 |
| tctgatgagc agttgaaatc tggaactgcc tctgtcgtgt gcctgctgaa taacttctat | 480 |
| cccagagagg ccaaagtaca gtggaaggtg gataacgccc tccaatcggg taactcccag | 540 |
| gagagtgtca cagagcagga cagcaaggac agcacctaca gcctcagcag caccctgacg | 600 |
| ctgagcaaag cagactacga gaaacacaaa gtctacgcct gcgaagtcac ccatcagggc | 660 |
| ctgtcctcgc ccgtcacaaa gagcttcaac aggggagagt gttaa | 705 |

```
<210> SEQ ID NO 6
<211> LENGTH: 16
<212> TYPE: PRT
<213> ORGANISM: Artificial Sequence
<220> FEATURE:
<223> OTHER INFORMATION: Isopeptag amino acid peptide tag

<400> SEQUENCE: 6

Thr Asp Lys Asp Met Thr Ile Thr Phe Thr Asn Lys Lys Asp Ala Glu
1               5                   10                  15

<210> SEQ ID NO 7
<211> LENGTH: 13
<212> TYPE: PRT
<213> ORGANISM: Artificial Sequence
<220> FEATURE:
<223> OTHER INFORMATION: Peptide tag

<400> SEQUENCE: 7

Ala His Ile Val Met Val Asp Ala Tyr Lys Pro Thr Lys
1               5                   10

<210> SEQ ID NO 8
<211> LENGTH: 17
<212> TYPE: PRT
<213> ORGANISM: Artificial Sequence
<220> FEATURE:
<223> OTHER INFORMATION: Anchoring domain (AD1) without cysteines

<400> SEQUENCE: 8

Gln Ile Glu Tyr Leu Ala Lys Gln Ile Val Asp Asn Ala Ile Gln Gln
1               5                   10                  15

Ala

<210> SEQ ID NO 9
<211> LENGTH: 44
<212> TYPE: PRT
<213> ORGANISM: Artificial Sequence
<220> FEATURE:
<223> OTHER INFORMATION: Dimerization and docking domain (DDD1) without
      cysteines

<400> SEQUENCE: 9

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 10
<211> LENGTH: 21
<212> TYPE: PRT
<213> ORGANISM: Artificial Sequence
<220> FEATURE:
<223> OTHER INFORMATION: Anchoring domain (AD1) with cysteines

<400> SEQUENCE: 10

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 11
```

```
<211> LENGTH: 45
<212> TYPE: PRT
<213> ORGANISM: Artificial Sequence
<220> FEATURE:
<223> OTHER INFORMATION: Dimerization and docking domain (DDD1) with
      cysteines

<400> SEQUENCE: 11

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 12
<211> LENGTH: 5
<212> TYPE: PRT
<213> ORGANISM: Artificial Sequence
<220> FEATURE:
<223> OTHER INFORMATION: Peptide linker sequence

<400> SEQUENCE: 12

Gly Gly Gly Gly Ser
1               5

<210> SEQ ID NO 13
<211> LENGTH: 4
<212> TYPE: PRT
<213> ORGANISM: Artificial Sequence
<220> FEATURE:
<223> OTHER INFORMATION: Peptide linker sequence

<400> SEQUENCE: 13

Gly Gly Gly Ser
1

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17
<211> LENGTH: 14
<212> TYPE: PRT
<213> ORGANISM: Artificial Sequence
<220> FEATURE:
<223> OTHER INFORMATION: Peptide linker sequence

<400> SEQUENCE: 17

Leu Val Gly Glu Ala Ala Ala Lys Glu Ala Ala Ala Lys Ala
1               5                   10
```

```
<210> SEQ ID NO 18
<211> LENGTH: 12
<212> TYPE: PRT
<213> ORGANISM: Artificial Sequence
<220> FEATURE:
<223> OTHER INFORMATION: Peptide linker sequence

<400> SEQUENCE: 18

Ala Glu Ala Ala Ala Lys Glu Ala Ala Ala Lys Ala
1               5                   10

<210> SEQ ID NO 19
<211> LENGTH: 16
<212> TYPE: PRT
<213> ORGANISM: Artificial Sequence
<220> FEATURE:
<223> OTHER INFORMATION: Peptide linker sequence

<400> SEQUENCE: 19

Glu Ala Ala Ala Lys Glu Ala Ala Ala Lys Glu Ala Ala Ala Lys Ala
1               5                   10                  15

<210> SEQ ID NO 20
<211> LENGTH: 18
<212> TYPE: PRT
<213> ORGANISM: Artificial Sequence
<220> FEATURE:
<223> OTHER INFORMATION: Peptide linker sequence

<400> SEQUENCE: 20

Lys Glu Ser Gly Ser Val Ser Ser Glu Gln Leu Ala Gln Phe Arg Ser
1               5                   10                  15

Leu Asp

<210> SEQ ID NO 21
<211> LENGTH: 14
<212> TYPE: PRT
<213> ORGANISM: Artificial Sequence
<220> FEATURE:
<223> OTHER INFORMATION: Peptide linker sequence

<400> SEQUENCE: 21

Glu Gly Lys Ser Ser Gly Ser Gly Ser Glu Ser Lys Ser Thr
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Peptide linker sequence

<400> SEQUENCE: 22

Gly Ser Ala Gly Ser Ala Ala Gly Ser Gly Glu Phe
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Peptide linker sequence

<400> SEQUENCE: 23

Ala Pro Ala Pro Ala Pro Ala Pro Ala Pro Ala Pro Ala Pro
1               5                   10
```

```
<210> SEQ ID NO 24
<211> LENGTH: 214
<212> TYPE: PRT
<213> ORGANISM: Artificial Sequence
<220> FEATURE:
<223> OTHER INFORMATION: Light chain of anti-CS1 antibody

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 222
<212> TYPE: PRT
<213> ORGANISM: Artificial Sequence
<220> FEATURE:
<223> OTHER INFORMATION: Heavy chain of anti-CS1 antibody Fab

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

```
Ala Arg Pro Asp Gly Asn Tyr Trp Tyr Phe Asp Val Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys
210                 215                 220

<210> SEQ ID NO 26
<211> LENGTH: 214
<212> TYPE: PRT
<213> ORGANISM: Artificial Sequence
<220> FEATURE:
<223> OTHER INFORMATION: Light chain of anti-EGFRvIII antibody (Hu806)
      Fab

<400> SEQUENCE: 26

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Asp Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 27
<211> LENGTH: 217
<212> TYPE: PRT
<213> ORGANISM: Artificial Sequence
<220> FEATURE:
<223> OTHER INFORMATION: Heavy chain of anti-EGFRvIII antibody (Hu806)
      Fab

<400> SEQUENCE: 27
```

| | | | | | | | | | | | | | | | |
|---|---|---|---|---|---|---|---|---|---|---|---|---|---|---|---|
| Gln | Leu | Gln | Glu | Ser | Gly | Pro | Gly | Leu | Val | Lys | Pro | Ser | Gln | Thr | Leu |
| 1 | | | | 5 | | | | | 10 | | | | | 15 | |
| Ser | Leu | Thr | Cys | Thr | Val | Ser | Gly | Tyr | Ser | Ile | Ser | Ser | Asp | Phe | Ala |
| | | | 20 | | | | | 25 | | | | | 30 | | |
| Trp | Asn | Trp | Ile | Arg | Gln | Pro | Pro | Gly | Lys | Gly | Leu | Glu | Trp | Met | Gly |
| | | | 35 | | | | | 40 | | | | | 45 | | |
| Tyr | Ile | Ser | Tyr | Ser | Gly | Asn | Thr | Arg | Tyr | Gln | Pro | Ser | Leu | Lys | Ser |
| | 50 | | | | | 55 | | | | | 60 | | | | |
| Arg | Ile | Thr | Ile | Ser | Arg | Asp | Thr | Ser | Lys | Asn | Gln | Phe | Phe | Leu | Lys |
| 65 | | | | | 70 | | | | | 75 | | | | | 80 |
| Leu | Asn | Ser | Val | Thr | Ala | Ala | Asp | Thr | Ala | Thr | Tyr | Tyr | Cys | Val | Thr |
| | | | | 85 | | | | | 90 | | | | | 95 | |
| Ala | Gly | Arg | Gly | Phe | Pro | Tyr | Trp | Gly | Gln | Gly | Thr | Leu | Val | Thr | Val |
| | | | 100 | | | | | 105 | | | | | 110 | | |
| Ser | Ser | Ala | Ser | Thr | Lys | Gly | Pro | Ser | Val | Phe | Pro | Leu | Ala | Pro | Ser |
| | | | 115 | | | | | 120 | | | | | 125 | | |
| Ser | Lys | Ser | Thr | Ser | Gly | Gly | Thr | Ala | Ala | Leu | Gly | Cys | Leu | Val | Lys |
| | 130 | | | | | 135 | | | | | 140 | | | | |
| Asp | Tyr | Phe | Pro | Glu | Pro | Val | Thr | Val | Ser | Trp | Asn | Ser | Gly | Ala | Leu |
| 145 | | | | | 150 | | | | | 155 | | | | | 160 |
| Thr | Ser | Gly | Val | His | Thr | Phe | Pro | Ala | Val | Leu | Gln | Ser | Ser | Gly | Leu |
| | | | | 165 | | | | | 170 | | | | | 175 | |
| Tyr | Ser | Leu | Ser | Ser | Val | Val | Thr | Val | Pro | Ser | Ser | Ser | Leu | Gly | Thr |
| | | | 180 | | | | | 185 | | | | | 190 | | |
| Gln | Thr | Tyr | Ile | Cys | Asn | Val | Asn | His | Lys | Pro | Ser | Asn | Thr | Lys | Val |
| | | | 195 | | | | | 200 | | | | | 205 | | |
| Asp | Lys | Lys | Val | Glu | Pro | Lys | Ser | Cys | | | | | | | |
| | 210 | | | | | 215 | | | | | | | | | |

```
<210> SEQ ID NO 28
<211> LENGTH: 214
<212> TYPE: PRT
<213> ORGANISM: Artificial Sequence
<220> FEATURE:
<223> OTHER INFORMATION: Light chain of anti-BCMA antibody (BCMA98) Fab

<400> SEQUENCE: 28
```

| | | | | | | | | | | | | | | | |
|---|---|---|---|---|---|---|---|---|---|---|---|---|---|---|---|
| Asp | Ile | Gln | Met | Thr | Gln | Ser | Pro | Ser | Ser | Leu | Ser | Ala | Ser | Val | Gly |
| 1 | | | | 5 | | | | | 10 | | | | | 15 | |
| Asp | Arg | Val | Thr | Ile | Thr | Cys | Arg | Ala | Asn | Gln | Gly | Ile | Ser | Asn | Asn |
| | | | 20 | | | | | 25 | | | | | 30 | | |
| Leu | Asn | Trp | Tyr | Gln | Gln | Lys | Pro | Gly | Lys | Ala | Pro | Lys | Pro | Leu | Ile |
| | | | 35 | | | | | 40 | | | | | 45 | | |
| Tyr | Tyr | Thr | Ser | Asn | Leu | Gln | Ser | Gly | Val | Pro | Ser | Arg | Phe | Ser | Gly |
| | 50 | | | | | 55 | | | | | 60 | | | | |
| Ser | Gly | Ser | Gly | Thr | Asp | Tyr | Thr | Leu | Thr | Ile | Ser | Ser | Leu | Gln | Pro |
| 65 | | | | | 70 | | | | | 75 | | | | | 80 |
| Glu | Asp | Phe | Ala | Thr | Tyr | Tyr | Cys | Gln | Gln | Phe | Thr | Ser | Leu | Pro | Tyr |
| | | | | 85 | | | | | 90 | | | | | 95 | |

-continued

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 29
<211> LENGTH: 224
<212> TYPE: PRT
<213> ORGANISM: Artificial Sequence
<220> FEATURE:
<223> OTHER INFORMATION: Heavy chain of anti-BCMA antibody (BCMA98) Fab

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Asp Met Ala Trp Val Arg Gln Ala Pro Gly Lys Gly Leu Val Trp Val
        35                  40                  45

Ser Ser Ile Thr Thr Gly Gly Gly Asp Thr Tyr Tyr Ala Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Val Tyr Tyr Cys
                85                  90                  95

Val Arg His Gly Tyr Tyr Asp Gly Tyr His Leu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

<210> SEQ ID NO 30

```
<211> LENGTH: 214
<212> TYPE: PRT
<213> ORGANISM: Artificial Sequence
<220> FEATURE:
<223> OTHER INFORMATION: Light Chain of anti-CD19 antibody

<400> SEQUENCE: 30

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 449
<212> TYPE: PRT
<213> ORGANISM: Artificial Sequence
<220> FEATURE:
<223> OTHER INFORMATION: Heavy Chain of anti-CD19 antibody IgG

<400> SEQUENCE: 31

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
```

```
                    100                 105                 110
Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 32
<211> LENGTH: 223
<212> TYPE: PRT
<213> ORGANISM: Artificial Sequence
<220> FEATURE:
<223> OTHER INFORMATION: Heavy Chain of anti-CD19 antibody Fab

<400> SEQUENCE: 32

Glu Val Lys Leu Gln Glu Ser Gly Pro Gly Leu Val Ala Pro Ser Gln
1               5                   10                  15
```

```
Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
            35                  40                  45

Gly Val Ile Trp Gly Ser Glu Thr Thr Tyr Tyr Asn Ser Ala Leu Lys
50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
                100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Val Glu Pro Lys Ser Cys
            210                 215                 220

<210> SEQ ID NO 33
<211> LENGTH: 28
<212> TYPE: PRT
<213> ORGANISM: Artificial Sequence
<220> FEATURE:
<223> OTHER INFORMATION: Synthetic VAAL K4 alpha helical coiled coil
      peptide

<400> SEQUENCE: 33

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 34
<211> LENGTH: 28
<212> TYPE: PRT
<213> ORGANISM: Artificial Sequence
<220> FEATURE:
<223> OTHER INFORMATION: Synthetic VAAL E4 alpha helical coiled coil
      peptide

<400> SEQUENCE: 34

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 35
<211> LENGTH: 723
<212> TYPE: DNA
<213> ORGANISM: Artificial Sequence
```

<220> FEATURE:
<223> OTHER INFORMATION: E4 Chimeric Receptor nucleotide sequence

<400> SEQUENCE: 35

| | |
|---|---|
| atggccttac cagtgaccgc cttgctcctg ccgctggcct tgctgctcca cgccgccagg | 60 |
| ccggaggttg ctgccctgga gaaggaggtg gctgcactgg agaaagaggt ggccgccctg | 120 |
| gaaaaagaag tggcagcctt ggagaaggaa agcaagtatg cccaccttg tccaccttgt | 180 |
| cccgatatct acatctgggc gcccttggcc gggacttgtg gggtccttct cctgtcactg | 240 |
| gttatcaccc tttactgcaa acggggcaga agaaactcc tgtatatatt caaacaacca | 300 |
| tttatgagac cagtacaaac tactcaagag gaagatggc gtagctgccg atttccagaa | 360 |
| gaagaagaag gaggatgtga actgagagtg aagttcagca ggagcgcaga cgcccccgcg | 420 |
| tacaagcagg gccagaacca gctctataac gagctcaatc taggacgaag agaggagtac | 480 |
| gatgttttgg acaagagacg tggccgggac cctgagatgg ggggaaagcc gagaaggaag | 540 |
| aaccctcagg aaggcctgta caatgaactg cagaaagata gatggcgga ggcctacagt | 600 |
| gagattggga tgaaaggcga gcgccggagg ggcaaggggc acgatggcct ttaccagggt | 660 |
| ctcagtacag ccaccaagga cacctacgac gcccttcaca tgcaggccct gccccctcgc | 720 |
| taa | 723 |

<210> SEQ ID NO 36
<211> LENGTH: 723
<212> TYPE: DNA
<213> ORGANISM: Artificial Sequence
<220> FEATURE:
<223> OTHER INFORMATION: K4 Chimeric Receptor nucleotide sequence

<400> SEQUENCE: 36

| | |
|---|---|
| atggccttac cagtgaccgc cttgctcctg ccgctggcct tgctgctcca cgccgccagg | 60 |
| ccgaaagtgg cagccctgaa ggagaaagtt gcggctctca agagaaagt ggctgcactg | 120 |
| aaagaaaagg ttgccgccct caaggaggaa agcaagtatg cccaccttg tccaccttgt | 180 |
| cccgatatct acatctgggc gcccttggcc gggacttgtg gggtccttct cctgtcactg | 240 |
| gttatcaccc tttactgcaa acggggcaga agaaactcc tgtatatatt caaacaacca | 300 |
| tttatgagac cagtacaaac tactcaagag gaagatggct gtagctgccg atttccagaa | 360 |
| gaagaagaag gaggatgtga actgagagtg aagttcagca ggagcgcaga cgcccccgcg | 420 |
| tacaagcagg gccagaacca gctctataac gagctcaatc taggacgaag agaggagtac | 480 |
| gatgttttgg acaagagacg tggccgggac cctgagatgg ggggaaagcc gagaaggaag | 540 |
| aaccctcagg aaggcctgta caatgaactg cagaaagata gatggcgga ggcctacagt | 600 |
| gagattggga tgaaaggcga gcgccggagg ggcaaggggc acgatggcct ttaccagggt | 660 |
| ctcagtacag ccaccaagga cacctacgac gcccttcaca tgcaggccct gccccctcgc | 720 |
| taa | 723 |

<210> SEQ ID NO 37
<211> LENGTH: 831
<212> TYPE: DNA
<213> ORGANISM: Artificial Sequence
<220> FEATURE:
<223> OTHER INFORMATION: Fmc63 HCCT E4 switch heavy chain nucleotide
      sequence

<400> SEQUENCE: 37

| | |
|---|---|
| atgtacagga tgcaactcct gtcttgcatt gcactaagtc ttgcacttgt cacgaattcg | 60 |

```
gaggtgaaac tgcaggagtc aggacctggc ctggtggcgc cctcacagag cctgtccgtc    120
acatgcactg tctcagggt ctcattaccc gactatggtg taagctggat tcgccagcct    180
ccacgaaagg gtctggagtg gctgggagta atatggggta gtgaaaccac atactataat    240
tcagctctca aatccagact gaccatcatc aaggacaact ccaagagcca agttttctta    300
aaaatgaaca gtctgcaaac tgatgacaca gccatttact actgtgccaa acattattac    360
tacggtggta gctatgctat ggactactgg ggccaaggaa cctcagtcac cgtctcctca    420
gcctccacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgact gtgccctcta gcagcttggg cacccagacc    660
tacatctgca acgtgaatca caagcccagc aacaccaagg tggacaagaa agttgagccc    720
aaatcttgtg gcggaggcgg gagcgaggtt gctgccctgg agaaggaggt ggctgcactg    780
gagaaagagg tggccgccct ggaaaaagaa gtggcagcct ggagaagtg a              831
```

<210> SEQ ID NO 38
<211> LENGTH: 832
<212> TYPE: DNA
<213> ORGANISM: Artificial Sequence
<220> FEATURE:
<223> OTHER INFORMATION: Fmc63 HCCT K4 switch heavy chain nucleotide
      sequence

<400> SEQUENCE: 38

```
atgtacagga tgcaactcct gtcttgcatt gcactaagtc ttgcacttgt cacgaattcg    60
gaggtgaaac tgcaggagtc aggacctggc ctggtggcgc cctcacagag cctgtccgtc    120
acatgcactg tctcagggt ctcattaccc gactatggtg taagctggat tcgccagcct    180
ccacgaaagg gtctggagtg gctgggagta atatggggta gtgaaaccac atactataat    240
tcagctctca aatccagact gaccatcatc aaggacaact ccaagagcca agttttctta    300
aaaatgaaca gtctgcaaac tgatgacaca gccatttact actgtgccaa acattattac    360
tacggtggta gctatgctat ggactactgg ggccaaggaa cctcagtcac cgtctcctca    420
gcctccacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgact gtgccctcta gcagcttggg cacccagacc    660
tacatctgca acgtgaatca caagcccagc aacaccaagg tggacaagaa agttgagccc    720
aaatcttgtg gcggaggcgg gagcaaagtg gcagccctga aggagaaagt gcggctctc    780 aaagagaaag tggctgcact gaaagaaaag gttgccgccc tcaaggagtg at            832
```

<210> SEQ ID NO 39
<211> LENGTH: 733
<212> TYPE: DNA
<213> ORGANISM: Artificial Sequence
<220> FEATURE:
<223> OTHER INFORMATION: Fmc63 HC WT switch heavy chain nucleotide
      sequence

<400> SEQUENCE: 39

```
atgtacagga tgcaactcct gtcttgcatt gcactaagtc ttgcacttgt cacgaattcg    60
```

```
gaggtgaaac tgcaggagtc aggacctggc ctggtggcgc cctcacagag cctgtccgtc      120
acatgcactg tctcagggt ctcattaccc gactatggtg taagctggat tcgccagcct      180
ccacgaaagg gtctggagtg gctgggagta atatggggta gtgaaaccac atactataat      240
tcagctctca aatccagact gaccatcatc aaggacaact ccaagagcca agttttctta      300
aaaatgaaca gtctgcaaac tgatgacaca gccatttact actgtgccaa acattattac      360
tacggtggta gctatgctat ggactactgg ggccaaggaa cctcagtcac cgtctcctca      420
gcctccacca agggcccatc ggtcttcccc ctggcaccct cctccaagag cacctctggg      480
ggcacagcgg ccctgggctg cctggtcaag gactacttcc ccgaaccggt gacggtgtcg      540
tggaactcag gcgccctgac cagcggcgtg cacaccttcc cggctgtcct acagtcctca      600
ggactctact ccctcagcag cgtggtgact gtgccctcta gcagcttggg cacccagacc      660
tacatctgca acgtgaatca caagcccagc aacaccaagg tggacaagaa agttgagccc      720
aaatcttgtt gat                                                         733

<210> SEQ ID NO 40
<211> LENGTH: 705
<212> TYPE: DNA
<213> ORGANISM: Artificial Sequence
<220> FEATURE:
<223> OTHER INFORMATION: Fmc63 LC WT switch light chain nucleotide
      sequence

<400> SEQUENCE: 40
atgtacagga tgcaactcct gtcttgcatt gcactaagtc ttgcacttgt cacgaattcg       60
gacatccaga tgacacagac tacatcctcc ctgtctgcct ctctgggaga cagagtcacc      120
atcagttgca gggcaagtca ggacattagt aaatatttaa attggtatca gcagaaacca      180
gatggaactg ttaaactcct gatctaccat acatcaagat tacactcagg agtcccatca      240
aggttcagtg gcagtgggtc tggaacagat tattctctca ccattagcaa cctggagcaa      300
gaagatattg ccacttactt ttgccaacag ggtaatacgc ttccgtacac gttcggaggg      360
gggaccaagc ttgagatcaa acgaactgtg gctgcaccat ctgtcttcat cttcccgcca      420
tctgatgagc agttgaaatc tggaactgcc tctgtcgtgt gcctgctgaa taacttctat      480
cccagagagg ccaaagtaca gtggaaggtg gataacgccc tccaatcggg taactcccag      540
gagagtgtca cagagcagga cagcaaggac agcacctaca gcctcagcag caccctgacg      600
ctgagcaaag cagactacga gaaacacaaa gtctacgcct gcgaagtcac ccatcagggc      660
ctgtcctcgc cgtcacaaa gagcttcaac aggggagagt gttga                      705

<210> SEQ ID NO 41
<211> LENGTH: 240
<212> TYPE: PRT
<213> ORGANISM: Artificial Sequence
<220> FEATURE:
<223> OTHER INFORMATION: E4 Chimeric Receptor

<400> SEQUENCE: 41

Met Ala Leu Pro Val Thr Ala Leu Leu Leu Pro Leu Ala Leu Leu Leu
1               5                   10                  15

His Ala Ala Arg Pro Glu Val Ala Ala Leu Glu Lys Glu Val Ala Ala
                20                  25                  30

Leu Glu Lys Glu Val Ala Ala Leu Glu Lys Glu Val Ala Ala Leu Glu
            35                  40                  45

Lys Glu Ser Lys Tyr Gly Pro Pro Cys Pro Pro Cys Pro Asp Ile Tyr
```

```
            50                  55                  60
Ile Trp Ala Pro Leu Ala Gly Thr Cys Gly Val Leu Leu Ser Leu
 65                  70                  75                  80

Val Ile Thr Leu Tyr Cys Lys Arg Gly Arg Lys Lys Leu Leu Tyr Ile
                 85                  90                  95

Phe Lys Gln Pro Phe Met Arg Pro Val Gln Thr Thr Gln Glu Glu Asp
                100                 105                 110

Gly Cys Ser Cys Arg Phe Pro Glu Glu Glu Glu Gly Gly Cys Glu Leu
                115                 120                 125

Arg Val Lys Phe Ser Arg Ser Ala Asp Ala Pro Ala Tyr Lys Gln Gly
                130                 135                 140

Gln Asn Gln Leu Tyr Asn Glu Leu Asn Leu Gly Arg Arg Glu Glu Tyr
145                 150                 155                 160

Asp Val Leu Asp Lys Arg Arg Gly Arg Asp Pro Glu Met Gly Gly Lys
                165                 170                 175

Pro Arg Arg Lys Asn Pro Gln Glu Gly Leu Tyr Asn Glu Leu Gln Lys
                180                 185                 190

Asp Lys Met Ala Glu Ala Tyr Ser Glu Ile Gly Met Lys Gly Glu Arg
                195                 200                 205

Arg Arg Gly Lys Gly His Asp Gly Leu Tyr Gln Gly Leu Ser Thr Ala
                210                 215                 220

Thr Lys Asp Thr Tyr Asp Ala Leu His Met Gln Ala Leu Pro Pro Arg
225                 230                 235                 240

<210> SEQ ID NO 42
<211> LENGTH: 240
<212> TYPE: PRT
<213> ORGANISM: Artificial Sequence
<220> FEATURE:
<223> OTHER INFORMATION: K4 Chimeric Receptor sequence

<400> SEQUENCE: 42

Met Ala Leu Pro Val Thr Ala Leu Leu Leu Pro Leu Ala Leu Leu Leu
 1               5                  10                  15

His Ala Ala Arg Pro Lys Val Ala Ala Leu Lys Glu Lys Val Ala Ala
                 20                  25                  30

Leu Lys Glu Lys Val Ala Ala Leu Lys Glu Lys Val Ala Ala Leu Lys
                 35                  40                  45

Glu Glu Ser Lys Tyr Gly Pro Pro Cys Pro Pro Cys Pro Asp Ile Tyr
 50                  55                  60

Ile Trp Ala Pro Leu Ala Gly Thr Cys Gly Val Leu Leu Ser Leu
 65                  70                  75                  80

Val Ile Thr Leu Tyr Cys Lys Arg Gly Arg Lys Lys Leu Leu Tyr Ile
                 85                  90                  95

Phe Lys Gln Pro Phe Met Arg Pro Val Gln Thr Thr Gln Glu Glu Asp
                100                 105                 110

Gly Cys Ser Cys Arg Phe Pro Glu Glu Glu Glu Gly Gly Cys Glu Leu
                115                 120                 125

Arg Val Lys Phe Ser Arg Ser Ala Asp Ala Pro Ala Tyr Lys Gln Gly
                130                 135                 140

Gln Asn Gln Leu Tyr Asn Glu Leu Asn Leu Gly Arg Arg Glu Glu Tyr
145                 150                 155                 160

Asp Val Leu Asp Lys Arg Arg Gly Arg Asp Pro Glu Met Gly Gly Lys
                165                 170                 175

Pro Arg Arg Lys Asn Pro Gln Glu Gly Leu Tyr Asn Glu Leu Gln Lys
```

```
                180             185                 190
Asp Lys Met Ala Glu Ala Tyr Ser Glu Ile Gly Met Lys Gly Glu Arg
            195                 200                 205

Arg Arg Gly Lys Gly His Asp Gly Leu Tyr Gln Gly Leu Ser Thr Ala
            210                 215                 220

Thr Lys Asp Thr Tyr Asp Ala Leu His Met Gln Ala Leu Pro Pro Arg
225                 230                 235                 240

<210> SEQ ID NO 43
<211> LENGTH: 276
<212> TYPE: PRT
<213> ORGANISM: Artificial Sequence
<220> FEATURE:
<223> OTHER INFORMATION: Fmc63 HCCT E4 switch heavy chain sequence

<400> SEQUENCE: 43

Met Tyr Arg Met Gln Leu Leu Ser Cys Ile Ala Leu Ser Leu Ala Leu
1               5                   10                  15

Val Thr Asn Ser Glu Val Lys Leu Gln Glu Ser Gly Pro Gly Leu Val
            20                  25                  30

Ala Pro Ser Gln Ser Leu Ser Val Thr Cys Thr Val Ser Gly Val Ser
            35                  40                  45

Leu Pro Asp Tyr Gly Val Ser Trp Ile Arg Gln Pro Pro Arg Lys Gly
    50                  55                  60

Leu Glu Trp Leu Gly Val Ile Trp Gly Ser Glu Thr Thr Tyr Tyr Asn
65                  70                  75                  80

Ser Ala Leu Lys Ser Arg Leu Thr Ile Ile Lys Asp Asn Ser Lys Ser
                85                  90                  95

Gln Val Phe Leu Lys Met Asn Ser Leu Gln Thr Asp Asp Thr Ala Ile
            100                 105                 110

Tyr Tyr Cys Ala Lys His Tyr Tyr Tyr Gly Gly Ser Tyr Ala Met Asp
        115                 120                 125

Tyr Trp Gly Gln Gly Thr Ser Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Gly Gly Gly Gly Ser Glu Val Ala Ala Leu Glu Lys Glu
                245                 250                 255

Val Ala Ala Leu Glu Lys Glu Val Ala Ala Leu Glu Lys Glu Val Ala
            260                 265                 270

Ala Leu Glu Lys
            275

<210> SEQ ID NO 44
<211> LENGTH: 276
<212> TYPE: PRT
```

<213> ORGANISM: Artificial Sequence
<220> FEATURE:
<223> OTHER INFORMATION: Fmc63 HCCT K4 switch heavy chain sequence

<400> SEQUENCE: 44

| Met | Tyr | Arg | Met | Gln | Leu | Leu | Ser | Cys | Ile | Ala | Leu | Ser | Leu | Ala | Leu |
|---|---|---|---|---|---|---|---|---|---|---|---|---|---|---|---|
| 1 | | | | 5 | | | | | 10 | | | | | 15 | |

| Val | Thr | Asn | Ser | Glu | Val | Lys | Leu | Gln | Glu | Ser | Gly | Pro | Gly | Leu | Val |
|---|---|---|---|---|---|---|---|---|---|---|---|---|---|---|---|
| | | | 20 | | | | | 25 | | | | | 30 | | |

| Ala | Pro | Ser | Gln | Ser | Leu | Ser | Val | Thr | Cys | Thr | Val | Ser | Gly | Val | Ser |
|---|---|---|---|---|---|---|---|---|---|---|---|---|---|---|---|
| | | 35 | | | | | 40 | | | | | 45 | | | |

| Leu | Pro | Asp | Tyr | Gly | Val | Ser | Trp | Ile | Arg | Gln | Pro | Pro | Arg | Lys | Gly |
|---|---|---|---|---|---|---|---|---|---|---|---|---|---|---|---|
| 50 | | | | | 55 | | | | | 60 | | | | | |

| Leu | Glu | Trp | Leu | Gly | Val | Ile | Trp | Gly | Ser | Glu | Thr | Thr | Tyr | Tyr | Asn |
|---|---|---|---|---|---|---|---|---|---|---|---|---|---|---|---|
| 65 | | | | 70 | | | | | 75 | | | | | 80 | |

| Ser | Ala | Leu | Lys | Ser | Arg | Leu | Thr | Ile | Ile | Lys | Asp | Asn | Ser | Lys | Ser |
|---|---|---|---|---|---|---|---|---|---|---|---|---|---|---|---|
| | | | | 85 | | | | | 90 | | | | | 95 | |

| Gln | Val | Phe | Leu | Lys | Met | Asn | Ser | Leu | Gln | Thr | Asp | Asp | Thr | Ala | Ile |
|---|---|---|---|---|---|---|---|---|---|---|---|---|---|---|---|
| | | | | 100 | | | | | 105 | | | | | 110 | |

| Tyr | Tyr | Cys | Ala | Lys | His | Tyr | Tyr | Tyr | Gly | Gly | Ser | Tyr | Ala | Met | Asp |
|---|---|---|---|---|---|---|---|---|---|---|---|---|---|---|---|
| | | | 115 | | | | | 120 | | | | | 125 | | |

| Tyr | Trp | Gly | Gln | Gly | Thr | Ser | Val | Thr | Val | Ser | Ser | Ala | Ser | Thr | Lys |
|---|---|---|---|---|---|---|---|---|---|---|---|---|---|---|---|
| | 130 | | | | | 135 | | | | | 140 | | | | |

| Gly | Pro | Ser | Val | Phe | Pro | Leu | Ala | Pro | Ser | Ser | Lys | Ser | Thr | Ser | Gly |
|---|---|---|---|---|---|---|---|---|---|---|---|---|---|---|---|
| 145 | | | | | 150 | | | | | 155 | | | | | 160 |

| Gly | Thr | Ala | Ala | Leu | Gly | Cys | Leu | Val | Lys | Asp | Tyr | Phe | Pro | Glu | Pro |
|---|---|---|---|---|---|---|---|---|---|---|---|---|---|---|---|
| | | | | 165 | | | | | 170 | | | | | 175 | |

| Val | Thr | Val | Ser | Trp | Asn | Ser | Gly | Ala | Leu | Thr | Ser | Gly | Val | His | Thr |
|---|---|---|---|---|---|---|---|---|---|---|---|---|---|---|---|
| | | | 180 | | | | | 185 | | | | | 190 | | |

| Phe | Pro | Ala | Val | Leu | Gln | Ser | Ser | Gly | Leu | Tyr | Ser | Leu | Ser | Ser | Val |
|---|---|---|---|---|---|---|---|---|---|---|---|---|---|---|---|
| | | 195 | | | | | 200 | | | | | 205 | | | |

| Val | Thr | Val | Pro | Ser | Ser | Ser | Leu | Gly | Thr | Gln | Thr | Tyr | Ile | Cys | Asn |
|---|---|---|---|---|---|---|---|---|---|---|---|---|---|---|---|
| | 210 | | | | | 215 | | | | | 220 | | | | |

| Val | Asn | His | Lys | Pro | Ser | Asn | Thr | Lys | Val | Asp | Lys | Lys | Val | Glu | Pro |
|---|---|---|---|---|---|---|---|---|---|---|---|---|---|---|---|
| 225 | | | | | 230 | | | | | 235 | | | | | 240 |

| Lys | Ser | Cys | Gly | Gly | Gly | Ser | Lys | Val | Ala | Ala | Leu | Lys | Glu | Lys |
|---|---|---|---|---|---|---|---|---|---|---|---|---|---|---|
| | | | | 245 | | | | | 250 | | | | | 255 |

| Val | Ala | Ala | Leu | Lys | Glu | Lys | Val | Ala | Ala | Leu | Lys | Glu | Lys | Val | Ala |
|---|---|---|---|---|---|---|---|---|---|---|---|---|---|---|---|
| | | | 260 | | | | | 265 | | | | | 270 | | |

| Ala | Leu | Lys | Glu |
|---|---|---|---|
| | | | 275 |

<210> SEQ ID NO 45
<211> LENGTH: 234
<212> TYPE: PRT
<213> ORGANISM: Artificial Sequence
<220> FEATURE:
<223> OTHER INFORMATION: Fmc63 HC WT Heavy Chain sequence

<400> SEQUENCE: 45

| Met | Tyr | Arg | Met | Gln | Leu | Leu | Ser | Cys | Ile | Ala | Leu | Ser | Leu | Ala | Leu |
|---|---|---|---|---|---|---|---|---|---|---|---|---|---|---|---|
| 1 | | | | 5 | | | | | 10 | | | | | 15 | |

| Val | Thr | Asn | Ser | Asp | Ile | Gln | Met | Thr | Gln | Thr | Thr | Ser | Ser | Leu | Ser |
|---|---|---|---|---|---|---|---|---|---|---|---|---|---|---|---|
| | | | 20 | | | | | 25 | | | | | 30 | | |

| Ala | Ser | Leu | Gly | Asp | Arg | Val | Thr | Ile | Ser | Cys | Arg | Ala | Ser | Gln | Asp |
|---|---|---|---|---|---|---|---|---|---|---|---|---|---|---|---|
| | | 35 | | | | | 40 | | | | | 45 | | | |

```
Ile Ser Lys Tyr Leu Asn Trp Tyr Gln Gln Lys Pro Asp Gly Thr Val
        50                  55                  60

Lys Leu Leu Ile Tyr His Thr Ser Arg Leu His Ser Gly Val Pro Ser
 65                  70                  75                  80

Arg Phe Ser Gly Ser Gly Ser Gly Thr Asp Tyr Ser Leu Thr Ile Ser
                     85                  90                  95

Asn Leu Glu Gln Glu Asp Ile Ala Thr Tyr Phe Cys Gln Gln Gly Asn
                100                 105                 110

Thr Leu Pro Tyr Thr Phe Gly Gly Gly Thr Lys Leu Glu Ile Lys Arg
                115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 46
<211> LENGTH: 234
<212> TYPE: PRT
<213> ORGANISM: Artificial Sequence
<220> FEATURE:
<223> OTHER INFORMATION: Fmc63 LC WT Light Chain sequence

<400> SEQUENCE: 46

Met Tyr Arg Met Gln Leu Leu Ser Cys Ile Ala Leu Ser Leu Ala Leu
 1                   5                  10                  15

Val Thr Asn Ser Asp Ile Gln Met Thr Gln Thr Thr Ser Ser Leu Ser
                 20                  25                  30

Ala Ser Leu Gly Asp Arg Val Thr Ile Ser Cys Arg Ala Ser Gln Asp
             35                  40                  45

Ile Ser Lys Tyr Leu Asn Trp Tyr Gln Gln Lys Pro Asp Gly Thr Val
        50                  55                  60

Lys Leu Leu Ile Tyr His Thr Ser Arg Leu His Ser Gly Val Pro Ser
 65                  70                  75                  80

Arg Phe Ser Gly Ser Gly Ser Gly Thr Asp Tyr Ser Leu Thr Ile Ser
                     85                  90                  95

Asn Leu Glu Gln Glu Asp Ile Ala Thr Tyr Phe Cys Gln Gln Gly Asn
                100                 105                 110

Thr Leu Pro Tyr Thr Phe Gly Gly Gly Thr Lys Leu Glu Ile Lys Arg
                115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175
```

```
Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 47
<211> LENGTH: 273
<212> TYPE: PRT
<213> ORGANISM: Artificial Sequence
<220> FEATURE:
<223> OTHER INFORMATION: 2X-E4 Chimeric Receptor sequence

<400> SEQUENCE: 47

Met Ala Leu Pro Val Thr Ala Leu Leu Leu Pro Leu Ala Leu Leu Leu
1               5                   10                  15

His Ala Ala Arg Pro Glu Val Ala Ala Leu Glu Lys Glu Val Ala Ala
            20                  25                  30

Leu Glu Lys Glu Val Ala Ala Leu Glu Lys Glu Val Ala Ala Leu Glu
        35                  40                  45

Lys Gly Gly Gly Ser Glu Val Ala Ala Leu Glu Lys Glu Val Ala
    50                  55                  60

Ala Leu Glu Lys Glu Val Ala Ala Leu Glu Lys Glu Val Ala Ala Leu
65                  70                  75                  80

Glu Lys Glu Ser Lys Tyr Gly Pro Pro Cys Pro Pro Cys Pro Asp Ile
                85                  90                  95

Tyr Ile Trp Ala Pro Leu Ala Gly Thr Cys Gly Val Leu Leu Leu Ser
            100                 105                 110

Leu Val Ile Thr Leu Tyr Cys Lys Arg Gly Arg Lys Lys Leu Leu Tyr
        115                 120                 125

Ile Phe Lys Gln Pro Phe Met Arg Pro Val Gln Thr Thr Gln Glu Glu
    130                 135                 140

Asp Gly Cys Ser Cys Arg Phe Pro Glu Glu Glu Glu Gly Gly Cys Glu
145                 150                 155                 160

Leu Arg Val Lys Phe Ser Arg Ser Ala Asp Ala Pro Ala Tyr Lys Gln
                165                 170                 175

Gly Gln Asn Gln Leu Tyr Asn Glu Leu Asn Leu Gly Arg Arg Glu Glu
            180                 185                 190

Tyr Asp Val Leu Asp Lys Arg Arg Gly Arg Asp Pro Glu Met Gly Gly
        195                 200                 205

Lys Pro Arg Arg Lys Asn Pro Gln Glu Gly Leu Tyr Asn Glu Leu Gln
    210                 215                 220

Lys Asp Lys Met Ala Glu Ala Tyr Ser Glu Ile Gly Met Lys Gly Glu
225                 230                 235                 240

Arg Arg Arg Gly Lys Gly His Asp Gly Leu Tyr Gln Gly Leu Ser Thr
                245                 250                 255

Ala Thr Lys Asp Thr Tyr Asp Ala Leu His Met Gln Ala Leu Pro Pro
            260                 265                 270

Arg

<210> SEQ ID NO 48
<211> LENGTH: 273
<212> TYPE: PRT
```

<213> ORGANISM: Artificial Sequence
<220> FEATURE:
<223> OTHER INFORMATION: 2X-K4 Chimeric Receptor sequence

<400> SEQUENCE: 48

```
Met Ala Leu Pro Val Thr Ala Leu Leu Leu Pro Leu Ala Leu Leu
1               5                   10                  15

His Ala Ala Arg Pro Lys Val Ala Ala Leu Lys Glu Lys Val Ala Ala
                20                  25                  30

Leu Lys Glu Lys Val Ala Ala Leu Lys Glu Lys Val Ala Ala Leu Lys
            35                  40                  45

Glu Gly Gly Gly Gly Ser Lys Val Ala Ala Leu Lys Glu Lys Val Ala
        50                  55                  60

Ala Leu Lys Glu Lys Val Ala Ala Leu Lys Glu Lys Val Ala Ala Leu
65                  70                  75                  80

Lys Glu Glu Ser Lys Tyr Gly Pro Pro Cys Pro Pro Cys Pro Asp Ile
                85                  90                  95

Tyr Ile Trp Ala Pro Leu Ala Gly Thr Cys Gly Val Leu Leu Leu Ser
                100                 105                 110

Leu Val Ile Thr Leu Tyr Cys Lys Arg Gly Arg Lys Lys Leu Leu Tyr
            115                 120                 125

Ile Phe Lys Gln Pro Phe Met Arg Pro Val Gln Thr Thr Gln Glu Glu
130                 135                 140

Asp Gly Cys Ser Cys Arg Phe Pro Glu Glu Glu Gly Gly Cys Glu
145                 150                 155                 160

Leu Arg Val Lys Phe Ser Arg Ser Ala Asp Ala Pro Ala Tyr Lys Gln
                165                 170                 175

Gly Gln Asn Gln Leu Tyr Asn Glu Leu Asn Leu Gly Arg Arg Glu Glu
                180                 185                 190

Tyr Asp Val Leu Asp Lys Arg Arg Gly Arg Asp Pro Glu Met Gly Gly
            195                 200                 205

Lys Pro Arg Arg Lys Asn Pro Gln Glu Gly Leu Tyr Asn Glu Leu Gln
        210                 215                 220

Lys Asp Lys Met Ala Glu Ala Tyr Ser Glu Ile Gly Met Lys Gly Glu
225                 230                 235                 240

Arg Arg Arg Gly Lys Gly His Asp Gly Leu Tyr Gln Gly Leu Ser Thr
                245                 250                 255

Ala Thr Lys Asp Thr Tyr Asp Ala Leu His Met Gln Ala Leu Pro Pro
            260                 265                 270

Arg
```

<210> SEQ ID NO 49
<211> LENGTH: 309
<212> TYPE: PRT
<213> ORGANISM: Artificial Sequence
<220> FEATURE:
<223> OTHER INFORMATION: Fmc63 HCCT 2X-E4 switch Heavy Chain sequence

<400> SEQUENCE: 49

```
Met Tyr Arg Met Gln Leu Leu Ser Cys Ile Ala Leu Ser Leu Ala Leu
1               5                   10                  15

Val Thr Asn Ser Glu Val Lys Leu Gln Glu Ser Gly Pro Gly Leu Val
                20                  25                  30

Ala Pro Ser Gln Ser Leu Ser Val Thr Cys Thr Val Ser Gly Val Ser
            35                  40                  45

Leu Pro Asp Tyr Gly Val Ser Trp Ile Arg Gln Pro Pro Arg Lys Gly
```

```
                    50                  55                  60

Leu Glu Trp Leu Gly Val Ile Trp Gly Ser Glu Thr Thr Tyr Tyr Asn
 65                  70                  75                  80

Ser Ala Leu Lys Ser Arg Leu Thr Ile Ile Lys Asp Asn Ser Lys Ser
                     85                  90                  95

Gln Val Phe Leu Lys Met Asn Ser Leu Gln Thr Asp Asp Thr Ala Ile
                    100                 105                 110

Tyr Tyr Cys Ala Lys His Tyr Tyr Gly Gly Ser Tyr Ala Met Asp
                115                 120                 125

Tyr Trp Gly Gln Gly Thr Ser Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Ser Leu Gly Thr Gln Thr Tyr Ile Cys Asn
                210                 215                 220

Val Asn His Lys Pro Ser Asn Thr Lys Val Asp Lys Lys Val Glu Pro
225                 230                 235                 240

Lys Ser Cys Gly Gly Gly Gly Ser Glu Val Ala Ala Leu Glu Lys Glu
                245                 250                 255

Val Ala Ala Leu Glu Lys Glu Val Ala Ala Leu Glu Lys Glu Val Ala
                260                 265                 270

Ala Leu Glu Lys Gly Gly Gly Gly Ser Glu Val Ala Ala Leu Glu Lys
                275                 280                 285

Glu Val Ala Ala Leu Glu Lys Glu Val Ala Ala Leu Glu Lys Glu Val
                290                 295                 300

Ala Ala Leu Glu Lys
305

<210> SEQ ID NO 50
<211> LENGTH: 309
<212> TYPE: PRT
<213> ORGANISM: Artificial Sequence
<220> FEATURE:
<223> OTHER INFORMATION: Fmc63 HCCT 2X-K4 switch Heavy Chain sequence

<400> SEQUENCE: 50

Met Tyr Arg Met Gln Leu Leu Ser Cys Ile Ala Leu Ser Leu Ala Leu
  1               5                  10                  15

Val Thr Asn Ser Glu Val Lys Leu Gln Glu Ser Gly Pro Gly Leu Val
                 20                  25                  30

Ala Pro Ser Gln Ser Leu Ser Val Thr Cys Thr Val Ser Gly Val Ser
                 35                  40                  45

Leu Pro Asp Tyr Gly Val Ser Trp Ile Arg Gln Pro Pro Arg Lys Gly
 50                  55                  60

Leu Glu Trp Leu Gly Val Ile Trp Gly Ser Glu Thr Thr Tyr Tyr Asn
 65                  70                  75                  80

Ser Ala Leu Lys Ser Arg Leu Thr Ile Ile Lys Asp Asn Ser Lys Ser
                     85                  90                  95

Gln Val Phe Leu Lys Met Asn Ser Leu Gln Thr Asp Asp Thr Ala Ile
```

```
                    100                 105                 110
Tyr Tyr Cys Ala Lys His Tyr Tyr Gly Gly Ser Tyr Ala Met Asp
            115                 120                 125

Tyr Trp Gly Gln Gly Thr Ser Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Gly Gly Gly Gly Ser Lys Val Ala Ala Leu Lys Glu Lys
                245                 250                 255

Val Ala Ala Leu Lys Glu Lys Val Ala Ala Leu Lys Glu Lys Val Ala
            260                 265                 270

Ala Leu Lys Glu Gly Gly Gly Ser Lys Val Ala Ala Leu Lys Glu
        275                 280                 285

Lys Val Ala Ala Leu Lys Glu Lys Val Ala Ala Leu Lys Glu Lys Val
    290                 295                 300

Ala Ala Leu Lys Glu
305

<210> SEQ ID NO 51
<211> LENGTH: 267
<212> TYPE: PRT
<213> ORGANISM: Artificial Sequence
<220> FEATURE:
<223> OTHER INFORMATION: Fmc63 LCCT E4 switch Light Chain sequence

<400> SEQUENCE: 51

Met Tyr Arg Met Gln Leu Leu Ser Cys Ile Ala Leu Ser Leu Ala Leu
1               5                   10                  15

Val Thr Asn Ser Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Lys Tyr Leu Asn Trp Tyr Gln Gln Lys Pro Asp Gly Thr Val
    50                  55                  60

Lys Leu Leu Ile Tyr His Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Tyr Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
```

```
                145                 150                 155                 160
Pro Arg Glu Ala Lys Val Gln Trp Lys Val Asp Asn Ala Leu Gln Ser
                    165                 170                 175

Gly Asn Ser Gln Glu Ser Val Thr Glu Gln Asp Ser Lys Asp Ser Thr
                    180                 185                 190

Tyr Ser Leu Ser Ser Thr Leu Thr Leu Ser Lys Ala Asp Tyr Glu Lys
                    195                 200                 205

His Lys Val Tyr Ala Cys Glu Val Thr His Gln Gly Leu Ser Ser Pro
                    210                 215                 220

Val Thr Lys Ser Phe Asn Arg Gly Glu Cys Gly Gly Gly Ser Glu
225                 230                 235                 240

Val Ala Ala Leu Glu Lys Glu Val Ala Ala Leu Glu Lys Glu Val Ala
                    245                 250                 255

Ala Leu Glu Lys Glu Val Ala Ala Leu Glu Lys
                    260                 265

<210> SEQ ID NO 52
<211> LENGTH: 267
<212> TYPE: PRT
<213> ORGANISM: Artificial Sequence
<220> FEATURE:
<223> OTHER INFORMATION: Fmc63 LCCT K4 Light Chain switch

<400> SEQUENCE: 52

Met Tyr Arg Met Gln Leu Leu Ser Cys Ile Ala Leu Ser Leu Ala Leu
1               5                   10                  15

Val Thr Asn Ser Asp Ile Gln Met Thr Gln Thr Thr Ser Ser Leu Ser
                20                  25                  30

Ala Ser Leu Gly Asp Arg Val Thr Ile Ser Cys Arg Ala Ser Gln Asp
                    35                  40                  45

Ile Ser Lys Tyr Leu Asn Trp Tyr Gln Gln Lys Pro Asp Gly Thr Val
            50                  55                  60

Lys Leu Leu Ile Tyr His Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
                    100                 105                 110

Thr Leu Pro Tyr Thr Phe Gly Gly Gly Thr Lys Leu Glu Ile Lys Arg
                    115                 120                 125

Thr Val Ala Ala Pro Ser Val Phe Ile Phe Pro Pro Ser Asp Glu Gln
                    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                    165                 170                 175

Gly Asn Ser Gln Glu Ser Val Thr Glu Gln Asp Ser Lys Asp Ser Thr
                    180                 185                 190

Tyr Ser Leu Ser Ser Thr Leu Thr Leu Ser Lys Ala Asp Tyr Glu Lys
                    195                 200                 205

His Lys Val Tyr Ala Cys Glu Val Thr His Gln Gly Leu Ser Ser Pro
                    210                 215                 220

Val Thr Lys Ser Phe Asn Arg Gly Glu Cys Gly Gly Gly Ser Lys
225                 230                 235                 240

Val Ala Ala Leu Lys Glu Lys Val Ala Ala Leu Lys Glu Lys Val Ala
```

Ala Leu Lys Glu Lys Val Ala Ala Leu Lys Glu
            260                 265

<210> SEQ ID NO 53
<211> LENGTH: 275
<212> TYPE: PRT
<213> ORGANISM: Artificial Sequence
<220> FEATURE:
<223> OTHER INFORMATION: Fmc63 HCNT E4 switch Heavy Chain sequence

<400> SEQUENCE: 53

Met Glu Val Ala Ala Leu Glu Lys Glu Val Ala Ala Leu Glu Lys Glu
1               5                   10                  15

Val Ala Ala Leu Glu Lys Glu Val Ala Ala Leu Glu Lys Gly Gly Gly
            20                  25                  30

Ser Tyr Arg Met Gln Leu Leu Ser Cys Ile Ala Leu Ser Leu Ala Leu
        35                  40                  45

Val Thr Asn Ser Glu Val Lys Leu Gln Glu Ser Gly Pro Gly Leu Val
    50                  55                  60

Ala Pro Ser Gln Ser Leu Ser Val Thr Cys Thr Val Ser Gly Val Ser
65                  70                  75                  80

Leu Pro Asp Tyr Gly Val Ser Trp Ile Arg Gln Pro Pro Arg Lys Gly
                85                  90                  95

Leu Glu Trp Leu Gly Val Ile Trp Gly Ser Glu Thr Thr Tyr Tyr Asn
            100                 105                 110

Ser Ala Leu Lys Ser Arg Leu Thr Ile Ile Lys Asp Asn Ser Lys Ser
        115                 120                 125

Gln Val Phe Leu Lys Met Asn Ser Leu Gln Thr Asp Asp Thr Ala Ile
    130                 135                 140

Tyr Tyr Cys Ala Lys His Tyr Tyr Gly Gly Ser Tyr Ala Met Asp
145                 150                 155                 160

Tyr Trp Gly Gln Gly Thr Ser Val Thr Val Ser Ser Ala Ser Thr Lys
                165                 170                 175

Gly Pro Ser Val Phe Pro Leu Ala Pro Ser Ser Lys Ser Thr Ser Gly
            180                 185                 190

Gly Thr Ala Ala Leu Gly Cys Leu Val Lys Asp Tyr Phe Pro Glu Pro
        195                 200                 205

Val Thr Val Ser Trp Asn Ser Gly Ala Leu Thr Ser Gly Val His Thr
    210                 215                 220

Phe Pro Ala Val Leu Gln Ser Ser Gly Leu Tyr Ser Leu Ser Ser Val
225                 230                 235                 240

Val Thr Val Pro Ser Ser Ser Leu Gly Thr Gln Thr Tyr Ile Cys Asn
                245                 250                 255

Val Asn His Lys Pro Ser Asn Thr Lys Val Asp Lys Lys Val Glu Pro
            260                 265                 270

Lys Ser Cys
        275

<210> SEQ ID NO 54
<211> LENGTH: 275
<212> TYPE: PRT
<213> ORGANISM: Artificial Sequence
<220> FEATURE:
<223> OTHER INFORMATION: Fmc63 HCNT K4 switch Heavy Chain sequence

<400> SEQUENCE: 54

Met Lys Val Ala Ala Leu Lys Glu Lys Val Ala Ala Leu Lys Glu Lys
1               5                   10                  15

Val Ala Ala Leu Lys Glu Lys Val Ala Ala Leu Lys Glu Gly Gly Gly
                20                  25                  30

Ser Tyr Arg Met Gln Leu Leu Ser Cys Ile Ala Leu Ser Leu Ala Leu
            35                  40                  45

Val Thr Asn Ser Glu Val Lys Leu Gln Glu Ser Gly Pro Gly Leu Val
    50                  55                  60

Ala Pro Ser Gln Ser Leu Ser Val Thr Cys Thr Val Ser Gly Val Ser
65                  70                  75                  80

Leu Pro Asp Tyr Gly Val Ser Trp Ile Arg Gln Pro Pro Arg Lys Gly
                85                  90                  95

Leu Glu Trp Leu Gly Val Ile Trp Gly Ser Glu Thr Thr Tyr Tyr Asn
            100                 105                 110

Ser Ala Leu Lys Ser Arg Leu Thr Ile Ile Lys Asp Asn Ser Lys Ser
            115                 120                 125

Gln Val Phe Leu Lys Met Asn Ser Leu Gln Thr Asp Asp Thr Ala Ile
            130                 135                 140

Tyr Tyr Cys Ala Lys His Tyr Tyr Gly Gly Ser Tyr Ala Met Asp
145                 150                 155                 160

Tyr Trp Gly Gln Gly Thr Ser Val Thr Val Ser Ser Ala Ser Thr Lys
                165                 170                 175

Gly Pro Ser Val Phe Pro Leu Ala Pro Ser Ser Lys Ser Thr Ser Gly
                180                 185                 190

Gly Thr Ala Ala Leu Gly Cys Leu Val Lys Asp Tyr Phe Pro Glu Pro
            195                 200                 205

Val Thr Val Ser Trp Asn Ser Gly Ala Leu Thr Ser Gly Val His Thr
    210                 215                 220

Phe Pro Ala Val Leu Gln Ser Ser Gly Leu Tyr Ser Leu Ser Ser Val
225                 230                 235                 240

Val Thr Val Pro Ser Ser Ser Leu Gly Thr Gln Thr Tyr Ile Cys Asn
                245                 250                 255

Val Asn His Lys Pro Ser Asn Thr Lys Val Asp Lys Lys Val Glu Pro
            260                 265                 270

Lys Ser Cys
        275

<210> SEQ ID NO 55
<211> LENGTH: 266
<212> TYPE: PRT
<213> ORGANISM: Artificial Sequence
<220> FEATURE:
<223> OTHER INFORMATION: Fmc63 LCNT E4 switch Light Chain sequence

<400> SEQUENCE: 55

Met Glu Val Ala Ala Leu Glu Lys Glu Val Ala Ala Leu Glu Lys Glu
1               5                   10                  15

Val Ala Ala Leu Glu Lys Glu Val Ala Ala Leu Glu Lys Gly Gly Gly
                20                  25                  30

Ser Tyr Arg Met Gln Leu Leu Ser Cys Ile Ala Leu Ser Leu Ala Leu
            35                  40                  45

Val Thr Asn Ser Asp Ile Gln Met Thr Gln Thr Thr Ser Ser Leu Ser
    50                  55                  60

Ala Ser Leu Gly Asp Arg Val Thr Ile Ser Cys Arg Ala Ser Gln Asp
65                  70                  75                  80

```
Ile Ser Lys Tyr Leu Asn Trp Tyr Gln Gln Lys Pro Asp Gly Thr Val
                85                  90                  95
Lys Leu Leu Ile Tyr His Thr Ser Arg Leu His Ser Gly Val Pro Ser
            100                 105                 110
Arg Phe Ser Gly Ser Gly Ser Gly Thr Asp Tyr Ser Leu Thr Ile Ser
            115                 120                 125
Asn Leu Glu Gln Glu Asp Ile Ala Thr Tyr Phe Cys Gln Gln Gly Asn
            130                 135                 140
Thr Leu Pro Tyr Thr Phe Gly Gly Gly Thr Lys Leu Glu Ile Lys Arg
145                 150                 155                 160
Thr Val Ala Ala Pro Ser Val Phe Ile Phe Pro Pro Ser Asp Glu Gln
                165                 170                 175
Leu Lys Ser Gly Thr Ala Ser Val Val Cys Leu Leu Asn Asn Phe Tyr
            180                 185                 190
Pro Arg Glu Ala Lys Val Gln Trp Lys Val Asp Asn Ala Leu Gln Ser
            195                 200                 205
Gly Asn Ser Gln Glu Ser Val Thr Glu Gln Asp Ser Lys Asp Ser Thr
            210                 215                 220
Tyr Ser Leu Ser Ser Thr Leu Thr Leu Ser Lys Ala Asp Tyr Glu Lys
225                 230                 235                 240
His Lys Val Tyr Ala Cys Glu Val Thr His Gln Gly Leu Ser Ser Pro
                245                 250                 255
Val Thr Lys Ser Phe Asn Arg Gly Glu Cys
            260                 265

<210> SEQ ID NO 56
<211> LENGTH: 266
<212> TYPE: PRT
<213> ORGANISM: Artificial Sequence
<220> FEATURE:
<223> OTHER INFORMATION: Fmc63 LCNT K4 Light Chain switch

<400> SEQUENCE: 56

Met Lys Val Ala Ala Leu Lys Glu Lys Val Ala Ala Leu Lys Glu Lys
1               5                   10                  15
Val Ala Ala Leu Lys Glu Lys Val Ala Ala Leu Lys Glu Gly Gly Gly
            20                  25                  30
Ser Tyr Arg Met Gln Leu Leu Ser Cys Ile Ala Leu Ser Leu Ala Leu
            35                  40                  45
Val Thr Asn Ser Asp Ile Gln Met Thr Gln Thr Thr Ser Ser Leu Ser
50                  55                  60
Ala Ser Leu Gly Asp Arg Val Thr Ile Ser Cys Arg Ala Ser Gln Asp
65                  70                  75                  80
Ile Ser Lys Tyr Leu Asn Trp Tyr Gln Gln Lys Pro Asp Gly Thr Val
                85                  90                  95
Lys Leu Leu Ile Tyr His Thr Ser Arg Leu His Ser Gly Val Pro Ser
            100                 105                 110
Arg Phe Ser Gly Ser Gly Ser Gly Thr Asp Tyr Ser Leu Thr Ile Ser
            115                 120                 125
Asn Leu Glu Gln Glu Asp Ile Ala Thr Tyr Phe Cys Gln Gln Gly Asn
            130                 135                 140
Thr Leu Pro Tyr Thr Phe Gly Gly Gly Thr Lys Leu Glu Ile Lys Arg
145                 150                 155                 160
Thr Val Ala Ala Pro Ser Val Phe Ile Phe Pro Pro Ser Asp Glu Gln
                165                 170                 175
```

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
    210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
            260                 265

<210> SEQ ID NO 57
<211> LENGTH: 275
<212> TYPE: PRT
<213> ORGANISM: Artificial Sequence
<220> FEATURE:
<223> OTHER INFORMATION: Fmc63 HCC1 E4 switch Heavy Chain sequence

<400> SEQUENCE: 57

Met Tyr Arg Met Gln Leu Leu Ser Cys Ile Ala Leu Ser Leu Ala Leu
1               5                   10                  15

Val Thr Asn Ser Glu Val Lys Leu Gln Glu Ser Gly Pro Gly Leu Val
            20                  25                  30

Ala Pro Ser Gln Ser Leu Ser Val Thr Cys Thr Val Ser Gly Val Ser
        35                  40                  45

Leu Pro Asp Tyr Gly Val Ser Trp Ile Arg Gln Pro Pro Arg Lys Gly
    50                  55                  60

Leu Glu Trp Leu Gly Val Ile Trp Gly Ser Glu Thr Thr Tyr Tyr Asn
65                  70                  75                  80

Ser Ala Leu Lys Ser Arg Leu Thr Ile Ile Lys Asp Asn Ser Lys Ser
                85                  90                  95

Gln Val Phe Leu Lys Met Asn Ser Leu Gln Thr Asp Asp Thr Ala Ile
            100                 105                 110

Tyr Tyr Cys Ala Lys His Tyr Tyr Gly Gly Ser Tyr Ala Met Asp
        115                 120                 125

Tyr Trp Gly Gln Gly Thr Ser Val Thr Val Ser Ser Ala Ser Thr Lys
130                 135                 140

Gly Pro Ser Val Phe Pro Leu Ala Pro Ser Ser Gly Gly Gly Gly Ser
145                 150                 155                 160

Glu Val Ala Ala Leu Glu Lys Glu Val Ala Ala Leu Glu Lys Glu Val
                165                 170                 175

Ala Ala Leu Glu Lys Glu Val Ala Ala Leu Glu Lys Gly Gly Ser Gly
            180                 185                 190

Gly Thr Ala Ala Leu Gly Cys Leu Val Lys Asp Tyr Phe Pro Glu Pro
        195                 200                 205

Val Thr Val Ser Trp Asn Ser Gly Ala Leu Thr Ser Gly Val His Thr
    210                 215                 220

Phe Pro Ala Val Leu Gln Ser Ser Gly Leu Tyr Ser Leu Ser Ser Val
225                 230                 235                 240

Val Thr Val Pro Ser Ser Ser Leu Gly Thr Gln Thr Tyr Ile Cys Asn
                245                 250                 255

Val Asn His Lys Pro Ser Asn Thr Lys Val Asp Lys Lys Val Glu Pro
            260                 265                 270

Lys Ser Cys
        275

<210> SEQ ID NO 58
<211> LENGTH: 275
<212> TYPE: PRT
<213> ORGANISM: Artificial Sequence
<220> FEATURE:
<223> OTHER INFORMATION: Fmc63 HCC1 K4 switch Heavy Chain sequence

<400> SEQUENCE: 58

Met Tyr Arg Met Gln Leu Leu Ser Cys Ile Ala Leu Ser Leu Ala Leu
1               5                   10                  15

Val Thr Asn Ser Glu Val Lys Leu Gln Glu Ser Gly Pro Gly Leu Val
            20                  25                  30

Ala Pro Ser Gln Ser Leu Ser Val Thr Cys Thr Val Ser Gly Val Ser
        35                  40                  45

Leu Pro Asp Tyr Gly Val Ser Trp Ile Arg Gln Pro Pro Arg Lys Gly
    50                  55                  60

Leu Glu Trp Leu Gly Val Ile Trp Gly Ser Glu Thr Thr Tyr Tyr Asn
65                  70                  75                  80

Ser Ala Leu Lys Ser Arg Leu Thr Ile Ile Lys Asp Asn Ser Lys Ser
                85                  90                  95

Gln Val Phe Leu Lys Met Asn Ser Leu Gln Thr Asp Asp Thr Ala Ile
            100                 105                 110

Tyr Tyr Cys Ala Lys His Tyr Tyr Tyr Gly Gly Ser Tyr Ala Met Asp
        115                 120                 125

Tyr Trp Gly Gln Gly Thr Ser Val Thr Val Ser Ser Ala Ser Thr Lys
    130                 135                 140

Gly Pro Ser Val Phe Pro Leu Ala Pro Ser Ser Gly Gly Gly Gly Ser
145                 150                 155                 160

Lys Val Ala Ala Leu Lys Glu Lys Val Ala Ala Leu Lys Glu Lys Val
                165                 170                 175

Ala Ala Leu Lys Glu Lys Val Ala Ala Leu Lys Glu Gly Gly Ser Gly
            180                 185                 190

Gly Thr Ala Ala Leu Gly Cys Leu Val Lys Asp Tyr Phe Pro Glu Pro
        195                 200                 205

Val Thr Val Ser Trp Asn Ser Gly Ala Leu Thr Ser Gly Val His Thr
    210                 215                 220

Phe Pro Ala Val Leu Gln Ser Ser Gly Leu Tyr Ser Leu Ser Ser Val
225                 230                 235                 240

Val Thr Val Pro Ser Ser Ser Leu Gly Thr Gln Thr Tyr Ile Cys Asn
                245                 250                 255

Val Asn His Lys Pro Ser Asn Thr Lys Val Asp Lys Lys Val Glu Pro
            260                 265                 270

Lys Ser Cys
        275

<210> SEQ ID NO 59
<211> LENGTH: 271
<212> TYPE: PRT
<213> ORGANISM: Artificial Sequence
<220> FEATURE:
<223> OTHER INFORMATION: Fmc63 LCC1A E4 switch Light Chain sequence

<400> SEQUENCE: 59

Met Tyr Arg Met Gln Leu Leu Ser Cys Ile Ala Leu Ser Leu Ala Leu
1               5                   10                  15

Val Thr Asn Ser Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Lys Tyr Leu Asn Trp Tyr Gln Gln Lys Pro Asp Gly Thr Val
50                  55                  60

Lys Leu Leu Ile Tyr His Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Tyr Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Gly Gly Gly Gly
            180                 185                 190

Ser Glu Val Ala Ala Leu Glu Lys Glu Val Ala Ala Leu Glu Lys Glu
        195                 200                 205

Val Ala Ala Leu Glu Lys Glu Val Ala Ala Leu Glu Lys Gly Gly Gly
210                 215                 220

Gly Ser Asp Ser Thr Tyr Ser Leu Ser Ser Thr Leu Thr Leu Ser Lys
225                 230                 235                 240

Ala Asp Tyr Glu Lys His Lys Val Tyr Ala Cys Glu Val Thr His Gln
                245                 250                 255

Gly Leu Ser Ser Pro Val Thr Lys Ser Phe Asn Arg Gly Glu Cys
            260                 265                 270

<210> SEQ ID NO 60
<211> LENGTH: 271
<212> TYPE: PRT
<213> ORGANISM: Artificial Sequence
<220> FEATURE:
<223> OTHER INFORMATION: Fmc63 LCC1A K4 switch Light Chain sequence

<400> SEQUENCE: 60

Met Tyr Arg Met Gln Leu Leu Ser Cys Ile Ala Leu Ser Leu Ala Leu
1               5                   10                  15

Val Thr Asn Ser Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Lys Tyr Leu Asn Trp Tyr Gln Gln Lys Pro Asp Gly Thr Val
50                  55                  60

Lys Leu Leu Ile Tyr His Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

```
Thr Leu Pro Tyr Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Gly Gly Gly Gly
            180                 185                 190

Ser Lys Val Ala Ala Leu Lys Glu Lys Val Ala Ala Leu Lys Glu Lys
        195                 200                 205

Val Ala Ala Leu Lys Glu Lys Val Ala Ala Leu Lys Glu Gly Gly Gly
        210                 215                 220

Gly Ser Asp Ser Thr Tyr Ser Leu Ser Ser Thr Leu Thr Leu Ser Lys
225                 230                 235                 240

Ala Asp Tyr Glu Lys His Lys Val Tyr Ala Cys Glu Val Thr His Gln
                245                 250                 255

Gly Leu Ser Ser Pro Val Thr Lys Ser Phe Asn Arg Gly Glu Cys
            260                 265                 270

<210> SEQ ID NO 61
<211> LENGTH: 28
<212> TYPE: PRT
<213> ORGANISM: Artificial Sequence
<220> FEATURE:
<223> OTHER INFORMATION: Synthetic E/K helical protein

<400> SEQUENCE: 61

Glu Val Ser Ala Leu Glu Lys Glu Val Ser Ala Leu Glu Lys Glu Val
1               5                   10                  15

Ser Ala Leu Glu Lys Glu Val Ser Ala Leu Glu Lys
            20                  25

<210> SEQ ID NO 62
<211> LENGTH: 28
<212> TYPE: PRT
<213> ORGANISM: Artificial Sequence
<220> FEATURE:
<223> OTHER INFORMATION: Synthetic E/K helical peptide

<400> SEQUENCE: 62

Lys Val Ser Ala Leu Lys Glu Lys Val Ser Ala Leu Lys Glu Lys Val
1               5                   10                  15

Ser Ala Leu Lys Glu Lys Val Ser Ala Leu Lys Glu
            20                  25

<210> SEQ ID NO 63
<211> LENGTH: 299
<212> TYPE: PRT
<213> ORGANISM: Artificial Sequence
<220> FEATURE:
<223> OTHER INFORMATION: Fmc63 LC BV E4 switch  light chain

<400> SEQUENCE: 63

Met Glu Val Ala Ala Leu Glu Lys Glu Val Ala Ala Leu Glu Lys Glu
1               5                   10                  15

Val Ala Ala Leu Glu Lys Glu Val Ala Ala Leu Glu Lys Gly Gly Gly
            20                  25                  30
```

Ser Tyr Arg Met Gln Leu Leu Ser Cys Ile Ala Leu Ser Leu Ala Leu
            35                  40                  45

Val Thr Asn Ser Asp Ile Gln Met Thr Gln Thr Thr Ser Ser Leu Ser
 50                  55                  60

Ala Ser Leu Gly Asp Arg Val Thr Ile Ser Cys Arg Ala Ser Gln Asp
 65                  70                  75                  80

Ile Ser Lys Tyr Leu Asn Trp Tyr Gln Gln Lys Pro Asp Gly Thr Val
                 85                  90                  95

Lys Leu Leu Ile Tyr His Thr Ser Arg Leu His Ser Gly Val Pro Ser
                100                 105                 110

Arg Phe Ser Gly Ser Gly Ser Gly Thr Asp Tyr Ser Leu Thr Ile Ser
            115                 120                 125

Asn Leu Glu Gln Glu Asp Ile Ala Thr Tyr Phe Cys Gln Gln Gly Asn
        130                 135                 140

Thr Leu Pro Tyr Thr Phe Gly Gly Gly Thr Lys Leu Glu Ile Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
    210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys Gly Gly Gly Gly Ser Glu
            260                 265                 270

Val Ala Ala Leu Glu Lys Glu Val Ala Ala Leu Glu Lys Glu Val Ala
        275                 280                 285

Ala Leu Glu Lys Glu Val Ala Ala Leu Glu Lys
    290                 295

<210> SEQ ID NO 64
<211> LENGTH: 308
<212> TYPE: PRT
<213> ORGANISM: Artificial Sequence
<220> FEATURE:
<223> OTHER INFORMATION: Fmc63 HC BV E4 switch light chain

<400> SEQUENCE: 64

Met Glu Val Ala Ala Leu Glu Lys Glu Val Ala Ala Leu Glu Lys Glu
1               5                   10                  15

Val Ala Ala Leu Glu Lys Glu Val Ala Ala Leu Glu Lys Gly Gly Gly
            20                  25                  30

Ser Tyr Arg Met Gln Leu Leu Ser Cys Ile Ala Leu Ser Leu Ala Leu
            35                  40                  45

Val Thr Asn Ser Glu Val Lys Leu Gln Glu Ser Gly Pro Gly Leu Val
 50                  55                  60

Ala Pro Ser Gln Ser Leu Ser Val Thr Cys Thr Val Ser Gly Val Ser
 65                  70                  75                  80

Leu Pro Asp Tyr Gly Val Ser Trp Ile Arg Gln Pro Pro Arg Lys Gly
                 85                  90                  95

```
Leu Glu Trp Leu Gly Val Ile Trp Gly Ser Glu Thr Thr Tyr Tyr Asn
                100                 105                 110

Ser Ala Leu Lys Ser Arg Leu Thr Ile Ile Lys Asp Asn Ser Lys Ser
            115                 120                 125

Gln Val Phe Leu Lys Met Asn Ser Leu Gln Thr Asp Asp Thr Ala Ile
        130                 135                 140

Tyr Tyr Cys Ala Lys His Tyr Tyr Gly Gly Ser Tyr Ala Met Asp
145             150                 155                 160

Tyr Trp Gly Gln Gly Thr Ser Val Thr Val Ser Ser Ala Ser Thr Lys
                165                 170                 175

Gly Pro Ser Val Phe Pro Leu Ala Pro Ser Ser Lys Ser Thr Ser Gly
            180                 185                 190

Gly Thr Ala Ala Leu Gly Cys Leu Val Lys Asp Tyr Phe Pro Glu Pro
        195                 200                 205

Val Thr Val Ser Trp Asn Ser Gly Ala Leu Thr Ser Gly Val His Thr
210                 215                 220

Phe Pro Ala Val Leu Gln Ser Ser Gly Leu Tyr Ser Leu Ser Ser Val
225                 230                 235                 240

Val Thr Val Pro Ser Ser Ser Leu Gly Thr Gln Thr Tyr Ile Cys Asn
            245                 250                 255

Val Asn His Lys Pro Ser Asn Thr Lys Val Asp Lys Lys Val Glu Pro
        260                 265                 270

Lys Ser Cys Gly Gly Gly Ser Glu Val Ala Ala Leu Glu Lys Glu
275                 280                 285

Val Ala Ala Leu Glu Lys Glu Val Ala Ala Leu Glu Lys Glu Val Ala
        290                 295                 300

Ala Leu Glu Lys
305

<210> SEQ ID NO 65
<211> LENGTH: 21
<212> TYPE: PRT
<213> ORGANISM: Artificial Sequence
<220> FEATURE:
<223> OTHER INFORMATION: Synthetic E/K helical peptide

<400> SEQUENCE: 65

Glu Ile Ala Ala Leu Glu Lys Glu Ile Ala Ala Leu Glu Lys Glu Ile
1               5                   10                  15

Ala Ala Leu Glu Lys
            20

<210> SEQ ID NO 66
<211> LENGTH: 28
<212> TYPE: PRT
<213> ORGANISM: Artificial Sequence
<220> FEATURE:
<223> OTHER INFORMATION: Synthetic E/K helical peptide

<400> SEQUENCE: 66

Glu Ile Ala Ala Leu Glu Lys Glu Ile Ala Ala Leu Glu Lys Glu Ile
1               5                   10                  15

Ala Ala Leu Glu Lys Glu Ile Ala Ala Leu Glu Lys
            20                  25

<210> SEQ ID NO 67
<211> LENGTH: 21
<212> TYPE: PRT
<213> ORGANISM: Artificial Sequence
```

-continued

```
<220> FEATURE:
<223> OTHER INFORMATION: Synthetic E/K helical peptide

<400> SEQUENCE: 67

Lys Ile Ala Ala Leu Lys Glu Lys Ile Ala Ala Leu Lys Glu Lys Ile
1               5                   10                  15

Ala Ala Leu Lys Glu
            20

<210> SEQ ID NO 68
<211> LENGTH: 28
<212> TYPE: PRT
<213> ORGANISM: Artificial Sequence
<220> FEATURE:
<223> OTHER INFORMATION: Synthetic E/K helical peptide

<400> SEQUENCE: 68

Lys Ile Ala Ala Leu Lys Glu Lys Ile Ala Ala Leu Lys Glu Lys Ile
1               5                   10                  15

Ala Ala Leu Lys Glu Lys Ile Ala Ala Leu Lys Glu
            20                  25

<210> SEQ ID NO 69
<211> LENGTH: 21
<212> TYPE: PRT
<213> ORGANISM: Artificial Sequence
<220> FEATURE:
<223> OTHER INFORMATION: Synthetic E/K helical peptide

<400> SEQUENCE: 69

Glu Ile Ser Ala Leu Glu Lys Glu Ile Ser Ala Leu Glu Lys Glu Ile
1               5                   10                  15

Ser Ala Leu Glu Lys
            20

<210> SEQ ID NO 70
<211> LENGTH: 28
<212> TYPE: PRT
<213> ORGANISM: Artificial Sequence
<220> FEATURE:
<223> OTHER INFORMATION: Synthetic E/K helical peptide

<400> SEQUENCE: 70

Glu Ile Ser Ala Leu Glu Lys Glu Ile Ser Ala Leu Glu Lys Glu Ile
1               5                   10                  15

Ser Ala Leu Glu Lys Glu Ile Ser Ala Leu Glu Lys
            20                  25

<210> SEQ ID NO 71
<211> LENGTH: 21
<212> TYPE: PRT
<213> ORGANISM: Artificial Sequence
<220> FEATURE:
<223> OTHER INFORMATION: Synthetic E/K helical peptide

<400> SEQUENCE: 71

Lys Ile Ser Ala Leu Lys Glu Lys Ile Ser Ala Leu Lys Glu Lys Ile
1               5                   10                  15

Ser Ala Leu Lys Glu
            20

<210> SEQ ID NO 72
<211> LENGTH: 28
<212> TYPE: PRT
```

```
<213> ORGANISM: Artificial Sequence
<220> FEATURE:
<223> OTHER INFORMATION: Synthetic E/K helical peptide

<400> SEQUENCE: 72

Lys Ile Ser Ala Leu Lys Glu Lys Ile Ser Ala Leu Lys Glu Lys Ile
 1               5                  10                  15

Ser Ala Leu Lys Glu Lys Ile Ser Ala Leu Lys Glu
            20                  25

<210> SEQ ID NO 73
<211> LENGTH: 21
<212> TYPE: PRT
<213> ORGANISM: Artificial Sequence
<220> FEATURE:
<223> OTHER INFORMATION: Synthetic E/K helical peptide

<400> SEQUENCE: 73

Glu Val Ala Ala Leu Glu Lys Glu Val Ala Ala Leu Glu Lys Glu Val
 1               5                  10                  15

Ala Ala Leu Glu Lys
            20

<210> SEQ ID NO 74
<211> LENGTH: 21
<212> TYPE: PRT
<213> ORGANISM: Artificial Sequence
<220> FEATURE:
<223> OTHER INFORMATION: Synthetic E/K helical peptide

<400> SEQUENCE: 74

Lys Val Ala Ala Leu Lys Glu Lys Val Ala Ala Leu Lys Glu Lys Val
 1               5                  10                  15

Ala Ala Leu Lys Glu
            20

<210> SEQ ID NO 75
<211> LENGTH: 21
<212> TYPE: PRT
<213> ORGANISM: Artificial Sequence
<220> FEATURE:
<223> OTHER INFORMATION: Synthetic E/K helical peptide

<400> SEQUENCE: 75

Glu Val Ser Ala Leu Glu Lys Glu Val Ser Ala Leu Glu Lys Glu Val
 1               5                  10                  15

Ser Ala Leu Glu Lys
            20

<210> SEQ ID NO 76
<211> LENGTH: 21
<212> TYPE: PRT
<213> ORGANISM: Artificial Sequence
<220> FEATURE:
<223> OTHER INFORMATION: Synthetic E/K helical peptide

<400> SEQUENCE: 76

Lys Val Ser Ala Leu Lys Glu Lys Val Ser Ala Leu Lys Glu Lys Val
 1               5                  10                  15

Ser Ala Leu Lys Glu
            20
```